(12) United States Patent
Miyazaki et al.

(10) Patent No.: US 10,246,478 B2
(45) Date of Patent: Apr. 2, 2019

(54) POLYENE MACROLIDE DERIVATIVE

(71) Applicant: Shionogi & Co., Ltd., Osaka-shi, Osaka (JP)

(72) Inventors: Keisuke Miyazaki, Toyonaka (JP); Kenji Takaya, Toyonaka (JP); Takafumi Ohara, Toyonaka (JP); Hideki Sugimoto, Toyonaka (JP); Manabu Fujitani, Toyonaka (JP); Yuki Ogata, Toyonaka (JP); Naoyuki Suzuki, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 0 days.

(21) Appl. No.: 15/315,646

(22) PCT Filed: Jun. 12, 2015

(86) PCT No.: PCT/JP2015/066976
§ 371 (c)(1),
(2) Date: Dec. 1, 2016

(87) PCT Pub. No.: WO2015/190587
PCT Pub. Date: Dec. 17, 2015

(65) Prior Publication Data
US 2017/0190729 A1    Jul. 6, 2017

(30) Foreign Application Priority Data
Jun. 12, 2014  (JP) .................. 2014-121341

(51) Int. Cl.
C07H 17/08 (2006.01)
C07H 23/00 (2006.01)
C07H 1/00 (2006.01)

(52) U.S. Cl.
CPC .............. *C07H 17/08* (2013.01); *C07H 1/00* (2013.01); *C07H 23/00* (2013.01)

(58) Field of Classification Search
CPC ................................ C07H 17/08; C07H 23/00
See application file for complete search history.

(56) References Cited

U.S. PATENT DOCUMENTS

| | | | |
|---|---|---|---|
| 4,783,527 A | 11/1988 | Falkowski et al. | |
| 5,100,876 A | 3/1992 | Driver et al. | |
| 5,314,999 A | 5/1994 | Seman et al. | |
| 5,514,662 A | 5/1996 | Seman | |
| 2004/0002465 A1 | 1/2004 | Bolard et al. | |
| 2010/0210576 A1 | 8/2010 | Wang | |

FOREIGN PATENT DOCUMENTS

| | | |
|---|---|---|
| EP | 0 031 722 A1 | 7/1981 |
| JP | 55-157598 A | 12/1980 |
| JP | 56-127394 A | 10/1981 |
| JP | 2-207093 A | 8/1990 |
| JP | 6-504295 A | 5/1994 |
| WO | WO 91/07421 A1 | 5/1991 |
| WO | WO 93/16090 A1 | 8/1993 |
| WO | WO 93/17034 A1 | 9/1993 |
| WO | WO 96/32404 A1 | 10/1996 |
| WO | WO 96/35701 A1 | 11/1996 |
| WO | WO 99/51274 A1 | 10/1999 |
| WO | WO 01/09758 A2 | 2/2001 |
| WO | WO 01/51061 A1 | 7/2001 |
| WO | WO 2007/096137 A1 | 8/2007 |
| WO | WO 2009/015541 A1 | 2/2009 |
| WO | WO 2012/085784 A2 | 6/2012 |
| WO | WO 2013/186384 A1 | 12/2013 |
| WO | WO 2015/054148 A1 | 4/2015 |
| WO | WO 2016/112243 A1 | 7/2016 |
| WO | WO 2016/168568 A1 | 10/2016 |

OTHER PUBLICATIONS

Umegawa et al., Tetrahedron Lett., 2007, 48, p. 3393-3396. (Year: 2007).*
International Preliminary Report on Patentability (form PCT/IB/373) and Written Opinion (form PCT/ISA/237) issued in PCT/JP2015/066976, dated Dec. 15, 2016, with English Translations thereof.
Adediran et al., "Synthesis of a Highly Water-Soluble Derivative of Amphotericin B with Attenuated Proinflammatory Activity", Molecular Pharmaceutics, vol. 6, No. 5, 2009, pp. 1582-1590.
Baginski et al., "Interaction of Amphotericin B and Its Selected Derivatives With Membranes: Molecular Modeling Studies", The Chemical Record, vol. 6, 2006, pp. 320-332.
Belakhov et al., "Synthesis and Antifungal Activity of N-Benzyl Derivatives of Amphotericin B", Pharmaceutical Chemistry Journal, vol. 41, No. 7, 2007, pp. 362-366.

(Continued)

*Primary Examiner* — Jonathan S Lau
(74) *Attorney, Agent, or Firm* — Birch, Stewart, Kolasch & Birch, LLP

(57) ABSTRACT

The present invention is the following Amphotericin B derivative:

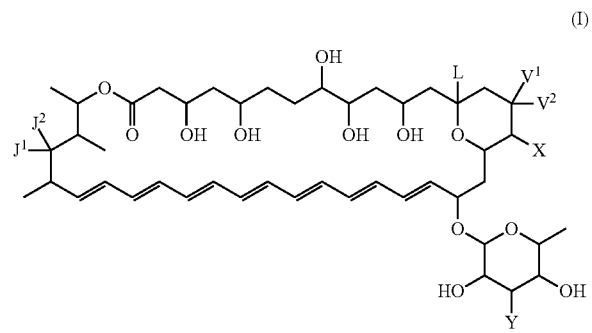

(I)

wherein each symbol is defined in description. The compound of the present invention has 16th position (X) is urea structure, cyclic structure, hydroxyalkyl or substituted monoalkylcarbamoyl. The compound of the present invention has antifungal activity.

42 Claims, No Drawings

(56) References Cited

OTHER PUBLICATIONS

Carmody et al., "Biosynthesis of Amphotericin Derivatives Lacking Exocyclic Carboxyl Groups", The Journal of Biological Chemistry, vol. 280, No. 41, Oct. 14, 2005, pp. 34420-34426.
Cereghetti et al., "Amphotericin B: 50 Years of Chemistry and Biochemistry", Synthesis, No. 6, 2006, pp. 914-942.
Cornely et al., "Liposomal Amphotericin B as Initial Therapy for Invasive Mold Infection: A Randomized Trial Comparing a High—Loading Dose Regimen with Standard Dosing (AmBiLoad Trial)", Clinical Infectious Diseases, vol. 44, 2007, pp. 1289-1297.
Czerwiński et al., "Amides of Polyene Macrolide Aureofacin Synthesis and Biological Properties", The Journal of Antibiotics, vol. XL, No. 7, Jul. 1987, pp. 1023-1027.
Czerwiński et al., "Amphotericin B 2-Morpholinoethylamide Diaspartate, A New Water Soluble Derivative of the Antibiotic Synthesis and Biological Properties", The Journal of Antibiotics, vol. XLIII, No. 6, Jun. 1990, pp. 680-683.
Czerwiński et al., "New N-Alkyl Derivatives of Amphotericin B Synthesis and Biological Properties", The Journal of Antibiotics, vol. 44, No. 9, Sep. 1991, pp. 979-984.
Czub et al., "Influence of a lipid bilayer on the conformational behavior of amphotericin B derivatives—A molecular dynamics study", Biophysical Chemistry, vol. 141, 2009, pp. 105-116.
Davis et al., "Nontoxic antimicrobials that evade drug resistance", Nature Chemical Biology, vol. 11, Jul. 2015, pp. 481-490.
Davis, "Non-toxic amphotericin B derivatization guided by a ligand-selective allosteric effects strategy", Biologically Related Molecules and Processes, Pub.# 344, ACS National Meeting & Exposition, Mar. 18, 2014, 1 page.
Driver et al., "Synthesis of 16-Decarboxy-16-Hydroxymethyl Amphotericin B—A Novel Antifungal Agent", Tetrahedron Letters, vol. 33, No. 30, 1992, pp. 4357-4360.
Ganis et al., "Polyene Macrolide Antibiotic Amphotericin B.[1] Crystal Structure of the N-Iodoacetyl Derivative", Journal of the American Chemical Society, vol. 93, No. 18, Sep. 8, 1971, pp. 4560-4564.
Grzybowska et al., "Hydrazides—A Novel Type of Derivatives of Polyene Macrolide Antifungal Antibiotics", The Journal of Antibiotics, vol. XLIII, No. 7, Jul. 1990, pp. 907-908.
Hutchinson et al., "Redesign of Polyene Macrolide Glycosylation: Engineered Biosynthesis of 19-(O)-Perosaminyl-Amphoteronolide B", Chemistry & Biology, vol. 17, Feb. 26, 2010, pp. 174-182.
International Search Report issued in PCT/JP2015/066976, dated Aug. 11, 2015.
MacPherson et al., "Adventures in Polyene Macrolide Chemistry: The Derivatisation of Amphotericin B", Recent Advances in the Chemistry of Anti-infective Agents, 1993, pp. 205-222.
Palacios et al., "A Post-PKS Oxidation of the Amphotericin B Skeleton Predicted to be Critical for Channel Formation Is Not Required for Potent Antifungal Activity", J. Am. Chem. Soc., vol. 129, 2007, pp. 13804-13805.
Palacios et al., "Synthesis-enabled functional group deletions reveal key underpinnings of amphotericin B ion channel and antifungal activities", PNAS, vol. 108, No. 17, Apr. 26, 2011, pp. 6733-6738.
Paquet et al., "Synthesis and In Vitro Biological Properties of Novel Cationic Derivatives of Amphotericin B", Chemistry A European Journal, vol. 14, 2008, pp. 2465-2481.
Parmegiani et al., "Comparative In Vitro and In Vivo Evaluation of N-D-Ornithyl Amphotericin B Methyl Ester, Amphotericin B Methyl Ester, and Amphotericin B", Antimicrobial Agents and Chemotherapy, vol. 31, No. 11, Nov. 1987, pp. 1756-1760.
Sedlák et al., "Synthesis and Characterisation of a New Amphotericin B—Methoxypoly(ethylene Glycol) Conjugate", Bioorganic and Medicinal Chemistry Letters, vol. 11, 2001, pp. 2833-2835.
Szpilman et al., "Synthesis and Biological Studies of 35-Deoxy Amphotericin B Methyl Ester", Angew. Chem. Int. Ed., vol. 47, 2008, pp. 4339-4342.
Szpilman et al., "Synthesis of 35-Deoxy Amphotericin B Methyl Ester: A Strategy for Molecular Editing", Angewandte Chemie Int. Ed., vol. 47, 2008, pp. 4335-4338.
Taylor et al., "Synthesis and Antifungal Selectivity of New Derivatives of Amphotericin B modified at the C-13 Position", The Journal of Antibiotics, vol. 46, No. 3, Mar. 1993, pp. 486-493.
Volmer et al., "Synthesis and biological evaluation of amphotericin B derivatives", Natural Product Reports, vol. 27, 2010, pp. 1329-1349.
Walsh et al., "Safety, Tolerance, and Pharmacokinetics of a Small Unilamellar Liposomal Formulation of Amphotericin B (AmBisome) in Neutropenic Patients", Antimicrobial Agents and Chemotherapy, vol. 42, No. 9, Sep. 1998, pp. 2391-2398.
Wright et al., "N-Aminoacyl Derivatives of Polyene Macrolide Antibiotics and Their Esters", The Journal of Antibiotics, vol. XXXV, No. 7, Jul. 1982, pp. 911-914.
Written Opinion of the International Searching Authority issued in PCT/JP2015/066976 (PCT/ISA/237), dated Aug. 11, 2015.
English translation of Office Action dated issued Apr. 25, 2018, in Chinese Patent Application No. 201580030105.4.

\* cited by examiner

POLYENE MACROLIDE DERIVATIVE

TECHNICAL FIELD

The present invention relates to polyene macrolide derivatives. Especially, the present invention relates to polyene macrolide derivatives which are useful for treatment or prevention against fungal infection of human or animals.

BACKGROUND ART

Amphotericin B is known as a drug having microbicidal effect by binding to ergosterol of cell membrane of fungi and forming ostium to membrane from long ago. Amphotericin B is used as formulation using deoxycholic acid or liposome due to its low water solubility and high toxicity. However, the formulation using deoxycholic acid is still high toxicity, so satisfactory administration and long-term treatment cannot be achieved. The formulation using liposome can greatly avoid possibility of hepatotoxicity and nephrotoxicity compared with the formulation using deoxycholic acid, but effective treatment is not still actually achieved because of decrease of drug efficacy (Non-patent Document 1, 2).

Therefore, chemical modification of amphotericin B has been tried for the improvement of its water solubility or the avoidance of its toxicity. For example, amphotericin B derivative having amide at 16th position (Patent Document 1, 3, 4, 5, 10) and ester derivative (Patent Document 2, 6, 7, 9, 11) are disclosed. In addition, amphotericin B derivatives having a modification at amino sugar part are disclosed as Patent Documents 1 to 4, 6 to 8, and 11. However, amphotericin B derivative having 16th position urea structure at is not disclosed in the above documents (Non-patent Document 3).

Moreover, amphotericin B derivatives having urea structure at 16th position wherein the end of urea is methyl, amino or carboxy are presented by Martin D Burke et al. at congress of American Chemical Society (ACS) on Mar. 18, 2014 (Non-patent Document 4), and such the derivatives were disclosed in Patent Document 11 and released as scientific journal (Non-patent Document 5). It was suggested there that amphotericin B derivative having amino at the end part has lower nephrotoxicity than that of having carboxy at the end part.

PRIOR ART REFERENCES

Patent Document

[Patent Document 1] WO 2007/096137
[Patent Document 2] WO 2001/051061
[Patent Document 3] WO 2001/009758
[Patent Document 4] WO 93/17034
[Patent Document 5] WO 96/32404
[Patent Document 6] WO 96/35701
[Patent Document 7] WO 99/51274
[Patent Document 8] WO 91/07421
[Patent Document 9] WO 2009/015541
[Patent Document 10] JP H55-157598
[Patent Document 11] WO 2015/054148

Non-Patent Document

[Non-patent Document 1] Antimicrobial Agents and Chemotherapy (1998), 42(9), 2391-2398
[Non-patent Document 2] Clinical Infectious Diseases (2007), 44(10), 1289-1297
[Non-patent Document 3] Natural Product Reports (2010), 27, 1329-1349
[Non-patent Document 4] 247th ACS National Meeting & Exposition Web Abstracts www.acs.org/content/acs/en/meetings/spring-2014/program.html) ORGN 334 Nontoxic amphotericin B derivatization guided by a ligand-selective allosteric effects strategy
[Non-patent Document 5] Nature chemical biology published online 1 Jun. 2015

SUMMARY OF THE INVENTION

Problems to be Solved by the Invention

The present invention is to provide amphotericin B derivatives having high antifungal activity against various fungi. Preferably, the present invention provides the derivatives having lower toxicity such as nephrotoxicity, hepatotoxicity and/or acute toxicity.

Means for Solving the Problem

The present invention solves the above problems by modifying 16th position (X) and amino-position (Y) of sugar chain of amphotericin B, and the following invention has been accomplished.
[1] A compound represented by formula (I):

[Chemical Formula 1]

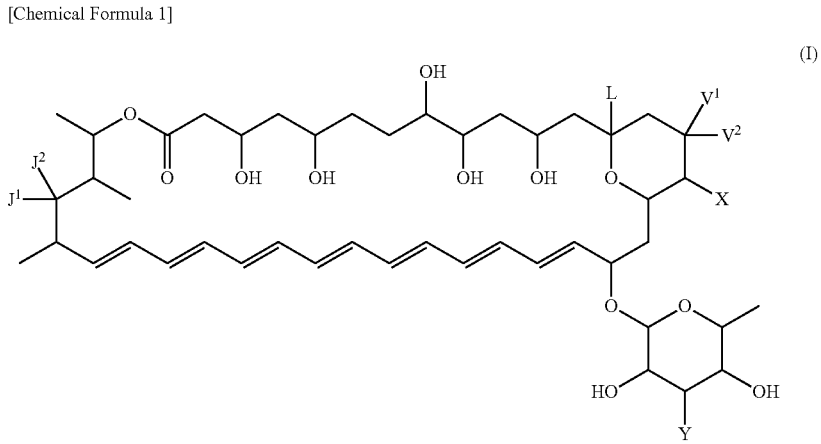

wherein X is a group of formula:

[Chemical Formula 2]

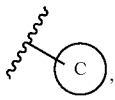
(II)

—N(R$^F$)—CO—X$^1$, hydroxyalkyl or a group of formula: —CO—NH(R$^X$)

wherein R$^X$ is substituted or unsubstituted non-aromatic heterocyclyloxyalkyl;

Ring C is substituted or unsubstituted aromatic carbocycle, substituted or unsubstituted non-aromatic carbocycle, substituted or unsubstituted aromatic heterocycle or substituted or unsubstituted non-aromatic heterocycle;

R$^F$ is hydrogen, substituted or unsubstituted alkyl, substituted or unsubstituted alkenyl or substituted or unsubstituted alkynyl; and X$^1$ is any one of following groups:

[Chemical Formula 3]

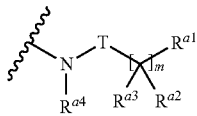
(III)

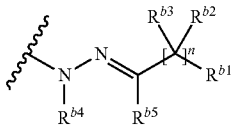
(IV)

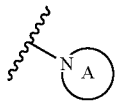
(V)

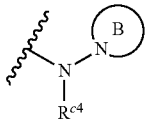
(VI)

L, J$^1$ and V$^1$ are each independently hydrogen, halogen, hydroxy, substituted or unsubstituted amino or substituted or unsubstituted alkyloxy;

J$^2$ and V$^2$ are each independently hydrogen, substituted or unsubstituted alkyl, substituted or unsubstituted alkenyl or substituted or unsubstituted alkynyl;

or J$^1$ and J$^2$ and/or V$^1$ and V$^2$ may be taken together to form oxo;

R$^{a1}$ and R$^{b1}$ are each independently, hydrogen, halogen, hydroxy, carboxy, substituted or unsubstituted amino, formyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkyl ammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted dialkynylphosphonyl, substituted or unsubstituted alkylcarbonyloxy, substituted or unsubstituted alkynylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl;

R$^{a2}$ and R$^{b2}$ are each independently hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl;

R$^{a3}$ and R$^{b3}$ are each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl;

or R$^{a2}$ and R$^{a3}$ and/or R$^{b2}$ and R$^{b3}$ are each independently may be taken together to form oxo, substituted or unsubstituted imino or thioxo, or may be taken together with neighboring atoms to form substituted or unsubstituted non-aromatic carbocycle or substituted or unsubstituted non-aromatic heterocycle;

R$^{a4}$, R$^{b4}$ and R$^{c4}$ are each independently, hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl;

$R^{b5}$ is hydrogen, substituted or unsubstituted alkyl, substituted or unsubstituted alkenyl or substituted or unsubstituted alkynyl;

Ring A and Ring B are each independently, substituted or unsubstituted nitrogen-containing aromatic heterocycle or substituted or unsubstituted nitrogen-containing non-aromatic heterocycle;

T is a bond, —N($R^{a5}$)— or —O—;

$R^{a5}$ is hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl or substituted or unsubstituted alkynylcarbonyl;

m and n are each independently an integer of 0 to 10;

Y is any one of following groups

[Chemical Formula 4]

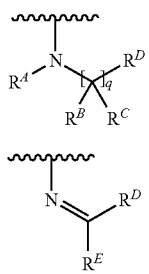

(VII)

(VIII)

$R^A$ is hydrogen, substituted or unsubstituted alkyl, substituted or unsubstituted alkenyl or substituted or unsubstituted alkynyl;

$R^B$ and $R^C$ are each independently hydrogen, hydroxy, substituted or unsubstituted amino, substituted or unsubstituted alkyl, substituted or unsubstituted alkenyl or substituted or unsubstituted alkynyl;

or $R^B$ and $R^C$ may be taken together to form oxo, substituted or unsubstituted imino or thioxo, or may be taken together with neighboring atoms to form substituted or unsubstituted non-aromatic carbocycle or substituted or unsubstituted non-aromatic heterocycle;

$R^D$ is hydrogen, hydroxy, carboxy, substituted or unsubstituted amino, substituted or unsubstituted carbamoyl, substituted or unsubstituted amidino, substituted or unsubstituted guanidino, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl;

$R^E$ is hydrogen, hydroxy or substituted or unsubstituted amino;

q is an integer of 0 to 10;

provided that the following compounds are excluded:
(i) The compounds which X is —$CH_2$—OH; and Y is —$NH_2$;
(ii) The compounds which X is either of following groups; and Y is any one of —$NH_2$; a group of formula:

[Chemical Formula 5]

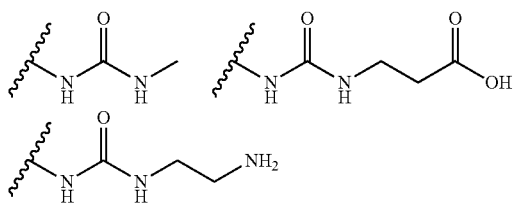

or a pharmaceutically acceptable salt thereof.

[2] The compound or its pharmaceutically acceptable salt according to the above item [1], wherein X is

[Chemical Formula 6]

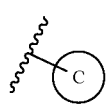

(II)

or —N($R^F$)—CO—$X^1$

[3] The compound or its pharmaceutically acceptable salt according to the above item [1] or [2], wherein $J^1$, L and $V^1$ are hydroxy; and $J^2$ and $V^2$ are hydrogen.

[4] The compound or its pharmaceutically acceptable salt according to any one of the above items [1] to [3], wherein X is a group of formula: —N($R^F$)—CO—$X^1$; $X^1$ is a group represented by formula (III); and T is a bond.

[5] The compound or its pharmaceutically acceptable salt according to the above item [4], wherein $R^{a1}$ is halogen, hydroxy, carboxy, substituted or unsubstituted amino, substituted or unsubstituted aromatic heterocyclylamino, substituted or unsubstituted non-aromatic heterocyclylamino, substituted or unsubstituted alkylammonium, carbamoyl, sulfamoyl, sulfo, cyano, substituted or unsubstituted ureido, guanidino, substituted or unsubstituted alkyloxy, substituted or unsubstituted non-aromatic heterocyclyloxy, substituted or unsubstituted alkylphosphonyl, substituted sulfamoyl, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl;

wherein said substituted or unsubstituted amino is selected from unsubstituted amino, hydroxyamino, sulfamoylamino, substituted or unsubstituted alkylamino, substituted or unsubstituted alkylsulfonylamino, substituted or unsubstituted non-aromatic carbocyclylcarbonylamino, substituted or unsubstituted aromatic carbocyclylcarbonylamino, substituted or unsubstituted aromatic heterocyclylcarbonylamino and substituted or unsubstituted non-aromatic heterocyclylcarbonylamino;

wherein said substituted or unsubstituted ureido is selected from ureido, substituted or unsubstituted alkylureido, substituted or unsubstituted aromatic heterocyclylureido and substituted or unsubstituted aromatic heterocyclylureido; and wherein said substituted sulfamoyl is substituted or unsubstituted aromatic heterocyclylsulfamoyl.

[6] The compound or its pharmaceutically acceptable salt according to the above item [4] or [5], wherein $R^{a2}$ are each independently hydrogen, halogen, hydroxy, carboxy, amino, carbamoyl, substituted or unsubstituted alkyl, substituted or unsubstituted non-aromatic heterocyclyloxyalkyl or substituted or unsubstituted alkylcarbonyl;

$R^{a3}$ are each independently, hydrogen, halogen, substituted or unsubstituted alkyl or substituted or unsubstituted non-aromatic heterocyclyloxyalkyl;

or $R^{a2}$ and $R^{a3}$ may be taken together to form oxo, or may be taken together with neighboring atoms to form non-aromatic carbocycle or non-aromatic heterocycle.

[7] The compound or its pharmaceutically acceptable salt according to any one of the above items [4] to [6], wherein $R^{a4}$ is hydrogen, hydroxy, amino, substituted or unsubstituted alkyl or substituted or unsubstituted non-aromatic carbocyclyl.

[8] The compound or its pharmaceutically acceptable salt according to any one of the above items [1] to [3] wherein X is a group of formula: —N($R^F$)—CO—$X^1$; $X^1$ is a group represented by formula (III); and T is —N($R^{a5}$)— or —O—.

[9] The compound or its pharmaceutically acceptable salt according to the above item [8], wherein $R^{a1}$ is hydroxy, carboxy, substituted amino, substituted or unsubstituted aromatic heterocyclylamino, formyl, carbamoyl, cyano, guanidino, substituted or unsubstituted alkyloxy, substituted or unsubstituted non-aromatic heterocyclyloxy, substituted or unsubstituted alkylcarbonyl, substituted or unsubstituted alkyloxycarbonyl, substituted or unsubstituted alkylsulfonyl, substituted or unsubstituted aromatic heterocyclylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted ureido;

wherein said substituted amino is hydroxyamino or substituted or unsubstituted alkylamino; and wherein said substituted ureido is substituted or unsubstituted aromatic heterocyclylureido.

[10] The compound or its pharmaceutically acceptable salt according to the above item [8] or [9], wherein $R^{a2}$ are each independently hydrogen, hydroxy or substituted or unsubstituted alkyl;

$R^{a3}$ are each independently hydrogen or substituted or unsubstituted alkyl; or $R^{a2}$ and $R^{a3}$ may be taken together to form oxo or thioxo, or may be taken together with neighboring atoms to form substituted or unsubstituted non-aromatic carbocycle.

[11] The compound or its pharmaceutically acceptable salt according to any one of the above items [8] to [10], wherein $R^{a4}$ is hydrogen.

[12] The compound or its pharmaceutically acceptable salt according to any one of the above items [1] to [3], wherein X is a group of formula: —N($R^F$)—CO—$X^1$; and $X^1$ is a group represented by formula (IV).

[13] The compound or its pharmaceutically acceptable salt according to the above item [12], wherein $R^{b1}$ is hydroxy.

[14] The compound or its pharmaceutically acceptable salt according to the above item [12] or [13], wherein n is 1 or 2; $R^{b2}$ are each independently hydrogen or hydroxy; and $R^{b3}$ is hydrogen.

[15] The compound or its pharmaceutically acceptable salt according to any one of the above items [12] to [14], wherein $R^{b4}$ is hydrogen; and $R^{b5}$ is hydrogen or substituted or unsubstituted alkyl.

[16] The compound or its pharmaceutically acceptable salt according to any one of the above items [1] to [3], wherein X is —N($R^F$)—CO—$X^1$; and $X^1$ is a group represented by formula (V).

[17] The compound according to the above item [16], wherein ring A is substituted or unsubstituted nitrogen-containing non-aromatic heterocycle.

[18] The compound according to any one of the above items [1] to [3], wherein X is a group of formula; —N($R^F$)—CO—$X^1$; and $X^1$ is a group represented by formula (VI).

[19] The compound or its pharmaceutically acceptable salt according to the above item [18], wherein ring B is substituted or unsubstituted nitrogen-containing non-aromatic heterocycle.

[20] The compound or its pharmaceutically acceptable salt according to the above item [18] or [19], wherein $R^{c4}$ is hydrogen.

[21] The compound or its pharmaceutically acceptable salt according to any one of the above items [1] to [20], wherein $R^F$ is hydrogen.

[22] The compound or its pharmaceutically acceptable salt according to any one of the above items [1] to [3], wherein X is a group represented by formula (II); and said group is represent by formula:

[Chemical Formula 7]

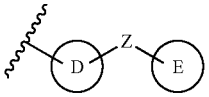

(IX)

ring D and ring E are each independently substituted or unsubstituted aromatic carbocycle, substituted or unsubstituted non-aromatic carbocycle, substituted or unsubstituted aromatic heterocycle or substituted or unsubstituted non-aromatic heterocycle; and Z is a bond, alkylene, —O—, —S— or —N(H)—.

[23] The compound or its pharmaceutically acceptable salt according to the above item [22], wherein ring D is substituted or unsubstituted aromatic heterocycle; and ring E is substituted or unsubstituted aromatic carbocycle or substituted or unsubstituted aromatic heterocycle.

[24] The compound or its pharmaceutically acceptable salt according to the above item [22] or [23], wherein Z is a bond.

[25] The compound or its pharmaceutically acceptable salt according to any one of the above items [22] to [24], wherein the substituent(s) on ring E is/are alkylamino.

[26] The compound or its pharmaceutically acceptable salt according to any one of the above items [1] to [25], wherein $R^A$ are each independently hydrogen or substituted or unsubstituted alkyl; $R^B$ are each independently hydrogen or hydroxy or substituted or unsubstituted amino; $R^C$ are each independently hydrogen or hydroxy or substituted or unsubstituted amino; or $R^B$ and $R^C$ may be taken together to form oxo, substituted or unsubstituted imino, hydroxyimino or cyanoimino;

$R^D$ is hydrogen, hydroxy, carboxy, substituted or unsubstituted amino, carbamoyl, guanidine, substituted or unsubstituted aromatic carbocyclyl, substituted or unsubstituted aromatic heterocyclyl or substituted or unsubstituted non-aromatic heterocyclyl;

$R^E$ is amino;

wherein said substituted or unsubstituted amino is unsubstituted amino or substituted or unsubstituted alkylamino;

wherein said substituted or unsubstituted imino is unsubstituted imino, hydroxyimino or cyanoimino.

[27] The compound or its pharmaceutically acceptable salt according to any one of the above items [1] to [25], wherein Y is $NH_2$.
[28] The compound or its pharmaceutically acceptable salt according to the above item [1], wherein X is hydroxyalkyl; and q is an integer of 0 to 10.
[29] The compound according to the above item [1], wherein X is a group of formula: —CO—NH($R^X$), and wherein $R^X$ is substituted or unsubstituted non-aromatic heterocyclyloxyalkyl.
[30] The compound or its pharmaceutically acceptable salt according to the above item [3], wherein X is a group of formula: —N($R^F$)—CO—$X^1$, wherein $X^1$ is a group represented by formula (III);

T is —N(H)—; $R^{a1}$ is carboxy, carbamoyl or substituted amino; $R^{a2}$ is each independently hydrogen or hydroxy; $R^{a3}$ and $R^{a4}$ are hydrogen; m is 2; and Y is $NH_2$.

[31] A pharmaceutical composition containing the compound or its pharmaceutically acceptable salt according to any one of the above items [1] to [30].

[32] A pharmaceutical composition of the above item [31] having antifungal activity.

[33] A compound represented by any one of formula (X), (XI), (XII), (XIII), (XVI) or (XVII):

[Chemical Formula 8]

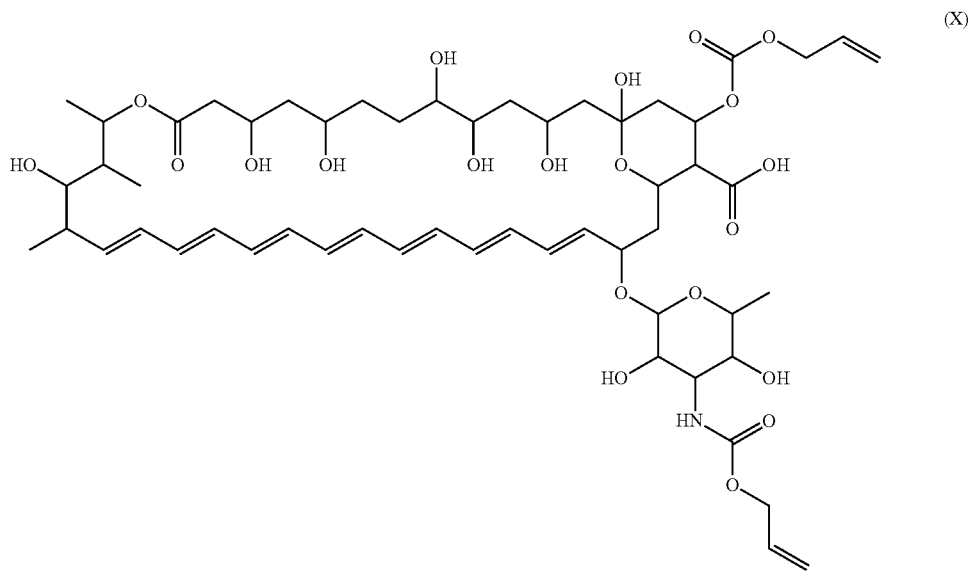

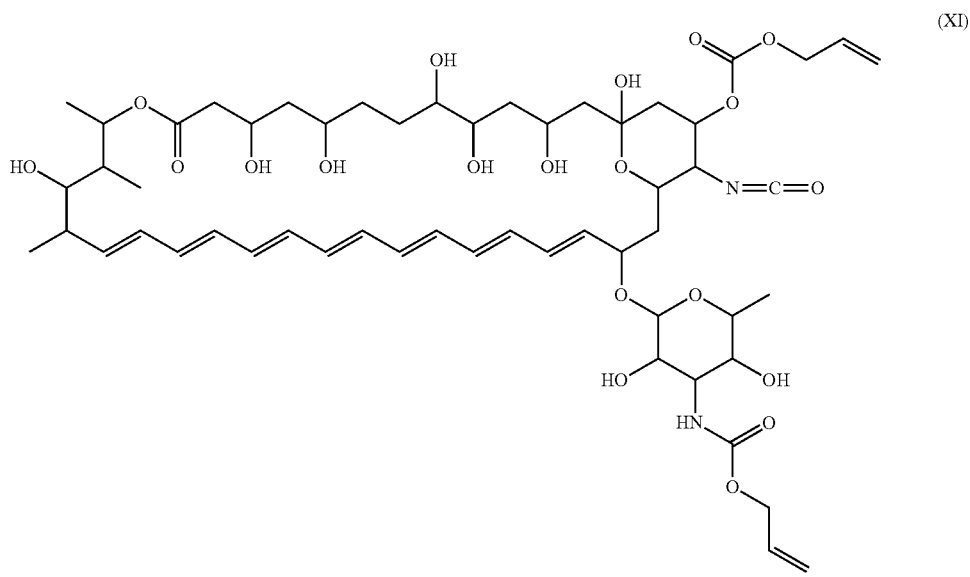

(XII)
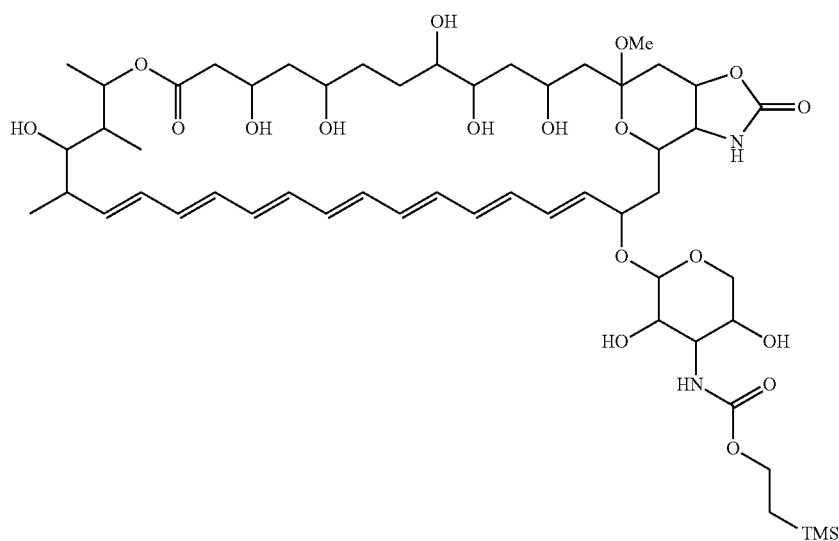
[Chemical Formula 9]
(XIII)
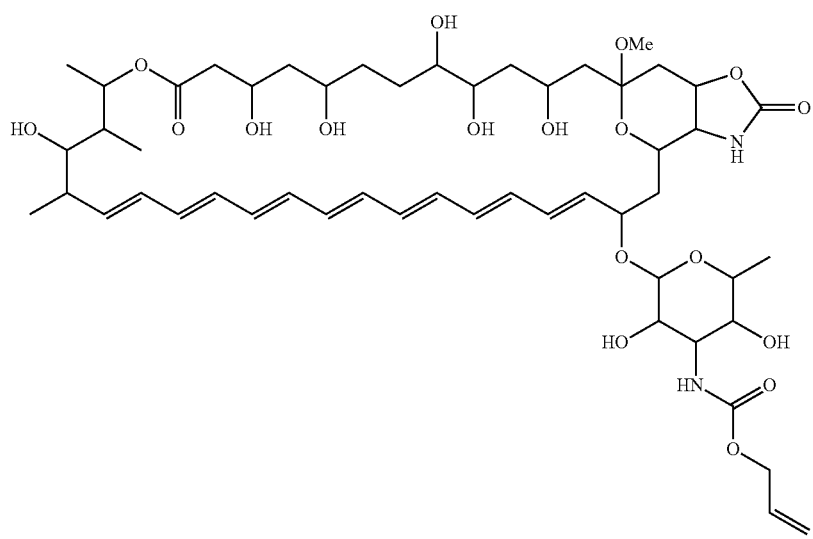

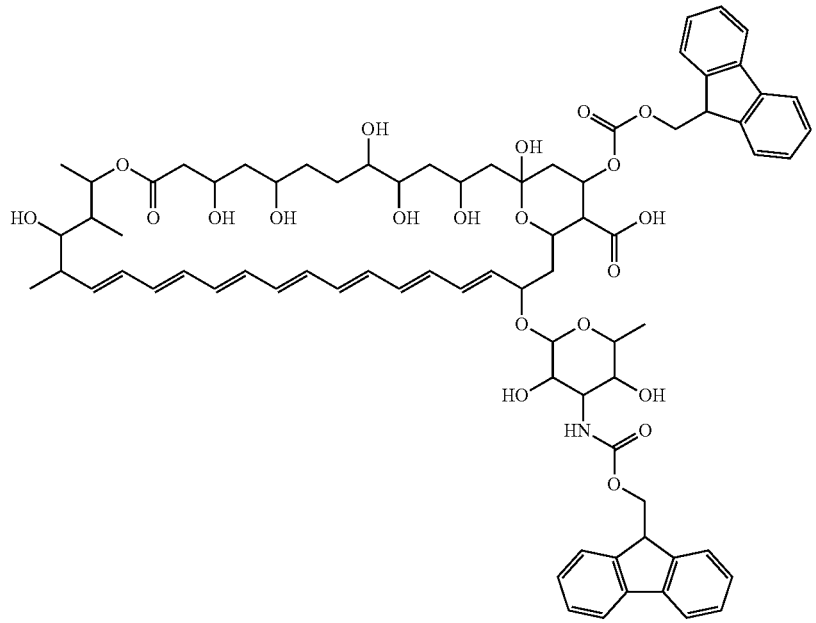

(XVI)

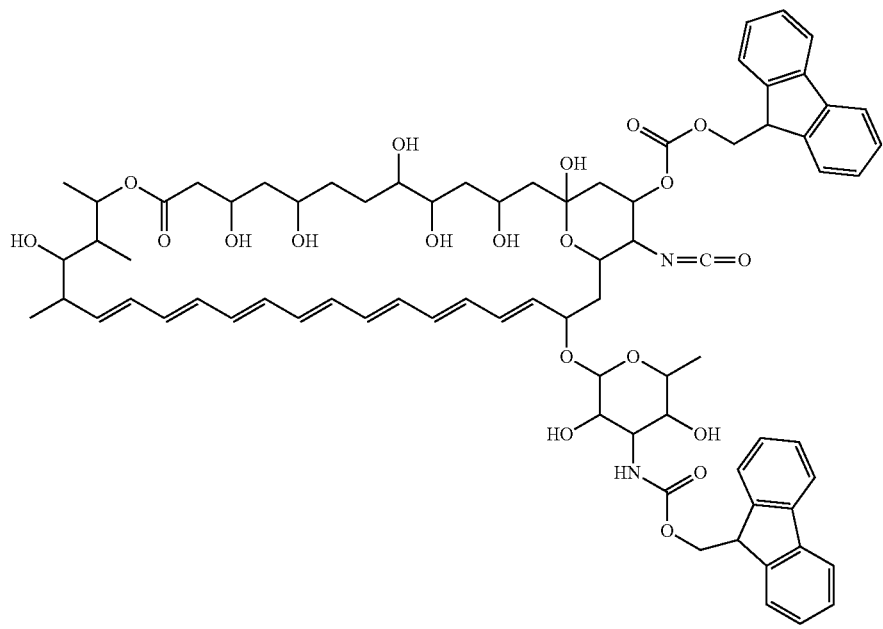

(XVII)

or its pharmaceutically acceptable salt.

[34] A process for the preparation of the compound according to any one of the above items [1] to [30], wherein X is a group of formula: —N(R$^F$)—CO—X$^1$, which is characterized in using the compound or its pharmaceutically acceptable salt according to the above item [33].

[35] The compound or its pharmaceutically acceptable salt according to any one of the above items [1] to [3], wherein said substituted or unsubstituted amino is selected from amino, hydroxyamino, sulfamoylamino, substituted or unsubstituted alkylamino, substituted or unsubstituted alkylsulfonylamino, substituted or unsubstituted aromatic carbocyclylcarbonylamino, substituted or unsubstituted non-aromatic carbocyclylcarbonylamino, substituted or unsubstituted aromatic heterocyclylcarbonylamino or substituted or unsubstituted non-aromatic heterocyclylcarbonylamino.

[36] The compound or its pharmaceutically acceptable salt according to any one of the above items [1] to [3], wherein said substituted or unsubstituted carbamoyl is unsubstituted carbamoyl or substituted or unsubstituted alkylcarbamoyl.

[37] The compound or its pharmaceutically acceptable salt according to any one of the above items [1] to [3], wherein said substituted or unsubstituted sulfamoyl is selected from unsubstituted sulfamoyl, substituted or unsubstituted alkylsulfamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl or substituted or unsubstituted non-aromatic heterocyclylsulfamoyl.

[38] The compound or its pharmaceutically acceptable salt according to any one of the above items [1] to [3], wherein said substituted or unsubstituted ureido is selected from unsubstituted ureido, substituted or unsubstituted alkylureido, substituted or unsubstituted aromatic carbocyclylureido, substituted or unsubstituted non-aromatic carbocyclylureido, substituted or unsubstituted aromatic heterocyclylureido or substituted or unsubstituted non-aromatic heterocyclylureido.

[39] The compound or its pharmaceutically acceptable salt according to any one of the above items [1] to [3], wherein said substituted or unsubstituted alkyloxy is selected from substituted or unsubstituted aromatic carbocyclylalkyloxy, substituted or unsubstituted non-aromatic carbocyclylalkyloxy, substituted or unsubstituted aromatic heterocyclylalkyloxy or substituted or unsubstituted non-aromatic heterocyclylalkyloxy.

[40] The compound or its pharmaceutically acceptable salt according to any one of the above items [1] to [3], wherein said substituted or unsubstituted alkylsulfonyl is selected from unsubstituted alkylsulfonyl, substituted or unsubstituted aromatic carbocyclylalkylsulfonyl, substituted or unsubstituted non-aromatic carbocyclylalkylsulfonyl, substituted or unsubstituted aromatic heterocyclylalkylsulfonyl or substituted or unsubstituted non-aromatic heterocyclylalkylsulfonyl.

[41] The compound or its pharmaceutically acceptable salt according to any one of the above items [1] to [3], wherein said substituted or unsubstituted alkylcarbonyloxy is selected from unsubstituted alkylcarbonyloxy, substituted or unsubstituted aromatic carbocyclylalkylcarbonyloxy, substituted or unsubstituted non-aromatic carbocyclylalkylcarbonyloxy, substituted or unsubstituted aromatic heterocyclylalkylcarbonyloxy or substituted or unsubstituted non-aromatic heterocyclylalkylcarbonyloxy.

[42] The compound or its pharmaceutically acceptable salt according to any one of the above items [1] to [3], wherein said substituted or unsubstituted aromatic carbocyclyl is selected from unsubstituted aromatic carbocyclyl or substituted or unsubstituted alkylaminoaromatic carbocyclyl.

[43] The compound or its pharmaceutically acceptable salt according to any one of the above items [1] to [3], wherein said substituted or unsubstituted non-aromatic carbocyclyl is selected from unsubstituted non-aromatic carbocyclyl or substituted or unsubstituted alkylamino non-aromatic carbocyclyl.

[44] The compound or its pharmaceutically acceptable salt according to any one of the above items [1] to [3], wherein said substituted or unsubstituted aromatic heterocyclyl is selected from unsubstituted aromatic heterocyclyl or substituted or unsubstituted alkylaminoaromatic heterocyclyl.

[45] The compound or its pharmaceutically acceptable salt according to any one of the above items [1] to [3], wherein said substituted or unsubstituted non-aromatic heterocyclyl is selected from unsubstituted non-aromatic heterocyclyl or substituted or unsubstituted alkylamino non-aromatic heterocyclyl.

[46] The compound or its pharmaceutically acceptable salt according to any one of the above items [4] to [11], wherein m is an integer of 0 to 6.

[47] The compound or its pharmaceutically acceptable salt according to any one of the above items [12] to [15], wherein n is an integer of 0 to 6.

[48] A method for treating a fungal infection, which comprises administrating the effective doses for anti fungal of the compound according to any one of the above items [1] to [30] to human or animals.

[49] The compound or its pharmaceutically acceptable salt according to any one of the above items [1] to [30], for use in a medical treatment.

[50] The use of the compound or its pharmaceutically acceptable salt according to any one of the above items [1] to [30], for the manufacture of a medicament for treating or preventing a fungal infection.

Effect of the Invention

The compound of the present invention has antifungal activity against fungi. Moreover, the compound of the present invention has utility as a medicament, and it has preferably excellent effects of all or portion of the following points.
a) Low possibility of nephrotoxicity
b) Low possibility of hepatotoxicity
c) Low possibility of acute toxicity
d) High water solubility
e) Low possibility of hemolytic toxicity
f) Low possibility of cytotoxicity Also, the present invention provides useful intermediates useful for preparing antifungal agent efficiently. Compound (I) can be easily prepared by using the intermediates in high yield and by short-step.

EMBODIMENTS FOR CARRYING OUT THE INVENTION

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "hydroxyalkyl" means a group wherein one or more hydrogen atom(s) of "alkyl" described above are replaced with hydroxy. Examples include hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl, hydroxyethyl.

The term "haloalkyl" means a group wherein one or more "halogen" described above is bonded to the above "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

The term "alkenyl" includes a C2 to C15, preferably a C2 to C10, more preferably a C2 to C6 and further preferably a C2 to C4 linear or branched hydrocarbon group having one or more double bongs) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

The term "alkynyl" includes a C2 to C10, preferably a C2 to C8, more preferably a C2 to C6 and further preferably a C2 to C4 linear or branched hydrocarbon group having one or more triple bond(s) at any position(s). Furthermore, it may have double bond(s) at any position(s). Examples include ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

The term "alkylene" includes a C1 to C15, preferably a C1 to C10, more preferably a C1 to C6 and further preferably a C1 to C4 liner or branched bivalent hydrocarbon group. Examples include methylene, ethylene, trimethylene, propylene, tetramethylene, pentamethylene, hexamethylene and the like.

The term "aromatic carbocycle" means a cyclic aromatic hydrocarbon which is monocycle or polycycle having two or more rings. Examples include benzene, naphthalene, anthracene, phenanthrene and the like.

A preferred embodiment of "aromatic carbocycle" is benzene.

The term "aromatic carbocyclyl" means a monovalent group derived from "aromatic carbocycle" described above. Examples include phenyl, naphthyl, anthryl, phenanthryl and the like.

A preferred embodiment of "aromatic carbocyclyl" is phenyl.

The term "non-aromatic carbocycle" means a cyclic saturated hydrocarbon or a cyclic unsaturated non-aromatic hydrocarbon, which is monocycle or polycycle having two or more rings. Examples of the "non-aromatic carbocycle", which is polycycle having two or more rings, include a fused ring wherein a non-aromatic carbocycle, which is monocycle or polycycle having two or more rings, is fused with a ring of the above "aromatic carbocycle".

In addition, examples of the "non-aromatic carbocycle" also include a group having a bridge or a spiro ring as follows:

[Chemical Formula 10]

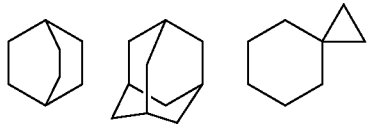

The non-aromatic carbocycle which is monocycle is preferably C3 to C16, more preferably C3 to C12 and further preferably C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.

Examples of non-aromatic carbocycle, which is polycycle having two or more rings, include indane, indene, asenafuchine, tetrahydronaphthalene, fluorene and the like.

The term "non-aromatic carbocyclyl" means a monovalent group derived from "non-aromatic carbocycle" described above.

The non-aromatic carbocyclyl which is monocyclic is preferably C3 to C16, more preferably C3 to C12 and further preferably C3 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

The term "aromatic heterocycle" means an aromatic cycle, which is monocycle or polycycle having two or more rings, containing one or more of heteroatom(s) selected independently from O, S and N. Examples of "aromatic heterocycle", which is polycycle having two or more rings, include a fused ring group wherein an aromatic heterocycle, which is monocycle or polycycle having two or more rings, is fused with a ring of the above "aromatic carbocycle".

The aromatic heterocycle, which is monocycle, is preferably a 5- to 8-membered and more preferably 5- to 6-membered ring. Examples include pyrroline, imidazoline, pyrazoline, pyridine, pyridazine, pyrimidine, pyrazine, triazole, triazine, tetorazorin, furan, isoxazole, oxazole, oxadiazole, isothiazole, thiazole, thiadiazole and the like.

Examples of aromatic heterocycle, which is bicyclic, include indoline, isoindoline, indazorine, indorizidine, quinoline, isoquinoline, cinnoline, phthalazine, quinazoline, naphthyridine, purine, pteridine, benzimidazole, benzisoxazole, benzoxazole, benzimidazole, oxadiazole, benzisothiazole, benzothiazole, benzothiadiazole, benzofuran, isobenzofuran, benzotriazole, imidazopyridine, triazolopyridine, imidazothiazole, pyladinopyridazole, oxazolopyridine, thiazolopyridine and the like.

Examples of aromatic heterocycle, which is polycycle having three or more rings, include carbazole, acridine, xanthene, phenothiazine, phenoxathiine, phenoxazine, dibenzofuran and the like.

The term "aromatic heterocyclyl" means a monovalent group derived from "aromatic heterocycle" described above.

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

Examples of aromatic heterocyclyl, which is polycyclic having three or more rings, include carbazolyl, acridinyl, xanthenyl, phenothiazinyl, phenoxathiinyl, phenoxazinyl, dibenzofuryl and the like.

The term "nitrogen-containing aromatic heterocycle" means an aromatic heterocycle, which is monocycle or polycycle having two or more rings, containing one or more nitrogen atom(s) furthermore may have one or more heteroatom(s) selected independently from O and/or S. The "nitrogen-containing aromatic heterocycle" is preferably "aromatic heterocycle" containing nitrogen atom(s) in the ring(s) of "aromatic heterocycle" exemplified above.

The term "non-aromatic heterocycle" means a non-aromatic cycle, which is monocycle or polycycle having two or more rings, containing one or more heteroatom(s) selected independently from O, S and N. Examples of "non-aromatic heterocycle", which is polycycle having two or more rings, include a fused ring wherein a non-aromatic heterocycle, which is monocycle or polycycle having two or more ring(s), is fused with a ring of the above "aromatic carbocycle", "non-aromatic carbocycle" and/or "aromatic heterocycle".

In addition, examples of the "non-aromatic heterocyclyl" also include a group having a bridge or a group to form a Spiro ring as follows:

[Chemical Formula 11]

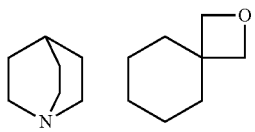

The non-aromatic heterocycle, which is monocycle, is preferably a 3- to 16-membered and more preferably 3- to 12-membered ring and further more preferably 3- to 8-membered ring. Examples include dioxane, thiirane, oxirane, oxetane, oxathiolane, azetidine, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxolane, oxepane, thiolane, thiazine and the like.

Examples of non-aromatic heterocycle, which is polycycle having two or more rings, include indoline, isoindoline, chromane, isochromane and the like.

The term "non-aromatic heterocyclyl" means a monovalent group derived from "non-aromatic heterocycle" described above.

The non-aromatic heterocyclyl, which is monocyclic, is preferably a 3- to 16-membered and more preferably 3- to 12-membered ring and further more preferably 3- to 8-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolyl, oxepanyl, thiolanyl, thiinyl, thiazinyl and the like.

Examples of non-aromatic heterocyclyl, which is polycyclic having two or more rings, include indolinyl, isoindolinyl, chromanyl, isochromanyl and the like.

The term "nitrogen-containing non-aromatic heterocycle" means a non-aromatic heterocycle, which is monocycle or polycycle having two or more rings, containing one or more nitrogen atom(s) furthermore may have one or more heteroatom(s) selected independently from O and/or S. The nitrogen-containing non-aromatic heterocycle, which is monocycle, is preferably a 3- to 16-membered and more preferably 3- to 12-membered ring and further more preferably 3- to 8-membered ring. Examples include azetidine, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, dihydrothiazole, tetrahydrothiazole, tetrahydroisothiazole, dihydrooxazine, hexahydroazepine, tetrahydrodiazepine, tetrahydropyridazine, hexahydropyrimidine, dioxazine, aziridine, thiazine, 1,4-diazepane, 1,4,7,10,13-pentaoxa-16-azacyclooctadecane, 1,4,7,10-tetraoxa-13-azacyclopentadecane and the like. Especially preferably, 1,4-diazepane, 1,4,7,10,13-pentaoxa-16-azacyclooctadecane, 1,4,7,10-tetraoxa-13-azacyclopentadecane, piperazine, morpholine, piperidine, pyrrolidine, thiazolidine, azetidine, pyrroline.

The term "aromatic carbocyclyloxy" means a group wherein "aromatic carbocycle" is bonded to an oxygen atom. Examples include phenyloxy, naphthyloxy and the like.

The term "non-aromatic carbocyclyloxy" means a group wherein "non-aromatic carbocycle" is bonded to an oxygen atom. Examples include cyclopropyloxy, cyclohexyloxy, cyclohexenyloxy and the like.

The term "aromatic heterocyclyloxy" means a group wherein "aromatic heterocycle" is bonded to an oxygen atom. Examples include pyridyloxy, oxazolyloxy and the like.

The term "non-aromatic heterocyclyloxy" means a group wherein "non-aromatic heterocycle" is bonded to an oxygen atom. Examples include piperidinyloxy, tetrahydrofuryloxy and the like.

The term "aromatic carbocyclylcarbonyl" means a group wherein "aromatic carbocycle" is bonded to carbonyl group. Examples include phenylcarbonyl, naphthylcarbonyl and the like.

The term "non-aromatic carbocyclylcarbonyl" means a group wherein "non-aromatic carbocycle" is bonded to carbonyl group. Examples include cyclopropylcarbonyl, cyclohexylcarbonyl, cyclohexenylcarbonyl and the like.

The term "aromatic heterocyclylcarbonyl" means a group wherein "aromatic heterocycle" is bonded to carbonyl group. Examples include pyridylcarbonyl, oxazolylcarbonyl, pyrazinecarbonyl and the like.

The term "non-aromatic heterocyclylcarbonyl" means a group wherein "non-aromatic heterocycle" is bonded to carbonyl group. Examples include piperidinylcarbonyl, tetrahydrofurylcarbonyl and the like.

The term "aromatic carbocyclylamino" means a group wherein the above "aromatic carbocycle" is replaced with one or two hydrogen atom(s) bonded to a nitrogen atom of an amino group. These two aromatic carbocycle may be the same or different. Examples include phenylamino, naphthylamino, diphenylamino and the like.

The term "non-aromatic carbocyclylamino" means a group wherein the above "non-aromatic carbocycle" is replaced with one or two hydrogen atom(s) bonded to a nitrogen atom of an amino group. These two non-aromatic carbocycle may be the same or different.

The term "aromatic heterocyclylamino" means a group wherein the above "aromatic heterocycle" is replaced with one or two hydrogen atom(s) bonded to a nitrogen atom of an amino group. These two aromatic heterocycle may be the same or different. Examples include pyridylamino, pyridazinylamino and the like.

The term "non-aromatic heterocyclylamino" means a group wherein the above "non-aromatic heterocycle" is replaced with one or two hydrogen atom(s) bonded to a nitrogen atom of an amino group. These two non-aromatic heterocycle may be the same or different.

The term "aromatic carbocyclylsulfonyl" means a group wherein "aromatic carbocycle" is bonded to sulfonyl group. Examples include phenylsulfonyl, naphthylsulfonyl and the like.

The term "non-aromatic carbocyclylsulfonyl" means a group wherein "non-aromatic carbocycle" is bonded to sulfonyl group. Examples include cyclopropylsulfonyl, cyclohexylsulfonyl, cyclohexenylsulfonyl and the like.

The term "aromatic heterocyclylsulfonyl" means a group wherein "aromatic heterocycle" is bonded to sulfonyl group. Examples include pyridylsulfonyl, oxazolylsulfonyl and the like.

The term "non-aromatic heterocyclylsulfonyl" means a group wherein "non-aromatic heterocycle" is bonded to sulfonyl group. Examples include piperidinylsulfonyl, tetrahydrofurylsulfonyl and the like.

The term "aromatic carbocyclylcarbonylamino" means a group wherein the above "aromatic carbocyclylcarbonyl" is replaced with one or two hydrogen atom(s) bonded to a nitrogen atom of an amino group. These two aromatic carbocyclyl may be the same or different. Examples include phenylcarbonylamino, naphthylcarbonylamino, di(phenylcarbonyl)amino and the like.

The term "non-aromatic carbocyclylcarbonylamino" means a group wherein the above "non-aromatic carbocyclylcarbonylamino" is replaced with one or two hydrogen atom(s) bonded to a nitrogen atom of an amino group. These two non-aromatic carbocyclyl may be the same or different. Examples include cyclopropylcarbonylamino, cyclohexylcarbonylamino, cyclohexenylcarbonylamino and the like.

The term "aromatic heterocyclylcarbonylamino" means a group wherein the above "aromatic heterocyclylcarbonyl" is replaced with one or two hydrogen atom(s) bonded to a nitrogen atom of an amino group. These two aromatic heterocyclyl may be the same or different. Examples include pyridylcarbonylamino, oxazolylcarbonylamino, pyrazinecarbonylamino and the like.

The term "non-aromatic heterocyclylcarbonylamino" means a group wherein the above "non-aromatic heterocyclylcarbonyl" is replaced with one or two hydrogen atom(s) bonded to a nitrogen atom of an amino group. These two non-aromatic heterocyclyl may be the same or different. Examples include piperidinylcarbonylamino, tetrahydrofurylcarbonylamino and the like.

The term "aromatic carbocyclylsulfamoyl" means a group wherein "aromatic carbocycle" is bonded to sulfamoyl group. Examples include phenylsulfamoyl, naphthylsulfamoyl and the like.

The term "non-aromatic carbocyclylsulfamoyl" means a group wherein "non-aromatic carbocycle" is bonded to sulfamoyl group. Examples include cyclopropylsulfamoyl, cyclohexylsulfamoyl and the like.

The term "aromatic heterocyclylsulfamoyl" means a group wherein "aromatic heterocycle" is bonded to sulfamoyl group. Examples include pyridylsulfamoyl, pyrazinesulfamoyl and the like.

The term "non-aromatic heterocyclylsulfamoyl" means a group wherein "non-aromatic heterocycle" is bonded to sulfamoyl group. Examples include piperidinylsulfamoyl, piperazinylsulfamoyl, pyrrolidinylsulfamoyl, tetrahydrofurylsulfamoyl and the like.

The term "aromatic carbocyclylureido" means a group wherein the above "aromatic carbocycle" is replaced with one or two hydrogen atom(s) bonded to a nitrogen atom of an ureido group. These two aromatic carbocycle may be the same or different.

The term "non-aromatic carbocyclylureido" means a group wherein the above "non-aromatic carbocycle" is replaced with one or two hydrogen atom(s) bonded to a nitrogen atom of an ureido group. These two non-aromatic carbocycle may be the same or different.

The term "aromatic heterocyclylureido" means a group wherein the above "aromatic heterocycle" is replaced with one or two hydrogen atom(s) bonded to a nitrogen atom of an ureido group. These two aromatic heterocycle may be the same or different.

The term "non-aromatic heterocyclylureido" means a group wherein the above "non-aromatic heterocycle" is replaced with one or two hydrogen atom(s) bonded to a nitrogen atom of an ureido group. These two non-aromatic heterocycle may be the same or different.

The term "alkylamino" means a group wherein one or two hydrogen atom(s) attached to a nitrogen atom of an amino group are replaced with one or two "alkyl" described above. These two alkyl groups may be the same or different. Examples include monomethylamino, monoethylamino, dimethylamino, diethylamino, N-methyl-N-ethylamino and the like.

The term "hydroxyamino" means a group wherein one or two hydrogen atom(s) attached to a nitrogen atom of an amino group are replaced with one or two hydroxy. Examples include monohydroxyamino, dihydroxyamino.

The term "sulfamoylamino" means a group wherein one or two hydrogen atom(s) attached to a nitrogen atom of an amino group are replaced with one or two sulfamoyl. Examples include monosulfamoylamino, disulfamoylamino.

The term "alkylammonium" means a group wherein one, two or three hydrogen atom(s) attached to a nitrogen atom of an ammonium group are replaced with one, two or three "alkyl" described above. These two or three alkyl groups may be the same or different. Examples include monomethylammonium, monoethylammonium, dimethylammonium, diethylammonium, triethylammonium, triethylammonium, N-methyl-N-ethyl-N-isopropylammonium and the like.

The term "alkylureido" means a group wherein one or two hydrogen atom(s) attached to a nitrogen atom of an ureido group are replaced with one or two "alkyl" described above. These two alkyl groups may be the same or different. Examples include monomethylureido, monoethylureido, dimethylureiclo, diethylureido, N-methyl-N-ethylureido and the like.

The term "alkylcarbamoyl" means a group wherein one or two hydrogen atom(s) attached to a nitrogen atom of a carbamoyl group are replaced with one or two "alkyl" described above. These two alkyl groups may be the same or different. Examples include monomethylcarbamoyl, monoethylcarbamoyl, dimethylcarbamoyl, diethylcarbamoyl, N-methyl-N-ethylcarbamoyl and the like.

The term "alkylsulfamoyl" means a group wherein one or two hydrogen atom(s) attached to a nitrogen atom of a sulfamoyl group are replaced with one or two "alkyl" described above. These two alkyl groups may be the same or different. Examples include monomethylsulfamoyl, monoethylsulfamoyl, dimethylsulfamoyl, diethylsulfamoyl, N-methyl-N-ethylsulfamoyl and the like.

The term "alkylphosphonyl" means a group wherein one or two hydrogen atom(s) attached to a nitrogen atom of a phosphonyl group are replaced with one or two "alkyl" described above. These two alkyl groups may be the same or different. Examples include monomethylphosphonyl, monoethylphosphonyl, dimethylphosphonyl, diethylphosphonyl, N-methyl-N-ethylphosphonyl and the like.

The term "aromatic carbocyclylalkyl" means an alkyl substituted with one or more "aromatic carbocyclyl" described above. Examples include benzyl, phenethyl, phenylpropyl, benzhydryl, trityl, naphthylmethyl and the like.

The term "non-aromatic carbocyclylalkyl" means an alkyl substituted with one or more "non-aromatic carbocyclyl" described above. The "non-aromatic carbocyclylalkyl" also includes "non-aromatic carbocyclylalkyl" wherein the alkyl part is substituted with the above "aromatic carbocyclyl". Examples include cyclopropylmethyl, cyclobutylmethyl, cyclopentylmethyl, cyclohexylmethyl and the like.

The term "aromatic heterocyclylalkyl" means an alkyl substituted with one or more "aromatic heterocyclyl" described above. The "aromatic heterocyclylalkyl" also includes "aromatic heterocyclylalkyl" wherein the alkyl part is substituted with the above "aromatic carbocyclyl" and/or "non-aromatic carbocyclyl". Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl and the like.

The term "non-aromatic heterocyclylalkyl" means an alkyl substituted with one or more "non-aromatic heterocyclyl" described above. The "non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". Examples include tetrahydropyranylmethyl, morpholinylethyl, piperidinylmethyl, piperazinylmethyl and the like.

The term "aromatic carbocyclylalkyloxy" means a group wherein a hydrogen atom of hydroxy is replaced with "aromatic carbocyclylalkyl" described above.

The term "non-aromatic carbocyclylalkyloxy" means a group wherein a hydrogen atom of hydroxy is replaced with "non-aromatic carbocyclylalkyl" described above.

The term "aromatic heterocyclylalkyloxy" means a group wherein a hydrogen atom of hydroxy is replaced with "aromatic heterocyclylalkyl" described above.

The term "non-aromatic heterocyclylalkyloxy" means a group wherein a hydrogen atom of hydroxy is replaced with "non-aromatic heterocyclylalkyl" described above.

The term "aromatic carbocyclylalkylsulfonyl" means a group wherein a hydrogen atom of sulfonyl group is replaced with "aromatic carbocyclylalkyl" described above.

The term "non-aromatic carbocyclylalkylsulfonyl" means a group wherein a hydrogen atom of sulfonyl group is replaced with "non-aromatic carbocyclylalkyl" described above.

The term "aromatic heterocyclylalkylsulfonyl" means a group wherein a hydrogen atom of sulfonyl group is replaced with "aromatic heterocyclylalkyl" described above.

The term "non-aromatic heterocyclylalkylsulfonyl" means a group wherein a hydrogen atom of sulfonyl group is replaced with "non-aromatic heterocyclylalkyl" described above.

The alkyl part of "alkyloxy", "alkylsulfonyl", "alkylphosphonyl", "alkyloxyalkyl", "alkyloxycarbonyl", "alkylcarbonyl", "alkylcarbonyloxy", "alkylimino", "alkylsulfonyl", "hydroxyalkyloxy", "hydroxyalkylamino", "carboxyalkyl", "carbamoylalkyl", "haloalkyloxy" or "alkylsulfonylamino" is also same as the above "alkyl".

The alkenyl part of "alkenyloxy", "alkenyloxycarbonyl", "alkenylcarbonyl", "alkenylcarbonyloxy", "alkenylsulfonyl", "alkenylimino" or "carboxyalkenyl" is also same as the above "alkenyl".

The alkynyl part of "alkynyloxy", "alkynyloxycarbonyl", "alkynylcarbonyl", "alkynylcarbonyloxy", "alkynylsulfonyl" or "alkynylimino" is also same as the above "alkynyl".

The alkyl part of "aromatic carbocyclylalkyloxy", "non-aromatic carbocyclylalkyloxy", "aromatic heterocyclylalkyloxy", "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl", "non-aromatic heterocyclylalkyloxycarbonyl", "non-aromatic carbocyclylalkylcarbonyl", "aromatic carbocyclylalkylcarbonyl", "aromatic heterocyclylalkylcarbonyl", "non-aromatic heterocyclylalkylcarbonyl", "aromatic carbocyclylalkylcarbonyloxy", "non-aromatic carbocyclylalkylcarbonyloxy", "aromatic heterocyclylalkylcarbonyloxy", "non-aromatic heterocyclylalkylcarbonyloxy", "aromatic carbocyclylalkylamino", "non-aromatic carbocyclylalkylamino", "aromatic heterocyclylalkylamino", "non-aromatic heterocyclylalkylamino", "aromatic carbocyclylalkylsulfonyl", "non-aromatic carbocyclylalkylsulfonyl", "aromatic heterocyclylalkylsulfonyl", "non-aromatic heterocyclylalkylsulfonyl", "aromatic carbocyclyloxyalkyl", "non-aromatic carbocyclyloxyalkyl", "aromatic heterocyclyloxyalkyl" and "non-aromatic heterocyclyloxyalkyl" is also same as the above "alkyl".

The alkenyl part of "aromatic carbocyclylalkenyl", "non-aromatic carbocyclylalkenyl", "aromatic heterocyclylalkenyl", "non-aromatic heterocyclylalkenyl", "aromatic carbocyclylalkenyloxy", "non-aromatic carbocyclylalkenyloxy", "aromatic heterocyclylalkenyloxy", "non-aromatic heterocyclylalkenyloxy", "aromatic carbocyclylalkenyloxyalkenyl", "non-aromatic carbocyclylalkenyloxyalkenyl", "aromatic heterocyclylalkenyloxyalkenyl", "non-aromatic heterocyclylalkenyloxyalkenyl", "aromatic carbocyclylalkenyloxycarbonyl", "non-aromatic carbocyclylalkenyloxycarbonyl", "aromatic heterocyclylalkenyloxycarbonyl", "non-aromatic heterocyclylalkenyloxycarbonyl", "aromatic carbocyclylalkenylcarbonyl", "non-aromatic carbocyclylalkenylcarbonyl", "aromatic heterocyclylalkenylcarbonyl", "non-aromatic heterocyclylalkenylcarbonyl", "aromatic carbocyclylalkenylcarbonyloxy", "non-aromatic carbocyclylalkenylcarbonyloxy", "aromatic heterocyclylalkenylcarbonyloxy", "now aromatic heterocyclylalkenylcarbonyloxy", "aromatic carbocyclylalkenylamino", "non-aromatic carbocyclylalkenylamino", "aromatic heterocyclylalkenylamino", "now aromatic heterocyclylalkenylamino", "aromatic carbocyclylalkenylsulfonyl", "non-aromatic carbocyclylalkenylsulfonyl", "aromatic heterocyclylalkenylsulfonyl", "non-aromatic heterocyclylalkenylsulfonyl", "aromatic carbocyclyloxyalkenyl", "non-aromatic carbocyclyloxyalkenyl", "aromatic heterocyclyloxyalkenyl" and "non-aromatic heterocyclyloxyalkenyl" is also same as the above "alkenyl".

The alkynyl part of "aromatic carbocyclylalkynyl", "non-aromatic carbocyclylalkynyl", "aromatic heterocyclylalkynyl", "non-aromatic heterocyclylalkynyl", "aromatic carbocyclylalkynyloxy", "non-aromatic carbocyclylalkynyloxy", "aromatic heterocyclylalkynyloxy", "non-aromatic heterocyclylalkynyloxy", "aromatic carbocyclylalkynyloxyalkynyl", "non-aromatic carbocyclylalkynyloxyalkynyl", "aromatic heterocyclylalkynyloxyalkynyl", "now aromatic heterocyclylalkynyloxyalkynyl", "aromatic carbocyclylalkynyloxycarbonyl", "non-aromatic carbocyclylalkynyloxycarbonyl", "aromatic heterocyclylalkynyloxycarbonyl", "non-aromatic heterocyclylalkynyloxycarbonyl", "aromatic carbocyclylalkynylcarbonyl", "non-aromatic carbocyclylalkynylcarbonyl", "aromatic heterocyclylalkynylcarbonyl", "non-aromatic heterocyclylalkynylcarbonyl", "aromatic carbocyclylalkynylcarbonyloxy", "non-aromatic carbocyclylalkynylcarbonyloxy", "aromatic heterocyclylalkynylcarbonyloxy", "now aromatic heterocyclylalkynylcarbonyloxy", "aromatic carbocyclylalkynylamino", "now aromatic carbocyclylalkynylamino", "aromatic heterocyclylalkynylamino", "now aromatic heterocyclylalkynylamino", "aromatic carbocyclylalkynylsulfonyl", "non-aromatic carbocyclylalkynylsulfonyl", "aromatic heterocyclylalkynylsulfonyl", "non-aromatic heterocyclylalkynylsulfonyl", "aromatic carbocyclyloxyalkynyl", "now aromatic carbocyclyloxyalkynyl", "aromatic heterocyclyloxyalkynyl" and "now aromatic heterocyclyloxyalkynyl" is also same as the above "alkynyl".

The aromatic carbocyclyl part of "aromatic carbocyclylalkyloxy", "aromatic carbocyclylalkyloxycarbonyl", "aromatic carbocyclylalkylcarbonyl", "aromatic carbocyclylalkylcarbonyloxy", "aromatic carbocyclylalkylamino", "aromatic carbocyclylalkylsulfonyl", "aromatic carbocycloxyalkyl", "aromatic carbocyclylalkenyl", "aromatic carbocyclylalkenyloxy", "aromatic carbocyclylalkenyloxyalkenyl", "aromatic carbocyclylalkenyloxycarbonyl", "aromatic carbocyclylalkenylcarbonyl", "aromatic carbocyclylalkenylcarbonyloxy", "aromatic carbocyclylalkenylamino", "aromatic carbocyclylalkenylsulfonyl", "aromatic carbocycloxyalkenyl", "aromatic carbocyclylalkynyl", "aromatic carbocyclylalkynyloxy", "aromatic carbocyclylalkynyloxyalkynyl", "aromatic carbocyclylalkynyloxycarbonyl", "aromatic carbocyclylalkynylcarbonyl", "aromatic carbocyclylalkynylcarbonyloxy", "aromatic carbocyclylalkynylamino", "aromatic carbocyclylalkynylsulfonyl" and "aromatic carbocycloxyalkynyl" is also same as the above "aromatic carbocyclyl".

The non-aromatic carbocyclyl part of "non-aromatic carbocyclylalkyloxy", "non- aromatic carbocyclylalkyloxycarbonyl", "non-aromatic carbocyclylalkylcarbonyl", "non-aromatic carbocyclylalkylcarbonyloxy", "non-aromatic carbocyclylalkylamino", "non-aromatic carbocyclylalkylsulfonyl", "non-aromatic carbocycloxyalkyl", "non-aromatic carbocyclylalkenyl", "non-aromatic carbocyclylalkenyloxy", "non-aromatic carbocyclylalkenyloxyalkenyl", "non-aromatic carbocyclylalkenyloxycarbonyl", "non-aromatic carbocyclylalkenylcarbonyl", "non-aromatic carbocyclylalkenylcarbonyloxy", "non-aromatic carbocyclylalkenylamino", "non-aromatic carbocyclylalkenylsulfonyl", "non-aromatic carbocycloxyalkenyl", "non-aromatic carbocyclylalkynyl", "non-aromatic carbocyclylalkynyloxy", "non-aromatic carbocyclylalkynyloxyalkynyl", "non-aromatic carbocyclylalkynyloxycarbonyl", "non-aromatic carbocyclylalkynylcarbonyl", "non-aromatic carbocyclylalkynylcarbonyloxy", "non-aromatic carbocyclylalkynylamino", "non-aromatic carbocyclylalkynylsulfonyl" and "non-aromatic carbocycloxyalkynyl" is also same as the above "non-aromatic carbocyclyl".

The aromatic heterocyclyl part of "aromatic heterocyclylalkyloxy", "aromatic heterocyclylalkyloxycarbonyl", "aromatic heterocyclylalkylcarbonyl", "aromatic heterocyclylalkylcarbonyloxy", "aromatic heterocyclylalkylamino", "aromatic heterocyclylalkylsulfonyl", "aromatic heterocycloxyalkyl", "aromatic heterocyclylalkenyl", "aromatic heterocyclylalkenyloxy", "aromatic heterocyclylalkenyloxyalkenyl", "aromatic heterocyclylalkenyloxycarbonyl", "aromatic heterocyclylalkenylcarbonyl", "aromatic heterocyclylalkenylcarbonyloxy", "aromatic heterocyclylalkenylamino", "aromatic heterocyclylalkenylsulfonyl", "aromatic heterocycloxyalkenyl", "aromatic heterocyclylalkynyl", "aromatic heterocyclylalkynyloxy", "aromatic heterocyclylalkynyloxyalkynyl", "aromatic heterocyclylalkynyloxycarbonyl", "aromatic heterocyclylalkynylcarbonyl", "aromatic heterocyclylalkynylcarbonyloxy", "aromatic heterocyclylalkynylamino", "aromatic heterocyclylalkynylsulfonyl" and "aromatic heterocycloxyalkynyl" is also same as the above "aromatic heterocyclyl".

The non-aromatic heterocyclyl part of "non-aromatic heterocyclylalkyloxy", "non-aromatic heterocyclylalkyloxycarbonyl", "non-aromatic heterocyclylalkylcarbonyl", "non-aromatic heterocyclylalkylcarbonyloxy", "non-aromatic heterocyclylalkylamino", "non-aromatic heterocyclylalkylsulfonyl", "non-aromatic heterocycloxyalkyl", "non-aromatic heterocyclylalkenyl", "non-aromatic heterocyclylalkenyloxy", "non-aromatic heterocyclylalkenyloxyalkenyl", "non-aromatic heterocyclylalkenyloxycarbonyl", "non-aromatic heterocyclylalkenylcarbonyl", "non-aromatic heterocyclylalkenylcarbonyloxy", "non-aromatic heterocyclylalkenylamino", "non-aromatic heterocyclylalkenylsulfonyl", "non-aromatic heterocycloxyalkenyl", "non-aromatic heterocyclylalkynyl", "non-aromatic heterocyclylalkynyloxy", "non-aromatic heterocyclylalkynyloxyalkynyl", "non-aromatic heterocyclylalkynyloxycarbonyl", "non-aromatic heterocyclylalkynylcarbonyl", "non-aromatic heterocyclylalkynylcarbonyloxy", "non-aromatic heterocyclylalkynylamino", "non-aromatic heterocyclylalkynylsulfonyl" and "non-aromatic heterocycloxyalkynyl" is also same as the above "non-aromatic heterocyclyl".

The term "alkylamino aromatic carbocyclyl", "alkylamino non-aromatic carbocyclyl", "alkylamino aromatic heterocyclyl" and "alkylamino non-aromatic heterocyclyl" means above "aromatic carbocyclyl", "non-aromatic carbocyclyl", "aromatic heterocyclyl" or "non-aromatic heterocyclyl" substituted one or more above "alkylamino".

Examples of the substituents of "substituted or unsubstituted amino", "substituted or unsubstituted carbamoyl", "substituted or unsubstituted sulfamoyl", "substituted or unsubstituted ureido", "substituted or unsubstituted amidino" and "substituted or unsubstituted guanidino" include same or different one or two group(s) selected from hydroxy, sulfamoyl, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl.

Especially preferably, same or different one or two group(s) selected from hydroxy, sulfamoyl, substituted or unsubstituted alkyl, substituted or unsubstituted alkylsulfonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyl, substituted or unsubstituted non-aromatic carbocyclyl, substituted or unsubstituted aromatic heterocyclyl and substituted or unsubstituted non-aromatic heterocyclyl are exemplified.

More preferably, same or different one or two group(s) selected from alkyl, hydroxy, hydroxyalkyl, alkylsulfonyl, alkylphosphonyl, sulfamoyl, aromatic carbocyclyl, non-aromatic carbocyclyl, aromatic heterocyclyl, non-aromatic heterocyclyl, aromatic carbocyclylcarbonyl, non-aromatic carbocyclylcarbonyl, aromatic heterocyclylcarbonyl and non-aromatic heterocyclylcarbonyl are exemplified.

Examples of the substituents of "substituted or unsubstituted alkylamino" include the substituents of above "substituted or unsubstituted alkyl". Preferably, halogen, hydroxy, carboxy, alkyloxycarbonyl, amino, alkylamino, carbamoyl, alkylimino, aromatic carbocyclyl, non-aromatic carbocyclyl, aromatic heterocyclyl, non-aromatic heterocyclyl, alkyloxyaromatic carbocyclyl, alkyloxynon-aromatic carbocyclyl, alkyloxyaromatic heterocyclyl and alkyloxynon-aromatic heterocyclyl are exemplified. One or more, preferably 1 to 4 same or different substituent(s) may be had at any position(s).

Examples of the substituents of "aromatic carbocyclyl", "non-aromatic carbocyclyl", "aromatic heterocyclyl" and "non-aromatic heterocyclyl" of "substituted aromatic carbocyclyl", "substituted non-aromatic carbocyclyl", "substituted aromatic heterocyclyl", "substituted non-aromatic heterocyclyl", "substituted aromatic carbocyclyl", "substituted non-aromatic carbocyclyl", "substituted aromatic heterocyclyl", "substituted non-aromatic heterocyclyl", "substituted aromatic carbocyclyloxy", "substituted non-aromatic carbocyclyloxy", "substituted aromatic heterocyclyloxy", "substituted non-aromatic heterocyclyloxy", "substituted aromatic carbocyclylcarbonyl", "substituted non-aromatic carbocyclylcarbonyl", "substituted aromatic heterocyclylcarbonyl", "substituted non-aromatic heterocyclylcarbonyl", "substituted aromatic carbocyclylamino", "substituted non-aromatic carbocyclylamino", "substituted aromatic heterocyclylamino", "substituted non-aromatic heterocyclylamino", "substituted aromatic carbocyclylsulfonyl", "substituted non-aromatic carbocyclylsulfonyl", "substituted aromatic heterocyclylsulfonyl", "substituted non-aromatic heterocyclylsulfonyl", "substituted non-aromatic heterocyclyloxyalkyl", "substituted non-aromatic heterocyclyloxyalkenyl", "substituted non-aromatic heterocyclyloxyalkynyl", "substituted nitrogen-containing aromatic heterocyclyl", "substituted nitrogen-containing non-aromatic heterocyclyl", "substituted aromatic carbocyclylcarbonylamino", "substituted non-aromatic carbocyclylcarbonylamino", "substituted aromatic heterocyclylcarbonylamino", "substituted non-aromatic heterocyclylcarbonylamino", "substituted aromatic carbocyclylsulfamoyl", "substituted non-aromatic carbocyclylsulfamoyl", "substituted aromatic heterocyclylsulfamoyl", "substituted non-aromatic heterocyclylsulfamoyl", "substituted aromatic carbocyclylureido", "substituted non-aromatic carbocyclylureido", "substituted aromatic heterocyclylureido", "substituted non-aromatic heterocyclylureido", "substituted aromatic carbocyclylalkyloxy", "substituted non-aromatic carbocyclylalkyloxy", "substituted aromatic heterocyclylalkyloxy", "substituted non-aromatic heterocyclylalkyloxy", "substituted aromatic carbocyclylalkylsulfonyl", "substituted non-aromatic carbocyclylalkylsulfonyl", "substituted aromatic heterocyclylalkylsulfonyl", "substituted non-aromatic heterocyclylalkylsulfonyl", "substituted aromatic carbocyclylalkylcarbonyloxy", "substituted non-aromatic carbocyclylalkylcarbonyloxy", "substituted aromatic heterocyclylalkylcarbonyloxy", "substituted non-aromatic heterocyclylalkylcarbonyloxy", "substituted alkylaminoaromatic carbocyclyl", "substituted alkylaminonon-aromatic carbocyclyl", "substituted alkylaminoaromatic heterocyclyl" and "substituted alkylaminonon-aromatic heterocyclyl" include halogen, cyano, alkyl, alkenyl, alkynyl, haloalkyl, hydroxyalkyl, carbamoylalkyl, haloalkenyl, hydroxyalkenyl, carbamoylalkenyl, carboxyalkyl, carboxyalkenyl, alkylcarbonyl, hydroxy, carboxy, oxo, thioxo, imino, alkylimino, alkyloxycarbonyl, amino, alkylamino (monoalkylamino, dialkylamino), hydroxyalkylamino, hydroxyalkyloxy, carbamoyl, sulfamoyl, alkylsulfonyl, alkyloxy, alkenylsulfonyl, alkenyloxy, amidino, aromatic carbocyclylalkyl, non-aromatic carbocyclylalkyl, aromatic heterocyclylalkyl, non-aromatic heterocyclylalkyl, aromatic carbocyclyloxyalkyl, non-aromatic carbocyclyloxyalkyl, aromatic heterocyclyloxyalkyl, non-aromatic carbocyclyloxyalkyl, aromatic carbocyclyl, non-aromatic carbocyclyl, aromatic heterocyclyl, non-aromatic heterocyclyl, aromatic carbocyclyl substituted with halogen, cyano, hydroxy, alkyl, haloalkyl, hydroxyalkyl, alkyloxy, haloalkyloxy and/or amino, non-aromatic carbocyclyl substituted with halogen, cyano, hydroxy, alkyl, haloalkyl, hydroxyalkyl, alkyloxy, haloalkyloxy and/or amino, aromatic heterocyclyl substituted with halogen, cyano, hydroxy, alkyl, haloalkyl, hydroxyalkyl, alkyloxy, haloalkyloxy and/or amino, non-aromatic heterocyclyl substituted with halogen, cyano, hydroxy, alkyl, haloalkyl, hydroxyalkyl, alkyloxy, haloalkyloxy and/or amino, aromatic carbocyclylalkyloxy, non-aromatic carbocyclylalkyloxy, aromatic heterocyclylalkyloxy, non-aromatic heterocyclylalkyloxy, aromatic carbocyclylalkyloxy substituted with halogen, cyano, hydroxy, alkyl, haloalkyl, hydroxyalkyl, alkyloxy, haloalkyloxy and/or amino, non-aromatic carbocyclylalkyloxy substituted with halogen, cyano, hydroxy, alkyl, haloalkyl, hydroxyalkyl, alkyloxy, haloalkyloxy and/or amino, aromatic heterocyclylalkyloxy substituted with halogen, cyano, hydroxy, alkyl, haloalkyl, hydroxyalkyl, alkyloxy, haloalkyloxy and/or amino, non-aromatic heterocyclylalkyloxy substituted with halogen, cyano, hydroxy, alkyl, haloalkyl, hydroxyalkyl, alkyloxy, haloalkyloxy and/or amino, aromatic carbocyclyloxy, non-aromatic carbocyclyloxy, aromatic heterocyclyloxy, non-aromatic heterocyclyloxy, aromatic carbocyclyloxy substituted with halogen, cyano, hydroxy, alkyl, haloalkyl, hydroxyalkyl, alkyloxy, haloalkyloxy and/or amino, non-aromatic carbocyclyloxy substituted with halogen, cyano, hydroxy, alkyl, haloalkyl, hydroxyalkyl, alkyloxy, haloalkyloxy and/or amino, aromatic heterocyclyloxy substituted with halogen, cyano, hydroxy, alkyl, haloalkyl, hydroxyalkyl, alkyloxy, haloalkyloxy and/or amino, non-aromatic heterocyclyloxy substituted with halogen, cyano, hydroxy, alkyl, haloalkyl, hydroxyalkyl, alkyloxy, haloalkyloxy and/or amino.

Preferably, halogen, alkyl, haloalkyl, hydroxyalkyl, carbamoylalkyl, carboxyalkenyl, hydroxy, carboxy, oxo, alkyloxycarbonyl, amino, alkylamino, hydroxyalkylamino, carbamoyl, sulfamoyl, alkylsulfonyl, alkyloxy, amidino, aromatic carbocyclylalkyl, non-aromatic carbocyclylalkyl, aromatic heterocyclylalkyl, non-aromatic heterocyclylalkyl, aromatic carbocyclyloxyalkyl, non-aromatic carbocyclyloxyalkyl, aromatic heterocyclyloxyalkyl, non-aromatic carbocyclyloxyalkyl, aromatic carbocyclyl, non-aromatic carbocyclyl, aromatic heterocyclyl, non-aromatic heterocyclyl, aromatic carbocyclyl substituted with halogen, alkyl, alkyloxy and/or amino, non-aromatic carbocyclyl substituted with halogen, alkyl, alkyloxy and/or amino, aromatic heterocyclyl substituted with halogen, alkyl, alkyloxy and/or amino, non-aromatic heterocyclyl substituted with halogen, alkyl, alkyloxy and/or amino, aromatic carbocyclylalkyloxy, non-aromatic carbocyclylalkyloxy, aromatic heterocyclylalkyloxy, non-aromatic heterocyclylalkyloxy, aromatic carbocyclylalkyloxy substituted with haloalkyl, non-aromatic carbocyclylalkyloxy substituted with haloalkyl, aromatic heterocyclylalkyloxy substituted with haloalkyl, non-aromatic heterocyclylalkyloxy substituted with haloalkyl, aromatic carbocyclyloxy, non-aromatic carbocyclyloxy, aromatic heterocyclyloxy, non-aromatic heterocyclyloxy, aromatic carbocyclyloxy substituted with hydroxy and/or hydroxyalkyl, non-aromatic carbocyclyloxy substituted with hydroxy or hydroxyalkyl, aromatic heterocyclyloxy substituted with hydroxy or hydroxyalkyl, non-aromatic heterocyclyloxy substituted with hydroxy or hydroxyalkyl are exemplified. One or more, preferably 1 to 4 same or different substituent(s) may be had at any position(s).

Examples of the substituents of "alkyl", "alkenyl" and "alkynyl" of "substituted alkyl", "substituted alkenyl", "substituted alkynyl", "substituted alkyloxy", "substituted alkenyloxy", "substituted alkynyloxy", "substituted alkylcarbonyl", "substituted alkenylcarbonyl", "substituted alkynylcarbonyl", "substituted alkylammonium", "substituted alkylsulfonyl", "substituted alkenylsulfonyl", "substituted alkynylsulfonyl", "substituted alkylphosphonyl", "substituted alkenylphosphonyl", "substituted alkynylphosphonyl", "substituted alkylcarbonyloxy", "substituted alkenylcarbonyloxy", "substituted alkynylcarbonyloxy", "substituted alkyloxycarbonyl", "substituted alkenyloxycarbonyl", "substituted alkynyloxycarbonyl", "substituted non-aromatic heterocyclyloxyalkyl", "substituted non-aromatic heterocyclyloxyalkenyl", "substituted non-aromatic heterocyclyloxyalkynyl", "substituted alkylamino", "substituted alkylsulfonylamino", "substituted alkylcarbamoyl", "substituted alkylsulfamoyl", "substituted alkylureido", "substituted aromatic carbocyclylalkyloxy", "substituted non-aromatic carbocyclylalkyloxy", "substituted aromatic heterocyclylalkyloxy", "substituted non-aromatic heterocyclylalkyloxy", "substituted aromatic carbocyclylalkylsulfonyl", "substituted non-aromatic carbocyclylalkylsulfonyl", "substituted aromatic heterocyclylalkylsulfonyl", "substituted non-aromatic heterocyclylalkylsulfonyl", "substituted aromatic carbocyclylalkylcarbonyloxy", "substituted non-aromatic carbocyclylalkylcarbonyloxy", "substituted aromatic heterocyclylalkylcarbonyloxy", "substituted non-aromatic heterocyclylalkylcarbonyloxy", "substituted alkylaminoaromatic carbocyclyl", "substituted alkylaminonon-aromatic carbocyclyl", "substituted alkylaminoaromatic heterocyclyl" and "substituted alkylaminonon-aromatic heterocyclyl" include halogen, cyano, hydroxy, carboxy, amino, alkylamino(monoalkylamino, dialkylamino), alkyloxy, haloalkyloxy, alkenyloxy, hydroxyalkyloxy, alkyloxycarbonyl, alkylsulfonyl, alkenylsulfonyl, carbamoyl, alkylimino, aromatic carbocyclyl, non-aromatic carbocyclyl, aromatic heterocyclyl, non-aromatic heterocyclyl, aromatic carbocyclyl substituted with halogen, cyano, hydroxy, alkyl, haloalkyl, hydroxyalkyl, alkyloxy, haloalkyloxy and/or amino, non-aromatic carbocyclyl substituted with halogen, cyano, hydroxy, alkyl, haloalkyl, hydroxyalkyl, alkyloxy, haloalkyloxy and/or amino, aromatic heterocyclyl substituted with halogen, cyano, hydroxy, alkyl, haloalkyl, hydroxyalkyl, alkyloxy, haloalkyloxy and/or amino, non-aromatic heterocyclyl substituted with halogen, cyano, hydroxy, alkyl, haloalkyl, hydroxyalkyl, alkyloxy, haloalkyloxy and/or amino.

Preferably, halogen, hydroxy, carboxy, amino, alkylamino, alkyloxy, hydroxyalkyloxy, alkyloxycarbonyl, alkylsulfonyl, carbamoyl, alkylimino, aromatic carbocyclyl, non-aromatic carbocyclyl, aromatic heterocyclyl, non-aromatic heterocyclyl, alkyloxyaromatic carbocyclyl, alkyloxynon-aromatic carbocyclyl, alkyloxyaromatic heterocyclyl and alkyloxynon-aromatic heterocyclyl are exemplified.

Especially preferably, hydroxy, carboxy, amino, alkylamino, alkyloxy, hydroxyalkyloxy, alkyloxycarbonyl, alkylsulfonyl, aromatic carbocyclyl, non-aromatic carbocyclyl, aromatic heterocyclyl and non-aromatic heterocyclyl are exemplified. One or more, preferably 1 to 4 same or different substituent(s) may be had at any position(s).

The "substituted aromatic carbocyclylalkyl", "substituted aromatic carbocyclyloxyalkyl", "substituted aromatic carbocyclylalkyloxy", "substituted aromatic carbocyclylalkyloxycarbonyl", "substituted aromatic carbocyclylalkylcarbonyl", "substituted aromatic carbocyclylalkylcarbonyloxy", "substituted aromatic carbocyclylalkylamino" and "substituted aromatic carbocyclylalkylsulfonyl" means the part of "aromatic carbocyclyl" and/or above "alkyl" are substituted.

The "substituted non-aromatic carbocyclylalkyl", "substituted non-aromatic carbocyclyloxyalkyl", "substituted non-aromatic carbocyclylalkyloxy", "substituted non-aromatic carbocyclylalkyloxycarbonyl", "substituted non-aromatic carbocyclylalkylcarbonyl", "substituted non-aromatic carbocyclylalkylcarbonyloxy", "substituted non-aromatic carbocyclylalkylamino" and "substituted non-aromatic carbocyclylalkylsulfonyl" means the part of above "non-aromatic carbocyclyl" and/or above "alkyl" are substituted.

The "substituted aromatic heterocyclylalkyl", "substituted aromatic heterocyclyloxyalkyl", "substituted aromatic heterocyclylalkyloxy", "substituted aromatic heterocyclylalkyloxycarbonyl", "substituted aromatic heterocyclylalkylcarbonyl", "substituted aromatic heterocyclylalkylcarbonyloxy", "substituted aromatic heterocyclylalkylamino" and "substituted aromatic heterocyclylalkylsulfonyl" means the part of above "aromatic heterocyclyl" and/or above "alkyl" are substituted.

The "substituted non-aromatic heterocyclylalkyl", "substituted non-aromatic heterocyclyloxyalkyl", "substituted non-aromatic heterocyclylalkyloxy", "substituted non-aromatic heterocyclylalkyloxycarbonyl", "substituted non-aromatic heterocyclylalkylcarbonyl", "substituted non-aromatic heterocyclylalkylcarbonyloxy", "substituted non-aromatic heterocyclylalkylamino" and "substituted or unsubstituted non-aromatic heterocyclylalkylsulfonyl" means the part of above "non-aromatic heterocyclyl" and/or above "alkyl" are substituted.

The "substituted non-aromatic heterocyclyloxyalkenyl" and "substituted non-aromatic heterocyclyloxyalkynyl" means the part of above "non-aromatic heterocyclyl", above "alkenyl" and/or above "alkynyl" are substituted.

Examples of "substituted or unsubstituted amino" include unsubstituted amino, hydroxyamino, sulfamoylamino, substituted or unsubstituted alkylamino, substituted or unsubstituted alkylsulfonylamino, substituted or unsubstituted carboxyamino, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino and the like.

Examples of "substituted or unsubstituted alkyloxy" include unsubstituted alkyloxy, substituted or unsubstituted aromatic carbocyclylalkyloxy, substituted or unsubstituted non-aromatic carbocyclylalkyloxy, substituted or unsubstituted aromatic heterocyclylalkyloxy, substituted or unsubstituted non-aromatic heterocyclylalkyloxy and the like.

Examples of "substituted or unsubstituted alkylsulfonyl" include unsubstituted alkylsulfonyl, substituted or unsubstituted aromatic carbocyclylalkylsulfonyl, substituted or unsubstituted non-aromatic carbocyclylalkylsulfonyl, substituted or unsubstituted aromatic heterocyclylalkylsulfonyl, substituted or unsubstituted non-aromatic heterocyclylalkylsulfonyl and the like.

Examples of "substituted or unsubstituted alkylcarbonyloxy" include unsubstituted alkylcarbonyloxy, substituted or unsubstituted aromatic carbocyclylalkylcarbonyloxy, substituted or unsubstituted non-aromatic carbocyclylalkylcarbonyloxy, substituted or unsubstituted aromatic heterocyclylalkylcarbonyloxy, substituted or unsubstituted non-aromatic heterocyclylalkylcarbonyloxy and the like.

Examples of "substituted or unsubstituted aromatic carbocyclyl" include unsubstituted aromatic carbocyclyl, substituted or unsubstituted alkylaminoaromatic carbocyclyl and the like.

Examples of "substituted or unsubstituted non-aromatic carbocyclyl" include unsubstituted non-aromatic carbocyclyl, substituted or unsubstituted alkylaminonon-aromatic carbocyclyl and the like.

Examples of "substituted or unsubstituted aromatic heterocyclyl" include unsubstituted aromatic heterocyclyl, substituted or unsubstituted alkylaminoaromatic heterocyclyl and the like.

Examples of "substituted or unsubstituted non-aromatic heterocyclyl" include unsubstituted non-aromatic heterocyclyl, substituted or unsubstituted alkylaminonon-aromatic heterocyclyl and the like.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on a carbon atom are substituted as below.

[Chemical Formula 12]

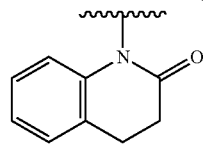

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylamino", "substituted or unsubstituted non-aromatic heterocyclylamino", "substituted or unsubstituted non-aromatic carbocyclylcarbonyl", "substituted or unsubstituted non-aromatic heterocyclylcarbonyl", "substituted or unsubstituted non-aromatic carbocyclylcarbonylamino", "substituted or unsubstituted non-aromatic heterocyclylcarbonylamino", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfamoyl", "substituted or unsubstituted non-aromatic heterocyclylsulfamoyl", "substituted or unsubstituted non-aromatic carbocyclylsulfonyl", "substituted or unsubstituted non-aromatic heterocyclylsulfonyl", "substituted or unsubstituted non-aromatic carbocyclylsulfamoyl", "substituted or unsubstituted non-aromatic heterocyclylsulfamoyl", "substituted or unsubstituted non-aromatic carbocyclylureido" and "substituted or unsubstituted non-aromatic heterocyclylureido" may be substituted with "oxo" as above.

Additionally, when "substituted or unsubstituted non-aromatic heterocyclyl" have a sulfur atom in ring, such sulfur atom may be substituted with "dioxo". In this case, it means a group wherein four hydrogen atoms on a sulfur atom are substituted as below.

[Chemical Formula 13]

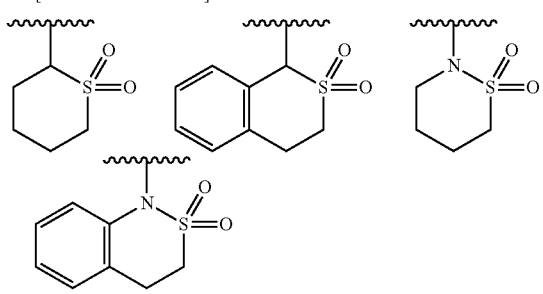

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylamino", "substituted or unsubstituted non-aromatic heterocyclylamino", "substituted or unsubstituted non-aromatic carbocyclylcarbonyl", "substituted or unsubstituted non-aromatic heterocyclylcarbonyl", "substituted or unsubstituted non-aromatic carbocyclylcarbonylamino", "substituted or unsubstituted non-aromatic heterocyclylcarbonylamino", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfamoyl", "substituted or unsubstituted non-aromatic heterocyclylsulfamoyl", "substituted or unsubstituted non-aromatic carbocyclylsulfonyl", "substituted or unsubstituted non-aromatic heterocyclylsulfonyl", "substituted or unsubstituted non-aromatic carbocyclylsulfamoyl", "substituted or unsubstituted non-aromatic heterocyclylsulfamoyl", "substituted or unsubstituted non-aromatic carbocyclylureido" and "substituted or unsubstituted non-aromatic heterocyclylureido" may be substituted with "sulfonyl" as above.

Preferred embodiments for the compound of formula (I) disclose below.

X is a group of formula:

[Chemical Formula 14]

(II)

a group of formula: —N($R^F$)—CO—$X^1$, hydroxyalkyl, or a group of formula: —CO—NH($R^X$)
wherein $R^X$ is substituted or unsubstituted non-aromatic heterocyclyloxyalkyl.

X is preferably, a group of formula: —N($R^F$)—CO—$X^1$, hydroxyalkyl or a group of formula: —CO—NH($R^X$)
wherein $R^X$ is substituted or unsubstituted non-aromatic heterocyclyloxyalkyl.

X is more preferably, a group of formula: —N($R^F$)—CO—$X^1$ or hydroxyalkyl.

X is especially preferably, a group of formula: —N($R^F$)—CO—$X^1$.

When X is hydroxyalkyl, Y is any one of following groups:

[Chemical Formula 15]

(VII)

(VIII)

Then q is an integer of 1 to 10.

$J^1$ is hydrogen, halogen, hydroxy, substituted or unsubstituted amino or substituted or unsubstituted alkyloxy.

$J^1$ is preferably, hydroxy, substituted or unsubstituted amino or substituted or unsubstituted alkyloxy.

$J^1$ is more preferably, hydroxy.

When $J^1$ is a substituted group, a preferable substituent on said substituted group is selected from alkyl, hydroxy, hydroxyalkyl and the like.

$J^2$ is preferably, hydrogen, substituted or unsubstituted alkyl, substituted or unsubstituted alkenyl or substituted or unsubstituted alkynyl.

$J^2$ is more preferably, hydrogen or substituted or unsubstituted alkyl.

$J^2$ is further preferably, hydrogen.

When $J^2$ is a substituted group, a preferable substituent on said substituted group is selected from alkyl, hydroxy, hydroxyalkyl and the like.

$J^1$ and $J^2$ may be taken together to form oxo.

L is hydrogen, halogen, hydroxy, substituted or unsubstituted amino or substituted or unsubstituted alkyloxy.

L is more preferably, hydroxy, substituted or unsubstituted amino or substituted or unsubstituted alkyloxy.

L is further preferably, hydroxy.

When L is a substituted group, a preferable substituent on said substituted group is selected from alkyl, hydroxy, hydroxyalkyl and the like.

$V^1$ is hydrogen, halogen, hydroxy, substituted or unsubstituted amino or substituted or unsubstituted alkyloxy.

$V^1$ is more preferably, hydroxy, substituted or unsubstituted amino or substituted or unsubstituted alkyloxy.

$V^1$ is further preferably, hydroxy.

When $V^1$ is a substituted group, a preferable substituent on said substituted group is selected from alkyl, hydroxy, hydroxyalkyl and the like.

$V^2$ is hydrogen, substituted or unsubstituted alkyl, substituted or unsubstituted alkenyl or substituted or unsubstituted alkynyl.

$V^2$ is more preferably, hydrogen or substituted or unsubstituted alkyl.

$V^2$ is further preferably, hydrogen.

When $V^2$ is a substituted group, a preferable substituent on said substituted group is selected from alkyl, hydroxy, hydroxyalkyl and the like.

$V^1$ and $V^2$ may be taken together to form oxo.

A group represented by formula (III) of X' group is explained as follows:

[Chemical Formula 16]

(III)

T is a bond, —N($R^{a5}$)— or —O—.
T is preferably, a bond or —N($R^{a5}$)—.
T is more preferably, —N($R^{a5}$)—.
When T is a bond, preferable embodiment is following.
$R^{a1}$ is hydrogen, halogen, hydroxy, carboxy, substituted or unsubstituted amino, substituted or unsubstituted alkylamino, folmyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted alkenylphosphonyl, substituted or unsubstituted alkynylphosphonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl.

$R^{a1}$ is preferably, hydrogen, halogen, hydroxy, carboxy, substituted or unsubstituted amino, substituted or unsubstituted alkylamino, substituted or unsubstituted carbamoyl, substituted or unsubstituted sulfamoyl, sulfo, cyano, substituted or unsubstituted ureido, guanidino, substituted or unsubstituted alkyloxy, substituted or unsubstituted alkylammonium, substituted or unsubstituted alkylphosphonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic heterocyclyloxy or substituted or unsubstituted aromatic heterocyclylamino.

$R^{a1}$ is more preferably, hydrogen, hydroxy, carboxy, amino, substituted or unsubstituted alkylamino, substituted or unsubstituted carbamoyl, cyano, substituted or unsubstituted ureido, substituted or unsubstituted alkylammonium, substituted or unsubstituted aromatic carbocyclyl, substituted or unsubstituted aromatic heterocyclyl, substituted or unsubstituted non-aromatic heterocyclyl.

When $R^{a1}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or hydroxy or non-aromatic heterocyclyloxy optionally substituted with hydroxyalkyl.

When $R^{a1}$ is a substituted group, a more preferable substituent on said substituted group is selected from unsubstituted alkyl, unsubstituted haloalkyl, amino, hydroxy, carboxy, unsubstituted hydroxyalkyl, unsubstituted carbamoylalkyl, unsubstituted alkyloxy, unsubstituted alkyloxycarbonyl, carbamoyl, unsubstituted alkylamino, hydroxyamino, unsubstituted hydroxyalkylamino, unsubstituted alkylimino, sulfamoyl, unsubstituted alkylsulfonyl, cyano, unsubstituted aromatic carbocyclyl, unsubstituted aromatic heterocyclyl, unsubstituted alkylaromatic heterocyclyl, unsubstituted alkyloxyaromatic carbocyclyl, aromatic carbocyclylalkyloxy optionally substituted with haloalkyl, aromatic carbocyclyl optionally substituted with halogen or aromatic heterocyclyl optionally substituted with amino.

When $R^{a1}$ is a substituted group, an especially preferable substituent on said substituted group is selected from hydroxy or unsubstituted hydroxyalkylamino.

$R^{a2}$ is each independently, hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a2}$ is preferably, each independently, hydrogen, halogen, hydroxy, carboxy, substituted or unsubstituted amino, substituted or unsubstituted carbamoyl, substituted or unsubstituted alkyl, substituted or unsubstituted alkyloxycarbonyl, or substituted or unsubstituted non-aromatic heterocyclyloxyalkyl.

$R^{a2}$ is more preferably, each independently, hydrogen, hydroxy, carboxy, substituted or unsubstituted amino or substituted or unsubstituted alkyl.

When $R^{a2}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a3}$ is each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a3}$ is preferably, each independently, hydrogen, halogen, substituted or unsubstituted alkyl or substituted or unsubstituted non-aromatic heterocyclyloxyalkyl.

$R^{a3}$ is more preferably, hydrogen.

When $R^{a3}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a2}$ and $R^{a3}$ may be each independently, taken together to form oxo, substituted or unsubstituted imino or thioxo, or may be taken together with neighboring atoms to form substituted or unsubstituted non-aromatic carbocycle or substituted or unsubstituted non-aromatic heterocycle.

$R^{a2}$ and $R^{a3}$ may be each independently, taken together to form oxo, or thioxo, or may be taken together with neighboring atoms to form substituted or unsubstituted non-aromatic carbocycle or substituted or unsubstituted non-aromatic heterocycle.

$R^{a2}$ and $R^{a3}$ may be each independently, taken together to form oxo, may be taken together with neighboring atoms to form substituted or unsubstituted non-aromatic carbocycle or substituted or unsubstituted non-aromatic heterocycle.

$R^{a4}$ is hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl.

$R^{a4}$ is preferably, hydrogen, hydroxy, substituted or unsubstituted amino, substituted or unsubstituted alkyl or substituted or unsubstituted non-aromatic carbocyclyl.

$R^{a4}$ is more preferably, hydrogen or hydroxy.

When $R^{a4}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

Especially preferable combination of ($R^{a1}$, $R^{a2}$, $R^{a3}$, $R^{a4}$, m) is following: (hydrogen, -, -, hydrogen, 0), (hydrogen, hydrogen, hydrogen, hydroxy, 1), (hydrogen, hydrogen, hydrogen, hydroxy, 2), (hydrogen, hydrogen, hydrogen, hydroxy, 3), (hydrogen, substituted or unsubstituted alkyl, hydrogen, hydrogen, 1), (hydrogen, substituted or unsubstituted alkyl, hydrogen, hydrogen, 2), (hydrogen, substituted or unsubstituted alkyl, hydrogen, hydrogen, 3), (hydrogen, substituted or unsubstituted alkyl, hydrogen, hydrogen, 4), (hydrogen, substituted or unsubstituted alkyl, hydrogen, hydrogen, 5), (hydrogen, substituted or unsubstituted alkyl, hydrogen, hydroxy, 1), (hydrogen, substituted or unsubstituted alkyl, hydrogen, hydroxy, 2), (hydrogen, carboxy, hydroxy, hydrogen, 1), (hydrogen, carboxy, hydroxy, hydrogen, 2), (hydrogen, carboxy, hydroxy, hydrogen, 3), (halogen, -, -, hydrogen, 0), (halogen, hydrogen, hydrogen, hydrogen, 1), (halogen, hydrogen, hydrogen, hydrogen, 2), (halogen, hydrogen, hydrogen, hydrogen, 3), (halogen, halogen, hydrogen, hydrogen, 1), (halogen, halogen, halogen, hydrogen, 2), (hydroxy, -, -, hydrogen, 0), (hydroxy, hydrogen, hydrogen, hydrogen, 1), (hydroxy, hydrogen, hydrogen, hydrogen, 2), (hydroxy, hydrogen, hydrogen, hydrogen, 3), (hydroxy, hydrogen, hydrogen, hydrogen, 4), (hydroxy, hydrogen, hydrogen, hydrogen, 5), (hydroxy, hydrogen, hydrogen, hydrogen, 6), (hydroxy, hydroxy, hydrogen, hydrogen, 1), (hydroxy, hydroxy, hydrogen, hydrogen, 2), (hydroxy, hydroxy, hydrogen, hydrogen, 3), (hydroxy, hydroxy, hydrogen, hydrogen, 4), (hydroxy, hydroxy, hydrogen, hydroxy, 1), (hydroxy, hydroxy, hydrogen, hydroxy, 2), (hydroxy, hydroxy, hydrogen, hydroxy, 3), (hydroxy, hydroxy, hydrogen, substituted or unsubstituted amino, 1), (hydroxy, hydroxy, hydrogen, substituted or unsubstituted amino, 2), (hydroxy, hydroxy, hydrogen, substituted or unsubstituted amino, 3), (hydroxy, substituted or unsubstituted hydroxyalkyl, hydrogen, hydrogen, 1), (hydroxy, substituted or unsubstituted hydroxyalkyl, hydrogen, hydrogen, 2), (hydroxy, substituted or unsubstituted hydroxyalkyl, hydrogen, hydrogen, 3), (hydroxy, substituted or unsubstituted hydroxyalkyl, substituted or unsubstituted alkyl, hydrogen, 1), (hydroxy, substituted or unsubstituted hydroxyalkyl, substituted or unsubstituted alkyl, hydrogen, 2), (hydroxy, substituted or unsubstituted hydroxyalkyl, hydrogen, substituted or unsubstituted amino, 1), (hydroxy, substituted or unsubstituted hydroxyalkyl, hydrogen, substituted or unsubstituted amino, 2), (hydroxy, carboxy, hydrogen, hydrogen, 1), (hydroxy, carboxy, hydrogen, hydrogen, 2), (hydroxy, carboxy, hydrogen, hydrogen, 3), (hydroxy, substituted or unsubstituted amino, hydrogen, hydrogen, 1), (hydroxy, substituted or unsubstituted amino, hydrogen, hydrogen, 2), (hydroxy, substituted or unsubstituted amino, hydrogen, hydrogen, 3), (hydroxy, substituted or unsubstituted amino, hydrogen, hydrogen, 4), (hydroxy, substituted or unsubstituted carbamoyl, hydrogen, hydrogen, 1), (hydroxy, substituted or unsubstituted carbamoyl, hydrogen, hydrogen, 2), (hydroxy, -, -, hydroxy, 0), (hydroxy, hydrogen, hydrogen, hydroxy, 1), (hydroxy, hydrogen, hydrogen, hydroxy, 2), (hydroxy, -, -, substituted or unsubstituted hydroxyalkyl, 0), (hydroxy, hydrogen, hydrogen, substituted or unsubstituted hydroxyalkyl, 1), (hydroxy, hydrogen, hydrogen, substituted or unsubstituted hydroxyalkyl, 2), (hydroxy, -, -, substituted or unsubstituted amino, 0), (hydroxy, hydrogen, hydrogen, substituted or unsubstituted amino, 1), (hydroxy, hydrogen, hydrogen, substituted or unsubstituted amino, 2), (carboxy, -, -, hydrogen, 0), (carboxy, hydrogen, hydrogen, hydrogen, 1), (carboxy, hydrogen, hydrogen, hydrogen, 2), (carboxy, hydrogen, hydrogen, hydrogen, 3), (carboxy, substituted or unsubstituted alkyl, hydrogen, hydrogen, 1), (carboxy, substituted or unsubstituted alkyl, hydrogen, hydrogen, 2), (carboxy, substituted or unsubstituted alkyl, hydrogen, hydrogen, 3), (carboxy, hydroxy, hydrogen, hydrogen, 1), (carboxy, hydroxy, hydrogen, hydrogen, 2), (carboxy, hydroxy, hydrogen, hydroxy, 1), (carboxy, hydroxy, hydrogen, hydroxy, 2), (carboxy, carboxy, hydrogen, hydrogen, 1), (carboxy, carboxy, hydrogen, hydrogen, 2), (carboxy, carboxy, hydroxy, hydrogen, 3), (carboxy, carboxy, hydroxy, hydrogen, 1), (carboxy, carboxy, hydroxy, hydrogen, 2), (carboxy, substituted or unsubstituted amino, hydrogen, hydrogen, 1), (carboxy, substituted or unsubstituted amino, hydrogen, hydrogen, 2), (carboxy, hydrogen, hydrogen, hydroxy, 1), (carboxy, hydrogen, hydrogen, hydroxy, 2), (carboxy, hydrogen, hydrogen, substituted or unsubstituted carboxyalkyl, 1), (substituted or unsubstituted carbamoyl, -, -, hydrogen, 0), (substituted or unsubstituted carbamoyl, hydrogen, hydrogen, hydrogen, 1), (substituted or unsubstituted carbamoyl, hydrogen, hydrogen, hydrogen, 2), (substituted or unsubstituted carbamoyl, substituted or unsubstituted alkyl, hydrogen, hydrogen, 1), (substituted or unsubstituted carbamoyl, substituted or unsubstituted alkyl, hydrogen, hydrogen, 2), (substituted or unsubstituted carbamoyl, hydroxy, hydrogen, hydrogen, 1), (substituted or unsubstituted carbamoyl, hydroxy, hydrogen, hydrogen, 2), (substituted or unsubstituted carbamoyl, carboxy, hydrogen, hydrogen, 1), (substituted or unsubstituted carbamoyl, carboxy, hydrogen, hydrogen, 2), (substituted or unsubstituted carbamoyl, -, -, hydroxy, 0), (substituted or unsubstituted carbamoyl, hydrogen, hydrogen, hydroxy, 1), (substituted or unsubstituted alkyl, -, -, substituted or unsubstituted alkyl, 0), (substituted or unsubstituted amino, -, -, hydrogen, 0), (substituted or unsubstituted amino, hydrogen, hydrogen, hydrogen, 1), (substituted or unsubstituted amino, hydrogen, hydrogen, hydrogen, 2), (substituted or unsubstituted amino, hydrogen, hydrogen, hydrogen, 3), (substituted or unsubstituted amino, substituted or unsubstituted hydroxyalkyl, hydrogen, hydrogen, 1), (substituted or unsubstituted amino, substituted or unsubstituted hydroxyalkyl, hydrogen, hydrogen, 2), (substituted or unsubstituted alkylamino, -, -, hydrogen, 0), (substituted or unsubstituted alkylamino, hydrogen, hydrogen, hydrogen, 1), (substituted or unsubstituted alkylamino, hydrogen, hydrogen, hydrogen, 2), (substituted or unsubstituted alkylamino, hydrogen, hydrogen, hydrogen, 3), (substituted or unsubstituted alkylamino, substituted or unsubstituted alkyl, hydrogen, hydrogen, 1), (substituted or unsubstituted alkylamino, substituted or unsubstituted alkyl, hydrogen, hydrogen, 2), (substituted or unsubstituted alkylamino, substituted or unsubstituted alkyl, hydrogen, hydrogen, 3), (substituted or unsubstituted alkylamino, substituted or unsubstituted hydroxyalkyl, hydrogen, hydrogen, 1), (substituted or unsubstituted alkylamino, substituted or unsubstituted hydroxyalkyl, hydrogen, hydrogen, 2), (substituted or unsubstituted alkylamino, -, -, hydroxy, 0), (substituted or unsubstituted alkylamino, hydrogen, hydrogen, hydroxy, 1), (substituted or unsubstituted alkylamino, hydrogen, hydrogen, hydroxy, 2), (substituted or unsubstituted alkylsulfonylamino, -, -, hydrogen, 0), (substituted or unsubstituted alkylsulfonylamino, hydrogen, hydrogen, hydrogen, 1), (substituted or unsubstituted alkylsulfonylamino, hydrogen, hydrogen, hydrogen, 2), (substituted or unsubstituted alkylsulfonylamino, substituted or unsubstituted alkylaminoalkyl, hydrogen, hydrogen, 1), (substituted or unsubstituted alkylsulfonylamino, substituted or unsubstituted alkylaminoalkyl, hydrogen, hydrogen, 2), (hydroxyamino, -, -, hydrogen, 0), (hydroxyamino, hydrogen, hydrogen, hydrogen, 1), (hydroxyamino, hydrogen, hydrogen, hydrogen, 2), (substituted or unsubstituted ureido, -, -, hydrogen, 0), (substituted or unsubstituted ureido, hydrogen, hydrogen, hydrogen, 1), (substituted or unsubstituted ureido, hydrogen, hydrogen, hydrogen, 2), (substituted or unsubstituted ureido, hydrogen, hydrogen, hydrogen, 3), (substituted or unsubstituted alkylureido, -, -, hydrogen, 0), (substituted or unsubstituted alkylureido, hydrogen, hydrogen, hydrogen, 1), (substituted or unsubstituted alkylureido, hydrogen, hydrogen, hydrogen, 2), (substituted or unsubstituted alkyloxy, -, -, hydrogen, 0), (substituted or unsubstituted alkyloxy, hydrogen, hydrogen, hydrogen, 1), (substituted or unsubstituted alkyloxy, hydrogen, hydrogen, hydrogen, 2), (substituted or unsubstituted alkyloxy, hydrogen, hydrogen, hydrogen, 3), (substituted or unsubstituted alkyloxy, hydrogen, hydrogen, hydrogen, 4), (substituted or unsubstituted alkyloxy, substituted or unsubstituted alkyl, hydrogen, hydrogen, 1), (substituted or unsubstituted alkyloxy, substituted or unsubstituted alkyl, hydrogen, hydrogen, 2), (substituted or unsubstituted alkyloxy, substituted or unsubstituted alkyloxyalkyl, hydrogen, hydrogen, 1), (substituted or unsubstituted alkyloxy, substituted or unsubstituted alkyloxyalkyl, hydrogen, hydrogen, 2), (substituted or unsubstituted alkyloxy, substituted or unsubstituted alkyloxycarbonyl, hydrogen, hydrogen, 1), (substituted or unsubstituted alkyloxy, substituted or unsubstituted alkyloxycarbonyl, hydrogen, hydrogen, 2), (substituted or unsubstituted alkyloxy, substituted or unsubstituted alkyloxycarbonyl, hydrogen, hydrogen, 3), (substituted or unsubstituted alkyloxy, substituted or unsubstituted alkyloxycarbonyl, hydrogen, hydrogen, 4), (cyano, -, -, hydrogen, 0), (cyano, hydrogen, hydrogen, hydrogen, 1), (guanidino, -, -, hydrogen, 0), (guanidino, hydrogen, hydrogen, hydrogen, 1), (guanidino, hydrogen, hydrogen, hydrogen, 2), (guanidino, hydrogen, hydrogen, hydrogen, 3), (guanidino, hydrogen, hydrogen, hydrogen, 4), (sulfo, -, -, hydrogen, 0), (sulfo, hydrogen, hydrogen, hydrogen, 1), (sulfo, hydrogen, hydrogen, hydrogen, 2), (substituted or unsubstituted sulfamoyl, -, -, hydrogen, 0), (substituted or unsubstituted sulfamoyl, hydrogen, hydrogen, hydrogen, 1), (substituted or unsubstituted sulfamoyl, hydrogen, hydrogen, hydrogen, 2), (substituted or unsubstituted alkylphosphonyl, -, -, hydrogen, 0), (substituted or unsubstituted alkylphosphonyl, hydrogen, hydrogen, hydrogen, 1), (substituted or unsubstituted alkylphosphonyl, hydrogen, hydrogen, hydrogen, 2), (substituted or unsubstituted aromatic carbocyclyl, -, -, hydrogen, 0), (substituted or unsubstituted aromatic carbocyclyl, hydrogen, hydrogen, hydrogen, 1), (substituted or unsubstituted aromatic carbocyclyl, hydrogen, hydrogen, hydrogen, 2), (substituted or unsubstituted aromatic carbocyclyl, hydrogen, hydrogen, hydrogen, 3), (substituted or unsubstituted aromatic carbocyclyl, substituted or unsubstituted alkyloxycarbonyl, hydrogen, hydrogen, 1), (substituted or unsubstituted aromatic carbocyclyl, substituted or unsubstituted alkyloxycarbonyl, hydrogen, hydrogen, 2), (substituted or unsubstituted non-aromatic carbocyclyl, -, -, hydrogen, 0), (substituted or unsubstituted non-aromatic carbocyclyl, hydrogen, hydrogen, hydrogen, 1), (substituted or unsubstituted non-aromatic carbocyclyl, hydrogen, hydrogen, hydrogen, 2), (substituted or unsubstituted non-aromatic carbocyclyl, hydrogen, hydrogen, hydrogen, 3), (substituted or unsubstituted non-aromatic carbocyclyl, -, -, substituted or unsubstituted non-aromatic carbocyclyl, 0), (substituted or unsubstituted aromatic heterocyclyl, -, -, hydrogen, 0), (substituted or unsubstituted aromatic heterocyclyl, hydrogen, hydrogen, hydrogen, 1), (substituted or unsubstituted aromatic heterocyclyl, hydrogen, hydrogen, hydrogen, 2), (substituted or unsubstituted aromatic heterocyclyl, hydrogen, hydrogen, hydrogen, 3), (substituted or unsubstituted aromatic heterocyclyl, substituted or unsubstituted hydroxyalkyl, hydrogen, hydrogen, 1), (substituted or unsubstituted aromatic heterocyclyl, substituted or unsubstituted hydroxyalkyl, hydrogen, hydrogen, 2), (substituted or unsubstituted aromatic heterocyclyl, substituted or unsubstituted carbamoyl, hydrogen, hydrogen, 1), (substituted or unsubstituted aromatic heterocyclyl, substituted or unsubstituted carbamoyl, hydrogen, hydrogen, 2), (substituted or unsubstituted non-aromatic heterocyclyl, -, -, hydrogen, 0), (substituted or unsubstituted non-aromatic heterocyclyl, hydrogen, hydrogen, hydrogen, 1), (substituted or unsubstituted non-aromatic heterocyclyl, hydrogen, hydrogen, hydrogen, 2), (substituted or unsubstituted non-aromatic heterocyclyl, hydrogen, hydrogen, hydrogen, 3), (substituted or unsubstituted non-aromatic heterocyclyloxy, -, -, hydrogen, 0), (substituted or unsubstituted non-aromatic heterocyclyloxy, hydrogen, hydrogen, hydrogen, 1), (substituted or unsubstituted non-aromatic heterocyclyloxy, hydrogen, hydrogen, hydrogen, 2), (substituted or unsubstituted non-aromatic heterocyclyloxy, hydrogen, hydrogen, hydrogen, 3), (substituted or unsubstituted non-aromatic heterocyclyloxy, substituted or unsubstituted non-aromatic heterocyclyloxyalkyl, substituted or unsubstituted non-aromatic heterocyclyloxyalkyl, hydrogen, 1), (substituted or unsubstituted non-aromatic heterocyclyloxy, substituted or unsubstituted non-aromatic heterocyclyloxyalkyl, substituted or unsubstituted non-aromatic heterocyclyloxyalkyl, hydrogen, 2), (substituted or unsubstituted aromatic heterocyclylamino, -, -, hydrogen, 0), (substituted or unsubstituted aromatic heterocyclylamino, hydrogen, hydrogen, hydrogen, 1), (substituted or unsubstituted aromatic heterocyclylamino, hydrogen, hydrogen, hydrogen, 2), (substituted or unsubstituted aromatic heterocyclylcarbonylamino, -, -, hydrogen, 0), (substituted or unsubstituted aromatic heterocyclylcarbonylamino, hydrogen, hydrogen, hydrogen, 1), (substituted or unsubstituted aromatic heterocyclylcarbonylamino, hydrogen, hydrogen, hydrogen, 2), (substituted or unsubstituted aromatic heterocyclylureido, -, -, hydrogen, 0), (substituted or unsubstituted aromatic heterocyclylureido, hydrogen, hydrogen, hydrogen, 1) or (substituted or unsubstituted aromatic heterocyclylureido, hydrogen, hydrogen, hydrogen, 2).

When T is —N($R^{a5}$)—, preferable embodiment is following.

$R^{a1}$ is hydrogen, halogen, hydroxy, carboxy, substituted or unsubstituted amino, substituted or unsubstituted alkylamino, folmyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted alkenylphosphonyl, substituted or unsubstituted alkynylphosphonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl.

$R^{a1}$ is preferably, hydrogen, hydroxy, carboxy, substituted or unsubstituted amino, substituted or unsubstituted alkylamino, folmyl, substituted or unsubstituted carbamoyl, substituted or unsubstituted ureido, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylamino, substituted or unsubstituted aromatic heterocyclylamino or substituted or unsubstituted aromatic heterocyclylsulfonyl.

$R^{a1}$ is more preferably, hydrogen, hydroxy, carboxy, substituted or unsubstituted alkylamino, folmyl, substituted or unsubstituted carbamoyl, substituted or unsubstituted ureido, substituted or unsubstituted alkylsulfonyl, substituted or unsubstituted aromatic carbocyclyl, substituted or unsubstituted non-aromatic carbocyclyl, substituted or unsubstituted aromatic heterocyclyl or substituted or unsubstituted aromatic heterocyclylsulfonyl.

$R^{a1}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When $R^{a1}$ is a substituted group, a more preferable substituent on said substituted group is selected from halogen, haloalkyl, hydroxy, amino, carbamoyl or unsubstituted non-aromatic heterocyclyl.

When $R^{a1}$ is a substituted group, an especially preferable substituent on said substituted group is hydroxy.

$R^{a2}$ is each independently, hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a2}$ is preferably, each independently, hydrogen, or substituted or unsubstituted alkyl.

When $R^{a2}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a3}$ is each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a3}$ is preferably, hydrogen.

When $R^{a3}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a2}$ and $R^{a3}$ may be each independently, taken together to form oxo, substituted or unsubstituted imino or thioxo, or may be taken together with neighboring atoms to form substituted or unsubstituted non-aromatic carbocycle or substituted or unsubstituted non-aromatic heterocycle.

$R^{a2}$ and $R^{a3}$ may be each independently, taken together to form oxo, or thioxo, or may be taken together with neighboring atoms to form substituted or unsubstituted non-aromatic carbocycle.

$R^{a2}$ and $R^{a3}$ may be each independently, more preferably, each independently, taken together to form oxo or may be taken togethe rwith neighboring atoms to form substituted or unsubstituted non-aromatic carbocycle.

$R^{a4}$ is hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl.

$R^{a4}$ is more preferably, hydrogen.

When $R^{a4}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a5}$ is hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl or substituted or unsubstituted alkynylcarbonyl.

$R^{a5}$ is preferably, hydrogen or substituted or unsubstituted alkyl.

When $R^{a5}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

Especially preferable combination of ($R^{a1}$, $R^{a2}$, $R^{a3}$, $R^{a4}$, m) is following: (hydrogen, -, -, hydrogen, hydrogen, 0), (hydrogen, hydrogen, hydrogen, hydrogen, hydrogen, 1), (hydrogen, hydrogen, hydrogen, hydrogen, hydrogen, 2), (hydrogen, hydrogen, hydrogen, hydrogen, hydrogen, 3), (hydrogen, hydrogen, hydrogen, hydrogen, hydrogen, 4), (hydrogen, hydrogen, hydrogen, hydrogen, alkyl, 1), (hydrogen, substituted or unsubstituted alkyl, hydrogen, hydrogen, hydrogen, 1), (hydrogen, substituted or unsubstituted alkyl, hydrogen, hydrogen, hydrogen, 2), (hydrogen, substituted or unsubstituted alkyl, hydrogen, hydrogen, hydrogen, 3), (hydrogen, substituted or unsubstituted alkyl, hydrogen, hydrogen, hydrogen, 4), (hydrogen, substituted or unsubstituted alkyl, hydrogen, hydrogen, hydrogen, 5), (hydroxy, -, -, hydrogen, hydrogen, 0), (hydroxy, hydrogen, hydrogen, hydrogen, hydrogen, 1), (hydroxy, hydrogen, hydrogen, hydrogen, hydrogen, 2), (hydroxy, hydrogen, hydrogen, hydrogen, hydrogen, 3), (hydroxy, hydrogen, hydrogen, hydrogen, hydrogen, 4), (hydroxy, hydrogen, hydrogen, hydrogen, hydrogen, 5), (hydroxy, hydrogen, hydrogen, hydrogen, hydrogen, 6), (hydroxy, hydroxy, hydrogen, hydrogen, hydrogen, 1), (hydroxy, hydroxy, hydrogen, hydrogen, hydrogen, 2), (hydroxy, hydroxy, hydrogen, hydrogen, hydrogen, 3), (hydroxy, hydroxy, hydrogen, hydrogen, hydrogen, 4), (hydroxy, hydroxy, hydrogen, hydrogen, hydrogen, 5), (hydroxy, hydroxy, hydrogen, hydrogen, hydrogen, 6), (hydroxy, hydrogen, hydrogen, hydrogen, substituted or unsubstituted alkyl, 1), (hydroxy, hydroxy, hydrogen, hydrogen, substituted or unsubstituted alkyl, 2), (hydroxy, hydroxy, hydrogen, hydrogen, substituted or unsubstituted alkyl, 3), (hydroxy, hydroxy, substituted or unsubstituted alkyl, hydrogen, hydrogen, 1), (hydroxy, hydroxy, substituted or unsubstituted alkyl, hydrogen, hydrogen, 2), (hydroxy, hydroxy, substituted or unsubstituted alkyl, hydrogen, hydrogen, 3), (hydroxy, hydroxy, substituted or unsubstituted alkyl, hydrogen, hydrogen, 4), (hydroxy, substituted or unsubstituted hydroxyalkyl, hydrogen, hydrogen, hydrogen, 1), (hydroxy, substituted or unsubstituted hydroxyalkyl, hydrogen, hydrogen, 2), (hydroxy, substituted or unsubstituted hydroxyalkyl, hydrogen, hydrogen, hydrogen, 3), (hydroxy, substituted or unsubstituted hydroxyalkyl, substituted or unsubstituted alkyl, hydrogen, hydrogen, 1), (hydroxy, substituted or unsubstituted hydroxyalkyl, substituted or unsubstituted alkyl, hydrogen, hydrogen, 2), (hydroxy, substituted or unsubstituted hydroxyalkyl, substituted or unsubstituted alkyl, hydrogen, hydrogen, 3), (hydroxy, substituted or unsubstituted hydroxyalkyl, hydrogen, substituted or unsubstituted amino, hydrogen, 1), (hydroxy, substituted or unsubstituted hydroxyalkyl, hydrogen, substituted or unsubstituted amino, hydrogen, 2), (hydroxy, substituted or unsubstituted hydroxy, substituted or unsubstituted alkyl, hydrogen, hydrogen, 3), (hydroxy, substituted or unsubstituted carbamoyl, hydrogen, hydrogen, hydrogen, 1), (hydroxy, substituted or unsubstituted carbamoyl, hydrogen, hydrogen, hydrogen, 2), (hydroxy, substituted or unsubstituted non-aromatic carbocyclyl, hydrogen, hydrogen, hydrogen, 3), (carboxy, -, -, hydrogen, hydrogen, 0), (carboxy, hydrogen, hydrogen, hydrogen, hydrogen, 1), (carboxy, hydrogen, hydrogen, hydrogen, hydrogen, 2), (carboxy, hydrogen, hydrogen, hydrogen, hydrogen, 3), (carboxy, hydroxy, hydrogen, hydrogen, hydrogen, 1), (carboxy, hydroxy, hydrogen, hydrogen, hydrogen, 2), (carboxy, hydroxy, hydrogen, hydrogen, hydrogen, 3), (carboxy, -, -, hydrogen, substituted or unsubstituted carboxyalkyl, 0), (carboxy, hydrogen, hydrogen, hydrogen, substituted or unsubstituted carboxyalkyl, 1), (substituted or unsubstituted carbamoyl, -, -, hydrogen, hydrogen, 0), (substituted or unsubstituted carbamoyl, hydrogen, hydrogen, hydrogen, hydrogen, 1), (substituted or unsubstituted carbamoyl, hydrogen, hydrogen, hydrogen, hydrogen, 2), (substituted or unsubstituted alkylamino, -, -, hydrogen, hydrogen, 0), (substituted or unsubstituted alkylamino, hydrogen, hydrogen, hydrogen, hydrogen, 1), (substituted or unsubstituted alkylamino, hydrogen, hydrogen, hydrogen, hydrogen, 2), (substituted or unsubstituted alkylamino, hydrogen, hydrogen, hydrogen, hydrogen, 3), (substituted or unsubstituted alkylsulfonyl, -, -, hydrogen, hydrogen, 0), (substituted or unsubstituted alkylsulfonyl, hydrogen, hydrogen, hydrogen, hydrogen, 1), (substituted or unsubstituted alkylsulfonyl, hydrogen, hydrogen, hydrogen, hydrogen, 2), (hydroxyamino, -, -, hydrogen, hydrogen, 0), (hydroxyamino, hydrogen, hydrogen, hydrogen, hydrogen, 1), (hydroxyamino, hydrogen, hydrogen, hydrogen, hydrogen, 2), (substituted or unsubstituted alkyloxy, -, -, hydrogen, hydrogen, 0), (substituted or unsubstituted alkyloxy, hydrogen, hydrogen, hydrogen, hydrogen, 1), (substituted or unsubstituted alkyloxy, hydrogen, hydrogen, hydrogen, hydrogen, 2), (substituted or unsubstituted alkyloxy, hydrogen, hydrogen, hydrogen, hydrogen, 3), (substituted or unsubstituted alkyloxy, hydrogen, hydrogen, hydrogen, hydrogen, 4), (folmyl, -, -, hydrogen, hydrogen, 0), (substituted or unsubstituted alkylsulfonyl, -, -, hydrogen, hydrogen, 0), (substituted or unsubstituted aromatic carbocyclyl, -, -, hydrogen, hydrogen, 0), (substituted or unsubstituted aromatic carbocyclyl, hydrogen, hydrogen, hydrogen, 1), (substituted or unsubstituted aromatic carbocyclyl, hydrogen, hydrogen, hydrogen, hydrogen, 2), (substituted or unsubstituted aromatic carbocyclyl, hydrogen, hydrogen, hydrogen, hydrogen, 3), (substituted or unsubstituted non-aromatic carbocyclyl, -, -, hydrogen, hydrogen, 0), (substituted or unsubstituted non-aromatic carbocyclyl, hydrogen, hydrogen, hydrogen, 1), (substituted or unsubstituted non-aromatic carbocyclyl, hydrogen, hydrogen, hydrogen, hydrogen, 2), (substituted or unsubstituted non-aromatic carbocyclyl, hydrogen, hydrogen, hydrogen, hydrogen, 3), (substituted or unsubstituted aromatic heterocyclyl, -, -, hydrogen, hydrogen, 0), (substituted or unsubstituted aromatic heterocyclyl, hydrogen, hydrogen, hydrogen, hydrogen, 1), (substituted or unsubstituted aromatic heterocyclyl, hydrogen, hydrogen, hydrogen, hydrogen, 2), (substituted or unsubstituted aromatic heterocyclyl, hydrogen, hydrogen, hydrogen, hydrogen, 3), (substituted or unsubstituted non-aromatic heterocyclyloxy, substituted or unsubstituted non-aromatic heterocyclyloxyalkyl, substituted or unsubstituted non-aromatic heterocyclyloxyalkyl, hydrogen, hydrogen, 1), (substituted or unsubstituted non-aromatic heterocyclyloxy, substituted or unsubstituted non-aromatic heterocyclyloxyalkyl, substituted or unsubstituted non-aromatic heterocyclyloxyalkyl, hydrogen, hydrogen, 2), (substituted or unsubstituted aromatic carbocyclylamino, hydrogen, hydrogen, hydrogen, hydrogen, 1), (substituted or unsubstituted aromatic heterocyclylamino, -, -, hydrogen, hydrogen, 0), (substituted or unsubstituted aromatic heterocyclylamino, hydrogen, hydrogen, hydrogen, hydrogen, 1), (substituted or unsubstituted aromatic heterocyclylamino, hydrogen, hydrogen, hydrogen, hydrogen, 2), (substituted or unsubstituted aromatic heterocyclylsulfonyl, hydrogen, hydrogen, hydrogen, 0), (substituted or unsubstituted aromatic heterocyclylureido, -, -, hydrogen, hydrogen, 0), (substituted or unsubstituted aromatic heterocyclylureido, hydrogen, hydrogen, hydrogen, hydrogen, 1), (substituted or unsubstituted aromatic heterocyclylureido, hydrogen, hydrogen, hydrogen, hydrogen, 2) or (substituted or unsubstituted aromatic heterocyclylsulfonyl, -, -, hydrogen, hydrogen, 0).

When T is —O—, preferable embodiment is following.

$R^{a1}$ is hydrogen, halogen, hydroxy, carboxy, substituted or unsubstituted amino, substituted or unsubstituted alkylamino, folmyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted alkenylphosphonyl, substituted or unsubstituted alkynylphosphonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl.

$R^{a1}$ is preferably, hydrogen, hydroxy, carboxy, substituted or unsubstituted alkylamino, cyano, guanidino, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl or substituted or unsubstituted non-aromatic heterocyclyloxy.

$R^{a1}$ is more preferably, hydrogen, hydroxy, carboxy, guanidino, substituted or unsubstituted aromatic heterocyclyl or substituted or unsubstituted non-aromatic heterocyclyl.

When $R^{a1}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When $R^{a1}$ is a substituted group, a more preferable substituent on said substituted group is selected from preferable substituents is hydroxy, amino or unsubstituted hydroxyalkyl.

$R^{a2}$ is each independently, hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a2}$ is preferably, each independently, hydrogen, hydroxy or substituted or unsubstituted hydroxyalkyl.

$R^{a2}$ is more preferably, each independently, hydrogen or substituted or unsubstituted hydroxyalkyl.

When $R^{a2}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a3}$ is each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{a3}$ is preferably, hydrogen.

When $R^{a3}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{a2}$ and $R^{a3}$ may be each independently, taken together to form oxo, substituted or unsubstituted imino or thioxo, or may be taken together with neighboring atoms to form substituted or unsubstituted non-aromatic carbocycle or substituted or unsubstituted non-aromatic heterocycle.

$R^{a2}$ and $R^{a3}$ may be each independently, taken together to form oxo.

$R^{a4}$ is hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl.

$R^{a4}$ is preferably, hydrogen or substituted or unsubstituted alkyl.

When $R^{a4}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

Especially preferable combination of ($R^{a1}$, $R^{a2}$, $R^{a3}$, $R^{a4}$, m) is following: (hydrogen, -, -, hydrogen, 0), (hydrogen, hydrogen, hydrogen, hydrogen, 1), (hydrogen, hydrogen, hydrogen, hydrogen, 2), (hydrogen, hydrogen, hydrogen, hydrogen, 3), (hydrogen, hydrogen, hydrogen, hydrogen, 4), (hydroxy, -, -, hydrogen, 0), (hydroxy, hydrogen, hydrogen, hydrogen, 1), (hydroxy, hydrogen, hydrogen, hydrogen, 2), (hydroxy, hydrogen, hydrogen, hydrogen, 3), (hydroxy, hydrogen, hydrogen, hydrogen, 4), (hydroxy, hydrogen, hydrogen, hydrogen, 5), (hydroxy, hydrogen, hydrogen, hydrogen, 6), (hydroxy, hydroxy, hydrogen, hydrogen, 1), (hydroxy, hydroxy, hydrogen, hydrogen, 2), (hydroxy, hydroxy, hydrogen, hydrogen, 3), (hydroxy, hydroxy, hydrogen, hydrogen, 4), (hydroxy, hydroxy, hydrogen, hydrogen, 5), (hydroxy, hydroxy, hydrogen, hydrogen, 6), (hydroxy, substituted or unsubstitutedhydroxyalkyl, hydrogen, hydrogen, 1), (hydroxy, substituted or unsubstitutedhydroxyalkyl, hydrogen, hydrogen, 2), (hydroxy, substituted or unsubstitutedhydroxyalkyl, hydrogen, hydrogen, 3), (cyano, hydroxy, hydrogen, hydrogen, 1), (cyano, hydroxy, hydrogen, hydrogen, 2), (cyano, hydroxy, hydrogen, hydrogen, 3), (guanidino, -, -, hydrogen, 0), (guanidino, hydrogen, hydrogen, hydrogen, 1), (guanidino, hydrogen, hydrogen, hydrogen, 2), (substituted or unsubstitutedalkylamino, -, -, hydrogen, 0), (substituted or unsubstitutedalkylamino, hydrogen, hydrogen, hydrogen, 1), (substituted or unsubstitutedalkylamino, hydrogen, hydrogen, hydrogen, 2), (substituted or unsubstitutedalkylamino, hydrogen, hydrogen, hydrogen, 3), (substituted or unsubstitutedalkyloxy, -, -, hydrogen, 0), (substituted or unsubstitutedalkyloxy, hydrogen, hydrogen, hydrogen, 1), (substituted or unsubstitutedalkyloxy, hydrogen, hydrogen, hydrogen, 2), (substituted or unsubstitutedalkyloxy, hydrogen, hydrogen, hydrogen, 3), (substituted or unsubstitutedalkyloxy, hydrogen, hydrogen, hydrogen, 4), (substituted or unsubstitutedaromatic heterocyclyl, -, -, hydrogen, 0), (substituted or unsubstitutedaromatic heterocyclyl, hydrogen, hydrogen, hydrogen, 1), (substituted or unsubstitutedaromatic heterocyclyl, hydrogen, hydrogen, hydrogen, 2), (substituted or unsubstitutedaromatic heterocyclyl, hydrogen, hydrogen, hydrogen, 3), (substituted or unsubstitutednon-aromatic heterocyclyl, -, -, hydrogen, 0), (substituted or unsubstitutednon-aromatic heterocyclyl, hydrogen, hydrogen, hydrogen, 1) or (substituted or unsubstitutednon-aromatic heterocyclyl, hydrogen, hydrogen, hydrogen, 2).

m is an integer of 0~10.
m is preferably, an integer of 0~6.
m is more preferably, an integer of 0~4.

A group represented by formula (IV) of $X^1$ group is described as follows:

[Chemical Formula 17]

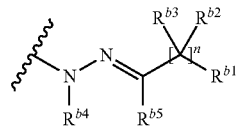

(IV)

$R^{b1}$ is hydrogen, halogen, hydroxy, carboxy, substituted or unsubstituted amino, folmyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted alkenylphosphonyl, substituted or unsubstituted alkynylphosphonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl.

$R^{b1}$ is preferably, hydroxy.

When $R^{b1}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{b2}$ is each independently, hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{b2}$ is preferably, each independently, hydrogen or hydroxy.

When $R^{b2}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{b3}$ is each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl.

$R^{b3}$ is preferably, hydrogen.

When $R^{b3}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{b2}$ and $R^{b3}$ may be each independently, taken together to form oxo, substituted or unsubstituted imino or thioxo, or may be taken together with neighboring atoms to form substituted or unsubstituted non-aromatic carbocycle or substituted or unsubstituted non-aromatic heterocycle.

$R^{b4}$ is hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl.

$R^{b4}$ is preferably, hydrogen.

When $R^{b4}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^{b5}$ is hydrogen, substituted or unsubstituted alkyl, substituted or unsubstituted alkenyl or substituted or unsubstituted alkynyl.

$R^{b5}$ is preferably, hydrogen or substituted or unsubstituted alkyl.

When $R^{b5}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

n is preferably, an integer of 0~10.
n is more preferably, an integer of 0~6.
n is further preferably, an integer of 0~2.

Especially preferable combination of ($R^{b1}$, $R^{b2}$, $R^{b3}$, $R^{b4}$, $R^{b5}$, m) is following:

(hydroxy, hydroxy, hydrogen, hydrogen, hydrogen, 1), (hydroxy, hydroxy, hydrogen, hydrogen, hydrogen, 2), (hydroxy, hydroxy, hydrogen, hydrogen, hydrogen, 3), (hydroxy, hydroxy, hydrogen, hydrogen, hydrogen, 4), (hydroxy, hydroxy, hydrogen, hydrogen, hydrogen, 5), (hydroxy, hydroxy, hydrogen, hydrogen, hydrogen, 6), (hydroxy, hydrogen, hydrogen, hydrogen, substituted or unsubstituted hydroxyalkyl, 1) or (hydroxy, hydrogen, hydrogen, hydrogen, substituted or unsubstituted hydroxyalkyl, 2).

A group represented by formula (V) of $X^1$ group is described as follows:

[Chemical Formula 18]

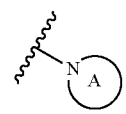

(V)

A ring is substituted or unsubstituted nitrogen-containing aromatic heterocycle or substituted or unsubstituted nitrogen-containing non-aromatic heterocycle.

A ring is preferably, 3- to 16-membered, more preferably 3- to 12-membered, further preferably 3- to 8-membered, substituted or unsubstituted nitrogen-containing non-aromatic heterocycle.

When A ring is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When A ring is a substituted group, a more preferable substituent on said substituted group is selected from hydroxy, carboxy, unsubstituted carboxyalkenyl, unsubstituted hydroxyalkyl, unsubstituted alkylamino, unsubstituted hydroxyalkylamino, carbamoyl, unsubstituted aromatic carbocyclyl, unsubstituted aromatic carbocyclylalkyl, unsubstituted non-aromatic heterocyclylalkyl, unsubstituted aromatic carbocyclyloxyalkyl or hydroxy or non-aromatic heterocyclyloxy optionally substituted with hydroxyalkyl.

When A ring is a substituted group, a especially preferable substituent on said substituted group is selected from hydroxy, carboxy, hydroxyalkylamino or non-aromatic heterocyclyloxy optionally substituted with hydroxy or hydroxyalkyl.

A group represented by formula (VI) of $X^1$ group is described as follows:

[Chemical Formula 19]

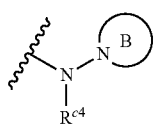

(VI)

B ring is preferably, substituted or unsubstituted nitrogen-containing aromatic heterocycle or substituted or unsubstituted nitrogen-containing non-aromatic heterocycle.

B ring is preferably, 3- to 16-membered, more preferably 3- to 12-membered, further preferably 3- to 8-membered, substituted or unsubstituted nitrogen-containing non-aromatic heterocycle.

When B ring is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When B ring is a substituted group, a more preferable substituent on said substituted group is selected from unsubstituted alkyl or hydroxyalkyl.

$R^{c4}$ is preferably, hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl.

$R^{c4}$ is more preferably, hydrogen.

When $R^{c4}$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

A group represented by formula (II) of X group is described as follows:

[Chemical Formula 20]

(II)

C ring is preferably, substituted or unsubstituted aromatic carbocycle, substituted or unsubstituted non-aromatic carbocycle, substituted or unsubstituted aromatic heterocycle or substituted or unsubstituted non-aromatic heterocycle.

C ring is preferably, 5- or 6-membered substituted or unsubstituted aromatic heterocycle.

When C ring is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When C ring is a substituted group, a more preferable substituent on said substituted group is selected from unsubstituted aromatic carbocyclyl or unsubstituted aromatic heterocyclyl.

A group represented by formula (IX) of X group is described as follows:

[Chemical Formula 21]

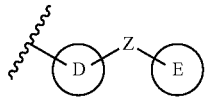

(IX)

D ring is preferably, substituted or unsubstituted aromatic carbocycle, substituted or unsubstituted non-aromatic carbocycle, substituted or unsubstituted aromatic heterocycle or substituted or unsubstituted non-aromatic heterocycle.

D ring is more preferably, 5- or 6-membered unsubstituted aromatic heterocycle.

When D ring is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

E ring is preferably, substituted or unsubstituted aromatic carbocycle, substituted or unsubstituted non-aromatic carbocycle, substituted or unsubstituted aromatic heterocycle or substituted or unsubstituted non-aromatic heterocycle.

E ring is more preferably, 5- or 6-membered substituted or unsubstituted aromatic carbocycle or substituted or unsubstituted aromatic heterocycle.

When E ring is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When E ring is a substituted group, a more preferable substituent on said substituted group is selected from unsubstituted alkylamino.

Z is preferably, a bond, alkylene, —O—, —S— or —N(H)—.

Z is more preferably, a bond.

A group represented by formula (VII) and formula (VIII) of Y group is described as follows:

[Chemical Formula 22]

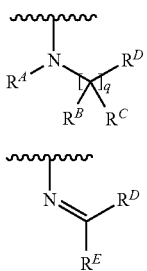

(VII)

(VIII)

$R^A$ is hydrogen, substituted or unsubstituted alkyl, substituted or unsubstituted alkenyl or substituted or unsubstituted alkynyl.

$R^A$ is preferably, hydrogen or substituted or unsubstituted alkyl.

$R^A$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^B$ is each independently, hydrogen, hydroxy, substituted or unsubstituted amino, substituted or unsubstituted alkyl, substituted or unsubstituted alkenyl or substituted or unsubstituted alkynyl.

$R^B$ is preferably, hydrogen, hydroxy or substituted or unsubstituted amino.

When $R^B$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^C$ is each independently, hydrogen, hydroxy, substituted or unsubstituted amino, substituted or unsubstituted alkyl, substituted or unsubstituted alkenyl or substituted or unsubstituted alkynyl.

$R^C$ is preferably, hydrogen.

When $R^C$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^B$ and $R^C$ may be preferably, each independently, taken together to form oxo, substituted or unsubstituted imino or thioxo, or may be taken together with neighboring atoms to form substituted or unsubstituted non-aromatic carbocycle or substituted or unsubstituted non-aromatic heterocycle.

$R^B$ and $R^C$ may be more preferably, each independently, taken together to form oxo, unsubstituted imino, cyanoimino or hydroxyimino.

$R^D$ is preferably, hydrogen, hydroxy, carboxy, substituted or unsubstituted amino, substituted or unsubstituted alkylamino, substituted or unsubstituted carbamoyl, substituted or unsubstituted amidino, substituted or unsubstituted guanidino, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl.

$R^D$ is more preferably, hydrogen, hydroxy, carboxy, substituted or unsubstituted amino, substituted or unsubstituted alkylamino, substituted or unsubstituted carbamoyl, guanidino, substituted or unsubstituted aromatic carbocyclyl, substituted or unsubstituted aromatic heterocyclyl or substituted or unsubstituted non-aromatic heterocyclyl.

When $R^D$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

When $R^D$ is a substituted group, a more preferable substituent on said substituted group is selected from alkyl, hydroxy, amino, alkylamino or amidino.

q is preferably, an integer of 0~10.

q is more preferably, an integer of 0~6.

$R^E$ is preferably, hydrogen, hydroxy or substituted or unsubstituted amino.

$R^E$ is more preferably, substituted or unsubstituted amino.

When $R^E$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

$R^F$ is preferably, hydrogen, substituted or unsubstituted alkyl, substituted or unsubstituted alkenyl or substituted or unsubstituted alkynyl.

$R^F$ is more preferably, hydrogen.

When $R^F$ is a substituted group, a preferable substituent on said substituted group is selected from halogen, hydroxy, carboxy, carboxyalkyl, carboxyalkenyl, amino, carbamoyl, carbamoylalkyl, cyano, sulfamoyl, amidino, alkyl, haloalkyl, hydroxyalkyl, hydroxyalkylamino, hydroxyalkyloxy, alkyloxy, alkylcarbonyl, alkylamino, alkylsulfonyl, alkylimino, alkyloxycarbonyl, aromatic carbocyclyl, aromatic heterocyclyl, non-aromatic heterocyclyl, aromatic carbocyclyloxyalkyl, aromatic carbocyclylalkyl, non-aromatic heterocyclylalkyl, aromatic heterocyclyl optionally substituted with alkyl, aromatic carbocyclyl optionally substituted with alkyloxy, aromatic heterocyclyl optionally substituted with amino, aromatic carbocyclyl optionally substituted with halogen, aromatic carbocyclylalkyloxy optionally substituted with haloalkyl or non-aromatic heterocyclyloxy optionally substituted with hydroxy or hydroxyalkyl.

Y includes, for example, following groups:

[Chemical Formula 23]

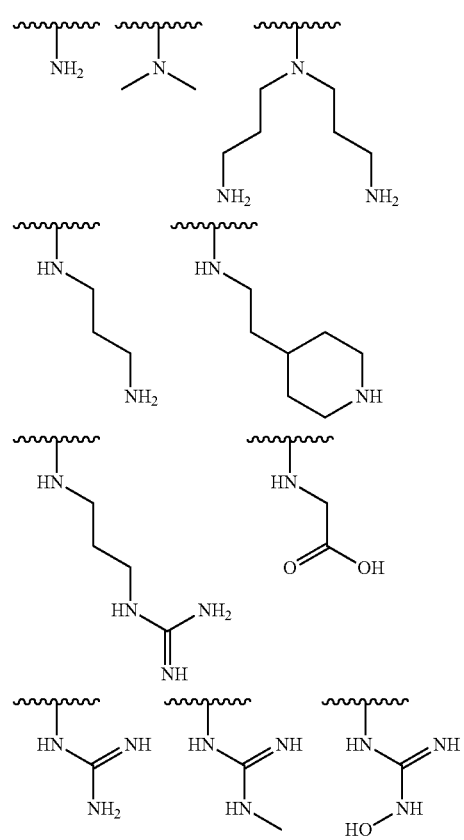

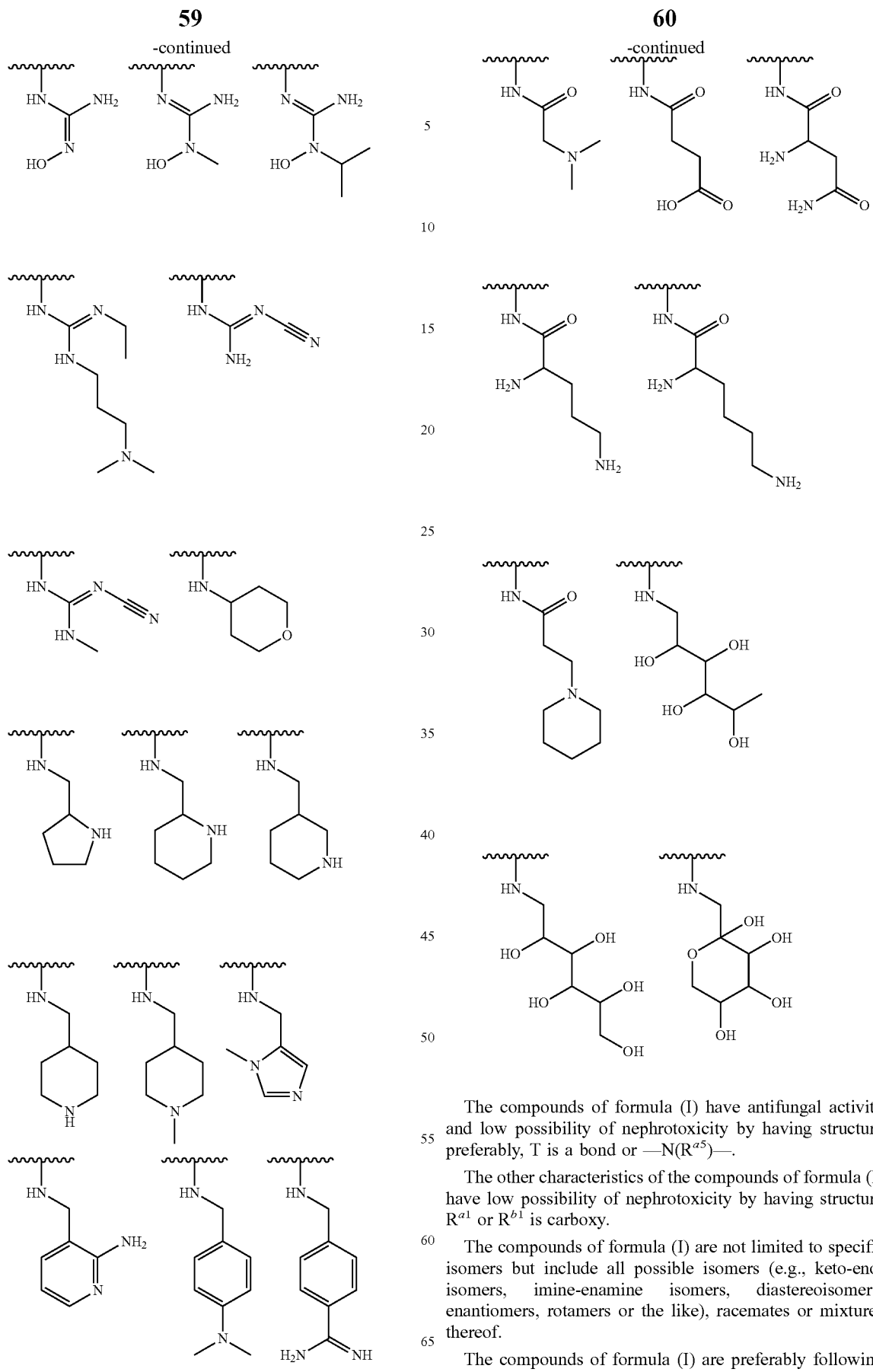

The compounds of formula (I) have antifungal activity and low possibility of nephrotoxicity by having structure preferably, T is a bond or —N(R$^{a5}$)—.

The other characteristics of the compounds of formula (I) have low possibility of nephrotoxicity by having structure R$^{a1}$ or R$^{b1}$ is carboxy.

The compounds of formula (I) are not limited to specific isomers but include all possible isomers (e.g., keto-enol isomers, imine-enamine isomers, diastereoisomers, enantiomers, rotamers or the like), racemates or mixtures thereof.

The compounds of formula (I) are preferably following structure.

[Chemical Formula 24]

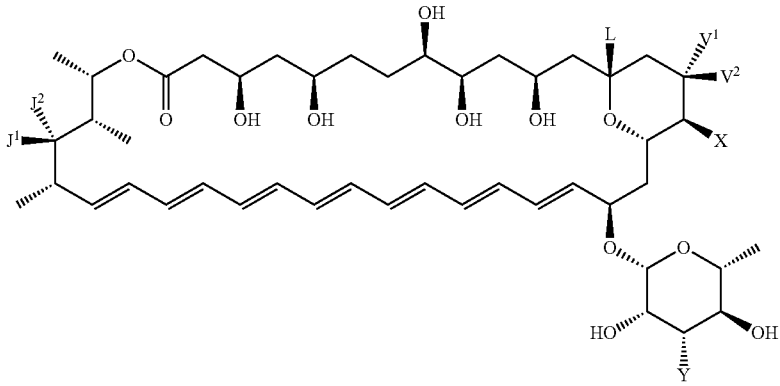

One or more hydrogen, carbon and/or other atoms in the compounds of formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2$H, $^3$H, $^{11}$C, $^{13}$C, $^{14}$C, $^{18}$N, $^{18}$O, $^{17}$O, $^{31}$P, $^{32}$P, $^{35}$S, $^{18}$F, $^{123}$I and $^{36}$Cl respectively. The compounds of formula (I) include compounds replaced with these isotopes. The compounds replaced with the above isotopes are useful as medicines and include all of radiolabeled compounds of the compound of formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of formula (I) can be prepared using well-known methods in this field of the invention. For example, a tritium-labeled compound of formula (I) can be prepared by introducing a tritium to a certain compound of formula (I), through a catalytic dehalogenation reaction using a tritium. This method comprises reacting with an appropriately-halogenated precursor of the compound of formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C.

The pharmaceutically acceptable salts of the compounds of formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of formula (I) of the present invention or its pharmaceutically acceptable salts may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of formula (I). When the compounds of formula (I) or its pharmaceutically acceptable salts are allowed to stand in the atmosphere, the compounds may absorb water, resulting in attachment of adsorbed water or formation of hydrates. Recrystallization of the compounds of formula (I) or its pharmaceutically acceptable salts may produce crystal polymorphs.

The compounds of formula (I) of the present invention or its pharmaceutically acceptable salts may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of formula (I) through enzymatic oxidation, reduction, hydrolysis or the like under physiological conditions in vivo, compounds that are converted to the compounds of formula (I) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of formula (I) or its pharmaceutically acceptable salts have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride or mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, $p-CH_3O-PhSO_3-$, $PhSO_3-$ and $p-CH_3PhSO_3$.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrated tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/clay. For parenteral administration, although the dosage highly varies with administration routes, a usual dosage is 0.005 to 10 and preferably 0.01 to 1 mg/kg/day. The dosage may be administered in one to several divisions per day.

The compounds of formula (I) is useful as therapeutic agent for fungal infection such as fungemia, fungal respiratory disease, fungal meningitis, disseminated mycosis by *Aspergillus* genus, *Candida* genus, *Cryptococcus* genus, *Mucor* genus, *Absidia* genus, *Rhizopus* genus, *Rhizomucor* genus, *Cladosporium* genus, *Cladophialophora* genus, *Fonsecaea* genus, *Phialophora* genus, *Exophiala* genus, *Coccidioides* genus, *Histoplasma* genus or *Blastomyces* genus.
(Synthetic Methods for the Compounds of the Present Invention)

For example, the compounds of formula (I) of the present invention can be prepared by the general synthetic methods described below. The methods for extraction, purification and the like may be carried out by using the usual method for the experiments of organic chemistry. Since chemical modification of $J^1$, $J^2$, $V^1$, $V^2$ and L had been performed in amphotericin B derivative, these can be referred.

Commercial regents can be used as starting materials, or starting materials can be synthesized by referring to the known methods in this field.

In this description, meaning of each abbreviation is as follows:
Alloc: Allyloxycarbonyl
Alloc-OSu: Allyl n-sccinimidyl carbonate
Alloc-Cl: Allyloxycarbonylchloride
AMB: Amphotericin B
Boc: tert-Butoxycarbonyl
CSA: 10-Camphorsulfonic acid
TBS: tert-Butyldimethylsilyl
DEAD: Diethyl azodicarboxylate
DMAD: Dimethyl azodicarboxylate
DMSO: Dimethyl sulfoxide
DIEA: N,N-Diisopropylethylamine
DMF: N,N-Dimethylformamide
DMA: N,N-Dimethylacetamide
EDC: 1-Ethyl-3-(3-dimethylaminopropyl)carbodiimide
NMP: N-methylpyrrolidone
Fmoc: 9-Fluorenylmethyloxycarbonyl
Teoc: 2-(Trimethylsilyl)ethoxymethyl chloride
TBAF: Tetrabutylammonium fluoride
TFA: Trifluoroacetic acid
HATU: O-(7-Azabenzotriazol-1-yl)-N,N,N',N'-tetramethyluronium Hexafluorophosphate
Pd(PPh$_3$)$_4$: Tetrakis(triphenylphosphine)palladium(0)
PPTS: Pyridinium p-Toluenesulfonate
PyBOP: (1H-Benzotriazole-1-yloxy)tripyrrolizinophosphonium hexafluorophosphate
(General Synthetic Method 1-1)

[Chemical Formula 25]

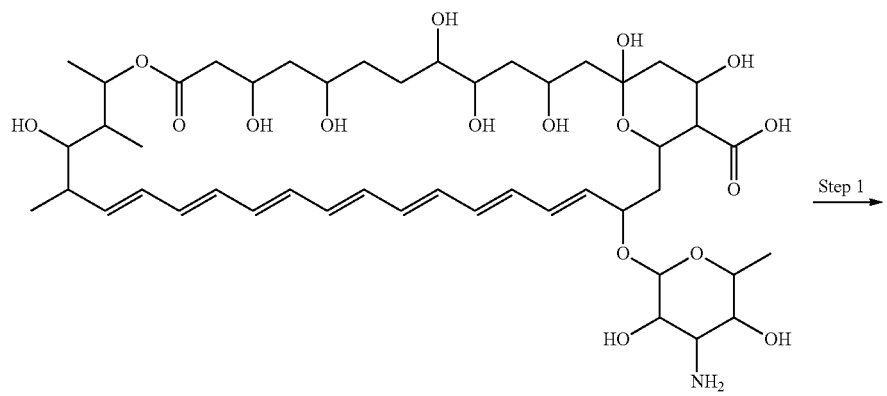

Step 1

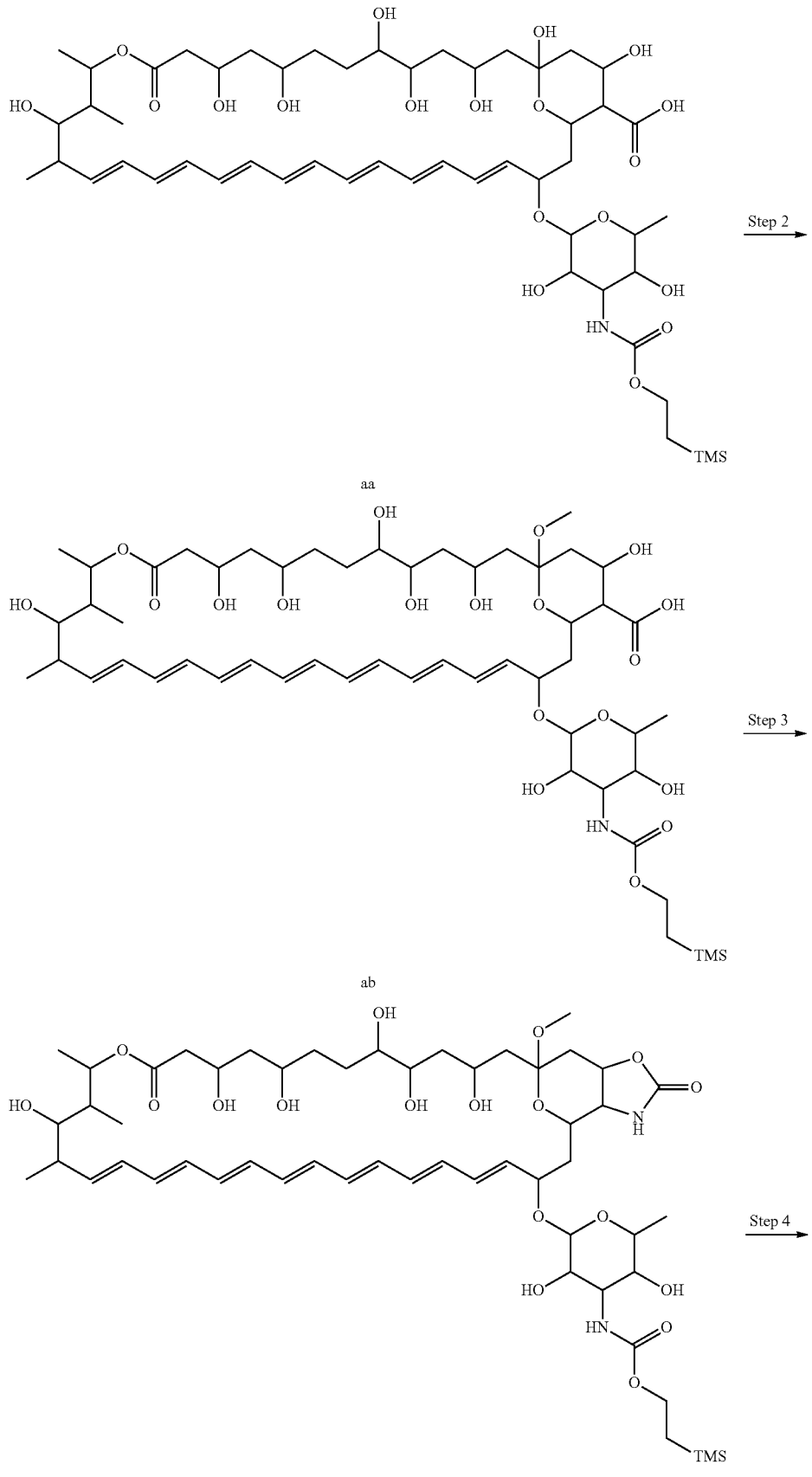

[Chemical Formula 26]
-continued
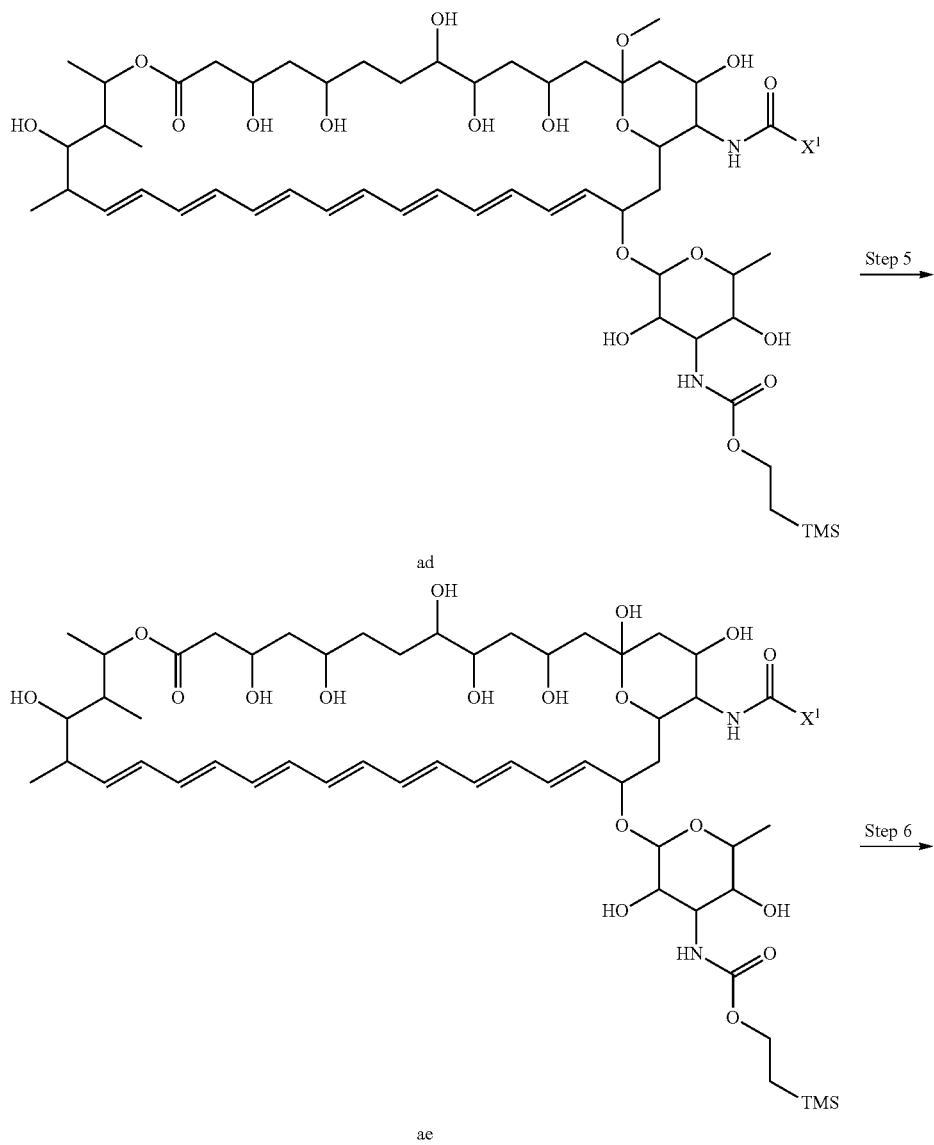
ad
→ Step 5
ae
→ Step 6
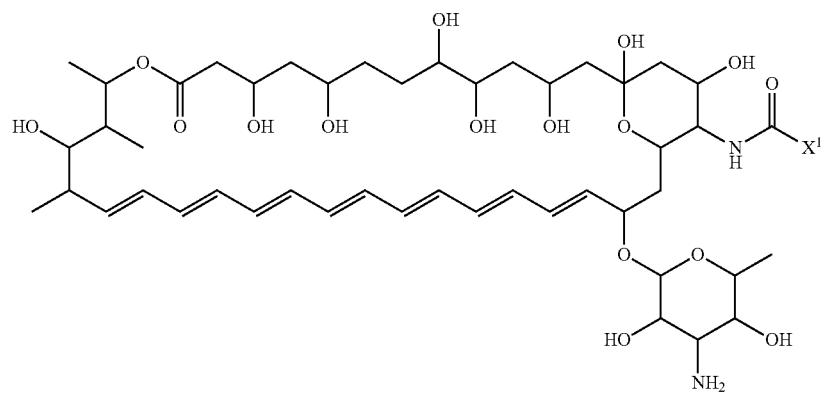
af Step 1

The compound aa can be synthesized by the reaction which tertiary amine such as triethylamine, DIEA, pyridine and the like and N-[2-(trimethylsilyl)-ethoxycarbonyloxy]succinimide are added dropwise to the commercially available amphotericin B in the solvent such as DMF, DMA, NMP, dichloromethane, tetrahydrofuran, acetonitrile and the like or solvent mixture thereof for 0.5 to 24 hours, preferably 1 to 5 hours at 20 to 30° C.

Step 2

The compound ab can be synthesized by the reaction which camphorsulfonic acid is added to the compound aa under ice cooling in the solvent such as tetrahydrofuran, ether and the like or solvent mixture thereof including methanol for 10 minutes to 6 hours, preferably 30 minutes to 3 hours at −30 to 10° C., preferably −15 to 0° C.

Step 3

The compound (XII) can be synthesized by the reaction which tertiary amine such as triethylamine, DIEA, pyridine and the like and diphenylphosphoryl azide are reacted to the compound ab in the solvent such as DMF, DMA, NMP, dichloromethane, tetrahydrofuran, acetonitrile and the like or solvent mixture thereof for 0.5 to 2 hours at 20 to 30° C., further for 1 to 6 hours, preferably 3 to 4 hours at 40 to 70° C., preferably 40 to 60° C.

Step 4

The compound ad can be synthesized by the reaction which the compound having amino group represented as $X^1$ such as primary amines, secondary amines, hydrazine, substituted hydrazine, alkoxy amine, amino acid and the like which is commercially available or can be synthesized according to the known methods is added to the compound (XII) in the solvent such as DMF, DMA, NMP, dichloromethane, tetrahydrofuran, acetonitrile and the like or solvent mixture thereof for 0.1 to 24 hours, preferably 1 to 12 hours at 20 to 70° C., preferably 20 to 40° C.

Step 5

The compound ae can be synthesized by the reaction which water is added, and PPTS is added to the compound ad in the solvent such as DMF, DMA, NMP, dichloromethane, acetonitrile and the like or solvent mixture thereof for 0.1 to 24 hours, preferably 1 to 6 hours at 20 to 40° C., preferably 20 to 30° C.

Step 6

The compound of can be synthesized by the commonly known deprotect reaction of carbamate protecting group of compound ae in the solvent such as DMF, DMA, NMP, dichloromethane, tetrahydrofuran, acetonitrile and the like or solvent mixture thereof.

(General Synthetic Method 1-2)

[Chemical Formula 27]

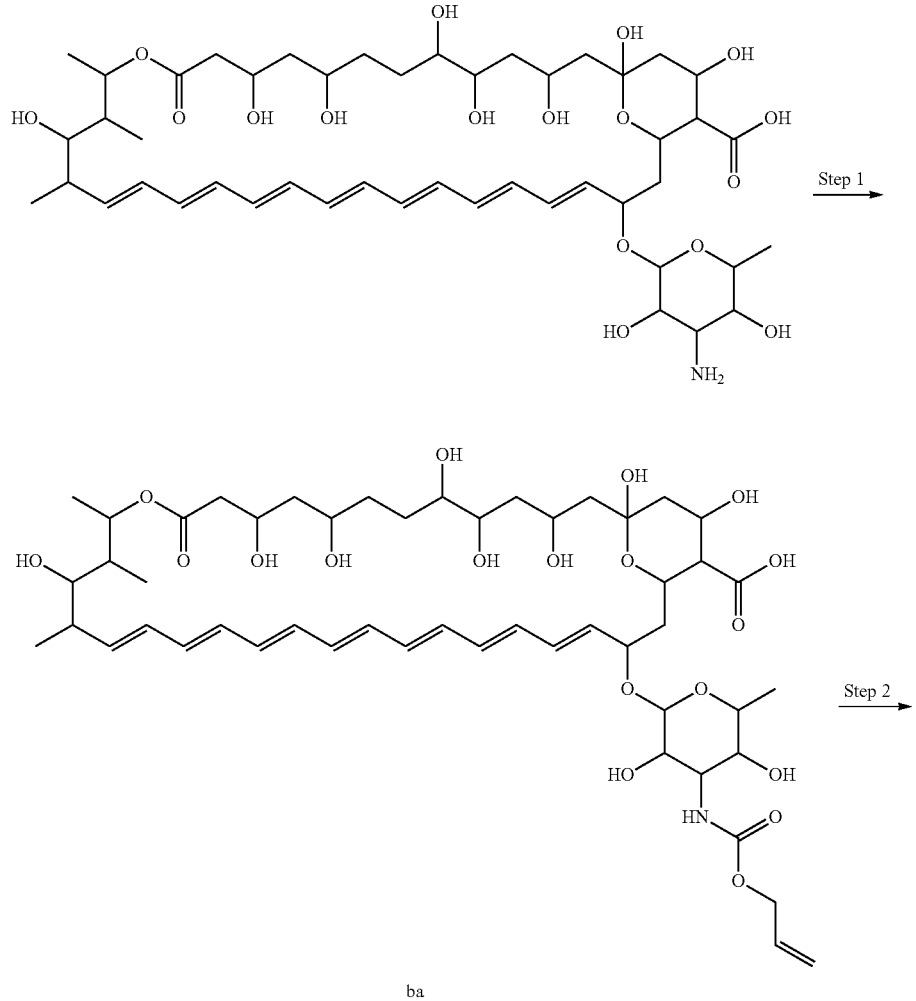

-continued
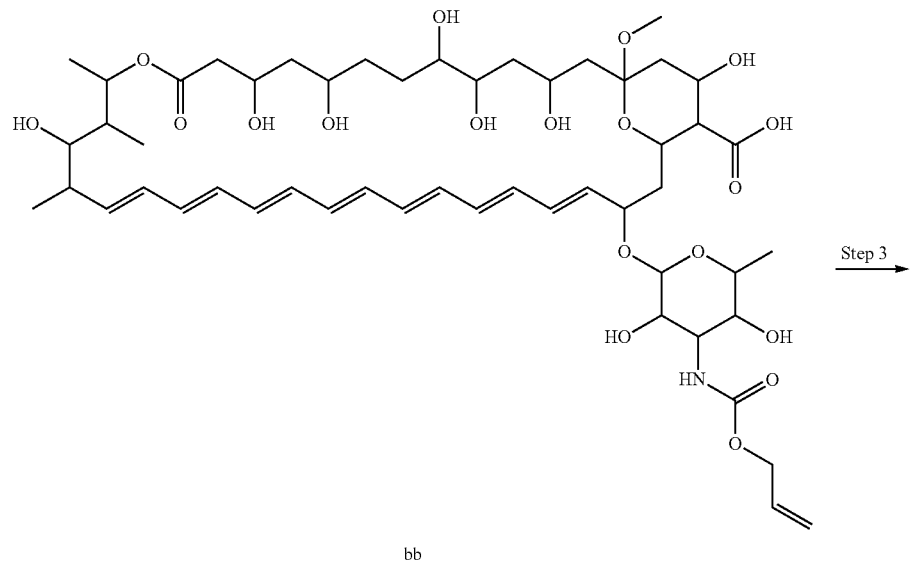
bb
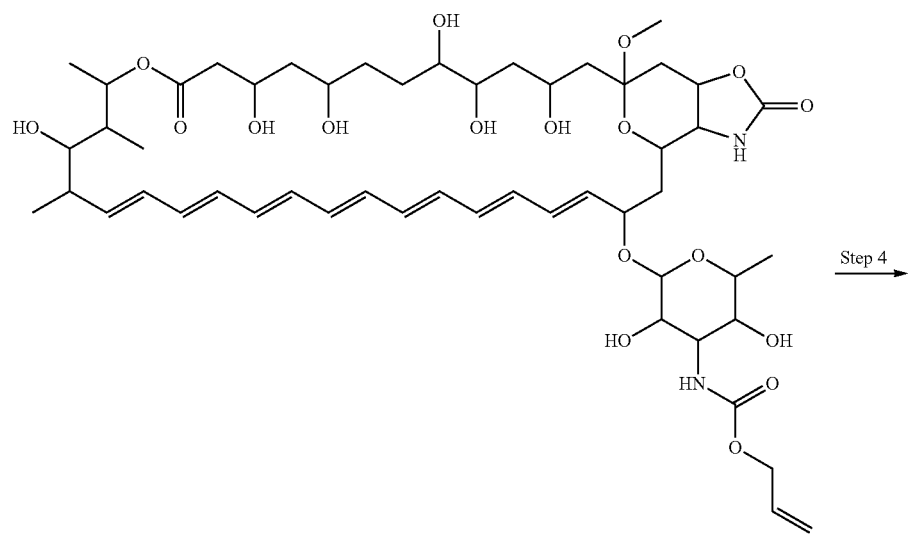
(XIII)
Step 3 →
Step 4 →

-continued
[Chemical Formula 28]
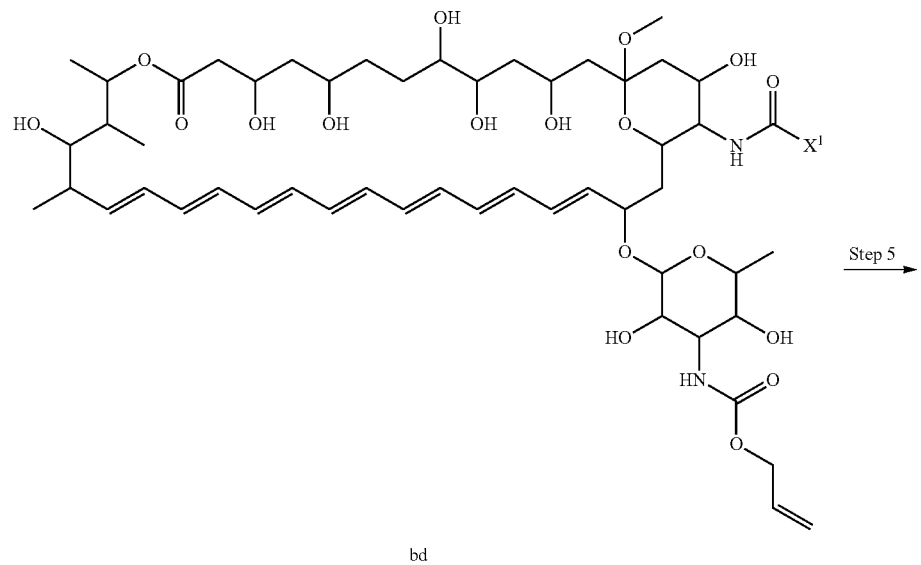
bd
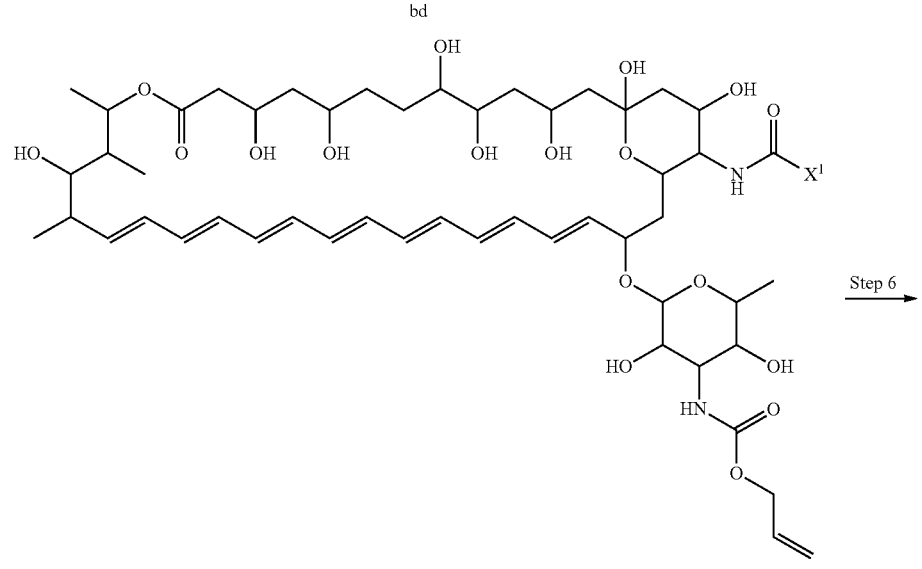
be
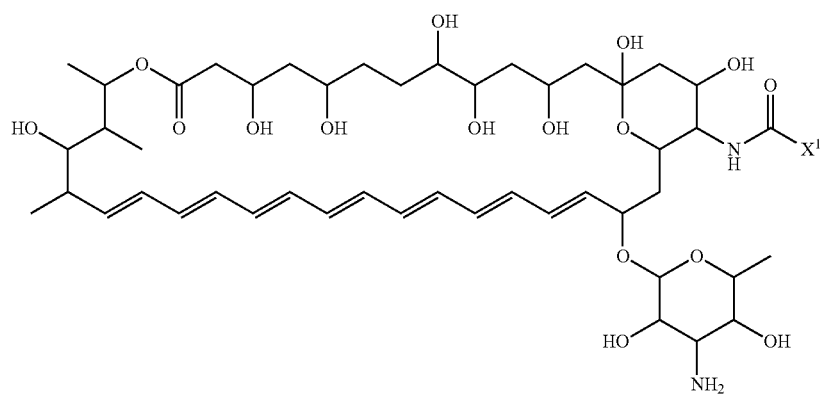
af

Step 1
The compound ba can be synthesized by the reaction which tertiary amine such as triethylamine, DIEA, pyridine and the like and N-(Allyloxycarbonyloxy)succinimide are added dropwise to the commercially available amphotericin B in the solvent such as DMF, DMA, NMP, dichloromethane, tetrahydrofuran, acetonitrile and the like or solvent mixture thereof for 0.5 to 24 hours, preferably 1 to 5 hours at 20 to 30° C.

Step 2
The compound bb can be synthesized by the reaction which camphorsulfonic acid is added to the compound ba under ice cooling in the solvent such as tetrahydrofuran, ether and the like or solvent mixture thereof including methanol for 10 minutes to 6 hours, preferably 30 minutes to 3 hours at −30 to 10° C., preferably −15 to 0° C.

Step 3
The compound (XIII) can be synthesized by the reaction which tertiary amine such as triethylamine, DIEA, pyridine and the like and diphenylphosphoryl azide are reacted to the compound bb in the solvent such as DMF, DMA, NMP, dichloromethane, tetrahydrofuran, acetonitrile and the like or solvent mixture thereof for 0.5 to 2 hours at 20 to 30° C., further for 1 to 6 hours, preferably 3 to 4 hours at 40 to 70° C., preferably 40 to 60° C.

Step 4
The compound bd can be synthesized by the reaction which the compound having amino group represented as $X^1$ such as primary amines, secondary amines, hydrazine, substituted hydrazine, alkoxy amine, amino acid and the like which is commercially available or can be synthesized according to the known methods is added to the compound (XIII) in the solvent such as DMF, DMA, NMP, dichloromethane, tetrahydrofuran, acetonitrile and the like or solvent mixture thereof for 0.1 to 24 hours, preferably 1 to 12 hours at 20 to 70° C., preferably 20 to 40° C.

Step 5
The compound be can be synthesized by the reaction which water is added, and PPTS is added to the compound bd in the solvent such as DMF, DMA, NMP, dichloromethane, tetrahydrofuran, acetonitrile and the like or solvent mixture thereof for 0.1 to 24 hours, preferably 1 to 6 hours at 20 to 40° C., preferably 20 to 30° C.

Step 6
The compound of can be synthesized by the commonly known deprotect reaction of carbamate protecting group of the compound be in the solvent such as DMF, DMA, NMP, dichloromethane, tetrahydrofuran, acetonitrile and the like or solvent mixture thereof.
(General Synthetic Method 1-3)

[Chemical Formula 29]

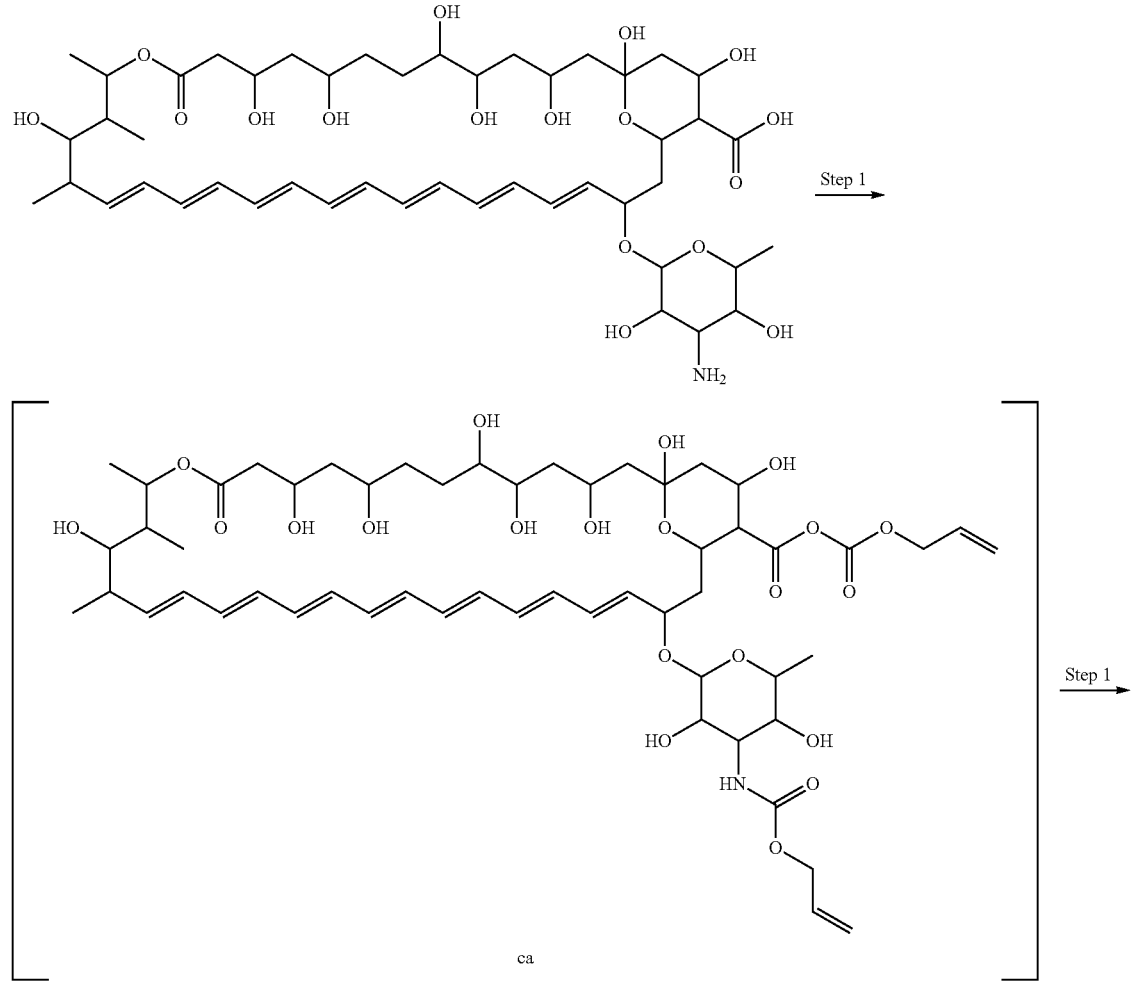

-continued
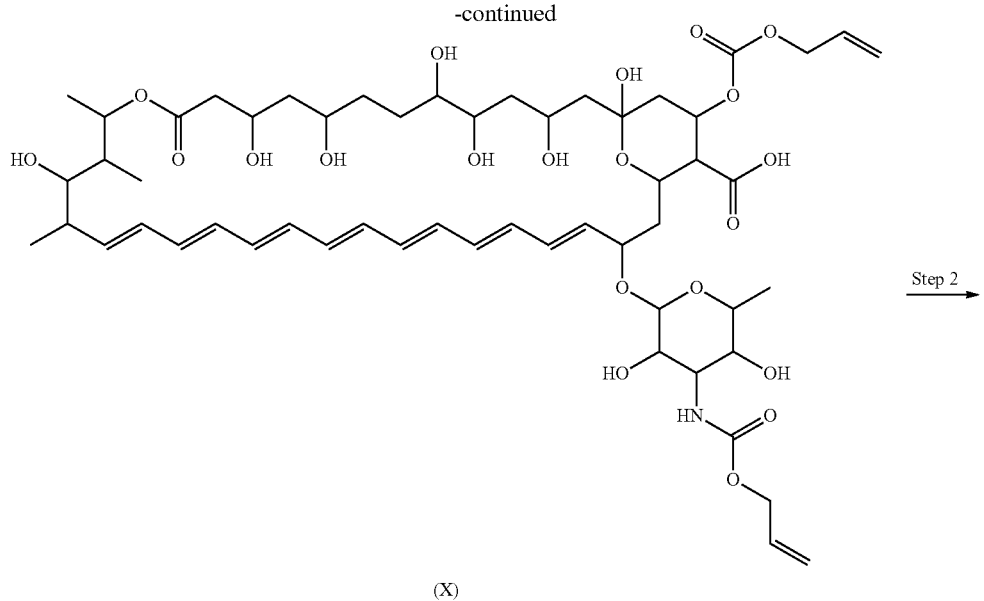
(X)
Step 2 →
[Chemical Formula 30]
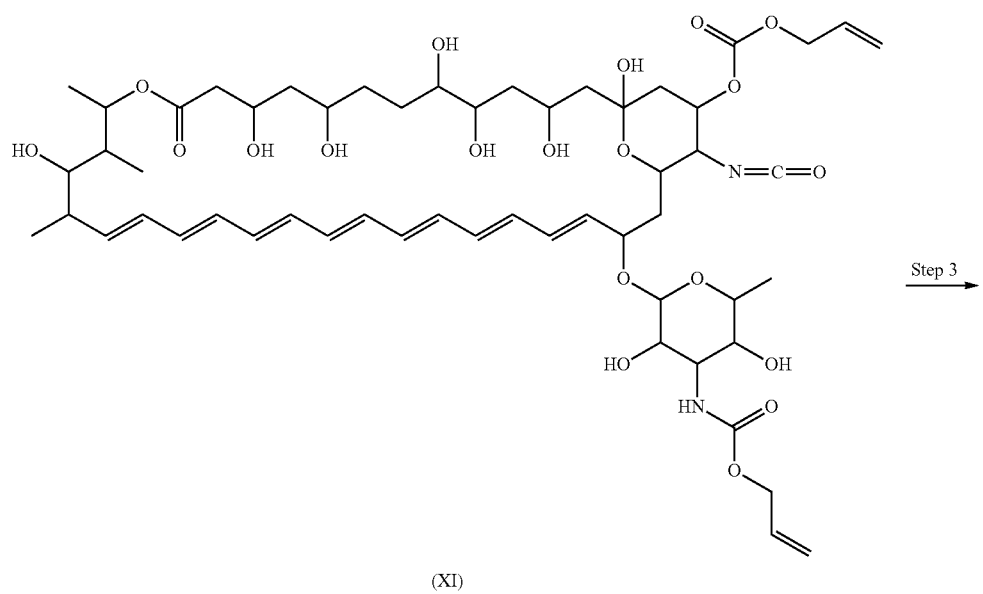
(XI)
Step 3 →

-continued

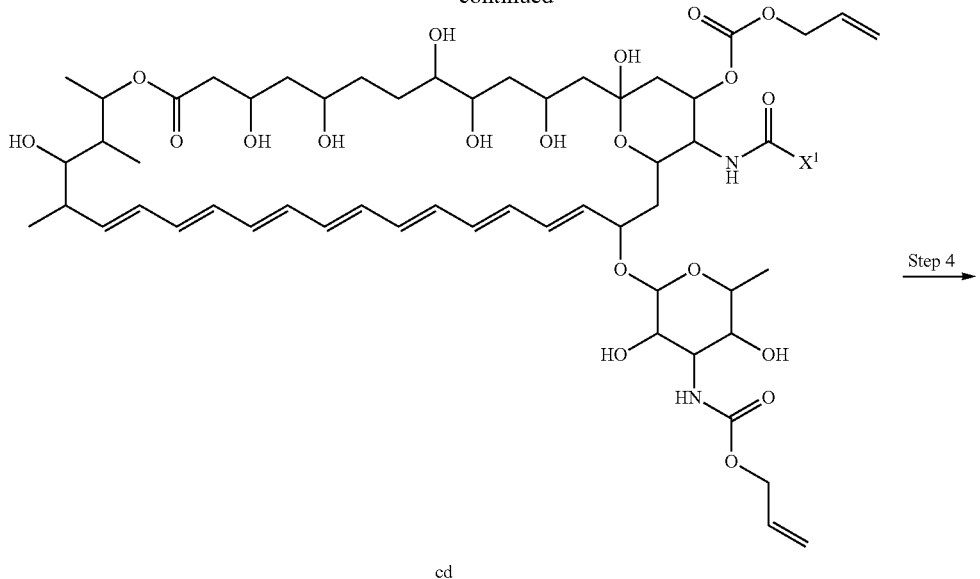

cd

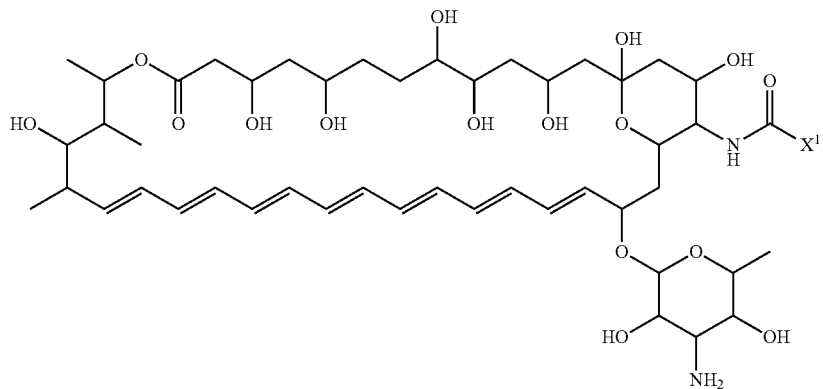

af

Step 1

Tertiary amine such as triethylamine, DIEA, pyridine and the like and allyloxycarbonyl chloride are added dropwise to the commercially available amphotericin B in the solvent such as DMF, DMA, NMP, dichloromethane, tetrahydrofuran, acetonitrile and the like or its solvent mixture for 0.5 to 6 hours, preferably 2 to 3 hours at 0 to 20° C., preferably 0 to 4° C. in the reaction mixture. Thereby, the anhydride intermediate ca can be synthesized.

The compound (X) can be synthesized by the intramolecular rearrangement of Alloc group with heating to 20 to 40° C., preferably 20 to 30° C. for 0.5 to 6 hours, preferably 2 to 4 hours.

Step 2

Tertiary amine such as triethylamine, DIEA, pyridine and the like and diphenylphosphoryl azide are reacted to the compound (X) in the solvent such as DMF, DMA, NMP, dichloromethane, tetrahydrofuran, acetonitrile and the like or solvent mixture thereof at 20 to 30° C. for 0.5 to 2 hours, further at 40 to 60° C. for 1 to 6 hours, preferably 2 to 4 hours. Thereby, the compound (XI) can be synthesized.

The compound (XI) can also be used as one-pot reaction of step 3 without purification.

Step 3

The compound having amino group such as primary amines, secondary amines, hydrazine, substituted hydrazine, alkoxy amine, amino acid and the like which is commercially available or can be synthesized according to the known methods is added to the compound (XI) in the solvent such as DMF, DMA, NMP, dichloromethane, tetrahydrofuran, acetonitrile and the like or solvent mixture thereof at −20 to 50° C., preferably 20 to 40° C. for 0.1 hours to 4 days, preferably 1 to 12 hours. Thereby, the compound cd can be synthesized.

Step 4

The compound of can be synthesized by the commonly known deprotect reaction of protecting group such as allyloxycarbonyl group of the compound cd in the solvent such as DMF, DMA, NMP, dichloromethane, tetrahydrofuran, acetonitrile and the like or solvent mixture thereof.

(General Synthetic Method 2)

[Chemical Formula 31]

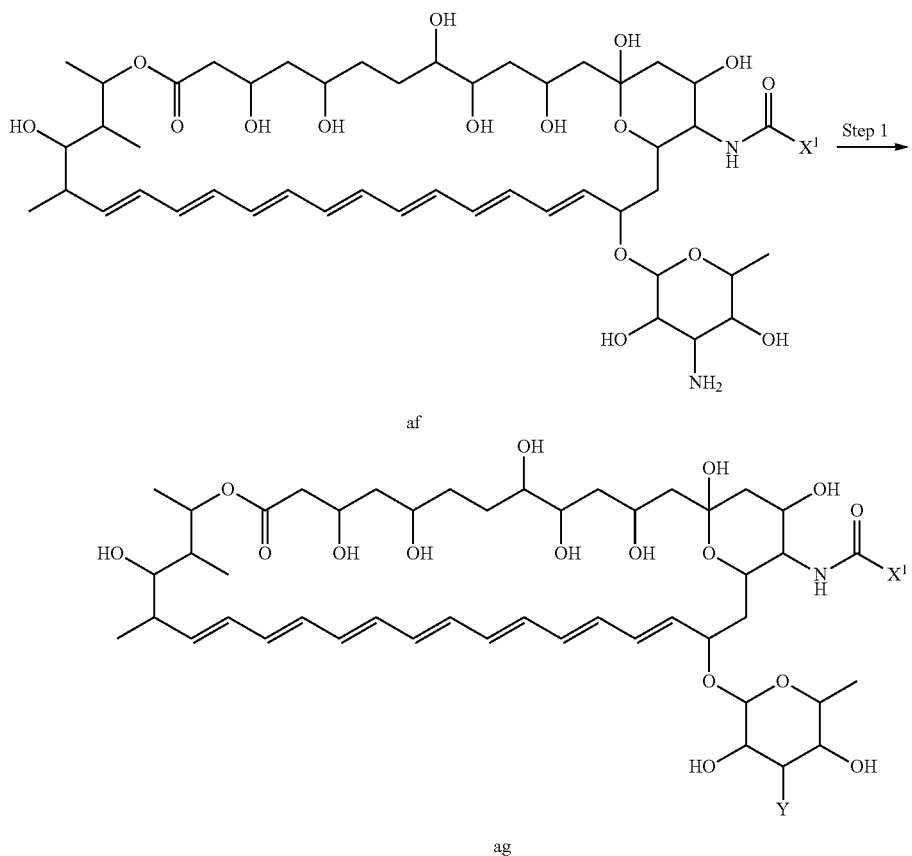

Step 1

The compound ag can be synthesized by the reaction which the compound having amino group such as primary amines, secondary amines, hydrazine, substituted hydrazine, alkoxy amine, amino acid and the like which is commercially available or can be synthesized according to the known methods is added to the compound of in the solvent such as DMF, DIEA, DMA, NMP, dichloromethane, tetrahydrofuran, acetonitrile and the like or solvent mixture thereof at −20 to 50° C., preferably 20 to 40° C. for 0.1 hours to 4 days, preferably 1 to 12 hours.

As above, the compound (I) having X represented —N(R$^F$)—CO—X$^1$ can be synthesized by using the intermediate of the present invention (X), (XI), (XII) or (XIII) easily, with high yield, with short steps. Various compound (I) can be synthesized from the obtained compound (I) by chemical modifying hydroxy part or sugar chain part and the like of core structure according to the known reaction.

the compound (I) represented as X is formula (II) can also be synthesized by inducing from carboxy group or isocyanate group.

(General Synthetic Method 3)

[Chemical Formula 32]

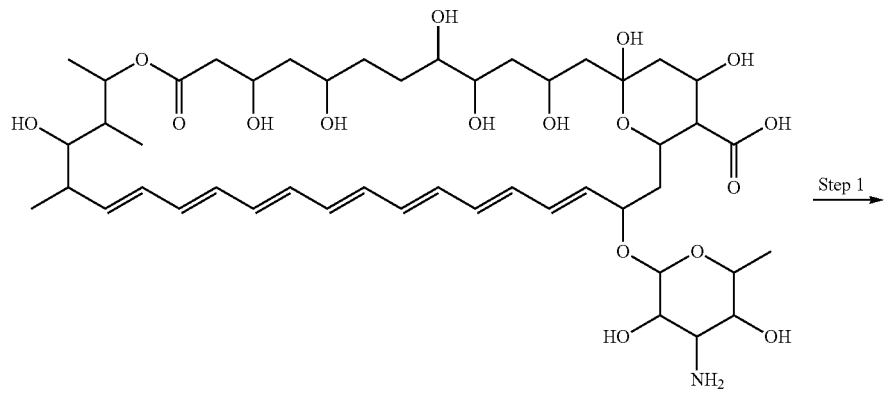

Step 1

-continued
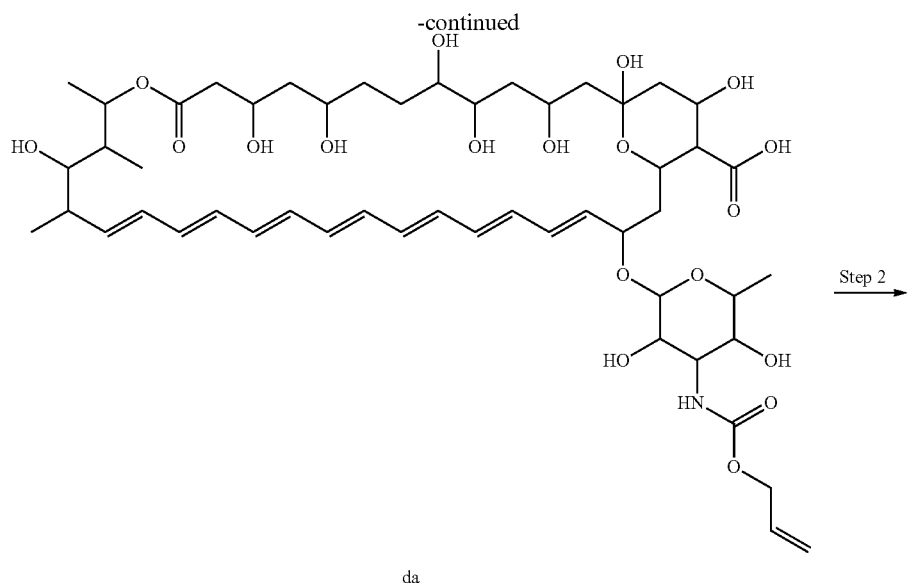
da
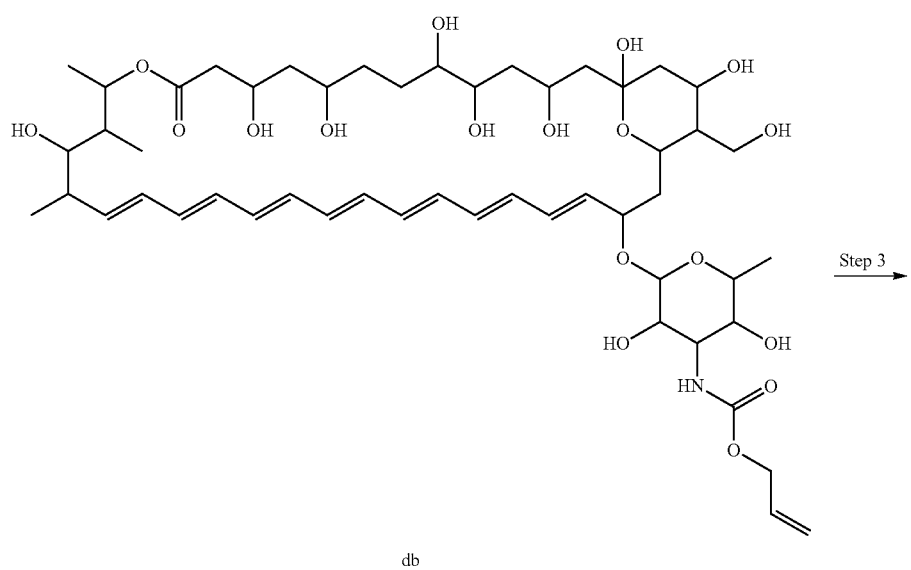
db
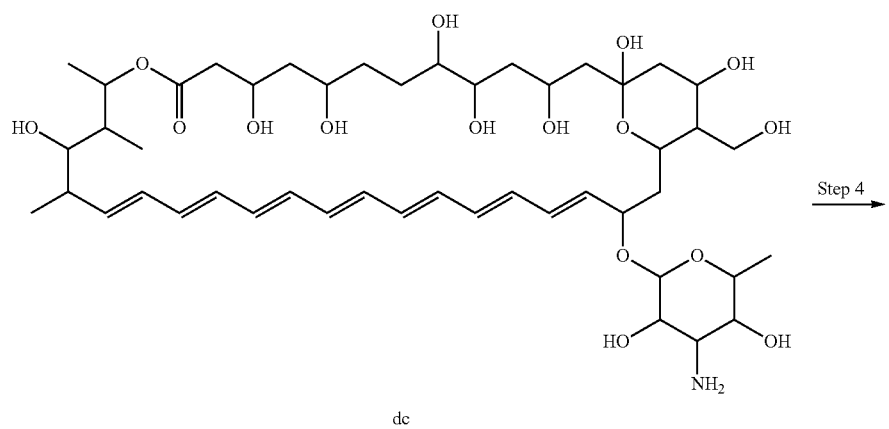
dc

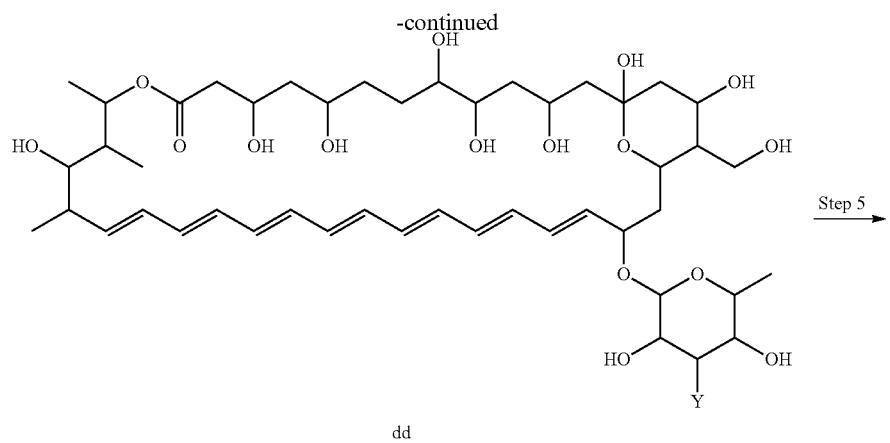

-continued dd

Step 1
The compound da can be synthesized by the reaction which tertiary amine such as triethylamine, DIEA, pyridine and the like and allyloxycarbonyl chloride or allyloxycarbonyl chloride succinimidediester are added dropwise to the commercially available amphotericin B in the solvent such as DMF, DMA, NMP, dichloromethane, tetrahydrofuran, acetonitrile and the like or solvent mixture thereof at 20 to 40° C., preferably 20 to 30° C. for 0.5 to 6 hours, preferably 2 to 4 hours at.

Step 2
The active ester is synthesized by the reacting the compound da with tertiary amine such as triethylamine, DIEA, pyridine and the like and phosphonium condensing agent such as PyBOP, BOP, BrOP, PyBrBOP and the like in the solvent such as DMF, DMA, NMP, dichloromethane, tetrahydrofuran, acetonitrile and the like or solvent mixture thereof at 0 to 20° C., preferably 0 to 10° C. for 0.5 to 4 hours, preferably 0.5 to 1 hours. After that, the compound db can be synthesized by the reaction which sodium borohydride or boron reducing agent equivalents thereof is added, and reacted at 0 to 20° C., preferably 0 to 10° C. for 0.5 to 4 hours, preferably 0.5 to 1 hours.

Step 3
The compound dc can be synthesized by the commonly known deprotect reaction of allyloxycarbonyl group of the compound db in the solvent such as DMF, DMA, NMP, dichloromethane, tetrahydrofuran, acetonitrile and the like or solvent mixture thereof.

Step 4
The compound dd can be synthesized by the reaction which the compound having amino group such as primary amines, secondary amines, hydrazine, substituted hydrazine, alkoxy amine, amino acid and the like which is commercially available or can be synthesized according to the known methods is added to the compound dc in the solvent such as DMF, DIEA, DMA, NMP, dichloromethane, tetrahydrofuran, acetonitrile and the like or solvent mixture thereof at −20 to 50° C., preferably 20 to 40° C. for 0.1 hours to 4 days, preferably 1 to 12 hours.

EXAMPLES

The present invention will be described in more detail with reference to, but not limited to, the following Examples, Reference Examples and Test Examples.

NMR analysis of each example was performed by 300 MHz using DMSO-$d_6$ or $CDCl_3$.

Reference Example 1

Synthesis of Compound III-a

[Chemical Formula 33]

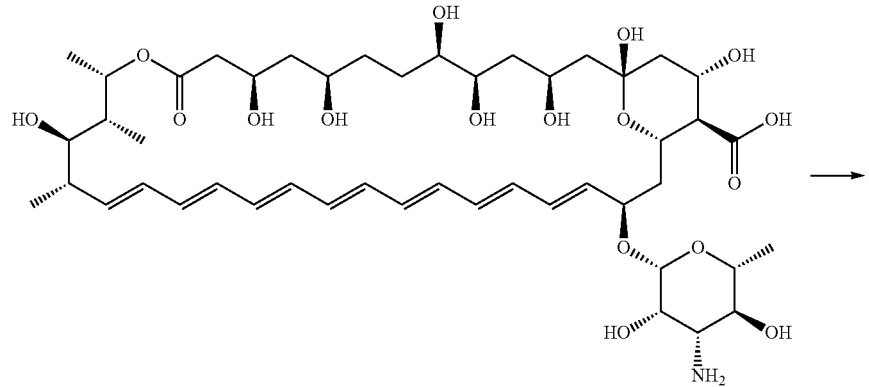

AMB

-continued
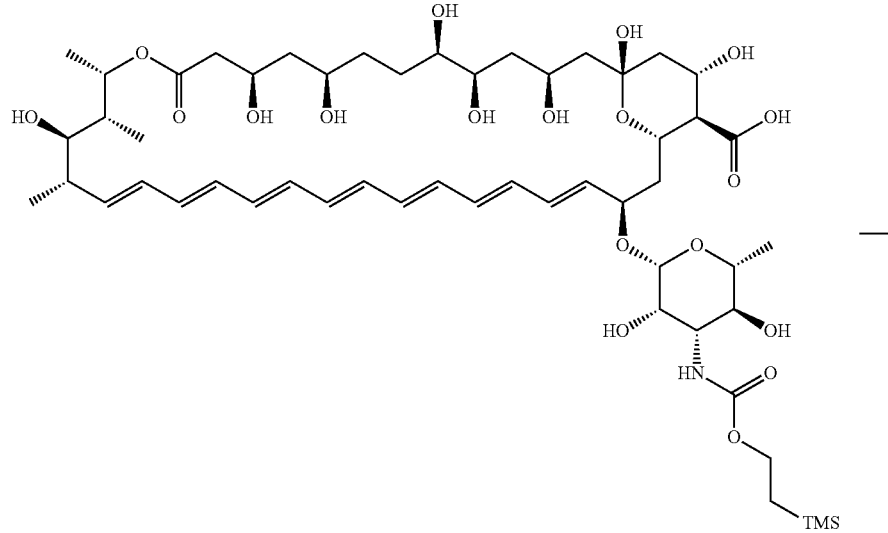
I-a
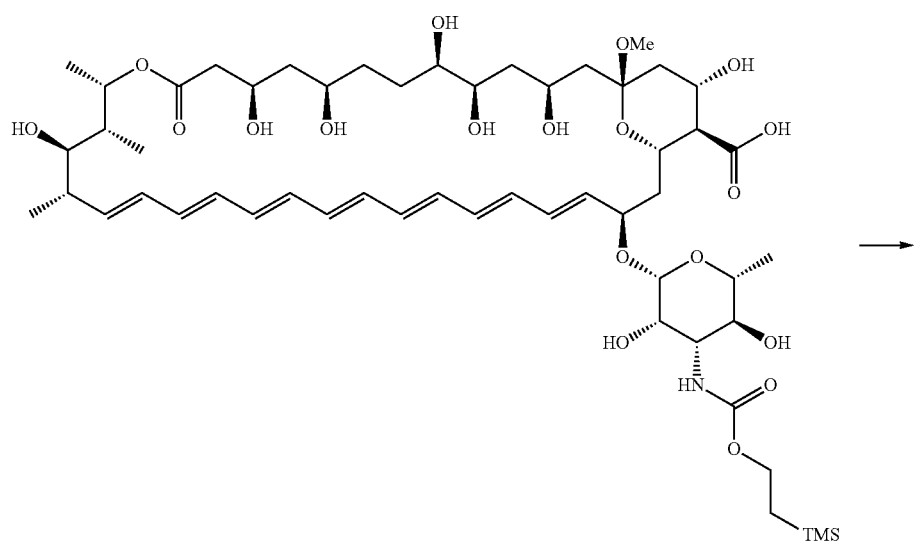
II-a

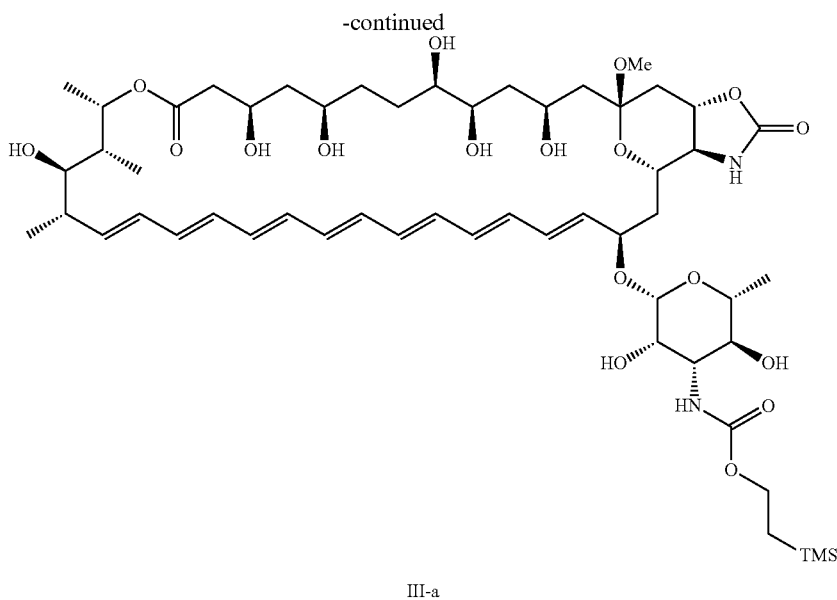

III-a

Step 1 Synthesis of Compound I-a

Amphotericin B (5 g, 5.41 mmol) was dissolved in DMF (25 mL) and added triethylamine (10 mL, 72.1 mmol) and N-[2-(trimethylsilyl)-ethoxycarbonyloxy]succinimide (3.51 g, 13.5 mmol), and the mixture was stirred for an hour at room temperature. Diisopropyl ether and acetonitrile were added, and the resulting solids were filtered. Compound I-a (7.11 g) was obtained as crude by evaporating in vacuo.

[M+Na]+=1090

Step 2 Synthesis of Compound II-a

Compound I-a (2 g, 1.87 mmol) was dissolved in methanol (20 mL), and stirred for 10 minutes in an ice-water bath. Camphorsulfonic acid (0.609 g, 2.62 mmol) was added and stirred for an hour in an ice-water bath. Methanol was removed by evaporating in vacuo, and the residue was resolved in a little methanol. The obtained methanol solution was added dropwise to diisopropyl ether (500 mL) to give Compound II-a (1.8 g, 89%).

Step 3 Synthesis of Compound III-a

Compound II-a (1.8 g, 1.66 mmol) was dissolved in DMF (10 mL) and added diphenylphosphoryl azide (1.075 mL, 4.99 mmol) and trimethylamine (1.2 mL, 8.32 mmol), and the mixture was stirred for an hour at room temperature, moreover, 3 hours at 40° C. The reaction mixture was powderized by adding dropwise to the solvent mixture of diisopropyl ether and methanol. The resulting residue was filtrated to give Compound III-a (1.37 g, 76%).

[M+Na]=1101

Reference Example 2

Synthesis of Compound III-b

[Chemical Formula 34]

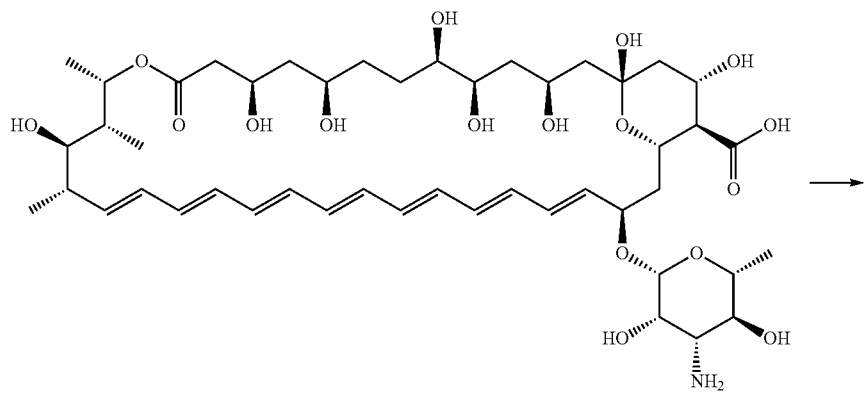

AMB

-continued
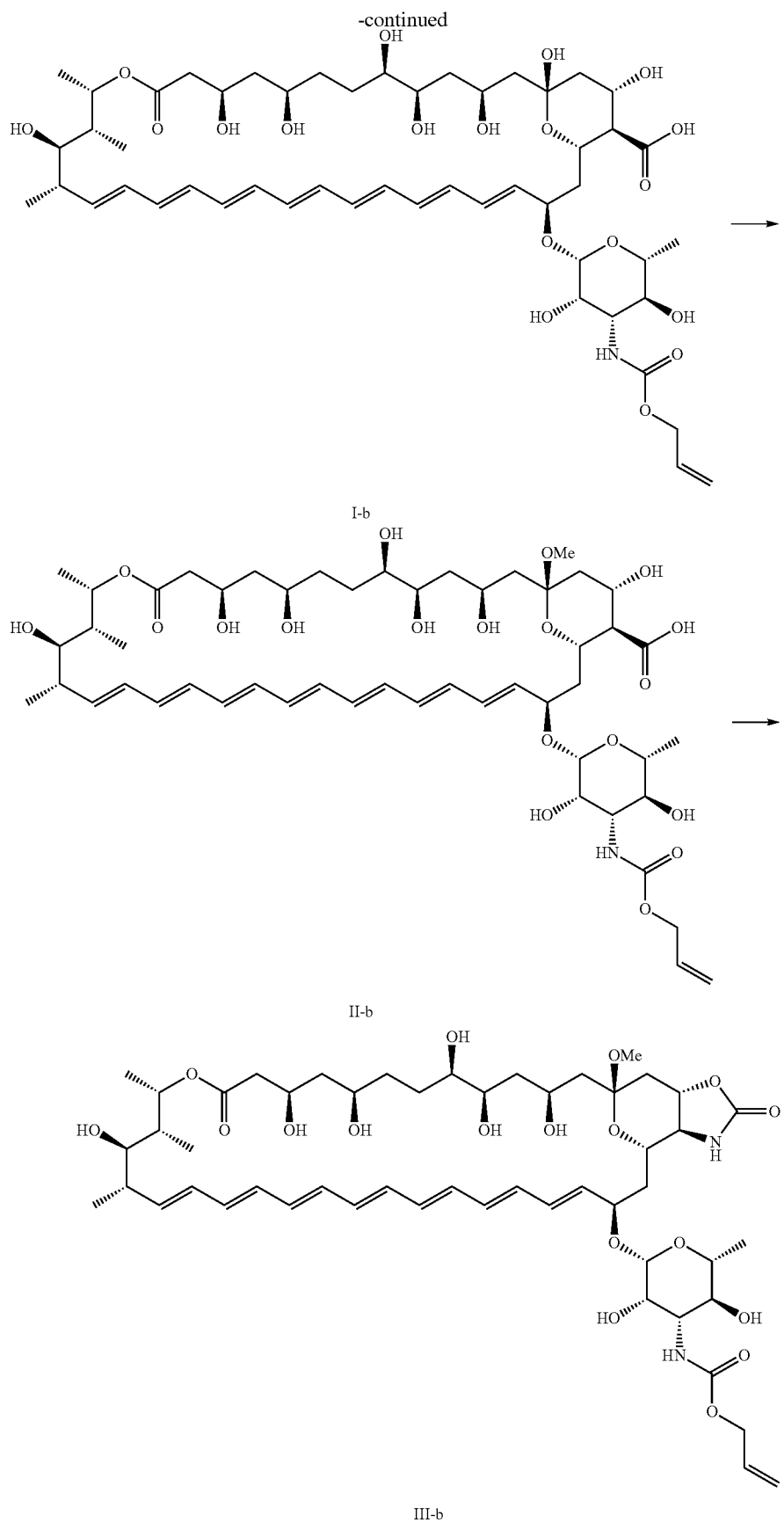
I-b
II-b
III-b

Step 1 Synthesis of Compound I-b

Amphotericin B (10.07 g, 10.9 mmol) was dissolved into N-methylpyrrolidone (50 mL) and methanol (50 mL) and added N,N-diisopropylethylamine (5.7 mL, 32.7 mmol) and Alloc-OSu (2.6 g, 13.1 mmol), and the mixture was stirred for 2 hours 30 minutes at room temperature. The reaction mixture was added to diisopropyl ether/methanol (10/1, 550 mL) and stirred strongly. The deposited powder was filtrated. The obtained solids was washed with isopropylether and evaporated in vacuo to give Compound I-b (11.58 g) as crude. The retention time of Compound I-b was 10.4 minutes by HPLC analysis (methanol/distilled water containing 0.1% PIC-B7=gradient from 70/30 to 100/0, flow speed 1 ml/min, wavelength of detection=385 nm). The retention time of raw material amphotericin B was 8.6 minutes under the same condition.

[M+Na]+=1032.5

Step 2 Synthesis of Compound II-b

Compound I-b (9.8 g, 7.78 mmol) was dissolved into tetrahydrofuran (150 mL) and methanol (150 mL) and cooled to 0° C. Camphorsulfonic acid (1.5 g, 6.45 mmol) was added in an ice-water bath, and the mixture was stirred for 2 hours 30 minutes. Triethylamine (1.12 mL, 6.45 mmol) was added, and reaction was quenched. The mixture was evaporated in vacuo to 50 mL by rotatory evaporator. The concentrated solution was added dropwise to diethylether/hexane (1/1, 1 L) with stirring. The obtained solids were filtrated to give Compound II-b (yellow powder, 12.48 g). The retention time of Compound II-b was 8.5 minutes by HPLC analysis (methanol/distilled water containing 0.1% PIC-B7=gradient from 70/30 to 100/0, flow speed 1 ml/min, wavelength of detection=385 nm).

Step 3 Synthesis of Compound III-b

Compound II-b (7.17 g, 7.01 mmol) was dissolved into DMF (36 mL) and added DIEA (7.35 mL, 42.1 mmol) and diphenylphosphoryl azide (4.52 mL, 21.4 mmol), and the mixture was stirred for an hour at room temperature, moreover, stirred 3 hours at 50° C. The reaction mixture was added dropwise to the solvent mixture of diisopropyl ether and methanol (10/1, 525 mL) to give powder. The obtained solids were filtrated to give Compound III-b (4.85 g, 87%). The retention time was 8.1 minutes by HPLC analysis (methanol/distilled water containing 0.1% PIC-B7=gradient from 70/30 to 100/0, flow speed 1 ml/min, wavelength of detection=385 nm).

[M+Na]+=1041.4

Reference Example 3-1

Synthesis of Compound I-A and Compound II-A

[Chemical Formula 35]

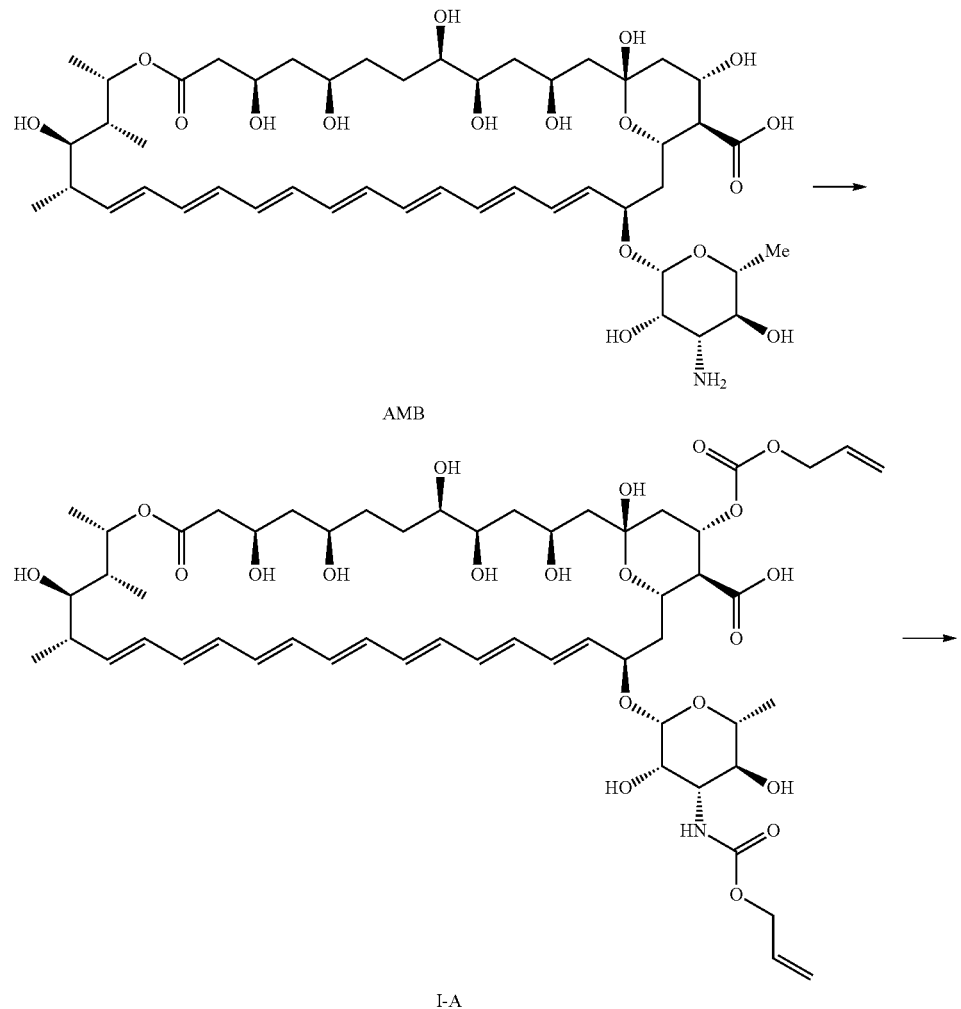

AMB

I-A

-continued

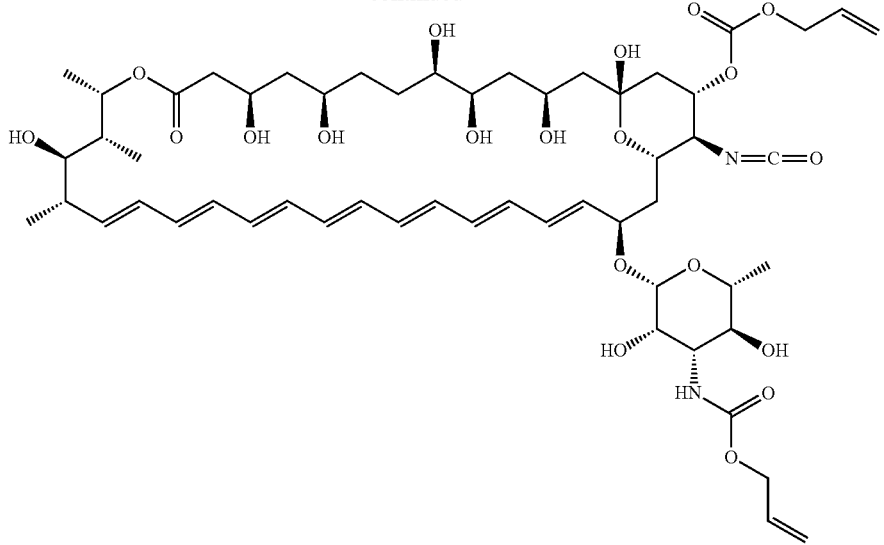

II-A

Step 1 Synthesis of Compound I-A

Amphotericin B (5 g, 5.41 mmol) was dissolved in DMF (50 mL), followed by the addition of DIEA (10 mL, 27.1 mmol). Allyloxycarbonyl chloride (3.51 g, 13.5 mmol) was added dropwise at 4° C. or below under control, and the mixture was stirred for 2 hours 50 minutes in an ice-water bath. After heating to room temperature, the mixture was stirred for 4 hours. The mixture was added dropwise to the solvent mixture of diisopropyl ether/methanol (4/1, 500 mL). After the mixture was incubated at room temperature, the obtained solids were filtrated to give Compound I-A (5.85 g). The retention time was 12.4 minutes by HPLC analysis (methanol/distilled water containing 0.1% PIC-B7=gradient from 70/30 to 100/0, flow speed 1 ml/min, wavelength of detection=385 nm).

[M+H]=1093.9

Step 2 Synthesis of Compound II-A

Compound I-A (5.28 g, 4.83 mmol) was dissolved into DMA (25 mL), followed by the addition of DIEA (1.26 mL, 7.25 mmol). Diphenylphosphoryl azide (1.56 mL, 7.25 mmol) was added, and the mixture was stirred for 2 hours 20 minutes at room temperature and further stirred for 2 hours at 50° C. After cooling to room temperature, the reaction mixture was diluted with acetonitrile (25 mL) and added diisopropyl ether (350 mL). The obtained solids was filtrated to give Compound II-A (5.01 g) as yellow powder. The retention time was 12.5 minutes by HPLC analysis (methanol/distilled water containing 0.1% PIC-B7=gradient from 70/30 to 100/0, flow speed 1 ml/min, wavelength of detection=385 nm).

Infrared absorption spectrometry (IR spectrum): 2141.85 ($cm^{-1}$) analysis: (C55H80N2O20)(C3H7NO)3.5(H2O)1

Calculated value: C 57.72; H, 7.88; N, 5.65 (%).

Actual value: C 57.81; H, 7.31; N, 6.03 (%).

Reference Example 3-2

Synthesis of Compound I-B, Compound II-B and Compound III-B

[Chemical Formula 36]

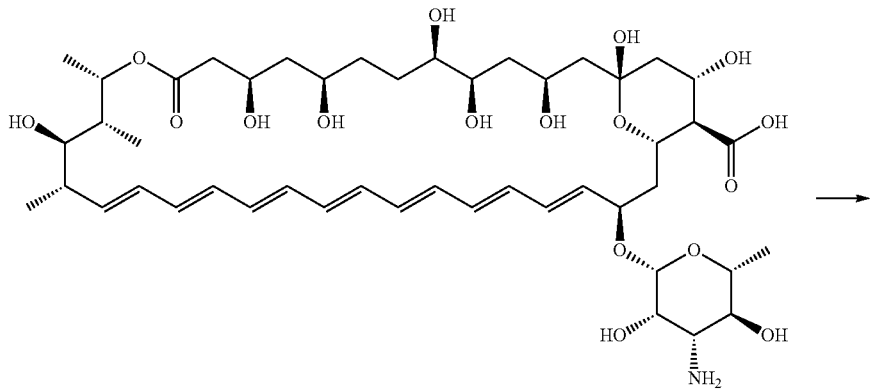

AMB

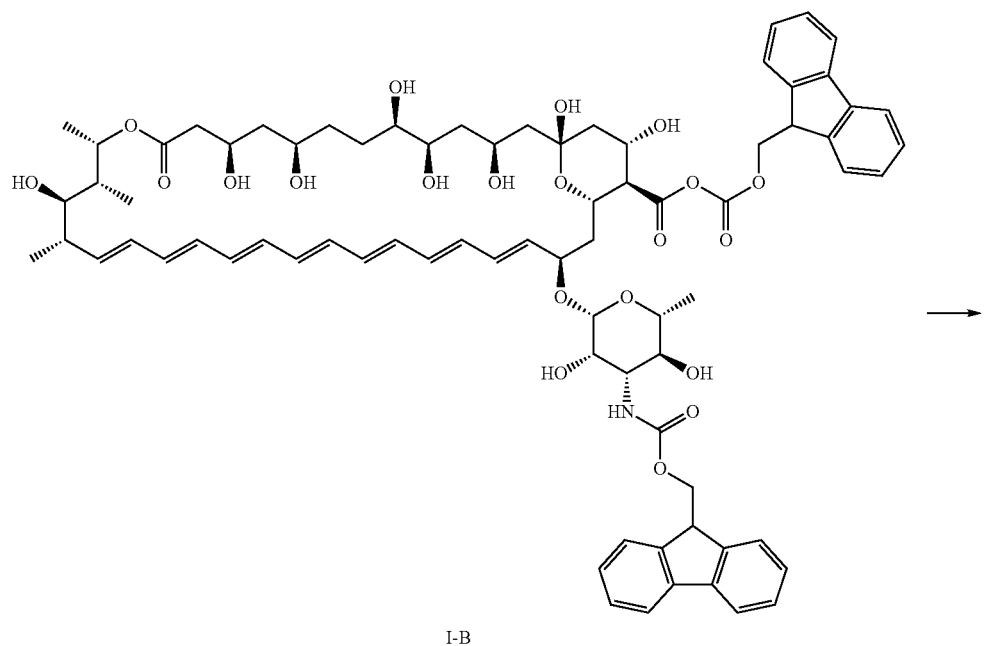
I-B
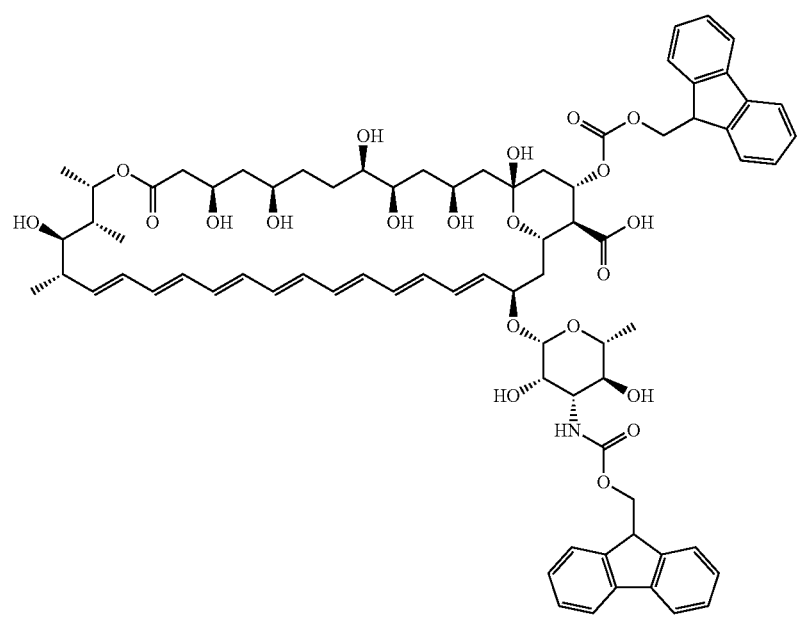
II-B

[Chemical Formula 37]

-continued

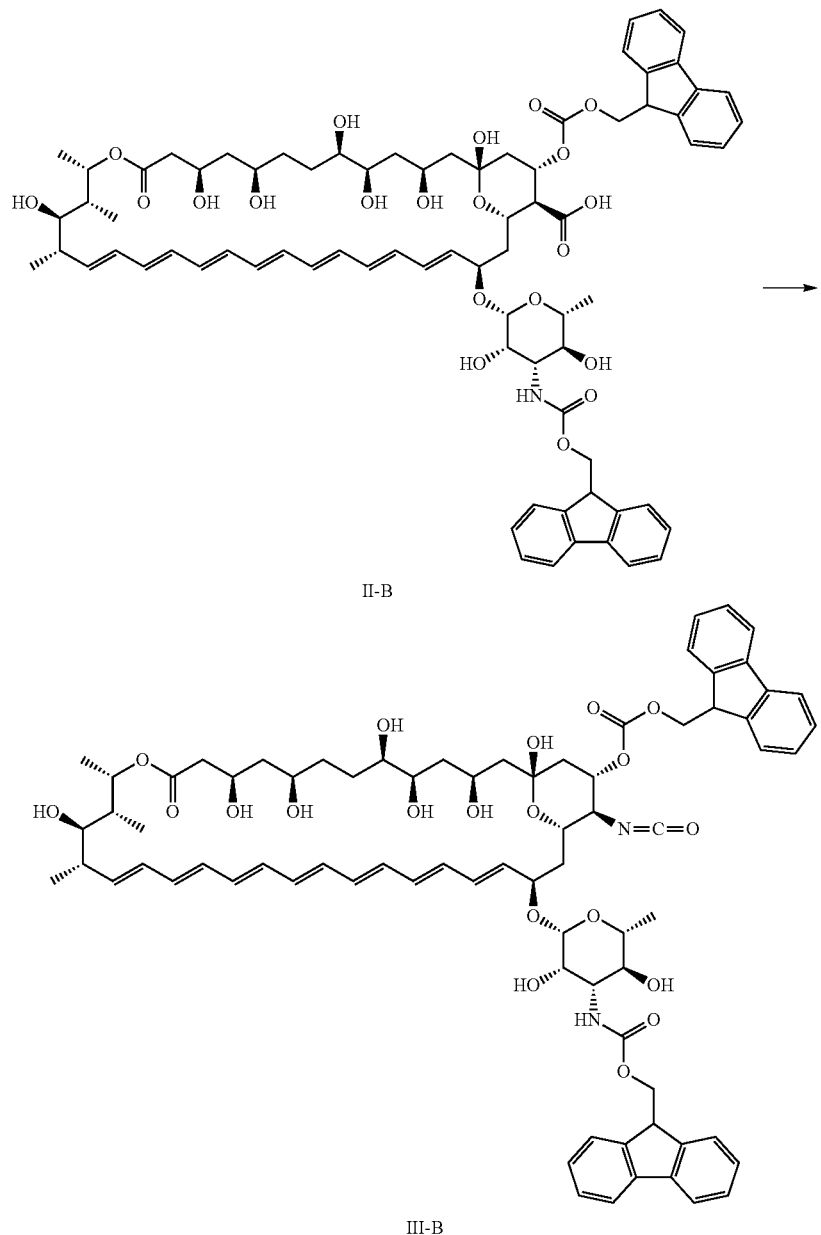

Step 1 Synthesis of Compound I-B

Amphotericin B (10.00 g, 10.82 mmol) was dissolved into DMA (78 mL), followed by the addition of DIEA (2.53 g, 19.58 mmol). 9-Fluorenylmethyloxycarbonylchloride (5.32 g, 20.6 mmol) was added carefully dropwise at 4° C. or below under control in an ice-water bath. After heating to room temperature, the mixture was stirred for an hour 30 minutes. After the mixture was added to the solution mixture of acetonitrile (100 mL) and DMA (3.6 mL), diisopropyl ether (500 mL) was added dropwise. The mixture was incubated at room temperature and filtrated to give crude Compound I-B (15.92 g, 11.63 mmol).

Step 2 Synthesis of Compound II-B

Compound I-B (10.00 g, 7.31 mmol) was dissolved into DMA (50 mL) and trimethylamine (0.506 mL, 3.65 mmol) was added. The mixture was stirred for an hour 40 minutes at room temperature. After acetonitrile (50 mL) was added, diisopropyl ether (500 mL) was added dropwise. After incubating at room temperature, the obtained powder was filtrated to give crude Compound II-B (8.79 g, 6.42 mmol). The crude Compound II-B (4.50 g, 3.29 mmol) was purified by silica-gel column chromatography by using chloroform/methanol (89/11) to give Compound II-B (2.02 g, 1.48 mmol). The retention time was 16.7 minutes by HPLC analysis (acetonitrile/distilled water containing 0.1% formic acid=gradient from 20/80 to 90/10, flow speed 1 ml/min, wavelength of detection=385 nm).

[M+Na]=1392

Step 3 Synthesis of Compound III-B

Compound II-B (1.50 g, 1.10 mmol) was dissolved into THF/DMA (1/4, 7.5 mL), followed by the addition of DIEA (325.5 µL, 1.86 mmol). Diphenylphosphoryl azide (400.5

μL, 1.86 mmol) was added, and the mixture was stirred for an hour at room temperature, in addition, stirred for 9.5 hours at 40° C. After cooling to room temperature, acetonitrile (25 mL) was added dropwise. After incubation at room temperature, the obtained powder was filtrated to give yellow powder Compound III-B (0.59 g, 0.435 mmol). The retention time was 17.2 minutes by HPLC analysis (methanol/distilled water containing 0.1% formic acid=gradient from 20/80 to 90/10, flow speed 1 ml/min, wavelength of detection=385 nm).

Infrared absorption spectrometry (IR spectrum): 2143 or 2165 (cm$^{-1}$)

Example 1

Synthesis of Compound I-1

[Chemical Formula 38]

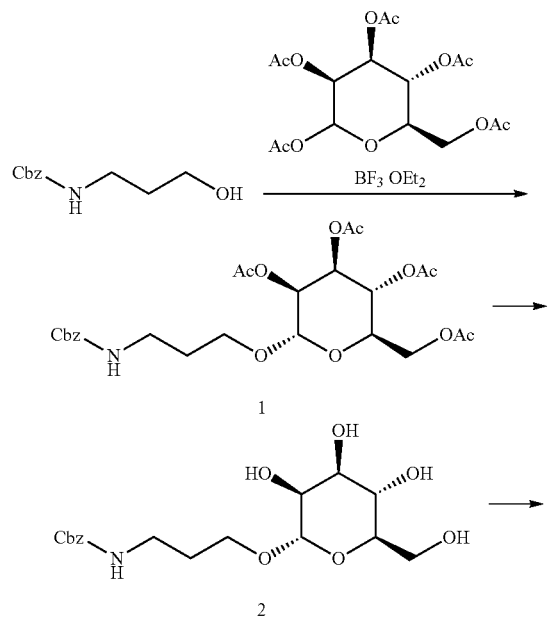

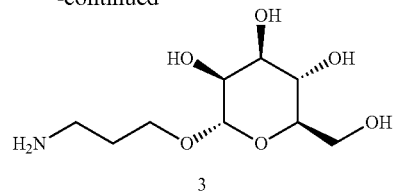

Step 1 Synthesis of Compound 1

Pentaacetylmannose (4 g, 10.25 mmol) and N-benzyloxy-carbonyl-aminopropanol (4.29 g, 20.49 mmol) were dissolved into dichloromethane (20 mL) and boron trifluoride diethyl ether complex (10.39 mL, 82 mmol) was added, and the mixture was stirred for 16 hours at room temperature. After the reaction was quenched by adding saturated sodium bicarbonate aqueous solution and 2 mol/L sodium hydroxide solution, the reaction mixture was extracted with ethyl acetate, and the organic phase was washed with water and brine. The organic phase was dried over with magnesium sulfate and filtrated and concentrated. The resulted residue was purified by silica-gel column chromatography (hexane-ethyl acetate) to give Compound 1 (2.55 g, 46%).

TLC: Rf=0.3 (hexane/ethyl acetate=1/1)

Step 2 Synthesis of Compound 2

Compound 1 (2.55 g, 4.73 mmol) was dissolved into methanol (10 mL), sodium methoxide (5.2 mol/L, 1.8 mL, 9.45 mmol) was added, and the mixture was stirred for 20 minutes at room temperature. After disappearance of raw material, Dowex was added, and the mixture was filtrated and concentrated and purified by silica-gel column chromatography (ethyl acetate, methanol) to give Compound 2 (1.3 g, 74%).

TLC: Rf=0.2 (chloroform/mthanol=4/1)

Step 3 Synthesis of Compound 3

Compound (1.3 g, 3.5 mmol) was dissolved into methanol (20 mL) and 5% Pd—C (373 mg, 0.175 mmol) was added, and the mixture was stirred for 15 hours under 1 atm of hydrogen. The mixture was filtrated and concentrated to give 3-aminopropyl-β-D-mannopyranoside (Compound 3, 840 mg). Crude Compound 3 was used to next reaction without purification.

[Chemical Formula 39]

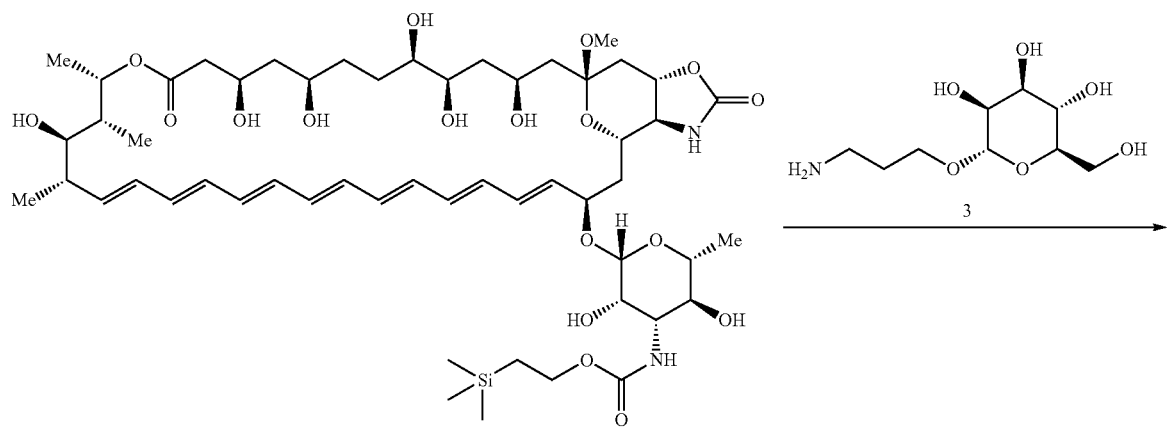

103 104
-continued
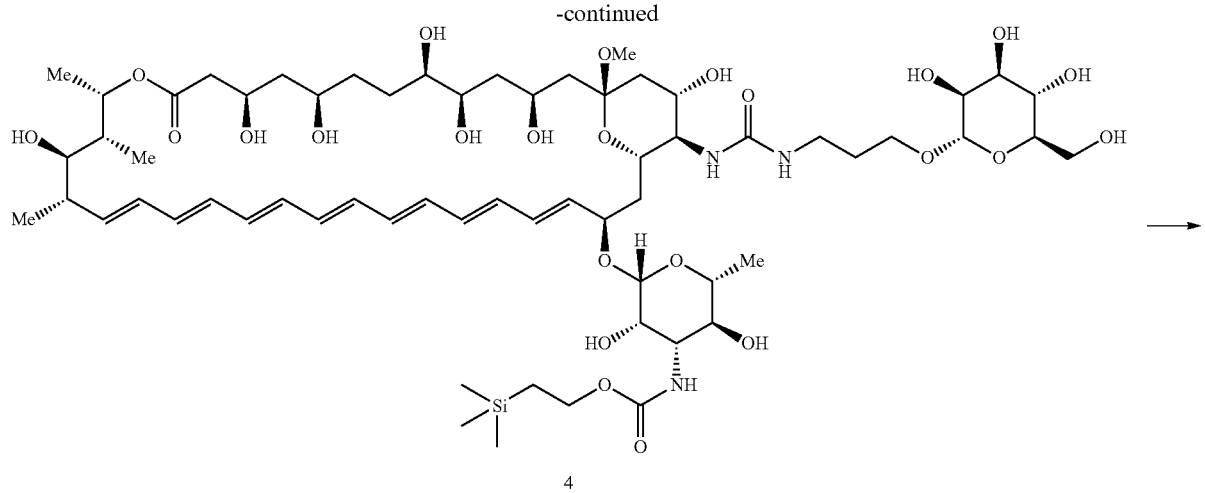
4
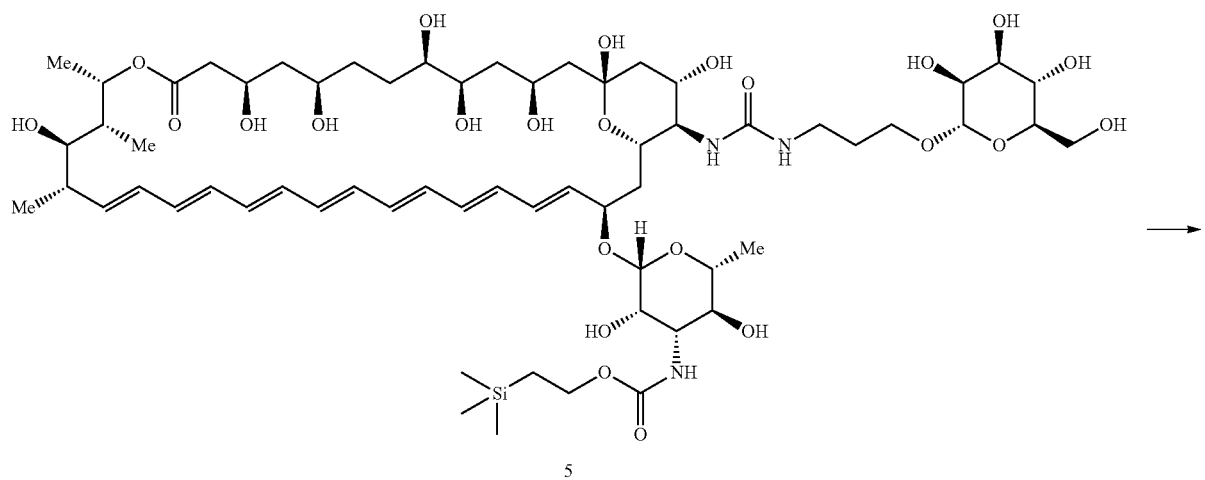
5
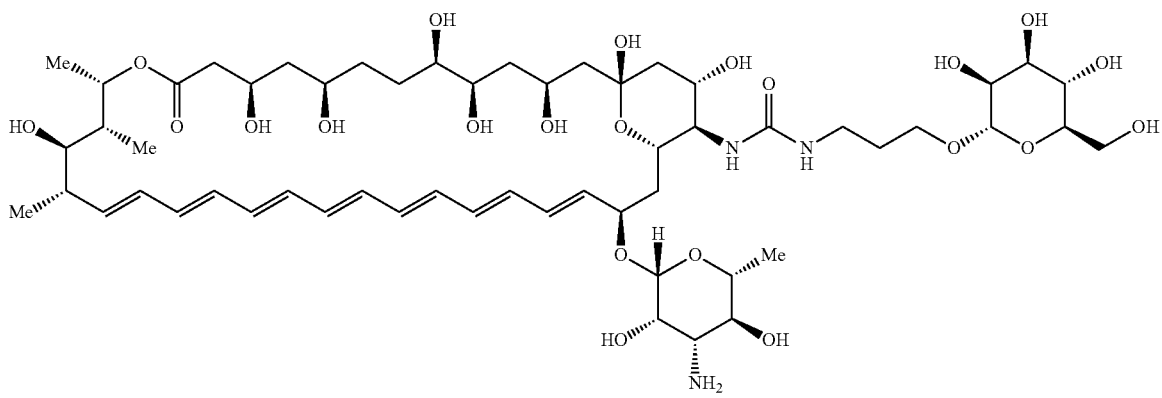
I-1

Step 4 Synthesis of Compound I-1

Compound III-a (500 mg, 0.463 mmol) and 3-aminopropyl-β-D-mannopyranoside (Compound 3) (154 mg, 0.649 mmol) were dissolved into DMF (5 mL) and DIEA (0.405 mL, 2.32 mmol) was added. The mixture was stirred for 2 hours at room temperature, moreover, stirred for 2 days at 40° C., moreover, stirred for 6 hours at 55° C. After disappearance of raw material, diisopropyl ether was added to give powder. Crude Compound 4 (497 mg) was obtained. Compound 4 (470 mg, 0.357 mmol) was dissolved to tetrahydrofuran (3 mL), water (3 mL) and DMF (0.3 mL) and PPTS (269 mg, 1.07 mmol) was added, and the mixture was stirred for an hour at room temperature. Diisopropyl ether was added to be powder to give crude Compound 5 (465 mg). The obtained Compound 5 (465 mg, 0.357 mmol) was dissolved into tetrahydrofuran (6 mL) and DMF (3 mL) and TBAF (1 mol/L, 1.78 mL) was added, and the mixture was stirred for 3 days at room temperature. The mixture was diluted by adding diisopropyl ether and purified by silica-gel column chromatography (chloroform/methanol/water=50/50/5 to 20/80/8). The obtained solids was dissolved into DMF (1 mL) again, and diisopropyl ether was added to solidify. Compound I-1 (44 mg, total yield 8%) was obtained.

LC/MS: 1158.6 [M+H]+

Elementary analysis: C56H91N3O22(C3H7N)0.9(H2O)7.1

Calculated value: C 52.78; H, 8.40; N, 4.09 (%).

Actual value: C 52.71; H, 8.40; N, 4.08 (%).

Example 2

Synthesis of Compound I-3

[Chemical Formula 40]

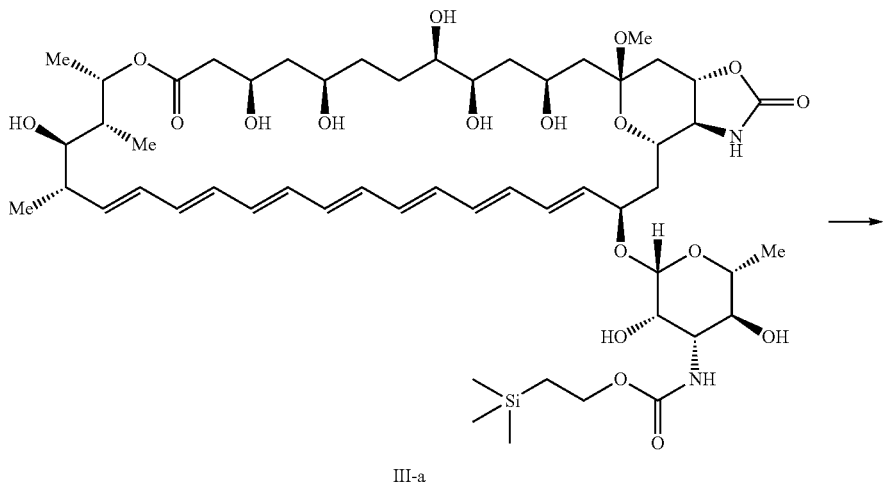

III-a

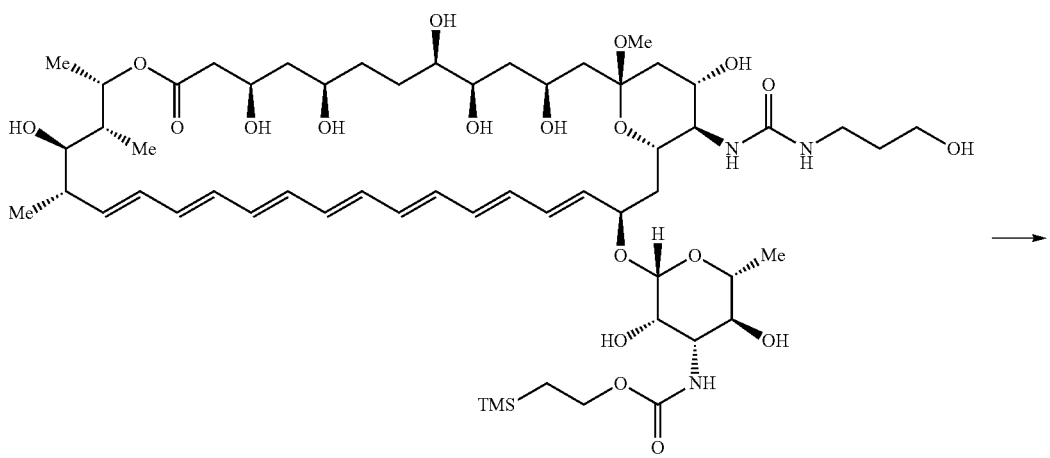

-continued

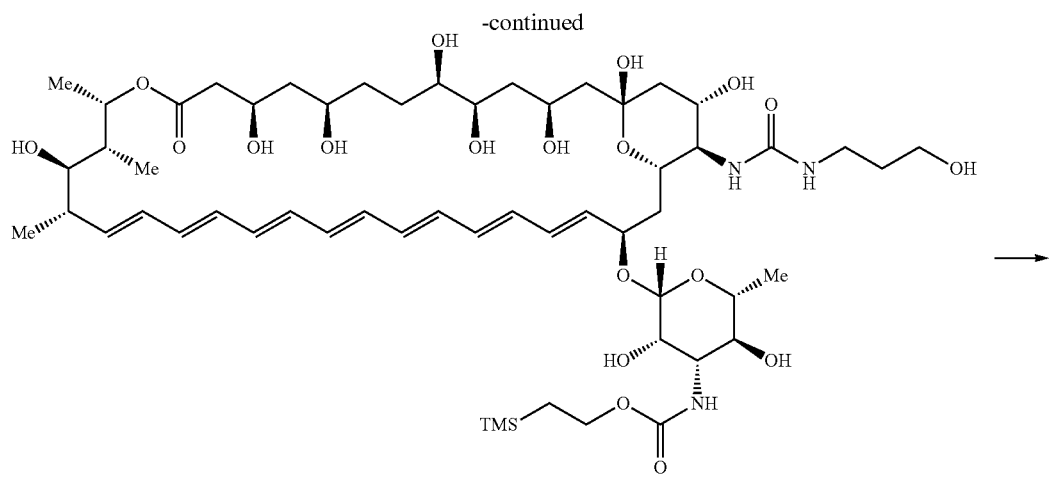

7

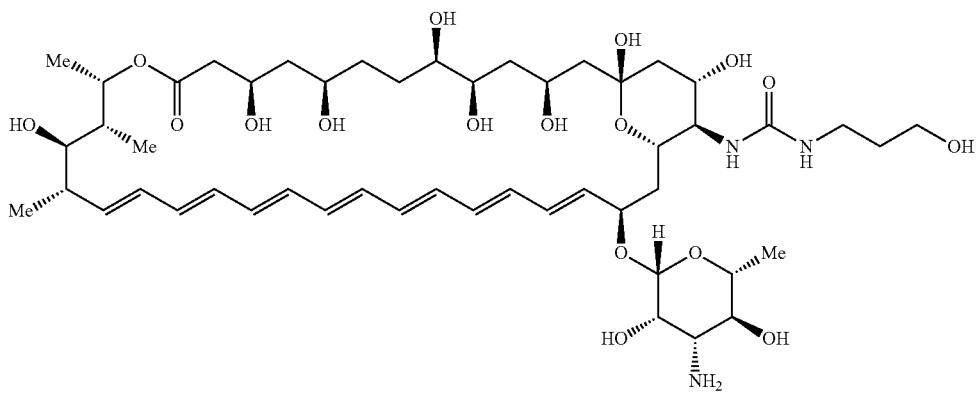

I-3

Compound III-a (420 mg, 0.389 mmol) was dissolved into DMF (5 mL) and added 3-aminopropanol (175 mg, 2.34 mmol), and the mixture was stirred for 2 hours at room temperature. The mixture was oil-outed by adding diisopropylether to give crude Compound 6 (365 mg). Compound 6 was dissolved into tetrahydrofuran (2 mL), DMF (1 ml) and water (0.5 mL) and added PPTS (238 mg, 0.948 mmol), and the mixture was stirred for 2 hours at room temperature. Compound 7 (360 mg) was obtained by adding diisopropylether to be powder. Compound 7 was dissolved into DMF (5 mL) and added TBAF (1 mol/L, 3.16 mL, 10 equivalent), and the mixture was stirred for overnight at room temperature. After the reaction mixture was oil-outed by adding diisopropylether, the mixture was purified by silica-gel column chromatography to give Compound I-3 (110 mg, total yield 28%)

LC/MS: 996.9 [M+H]+

Elementary analysis: C50H81N3O17(C3H7NO)1(H2O)4.3

Calculated value: C 55.51; H, 8.49; N, 4.89 (%).

Actual value: C 55.53; H, 8.61; N, 4.98 (%).

Example 3
Synthesis of Compound I-4
[Chemical Formula 41]
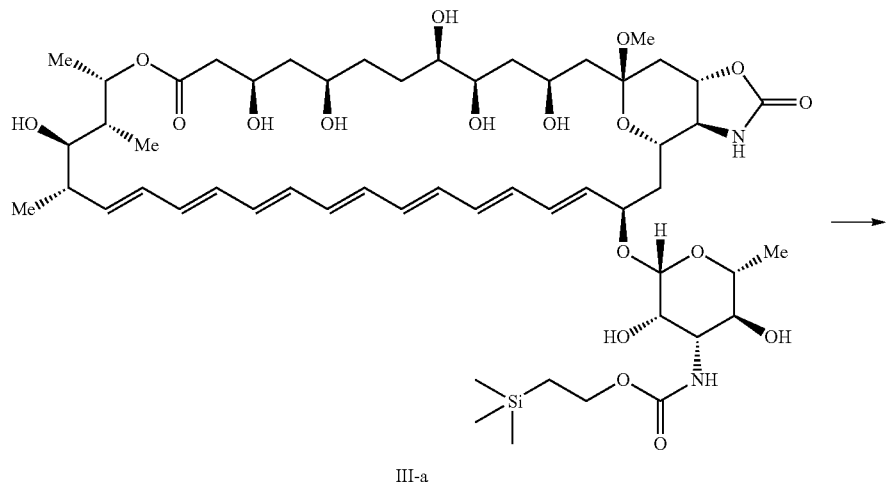
III-a
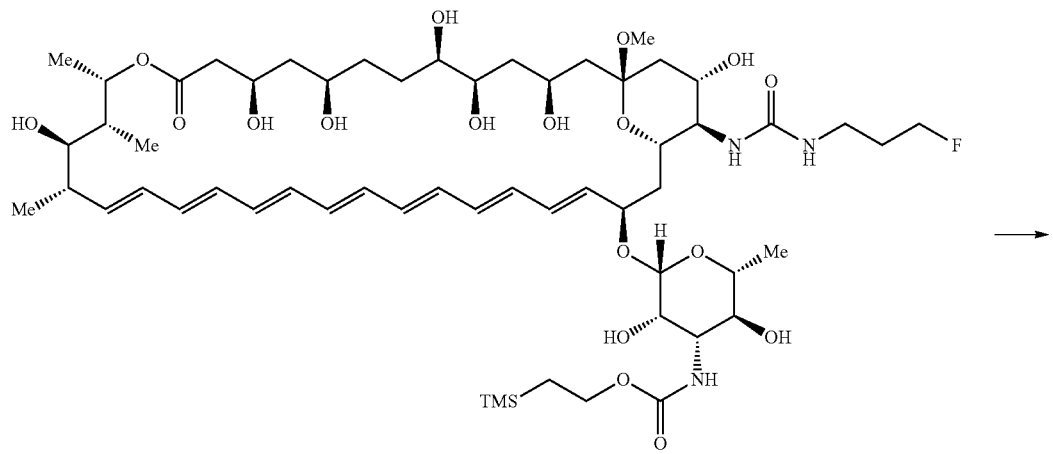
8
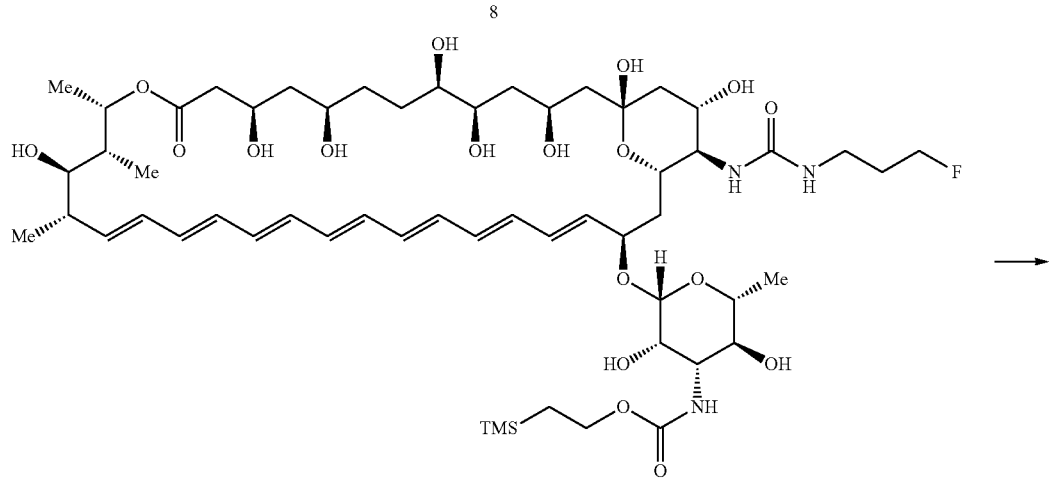
9

-continued

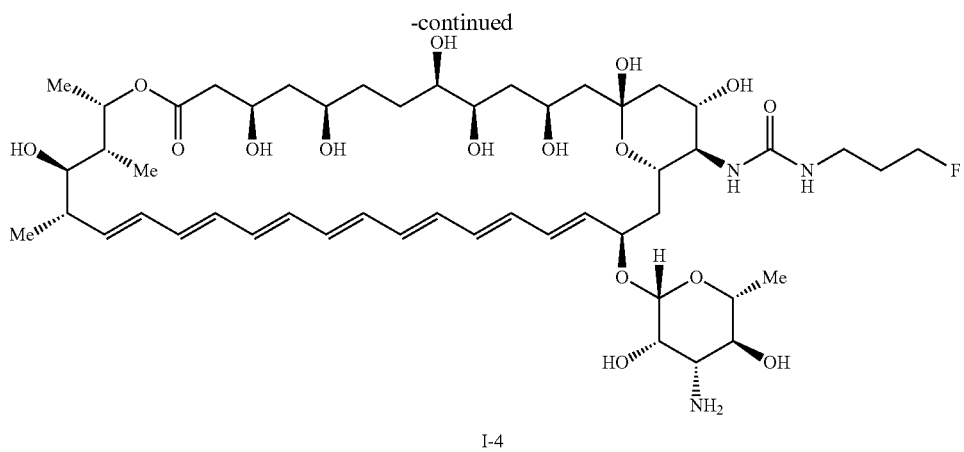

I-4

Compound III-a (400 mg, 0.371 mmol) was dissolved into DMF (5 mL) and added 3-fluoropropanpolamine hydrochloride (168 mg, 1.48 mmol) and trimethylamine (0.2 mL, 1.48 mmol), and the mixture was stirred for an hour at room temperature. Diisopropylethylamine (0.26 mL, 1.48 mmol) was added, and the mixture was stirred for 3 hours at room temperature. The crude Compound 8 (260 mg, 0.225 mmol) was obtained by adding diisopropylether to be oil-outed. Compound 8 (260 mg, 0.225 mmol) was dissolved into tetrahydrofuran (2 mL), DMF (1 mL) and water (0.5 mL) and added PPTS (169 mg, 0.674 mmol), and the mixture was stirred for 2 hours at room temperature. The obtained Compound 9 by adding diisopropylether to be oil-outed was used to next reaction without purification. Compound 9 (257 mg) was dissolved into DMF (3 mL) and added TBAF (1 mol/L, 2.2 mL), and the mixture was stirred for 24 hours at room temperature. The mixture was oil-outed by adding diisopropylether and purified by silica-gel column chromatography to give Compound I-4 (54 mg, total yield 15%).

LC/MS: 998.5 [M+H]+

Elementary analysis: (C50H80FN3O16)(C3H7NO)(H2O)3

Calculated value: C 56.57; H, 8.33; N, 4.98; F, 1.69 (%).
Actual value: C 56.20; H, 8.64; N, 4.94; F, 2.16 (%).

Example 4

Synthesis of Compound I-19

[Chemical Formula 42]

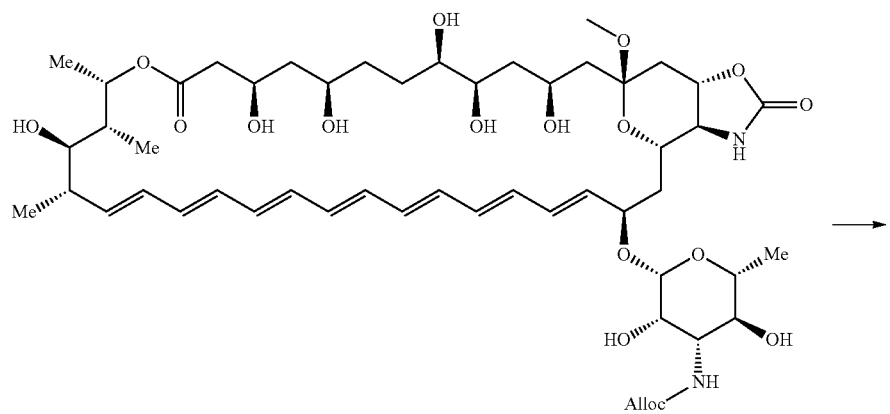

III-b

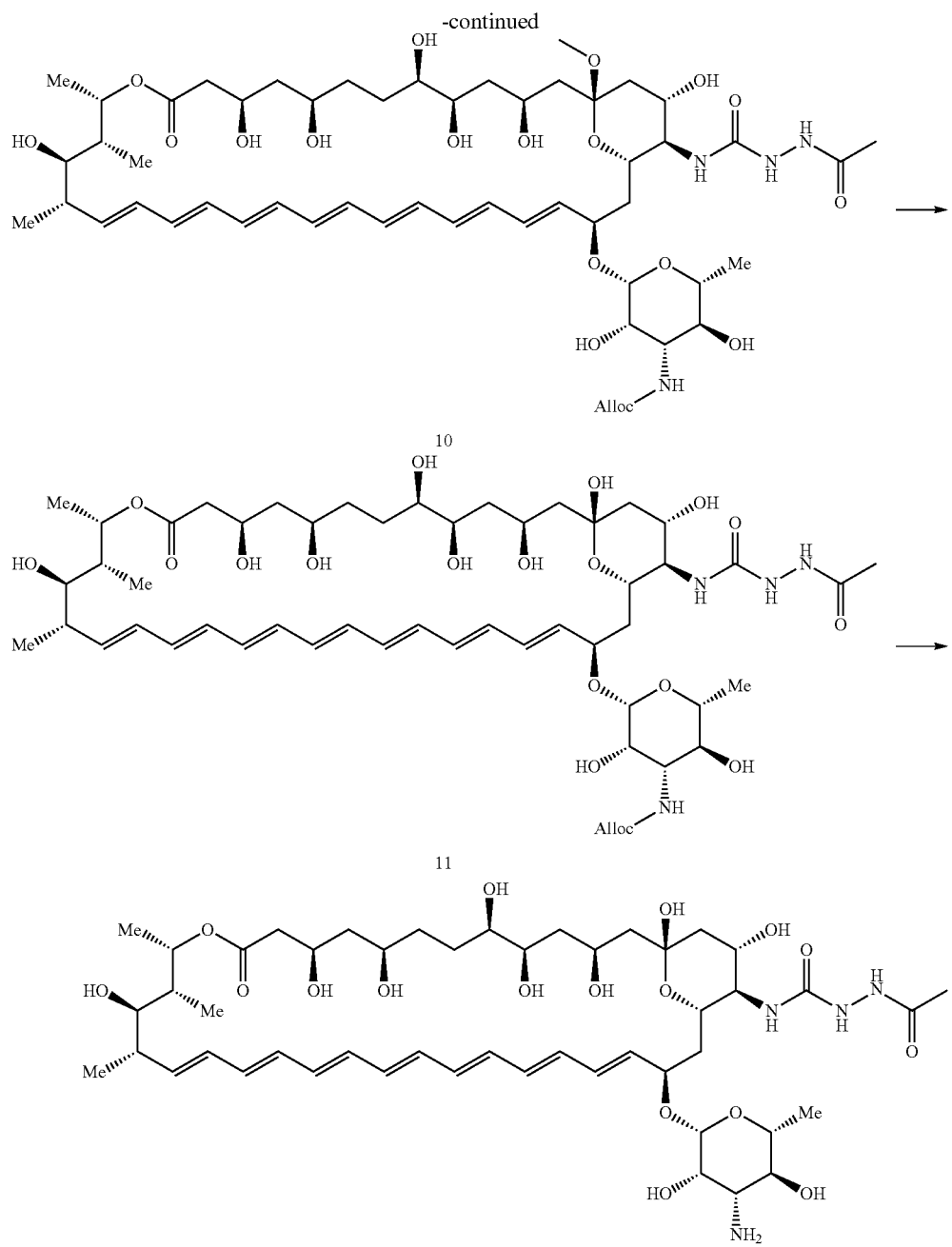

I-19

Compound III-b (2 g, 1.96 mmol) was dissolved into DMA (20 mL) and added DIEA (2 mL, 11.7 mmol) and acetohydrazide (0.58 g, 7.85 mmol), and the mixture was stirred for 12 hours at 70° C. After powderization by diisopropyl ether/methanol, the crude Compound 10 (1.79 g) was filtrated. The crude Compound 10 was used to next reaction without purification. Compound 10 (1.79 g, 1.64 mmol) was dissolved into tetrahydrofuran (10 mL), DMF (5 mL) and water (1.25 mL) and added PPTS (2.05 g, 8.19 mmol), and the mixture was stirred for an hour at room temperature. The reaction was quenched by trimethylamine (1.36 mL, 9.82 mmol). After concentration, the mixture was oil-outed by adding diisopropyl ether. The mixture was dissolved into chloroform and methanol. After aminosilica-gel was added, the mixture was purified by silica-gel column chromatography (aminosilica-gel, chloroform/methanol/water=80/20/2) to give Compound 11 (295 mg, 17%). Compound 11 (295 mg, 0.27 mmol) was dissolved into DMF (3 mL) and added morpholine (0.24 mL, 2.7 mmol) and Pd(PPh$_3$)$_4$ (93 mg, 0.091 mmol), and the mixture was stirred for 2 hours at room temperature. After powderization by adding diisopropyl ether/methanol (10/1), Compound I-19 (160 mg, 59%) was obtained by silica-gel column chromatography (chloroform/methanol/water=from 90/10/1 to 40/60/6).

LC-MS: m/z 995.5 [M+H]+

Elementary analysis: (C49H78N4O17)(C3H7NO)(H2O) 3.7

Calculated value: C 55.03; H, 8.21; N, 6.17 (%).
Actual value: C 54.97; H, 8.15; N, 6.53 (%).
Example 5
Synthesis of Compound I-36
[Chemical Formula 43]
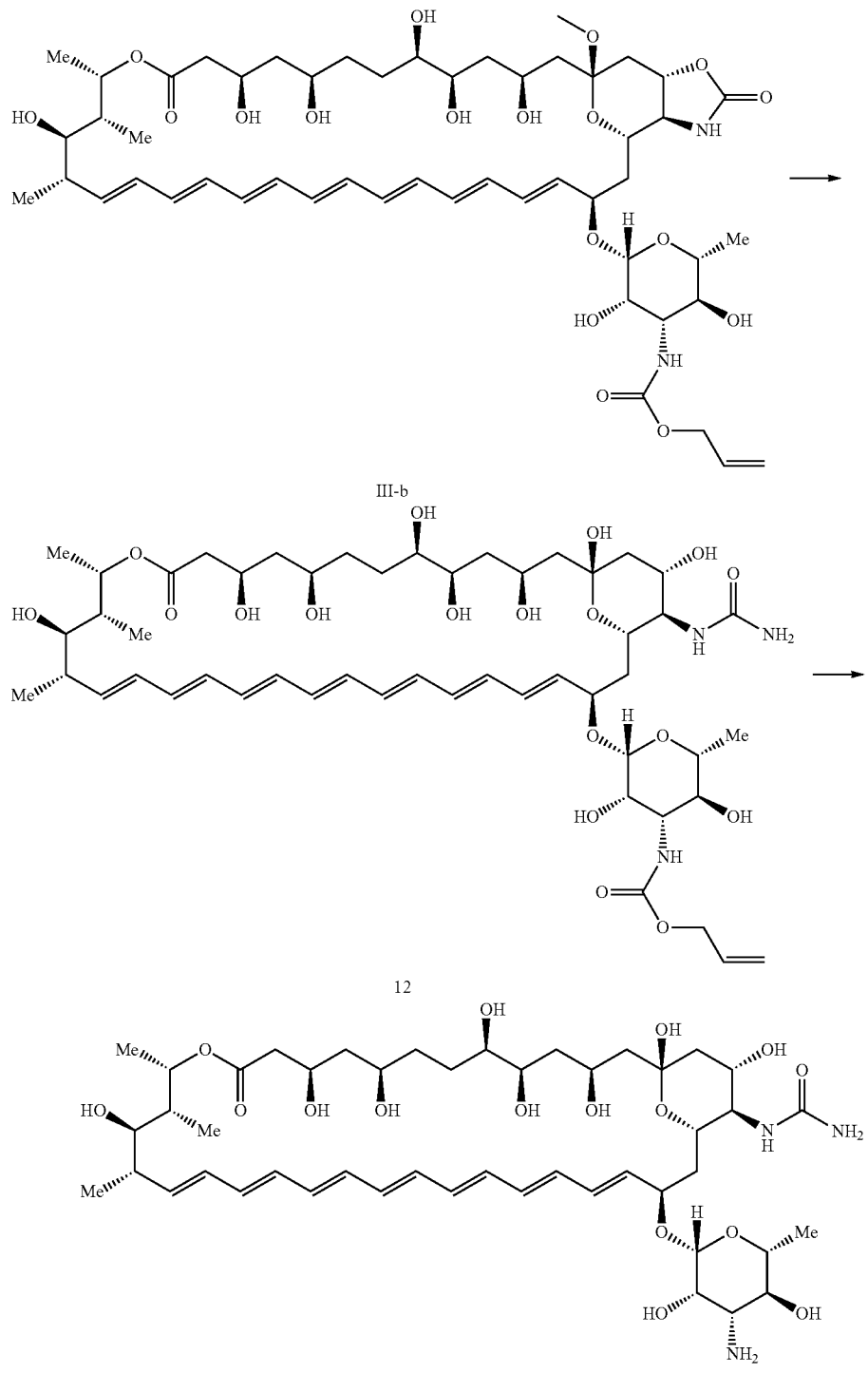

Step 1

Compound III-b (3.08 g, 1.87 mmol) was dissolved into DMA (20 mL) and added ammonia (2 mol/L, methanol solution, 15 mL, 30 mmol), and the mixture was stirred for 3 hours 20 minutes at room temperature. Furthermore, ammonia (2 mol/L, methanol solution, 15 mL, 30 mmol) was added, and the mixture was stirred for 2 hours 30 minutes at 45° C. Diisopropyl ether/methanol (10/1, 400 mL) was added to the reaction mixture to give yellow powder (2.14 g). The resulting powder was dissolved into tetrahydrofuran (10 mL), DMF (5 mL) and water (2.5 mL) and added PPTS (0.778 g, 3.1 mmol), and the mixture was stirred for 5 hours at room temperature. The reaction mixture was quenched by adding trimethylamine (0.429 mL, 3.1 mmol). The reaction mixture was added to hexane/diethyl ether (1/1, 1 L) to give crude Compound 12 (1.84 g) by powderization. The retention time was 9.5 minutes by HPLC analysis (methanol/distilled water containing 0.1% PIC-B7=gradient from 70/30 to 100/0, flow speed 1 ml/min, wavelength of detection=385 nm).

Step 2

Compound 12 (1.844 g, 1.804 mmol) was dissolved into DMF (11 mL) and added DMF (11 mL), morpholine (0.47 mL, 0.54 mmol) and Pd(PPh₃)₄ (104 mg, 0.009 mmol), and the mixture was stirred for 2 hours at room temperature. After powderization by adding diisopropyl ether, the mixture was purified by reverse-phase chromatography (HP20ss, hydrochloric acid aq (0.5 mM)/acetonitrile=100/0 to 70/30). After lyophilization, Compound I-36 (126 mg, 8%) was obtained. The retention time was 6.7 minutes by HPLC analysis (methanol/distilled water containing 0.1% PIC-B7=gradient from 70/30 to 100/0, flow speed 1 ml/min, wavelength of detection=385 nm).

LC-MS: m/z 938.5 [M+H]+

Elementary analysis: (C47H75N3O16)(HCl)0.7(H2O)6
Calculated value: C 52.67; H, 8.25; N, 3.92; Cl, 2.32.
Actual value: C 52.97; H, 8.01; N, 4.01; Cl, 2.62.

Example 6

Synthesis of Compound I-40

[Chemical Formula 44]

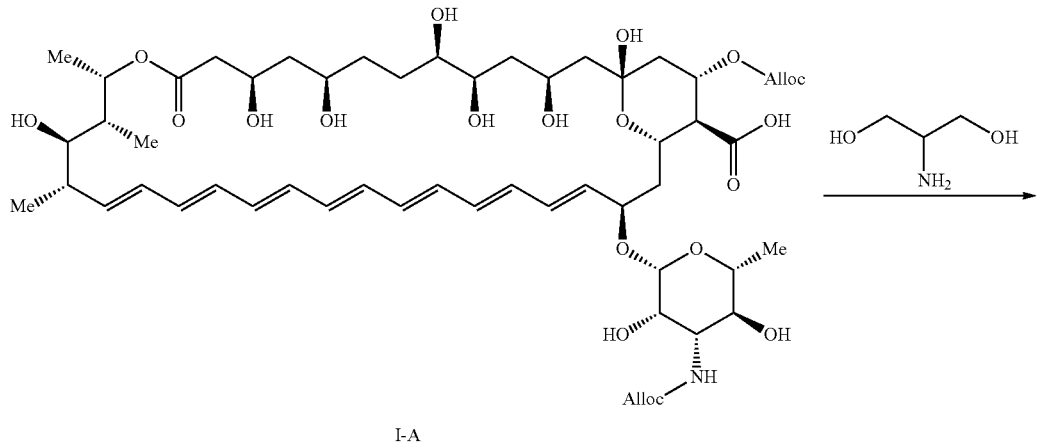

I-A

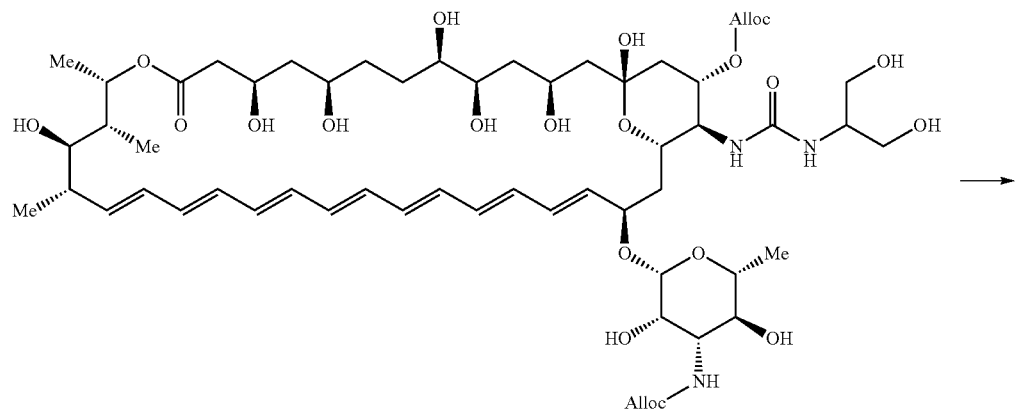

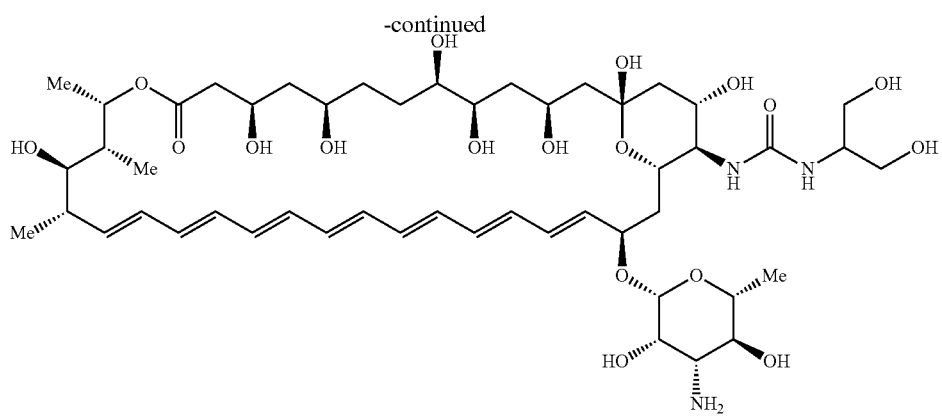

I-40

Compound I-A (1 g, 0.916 mmol) was dissolved into DMA (10 mL) and added DIEA (0.24 mL, 1.37 mmol) and diphenylphosphoryl azide (0.295 mL, 1.37 mmol), and the mixture was stirred for 3 hours at room temperature. After conversion to acid azide, curtius rearrangement was carried out by stirring for 30 minutes at 50° C. 2-aminopropane-1, 3-diol (250 mg, 2.75 mmol) was added and reacted against generated isocyanate in the reaction mixture, and the reaction mixture was stirred for 30 minutes. After the mixture was oil-outed by adding diisopropyl ether, the resulting residue was purified by silica-gel column chromatography (chloroform/methanol/water=95/5/0.5 to 50/50/5) to give Compound 13 (180 mg, 17%). Compound 13 (180 mg, 0.152 mmol) was dissolved into DMF (2 mL) and added morpholine (0.13 mL, 1.52 mmol) and Pd(PPh$_3$)$_4$ (17 mg, 0.015 mmol), and the mixture was stirred for 40 minutes at room temperature. Furthermore, Pd(PPh$_3$)$_4$ (17 mg, 0.015 mmol) was added, and the mixture was stirred for 20 minutes at room temperature. After powderization by adding diisopropyl ether/methanol (10/1), the mixture was purified by silica-gel column chromatography (amino silica-gel, chloroform/methanol/water=90/10/1 to 50/50/5) to give Compound I-40 (76 mg, 49%).

LC-MS: 1012.4 [M+H]+, 1034.5 [M+Na]+

Elementary analysis: C50H81N3O18(C3H7NO)1.3 (H2O)4.1

Calculated value: C 54.81; H, 8.39; N, 5.10 (%).

Actual value: C 54.85; H, 8.34; N, 5.08 (%).

Example 7

Synthesis of Compound I-59

[Chemical Formula 45]

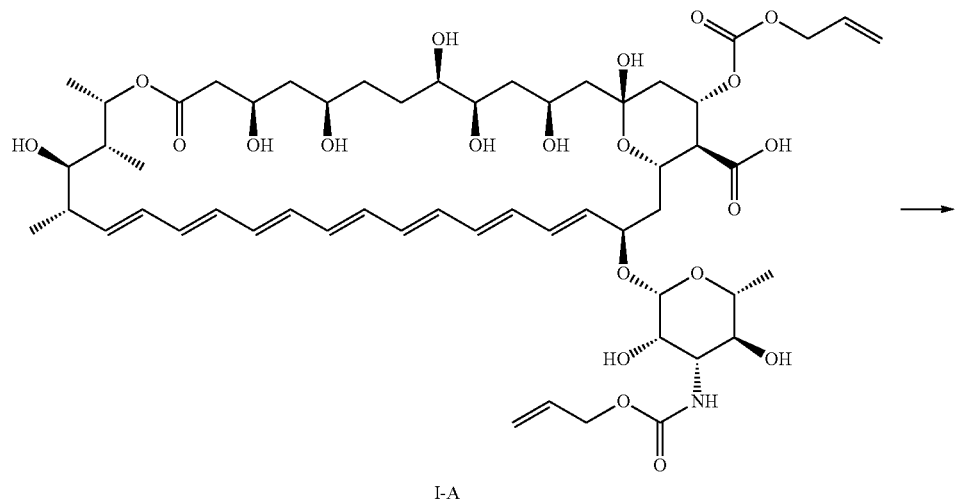

I-A

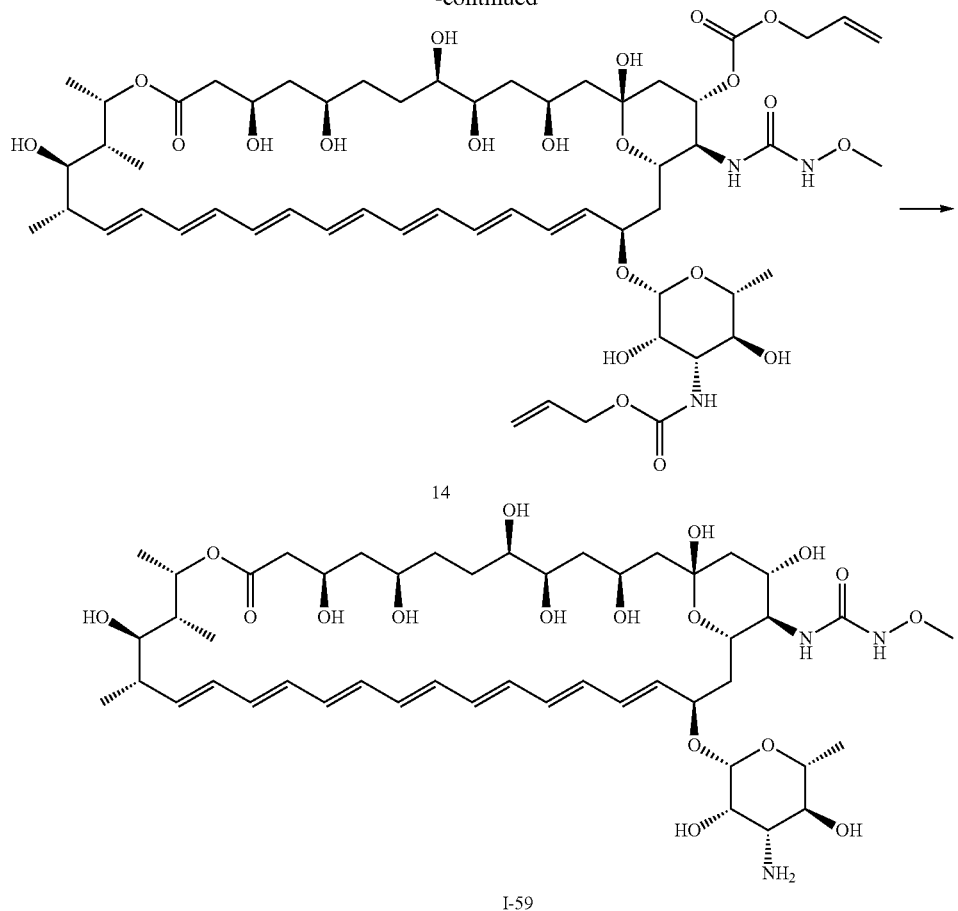

I-59

Step 1

Compound I-A (500 mg, 0.458 mmol) was dissolved into DMF (1.5 mL) and added DIEA (0.096 mL, 0.549 mmol) and diphenylphosphoryl azide (0.118 mL, 0.549 mmol), and the mixture was stirred for 2 hours 10 minutes at room temperature, in addition, stirred for 40 minutes at 50° C. O-Methylhydroxylamine hydrochloride (76 mg, 0.916 mmol) and DIEA (0.19 mL, 1.1 mmol) were added, and the mixture was stirred for 80 minutes at 50° C. After the mixture was oil-outed by adding diisopropyl ether, the resulting residue was purified by silica-gel column chromatography (chloroform/methanol/water=95/5/0.5 to 85/15/1.5, containing 0.2% triethylamine) to give Compound 14 (163 mg, 17%).

LC-MS: 1158.5 [M+Na]+

Step 2

Compound 14 (163 mg, 0.143 mmol) was dissolved into tetrahydrofuran (4 mL) and added water (0.4 mL). Morpholine (0.125 mL, 1.435 mmol) and Pd(PPh$_3$)$_4$ (8 mg, 0.007 mmol) were added, and the mixture was stirred for 2 hours at room temperature. After concentration, the mixture was evaporated in vacuo. The resulting residue was purified by silica-gel column chromatography to give Compound I-59 (60 mg, 43%).

LC-MS: m/z 968.5 [M+H]+

Elementary analysis: C48H77N3O17(H2O)3.5

Calculated value: C 55.91; H, 8.21; N, 4.07 (%).

Actual value: C 55.95; H, 8.13; N, 4.21 (%).

Example 8

Synthesis of Compound I-65

[Chemical Formula 46]

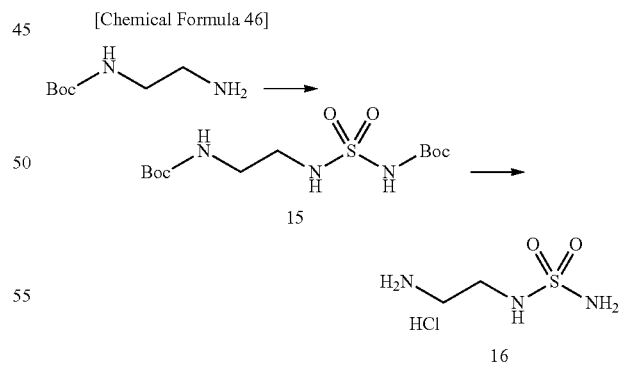

Tert-butanol (2.4 mL, 24.9 mmol) was dissolved into dichloromethane (20 mL) and cooled to −15° C. Chlorosulfonyl isocyanate (2.2 mL, 24.9 mmol) was added, and the mixture was stirred for 5 minutes at −15° C. as the solution A. The other side, tert-butyl 2-aminoethylcarbamate (2 g, 12.5 mmol) was dissolved into dichloromethane (20 mL) and added triethylamine (1.7 mL, 12.5 mmol) and cooled to −30° C. The solution A was added to the reaction mixture, the mixture was stirred for an hour at −15° C. by controlling inside temperature. After the reaction was quenched by saturated ammonium chloride aqueous solution, dichloromethane was removed by evaporating in vacuo, and the mixture was extracted by ethyl acetate. The organic phase was washed with brine and dried over with magnesium sulfate and filtrated. The mixture was condensed and filtrated to give Compound 15 (2.6 g, 61%). Compound 15 was dissolved into dichloromethane (20 mL) and added hydrochloric acid-dioxane (4 mol/L, 11.5 mL, 46 mmol), and the mixture was stirred for 4 hours at room temperature. The mixture was condensed to give Compound 16 (1.345 g, 7.66 mmol).

Compound I-A (2.5 g, 2.289 mmol) was dissolved into DMA (12 mL) and added DIEA (0.6 mL, 3.43 mmol) and diphenylphosphoryl azide (0.74 mL, 3.43 mmol), and the mixture was stirred for an hour at room temperature, furthermore, stirred for an hour at 50° C. The solution of 2-sulfamoylaminoethylamine hydrochloride (Compound 16, 1.345 g, 7.66 mmol) and DIEA (1.6 mL, 9.16 mmol) in DMA was added to the mixture, and the mixture was stirred for 30 minutes at room temperature. The mixture was oil-outed by adding diisopropyl ether and purified by silicagel column chromatography (chloroform/methanol/water=95/5/0.5 to 80/20/2) to give Compound 17 (250 mg, 9%). Compound 17 (250 mg) was dissolved into DMF (3

[Chemical Formula 47]

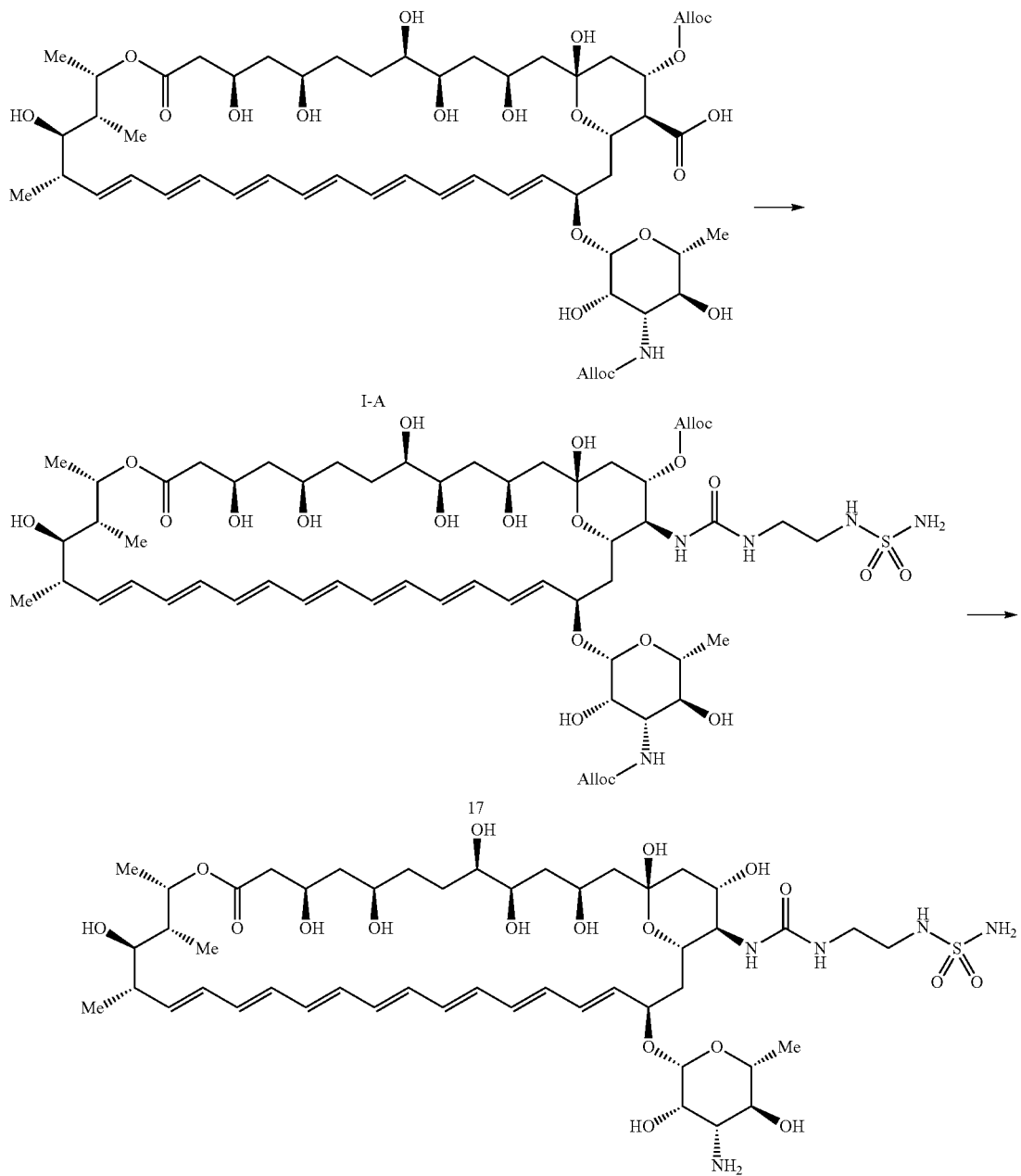

I-65 mL) and added morpholine (0.177 mL, 2.03 mmol) and Pd(PPh$_3$)$_4$ (24 mg, 0.02 mmol), and the mixture was stirred for an hour at room temperature. After powderization with diisopropyl ether/methanol (10/1), the resulted residue was purified by silica-gel column chromatography (amino silica-gel, chloroform/methanol/water=70/30/3 to 50/50/5) to give Compound I-65 (216 mg, 62%).

LC-MS: m/z 1060.5 [M+H]+, 1082.5 [M+Na]+ analysis: C49H81N5O18S(H2O)3.4(C3H7NO)0.4

Calculated value: C 52.40; H, 7.94; N, 6.57; S, 2.79 (%).
Actual value: C 52.40; H, 7.82; N, 6.60; S, 2.63 (%).

Example 9

Synthesis of Compound I-47

[Chemical Formula 48]

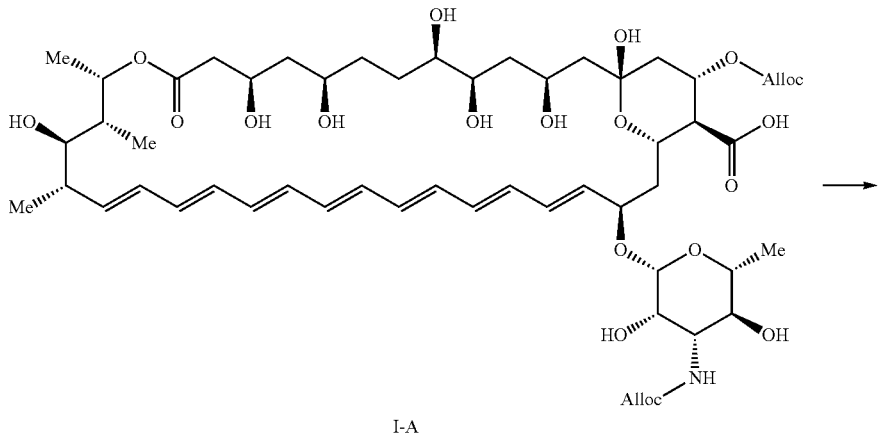

I-A

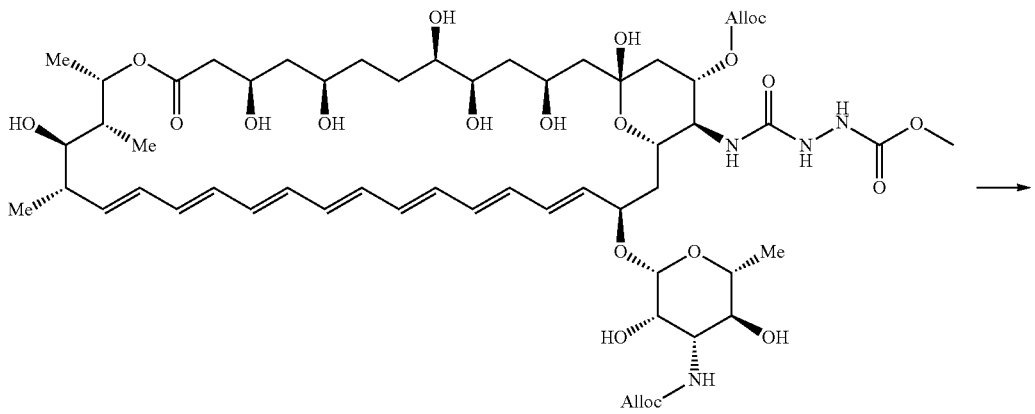

18

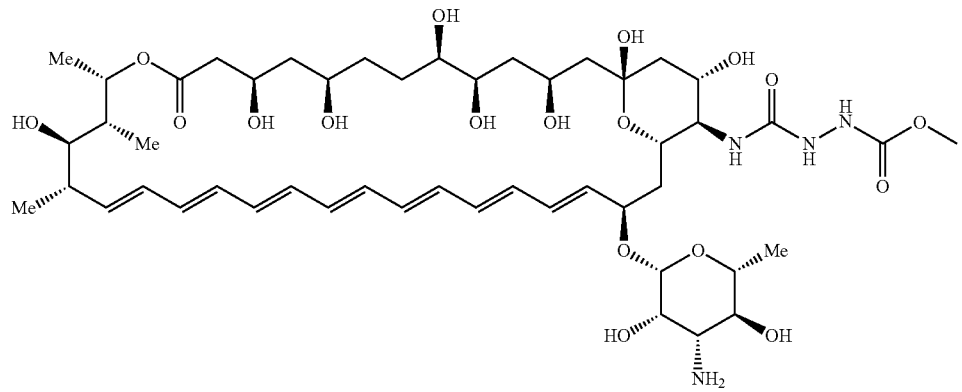

I-47

Compound I-A (1 g, 0.916 mmol) is dissolved into DMA (5 mL) and added DIEA (0.24 mL, 1.37 mmol) and diphenylphosphoryl azide (0.295 mL, 1.37 mmol), and the mixture was stirred for 40 minutes at room temperature, furthermore, stirred for an hour at 50° C. Methoxycarbonylhydrazine (247 mg, 2.75 mmol) was added, and the mixture was stirred for 2 hours at room temperature. The mixture was oil-outed with diisopropyl ether and purified by silica-gel column chromatography (chloroform/methanol/water=95/5/0.5 to 80/20/2) to give Compound 18 (311 mg, 29%). Compound 18 (311 mg, 0.264 mmol) was dissolved into DMF (5 mL) and added morpholine (0.46 mL, 5.2 mmol) and Pd(PPh$_3$)$_4$ (61 mg, 0.052 mmol), and the mixture was stirred for an hour at room temperature. After powderization with diisopropyl ether/methanol (10/1), the resulted residue was purified by silica-gel column chromatography (amino silica-gel, chloroform/methanol/water=70/30/3 to 50/50/5) to give Compound I-47 (89 mg, 33%).

LC-MS: m/z 1011.4 [M+H]+, 1033.4 [M+Na]+

Elementary analysis: (C49H78N4O18)(C3H7NO)(H2O)4

Calculated value: C 54.01; H, 8.11; N, 6.06 (%).

Actual value: C 54.00; H, 8.02; N, 6.22 (%).

Example 10

Synthesis of Compound I-78

[Chemical Formula 49]

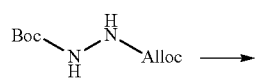

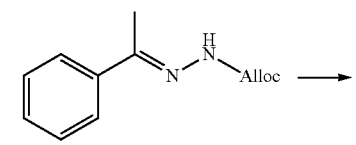

19

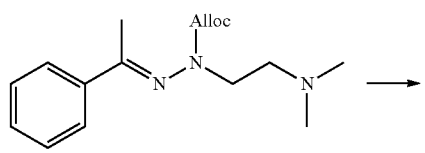

20

-continued

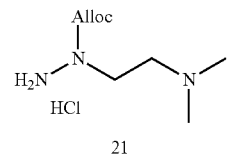

21

Step 1 Synthesis of Compound 19

1-Allyl 2-tert-butyl hydrazine-1,2-dicarboxylate (8.06 g, 37.3 mmol) was dissolved into dichloromethane (100 mL) and added hydrochloride-dioxane (4 mol/L, 28 mL), the mixture was stirred for 4 hours at room temperature. The resulted precipitate was filtrated to give Alloc hydrazine hydrochloride (5.2 g, 91%). The resulted Alloc hydrazine hydrochloride (4 g, 26.2 mmol) was dissolved into ethanol and added acetophenone (4.6 mL, 39.3 mmol), and the mixture was stirred for 6 hours under heat reflux. After evaporating in vacuo, ethyl acetate and water were added, and the mixture was extracted with ethyl acetate. After the organic phase was washed with saturated sodium hydrogen carbonate aqueous solution, the organic phase was dried out with magnesium sulfate and filtrated and condensed. The resulted solids were washed with hexane to give Compound 19 (3.2 g, 56%).

Step 2 Synthesis of Compound 20

Compound 19 (1.9 g, 8.71 mmol) was dissolved into tetrahydrofuran (40 mL). After sodium hydride (60%, 3.48 g, 87 mmol) was added in an ice-water bath, 2-bromoethyldimethylamine (7.94 g, 52.2 mmol) was added, and the mixture was stirred for 6 days. After the reaction was quenched by adding water, the reaction was extranced with dichloromethane. After the organic phase was washed with brine, the organic phase was dried up with magnesium sulfate and filtrated and condensed. The resulted residue was purified by column chromatography to give Compound 20 (2.17 g, 86%).

Step 3 Synthesis of Compound 21

Compound 20 (2.16 g, 7.46 mmol) was dissolved into dichloromethane (10 mL) and methanol (2 mL) and added hydrochloric acid-dioxane (4 mol/L, 5.6 mL). After the mixture was stirred, the mixture was condensed. After the resulted residue was dissolved into methanol, the mixture was oil-outed by adding diisopropyl ether to give crude Compound 21 (1.43 g). The crude Compound 21 was used to next reaction without purification.

[Chemical Formula 50]

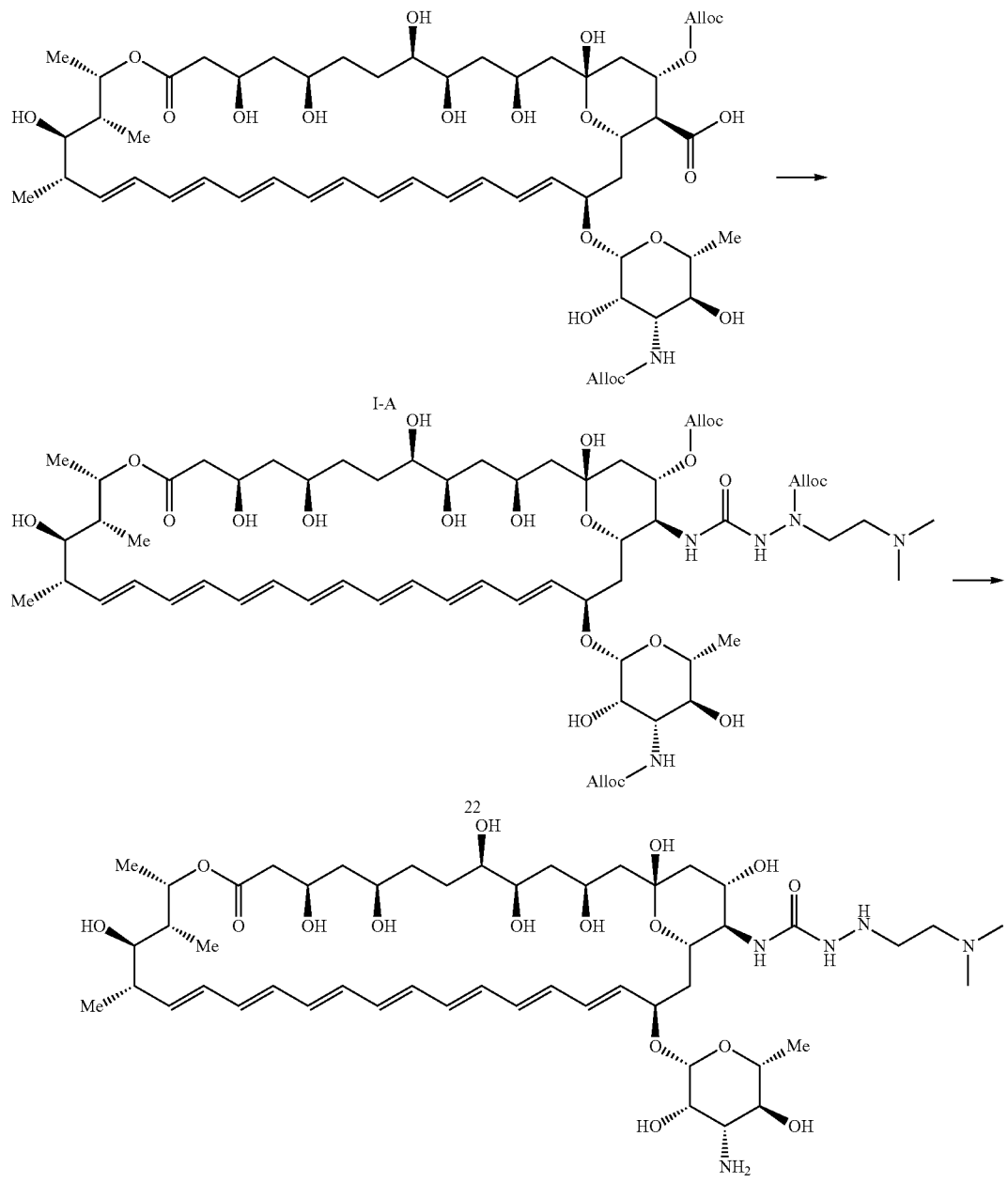

Compound I-A (2 g, 1.83 mmol) was dissolved into DMA (5 mL) and added DIEA (0.48 mL, 2.75 mmol) and diphenylphosphoryl azide (0.591 mL, 2.75 mmol), the mixture was stirred for 2 hours 30 minutes at room temperature, furthermore, stirred with heat for 2 hours at 50° C. DIEA (1.92 mL, 10.99 mmol) and allyl 1-(2-(dimethylamino)ethyl)hydrazine-1-carboxyrate hydrochloride 21 (1.43 g, 5.49 mmol) were added, and the mixture was stirred for 50 minutes at room temperature. The mixture was oil-outed by adding diisopropyl ether. The resulted gummy solids was purified by silica-gel column chromatography (chloroform/methanol/water=95/5/0.5 to 80/20/2) to give Compound 22 (960 mg, 41%). Compound 22 (960 mg, 0.752 mmol) was dissolved into DMF (10 mL) and added morpholine (0.65 mL, 7.52 mmol) and Pd(PPh$_3$)$_4$ (87 mg, 0.0075 mmol), and the mixture was stirred for 90 minutes at room temperature. After powderization with diisopropyl ether, the resulted powder was purified by silica-gel column chromatography (amino silica-gel, chloroform/methanol/water=70/30/3 to 20/80/8) to give Compound I-78 (156 mg, 20%).

LC-MS: m/z 1024.5 [M+H]+

Elementary analysis: C51H85N5O16(C3H7NO)0.7(H2O)3.4

Calculated value: C 56.11; H, 8.57; N, 7.02 (%).

Actual value: C 56.12; H, 8.45; N, 7.02 (%).

Example 11

Synthesis of Compound I-70

[Chemical Formula 51]

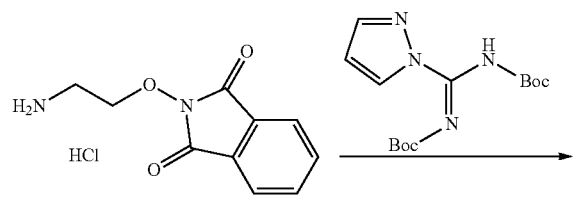

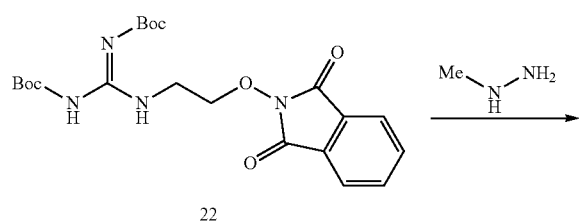

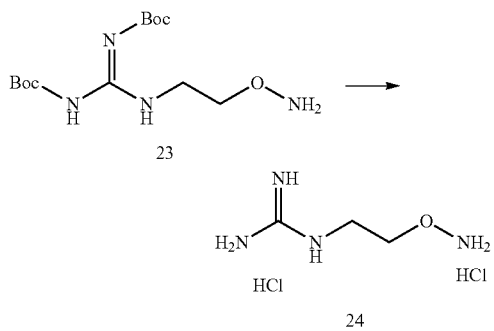

Step 1 Synthesis of Compound 22

2-(2-Aminoethoxy)isoindoline-1,3-dione hydrochloride (717 mg, 2.95 mmol) was dissolved into tetrahydrofuran (10 mL) and added DIEA (0.542 mL, 3.10 mmol) and N,N'-Di-Boc-1H-pyrazole-1-carboxamidine (963 mg, 3.10 mmol), the mixture was stirred for 30 minutes at room temperature. After adding DMF (10 mL), the mixture was stirred for 20 hours, further, stirred for 3 hours 40 minutes at 60° C. The reaction was quenched with saturated sodium bicarbonate aqueous solution, and the mixture was extracted with ethyl acetate. The organic phase was washed with water and brine, and dried up with sodium sulfate anhydrous and filtrated and condensed. The resulted residue was purified by silica-gel column chromatography (hexane/ethyl acetate=3/1) to give Compound 22 (856 mg, 65%, white frothy solid).

TLC: Rf=0.3 (hexane/ethyl acetate=3/1)

Step 2 Synthesis of Compound 23

Compound 22 (427 mg, 0.952 mmol) was dissolved into dichloromethane (5 mL) and added methylhydrazine (0.053 mL, 1.00 mmol), and the mixture was stirred for 4 hours 40 minutes at room temperature. After the resulted white solids were removed by filtration, the resulted filtrate was condensed to give white oily liquid. The resulted liquid was purified by silica-gel column chromatography (hexane/ethyl acetate=3/1 to 1/1) to give Compound 23 (180 mg, 59%, colorless and transparent liquid).

TLC: Rf=0.3 (hexane/ethyl acetate=1/1)

LC-MS: 319.4 [M+H]+

Step 3 Synthesis of Compound 24

Compound 23 (180 mg, 0.565 mmol) was dissolved into hydrochloric acid-dioxane (4 mol/L, 1.4 mL), and the mixture was stirred for an hour 40 minutes at room temperature. After confirming disappearance of raw materials by TLC, the solvent was removed by evaporating in vacuo. The resulted gummy solids were washed with hexane and dried up in vacuo to give Compound 24 (182 mg). The compound 24 was used to next reaction without purification.

[Chemical Formula 52]

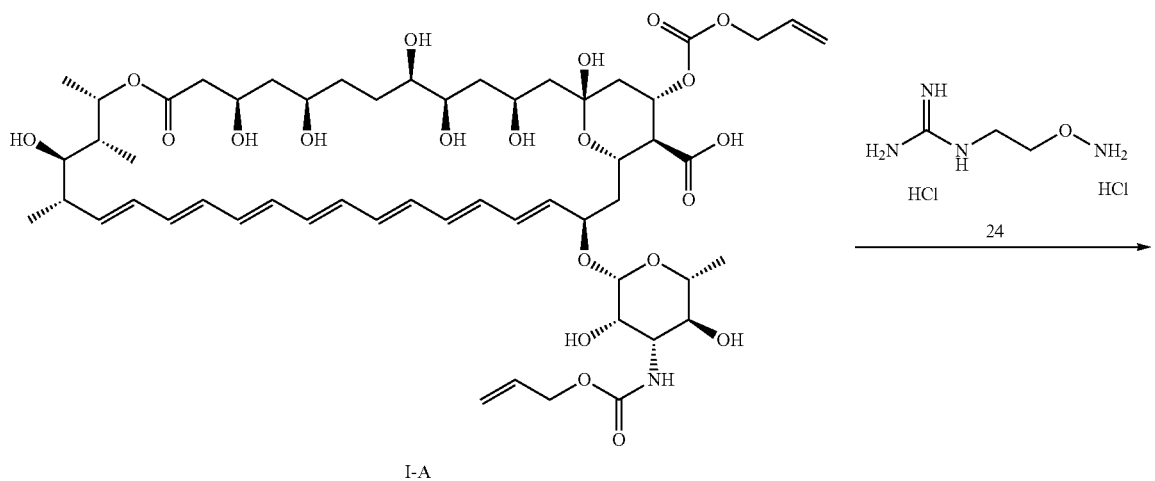

I-A

-continued

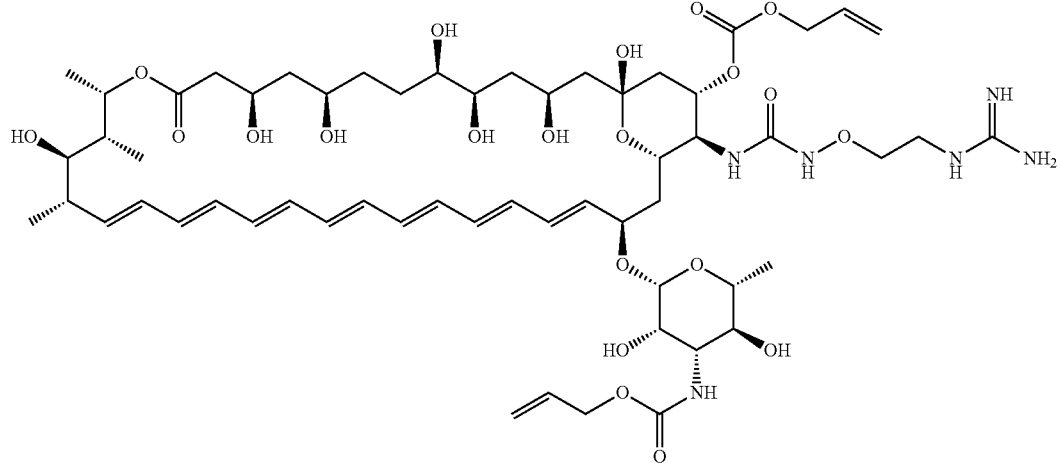

25

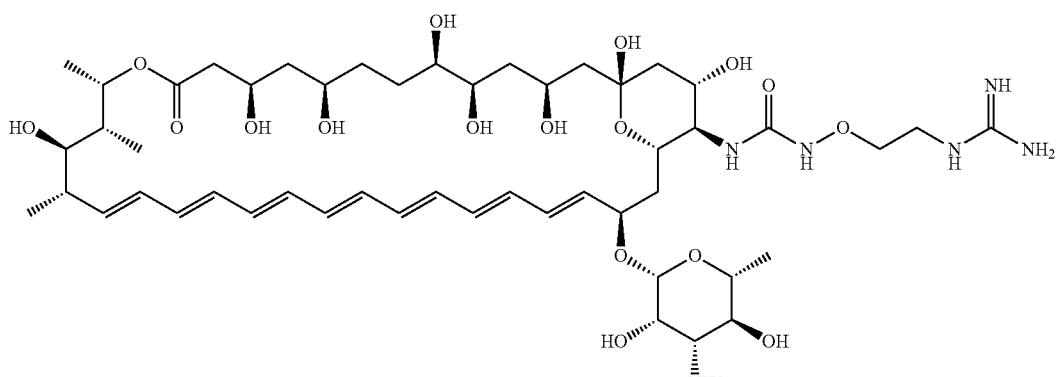

I-70

Step 1 Synthesis of Compound 25

Compound I-A (500 mg, 0.458 mmol) was dissolved into DMF (2 mL) and added DIEA (0.088 mL, 0.504 mmol) and diphenylphosphoryl azide (0.108 mL, 0.504 mmol), the mixture was stirred for 90 minutes at room temperature, further, stirred for 30 minutes at 50° C. DIEA (0.088 mL, 0.504 mmol) and 2-guanidinylethyloxyamine dihydrochloride (Compound 24, 163 mg, 0.504 mmol) were added, the mixture was stirred for an hour 40 minutes at 50° C. The mixture was oil-outed by adding diisopropyl ether and dried up by evaporating in vacuo. The resulted residue was purified by silica-gel column chromatography (chloroform/methanol/water=90/10/1 to 85/15/1.5) to give Compound 25 (209 mg, 38%).

LC-MS: m/z 1208.6 [M+H]+

Step 2 Synthesis of Compound I-70

Compound 25 (200 mg, 0.166 mmol) was dissolved into DMF (5 mL) and morpholine (0.10 mL, 1.16 mmol) and Pd(PPh$_3$)$_4$ (19.1 mg, 0.017 mmol) were added, and the mixture was stirred for 2 hours at room temperature. After powderization with diisopropyl ether, the resulted residue was purified by reverse-phase chromatography (HP20ss, acetonitrile/aqueous solution containing 0.05% formic acid=10/90 to 30/70) to give Compound I-70 (37 mg, 21%).

LC-MS: m/z 1039.5 [M+H]+

Example 12

Synthesis of Compound I-99

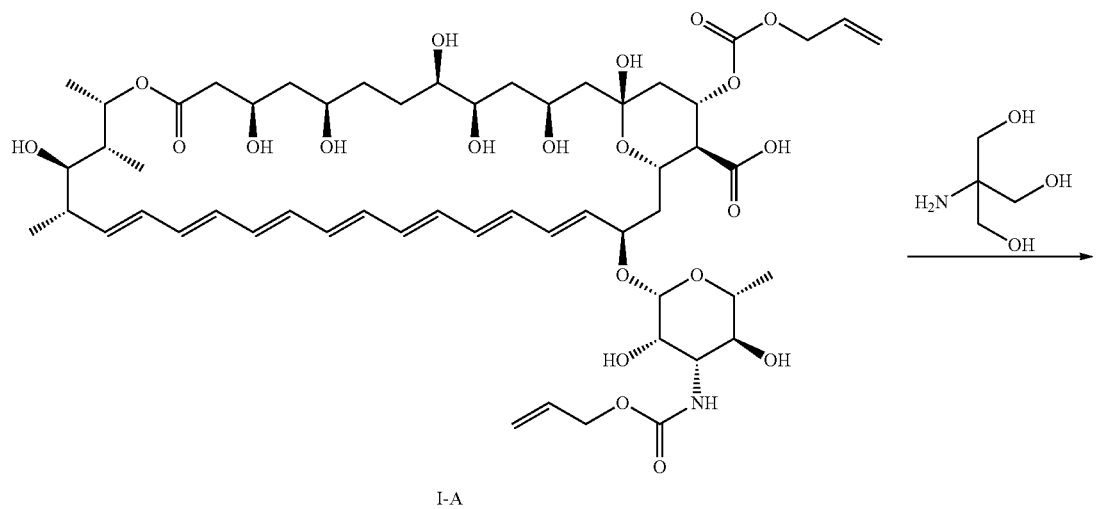

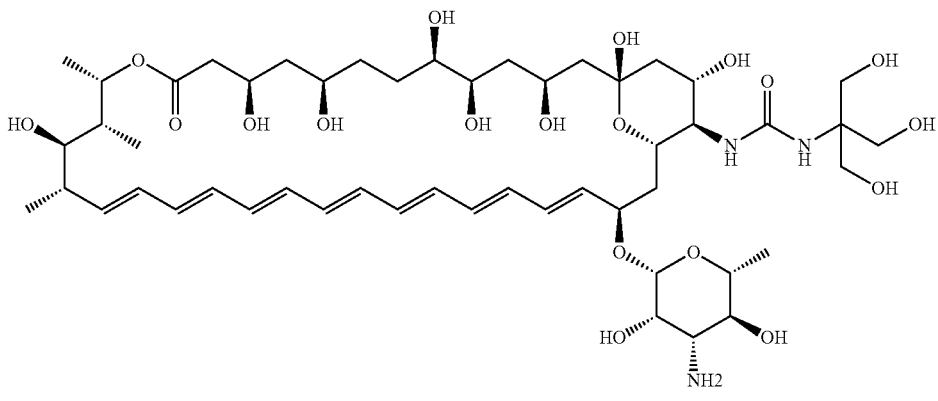

Compound I-A (1 g, 0.916 mmol) was dissolved into DMF (8 mL) and added DIEA (0.24 mL, 1.373 mmol) and diphenylphosphoryl azide (0.295 mL, 1.373 mmol), and the mixture was stirred for 2 hours at room temperature. 2-amino-2-(hydroxymethyl)propane-1,3-diol (222 mg, 1.831 mmol) was added, and the mixture was stirred for 30 minutes at 50° C. The mixture was oil-outed by adding diisopropyl ether, and the resulted residue was dried out by evaporating in vacuo. The resulted residue was purified by silica-gel column chromatography (chloroform/methanol/water=70/30/3) to give yellow powder (262 mg, 24%).

LC-MS: m/z 1211.2 [M+H]+

The resulted yellow powder was dissolved into DMF (5 mL) and morpholine (0.19 mL, 2.17 mmol) and Pd(PPh$_3$)$_4$ (25 mg, 0.022 mmol) were added, and the mixture was stirred for an hour at room temperature. After powderization with diisopropyl ether, the resulted powder was purified by silica-gel column chromatography (amino silica-gel, chloroform/methanol/water=60/40/4) to give Compound I-99 (110 mg, 48%).

LC-MS: m/z 1042.5 [M+H]+

Elementary analysis: (C51H83N3O19)(C3H7NO)0.9 (H2O)2

Calculated value: C 56.38; H, 8.22; N, 4.77 (%).

Actual value: C 56.16; H, 8.22; N, 5.08 (%).

Example 13

Synthesis of Compound I-101

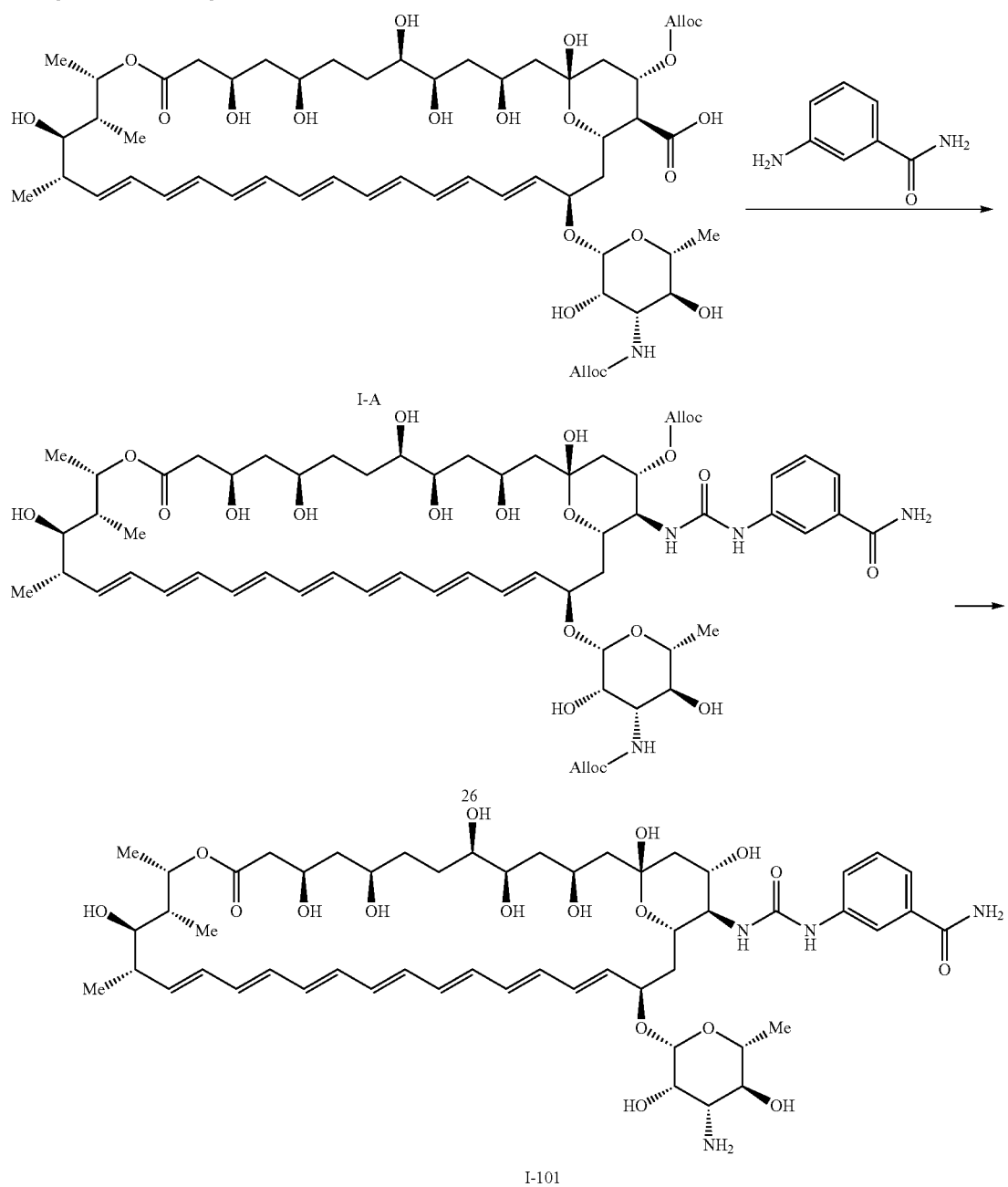

Compound I-A (1 g, 0.916 mmol) was dissolved into DMA (5 mL) and added DIEA (0.24 mL, 1.37 mmol) and diphenylphosphoryl azide (0.295 mL, 1.37 mmol), and the mixture was stirred for an hour at room temperature, further stirred for 2 hours at 50° C. 3-Aminobenzamido (374 mg, 2.753 mmol) and Bis tributyltin oxide (0.465 mL, 0.915 mmol) were added, and the mixture was stirred for 2 hours. The resulted residue by decantation adding diisopropyl ether was purified by silica-gel column chromatography (CHCl$_3$/MeOH/H$_2$O=80/20/2) to give Compound 26 (160 mg, 14%). Compound 26 (160 mg, 0.131 mmol) was dissolved into DMF (5 mL) and added morpholine (0.114 mL, 1.31 mmol) and Pd(PPh$_3$)$_4$ (15 mg, 0.013 mmol), and the mixture was stirred for 20 minutes at room temperature. After powderization by adding diisopropyl ether, the resulted powder was purified by silica-gel column chromatography (amino silica-gel, chloroform/methanol/water=90/10/1 to 70/30/3) to give Compound I-101 (59 mg, 43%).

LC/MS: m/z 1057.6 [M+H]+

Elementary analysis: C54H80N4O17(C3H7NO)0.4 (H2O)3.7

Calculated value: C 57.50; H, 7.88; N, 5.34 (%).

Actual value: C 57.46; H, 7.83; N, 5.37 (%).

Example 14

Synthesis of Compound I-41

[Chemical Formula 55]

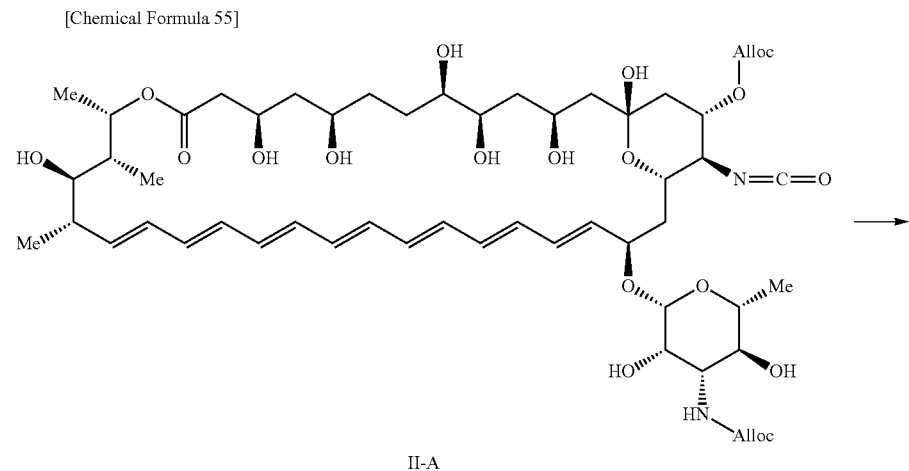

II-A

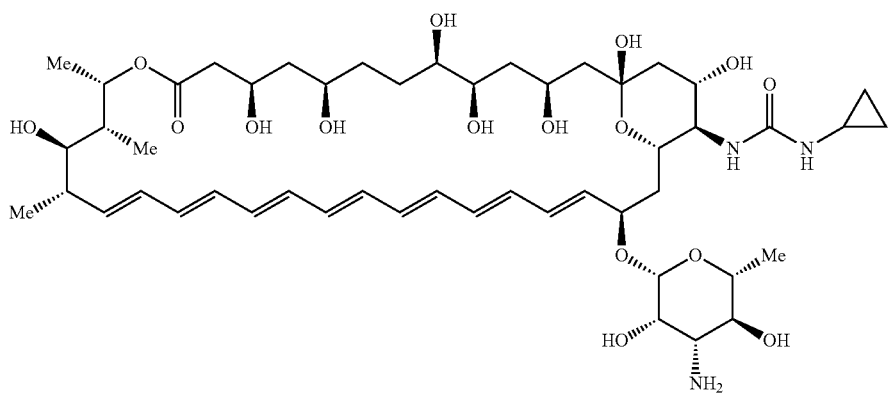

I-41

Compound II-A (3 g, 2.75 mmol) was dissolved into DMF (10 mL) and added cyclopropaneamine (157 mg, 2.75 mmol), the mixture was stirred for 2 hours at room temperature. The mixture was oil-outed with diisopropyl ether. The resulted residue was purified by silica-gel column chromatography (chloroform/methanol=70/30) to give Compound 14 (1 g, 31%). Compound 14 (1 g) was dissolved into DMF (5 mL) and added morpholine (0.76 mL, 8.72 mmol) and Pd(PPh$_3$)$_4$ (50 mg, 0.044 mmol), the mixture was stirred for an hour at room temperature. After powderization by adding diisopropylether/methanol (10/1), the resulted powder was purified by silica-gel column chromatography (amino silica-gel, chloroform/methanol/water=70/30/3 to 30/70/7) to give Compound I-41 (159 mg, 19%).

LC-MS: m/z 978.3 [M+H], 1000.4 [M+Na]+

Elementary analysis: C50H79N3O16(C3H7NO)0.7 (H2O)2.2, [C52.1H88.3N3.7O18.9]

FW: 1068.97

Calculated value: C 58.54; H, 8.33; N, 4.85 (%).

Actual value: C 58.52; H, 8.25; N, 4.83 (%).

Example 15

Synthesis of Compound I-5

[Chemical Formula 56]

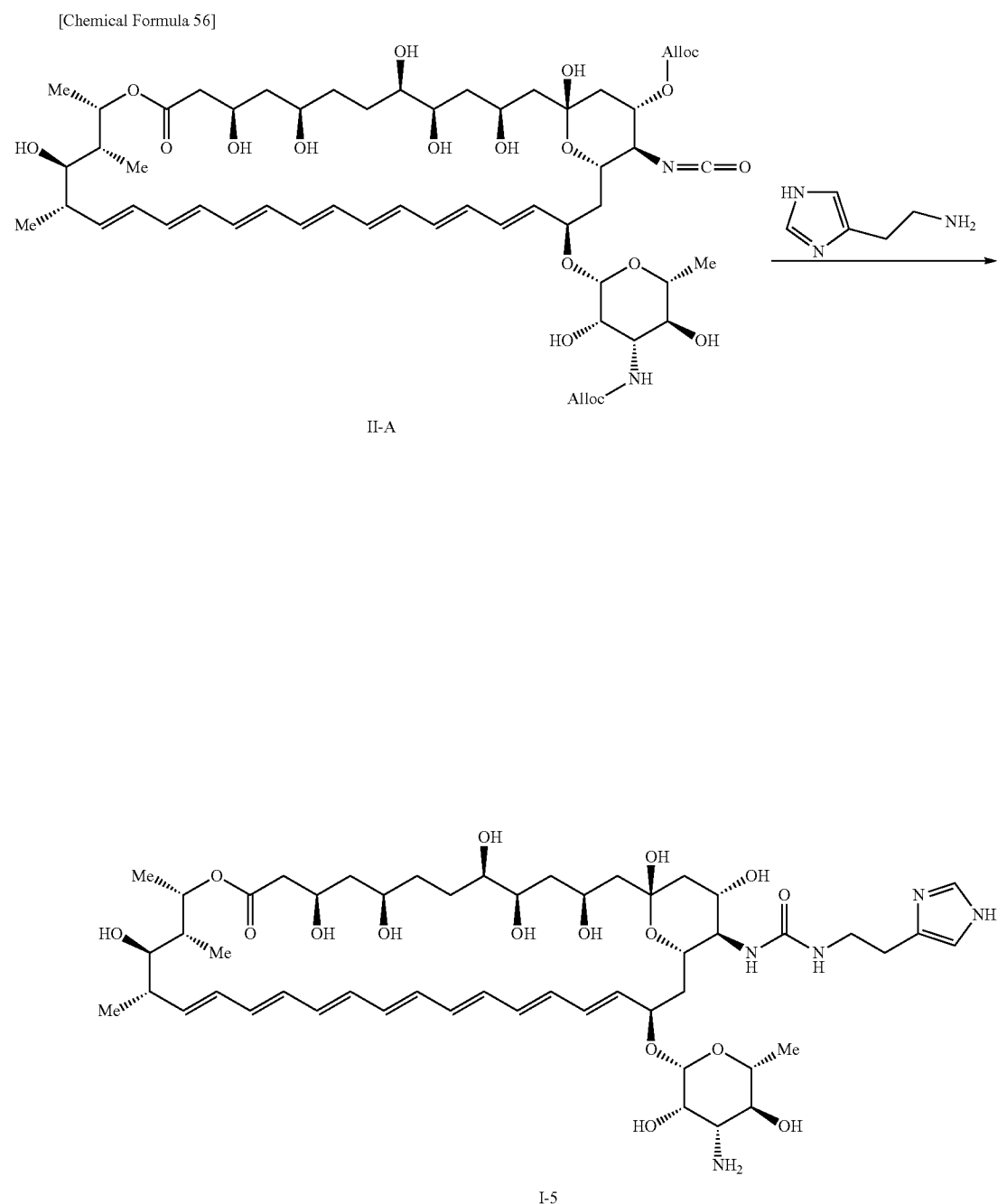

Compound II-A (6 g, 5.5 mmol) was dissolved into DMA and added histamine (918 mg, 8.26 mmol), and the mixture was stirred for a few hours at room temperature. After the mixture was oil-outed with diisopropyl ether, the resulted residue was purified by silica-gel column chromatography. The resulted powder (1.12 g) was dissolved into DMA (8 mL) and added morpholine (0.81 mL, 9.3 mmol) and Pd(PPh$_3$)$_4$ (54 mg, 0.047 mmol), and the mixture was stirred for 20 minutes under nitrogen atmosphere. After powderization, the resulted residue was purified by silica-gel column chromatography (amino silica-gel, chloroform/methanol/water) to give Compound I-5 (370 mg, 6%).

LC-MS: m/z 1032.5 [M+H]+

Elementary analysis: C52H81N5O16(C3H7NO)0.2 (H2O)2.5

Calculated value: C 57.86; H, 8.07; N, 6.67 (%).

Actual value: C 57.87; H, 8.07; N, 6.71 (%).

Example 16

Synthesis of Compound I-56

[Chemical Formula 57]

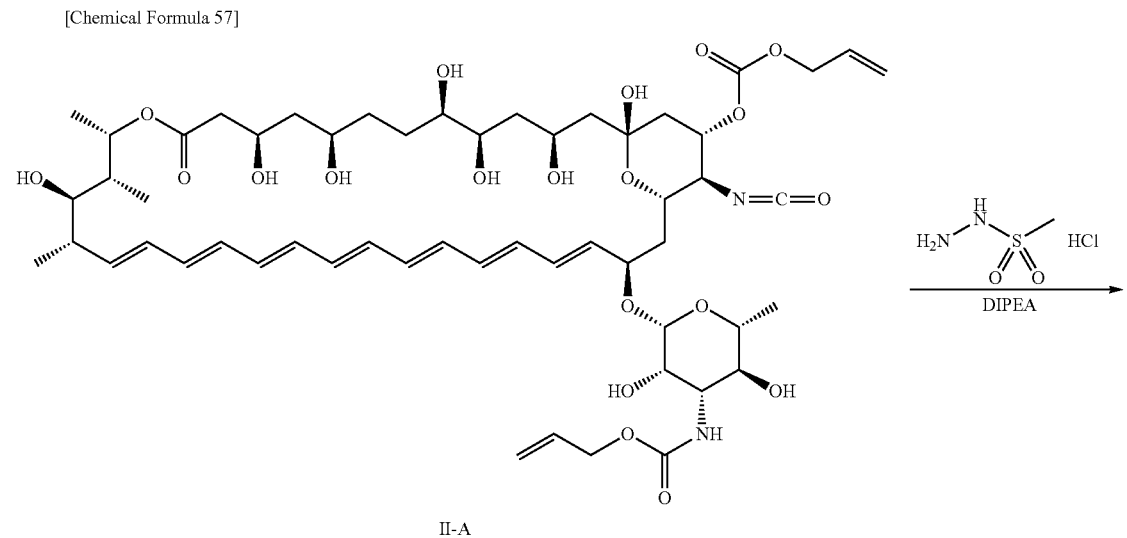

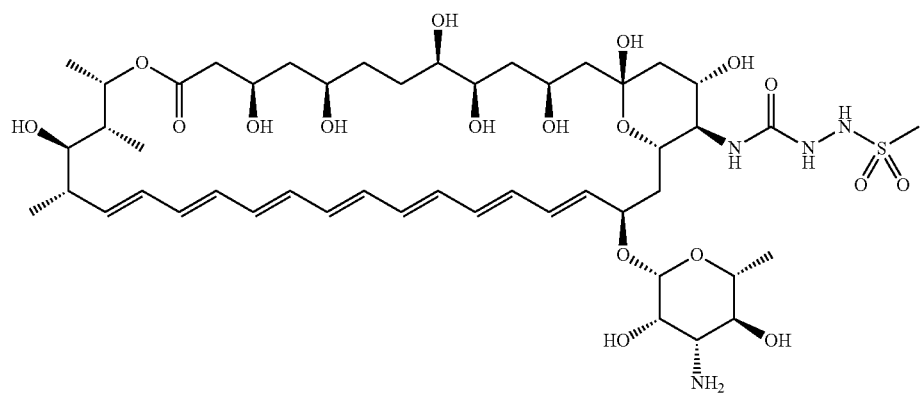

Compound II-A (13.1 g, 12.03 mmol) was dissolved into DMF (65 mL) and added methanesulfonylhydrazine hydrochloride (2.645 g, 18.04 mmol) and DIEA (6.3 mL, 36.1 mmol), and the mixture was stirred for 4 hours 25 minutes at room temperature. After the mixture was oil-outed with diisopropyl ether, the resulted residue was purified by silica-gel column chromatography (chloroform/methanol/water) to give yellow powder (1.05 g, 0.875 mmol). The yellow powder was dissolved into DMF (10 mL) and added morpholine (0.53 mL, 6.13 mmol) and Pd(PPh$_3$)$_4$ (51 mg, 0.044 mmol), and the mixture was stirred for 2 hours at room temperature. After the mixture was powderization with diisopropyl ether, the mixture was purified by silica-gel column chromatography (amino silica-gel, chloroform/methanol/water=50/50/5) to give Compound I-56 (284 mg, 0.062 mmol).

LC-MS: m/z 1031.5 [M+H]+

Elementary analysis: C48H78N4O18S(C3H7NO)0.1 (H2O)1.5

Calculated value: C 54.44; H, 7.73; N, 5.39 (%).

Actual value: C 54.46; H, 7.69; N, 5.37 (%).

Example 17

Synthesis of Compound I-60

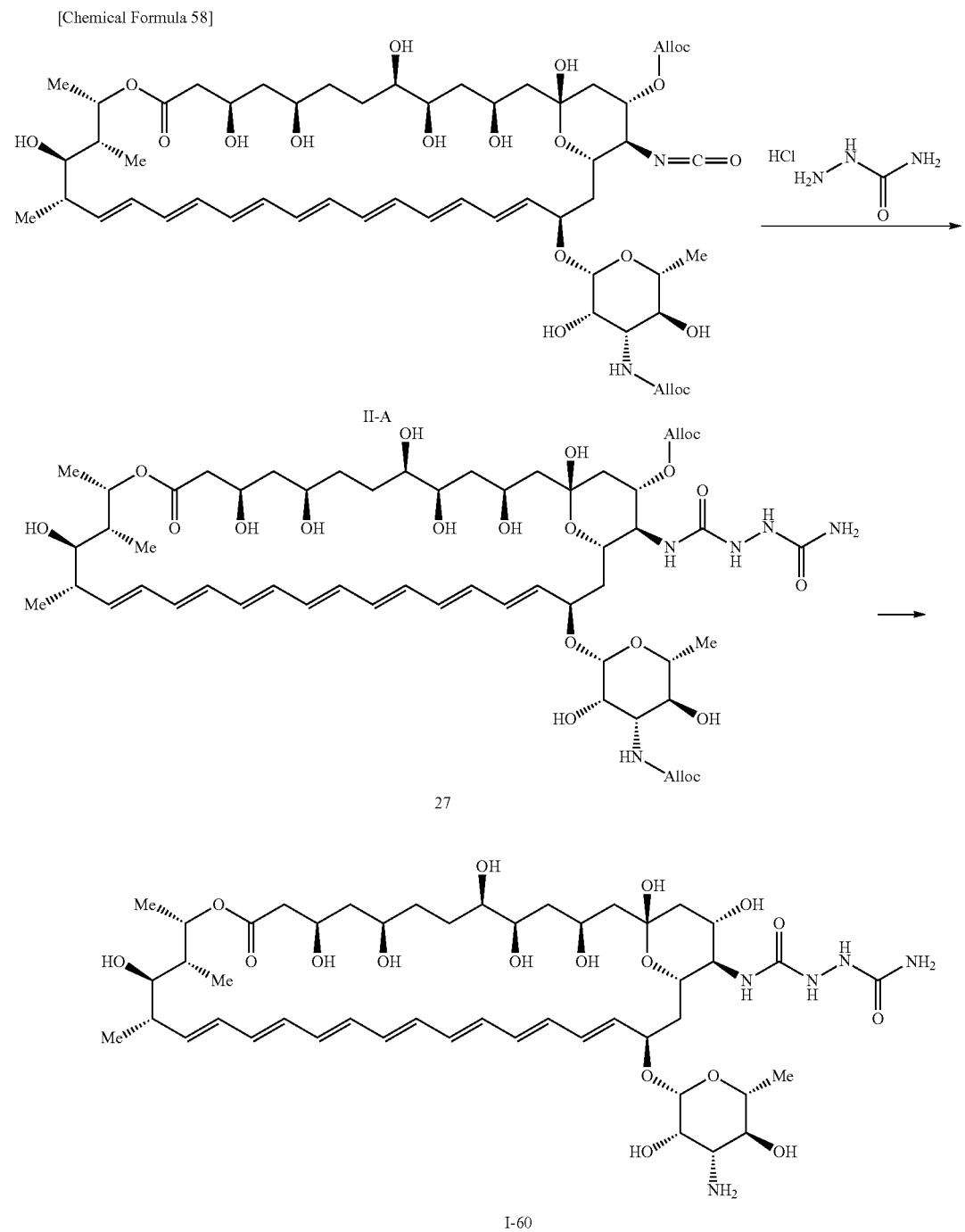

Compound II-A (17.8 g, 16.3 mmol) was dissolved into DMA (54 mL) and added DIEA (4.3 mL, 24.5 mmol) and hydrazinecarboxyamide hydrochloride (1.82 g, 16.3 mmol), and the mixture was stirred for an hour at room temperature. After the mixture was oil-outed with diisopropyl ether, the resulted residue was purified by silica-gel column chromatography (chloroform/methanol=92/8 to 70/30) to give Compound 27 (5.56 g, 19%). Compound 27 (5.56 g, 4.78 mmol) was dissolved into DMF (30 mL) and added morpholine (2.5 mL, 28.7 mmol) and Pd(PPh$_3$)$_4$ (166 mg, 0.143 mmol), the mixture was stirred for 30 minutes at room temperature. After the mixture was powderization with diisopropyl ether/methanol (10/1), the mixture was purified by silica-gel column chromatography (amino silica-gel, chloroform/methanol/water=70/30/3 to 50/50/5) to give Compound I-60 (1.85 g, 4%).

LC/MS: m/z 996.5 [M+H]+

Elementary analysis: C48H77N5O17(H2O)4.4,

Calculated value: C 53.61; H, 8.04; N, 6.51 (%).

Actual value: C 53.60; H, 8.07; N, 6.59 (%).

Example 18

Synthesis of Compound I-74

[Chemical Formula 59]

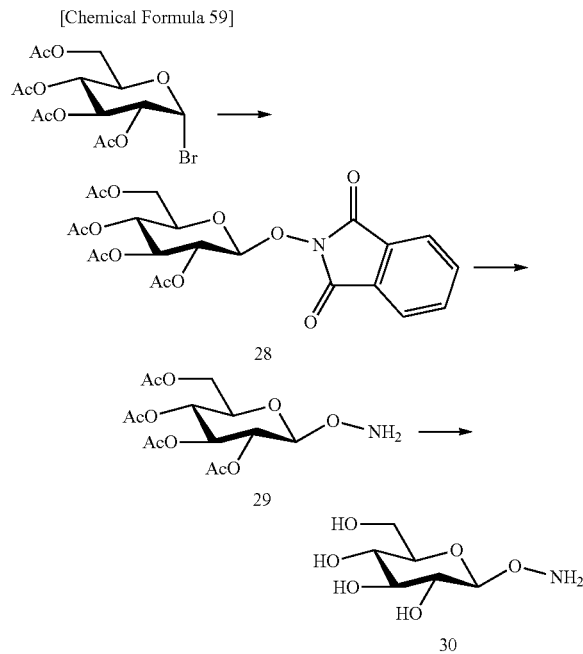

Step 1 Synthesis of Compound 28

2,3,4,6-tetra-O-acetyl-α-D-glucopyranosylbromide (5.346 g, 13 mmol) was dissolved into dichloromethane (100 mL) and added tetrabutyl ammonium hydrogen sulfate (4.11 g, 13 mmol) and further added the solution N-hydroxyphthalimide (10.6 g, 65 mmol) dissolved into sodium carbonate aqueous solution (1 mmol/L, 100 mL). The mixture was stirred for 20 hours at room temperature. After the obtained organic phase by extracting with dichloromethane was washed with saturated sodium bicarbonate aqueous solution and burine, the mixture was dried up with sodium sulfate anhydrous and filtrated and condensed. The resulted residue was purified by silica-gel column chromatography (dichloromethane/ethyl acetate=9/1) to give 2,3,4,6-tetra-O-acetyl-α-D-glucopyranosyloxyphthalimide, Compound 28 (980 mg, white foamy solids).

TLC: Rf=0.5 (dichloromethane/ethyl acetate=9/1)

Step 2 Synthesis of Compound 29

Compound 28 (872 mg, 1.767 mmol) was dissolved into methanol (18 mL) and added hydrazine monohydrate (0.086 mL, 1.767 mmol). After the mixture was stirred for 20 minutes at room temperature, the mixture was condensed. After ethyl acetate was added and impurities were removed, the filtrate was condensed. The resulted residue was purified by silica-gel column chromatography (hexane/ethyl acetate=1/2) to give 2,3,4,6-tetra-O-acetyl-α-D-glucopyranosyloxyamine, Compound 29 (516 mg, white foamy solids, 80%).

TLC: Rf=0.4 (hexane/ethyl acetate=1/2)

13C-NMR (CDCl3, 75 MHz) δ: 170.3, 169.8, 169.2, 169.1, 134.4, 123.7, 103.1, 72.7, 71.6, 69.5, 68.1, 61.6, 20.7, 20.6, 20.5: 1H-NMR(CDCl3, 300 MHz) δ:6.1-5.8 (br, 2H), 5.4-6.0 (m, 3H), 4.72 (d, 1H, J=8.1 Hz), 4.4-4.0 (m, 2H), 3.8-3.6 (d, 1H), 2.1-2.0 (m, 12H).

Step 3 Synthesis of Compound 30

Compound 29 (508 mg, 1.398 mmol) was dissolved into methanol (14 mL) and added sodium methoxide (1 mol/L, 0.22 mL), and the mixture was stirred for 3 hours at 0° C. Amberlite IR-120 was added and the reaction was quenched by neutralization. Water was added, and the mixture was filtered. The resulted filtrate was condensed and lyophilized to give Compound 30 (229 mg, light yellow solids, 80%).

1H-NMR(D2O, 300 MHz) δ: 7.58 (br, 2H), 4.21 (d, 1H, J=8.1 Hz), 3.7-2.9 (m, 6H).

[Chemical Formula 60]

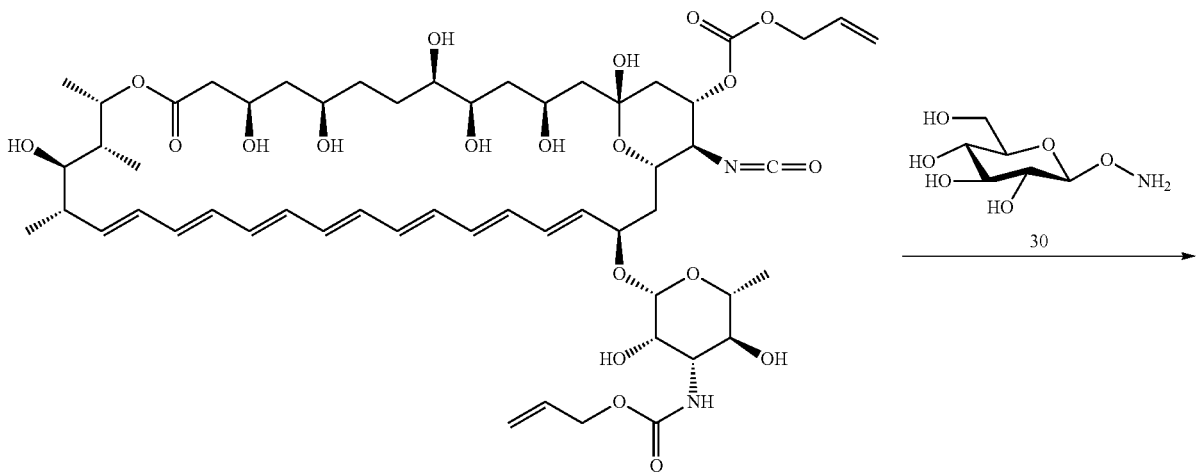

II-A

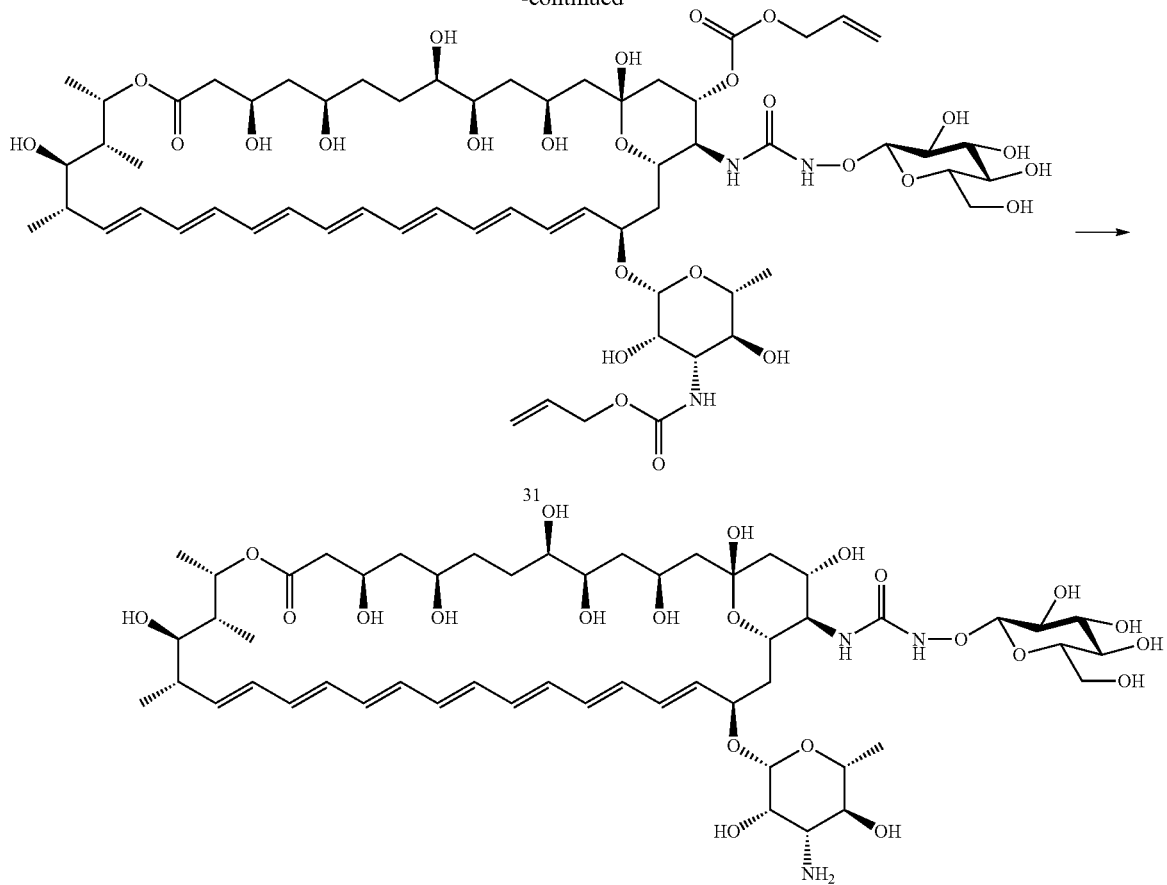

I-74

Step 1 Synthesis of Compound 31

Compound II-A (10.5 g, 9.64 mmol) was dissolved into DMA (60 mL), and DIEA (5.05 mL, 28.9 mmol) was added. Separately, the solution which β-glucose-1-oxyamine (Compound 30) (2.258 g, 11.57 mmol) was dissolved to water (10 mL) and DMA (5 mL) was prepared, and the prepared solution was added to the reaction mixture. The reaction mixture was stirred for an hour at room temperature, further stirred for 25 minutes at 40° C. After the mixture was oil-outed with diisopropyl ether, the resulted residue was purified by silica-gel column chromatography (chloroform/methanol/water=95/5/0.5 to 85/15/1.5) to give Compound 31 (2.43 g, 19%).

LC-MS: 1306.5 [M+H+]

Step 2 Synthesis of Compound I-74

Compound 16 (2.43 g, 1.892 mmol) was dissolved into DMF (30 mL) and added morpholine (1.65 mL, 18.9 mmol) and Pd(PPh$_3$)$_4$ (219 mg, 0.189 mmol), and the mixture was stirred for 3 hours at room temperature. After powderization by adding diisopropyl ether, the resulted powder was purified by silica-gel column chromatography (chloroform/methanol/water=85/15/1.5 to 30/70/7). The obtained fractions was condensed and lyophilized to give Compound I-74 (818 mg, 39%).

LC/MS: m/z 1116.5 [M+H]+

Elementary analysis; (C53H85N3O22)(H2O)2.3

Calculated value: C 54.99; H, 7.80; N, 3.63 (%).

Actual value: C 55.01; H, 7.88; N, 3.48 (%).

Example 19

Synthesis of Compound I-164

[Chemical Formula 61]

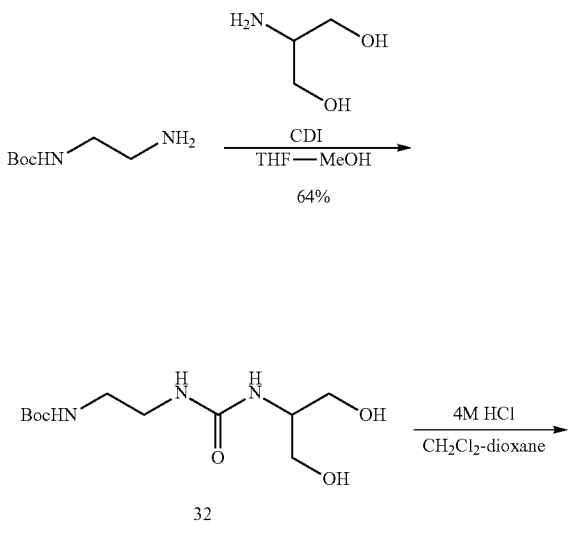

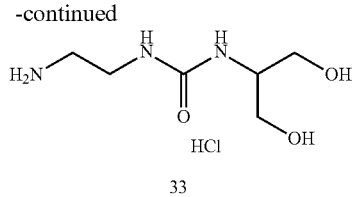

1,1'-Carbonyldiimidazole (1.316 g, 8.11 mmol) was dissolved into tetrahydrofuran (10 mL). After tert-butyl 2-aminoethylcarbamate (0.984 mL, 6.24 mmol) was added, the methanol (2 mL) solution including 2-aminopropane-1,3-diol (0.569 g, 6.24 mmol) was added to the mixture, and the mixture was stirred for an hour at 50° C., further stirred for an hour at 65° C. After concentration, the mixture was purified by silica-gel column chromatography to give Compound 32 (1.1 g, 64%). Compound 32 (1.1 g, 3.97 mmol) was dissolved into methanol (10 mL) and added hydrochloric acid-dioxane (4 mmol/L, 16 mL), and the mixture was stirred for 2 hours. The mixture was condensed to give Compound 33 (1.09 g). Compound 33 was used to next reaction without purification.

1H-NMR(D2O, 300 MHz)δ;3.9-3.7 (m, 1H), 3.7-3.5(m, 4H), 3.4-3.35 (m, 2H),3.34 (s, 2H), 3.15-3.05 (m, 2H).

[Chemical Formula 62]

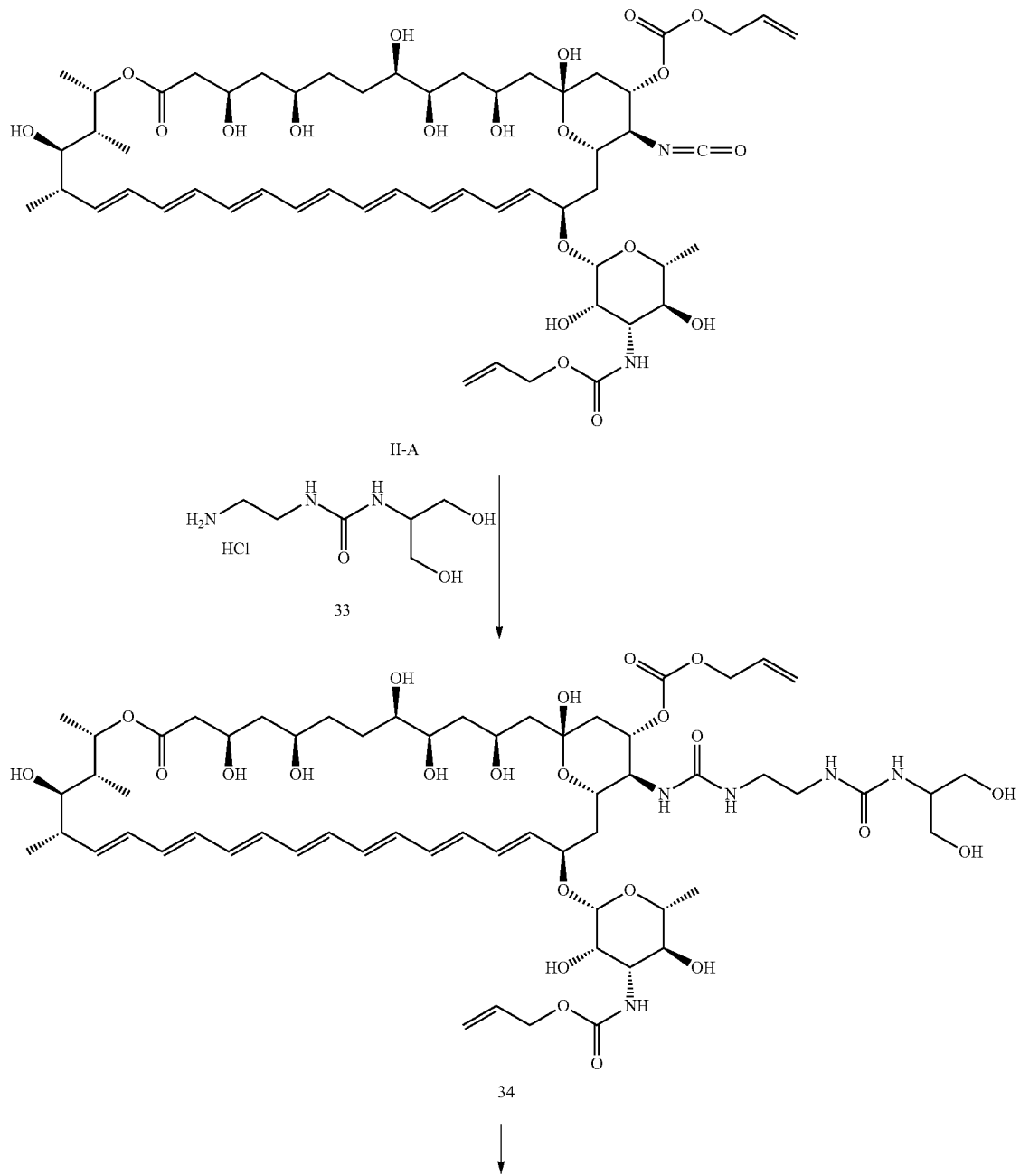

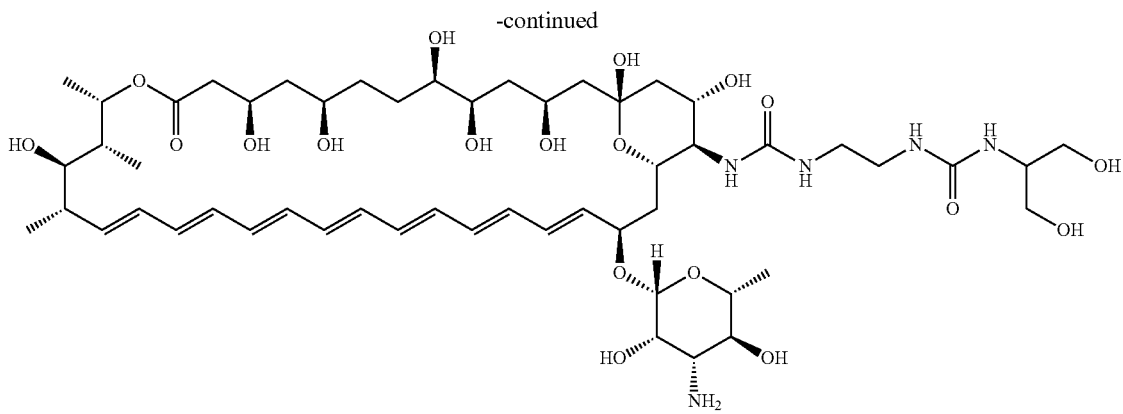

I-164

Compound II-A (1.5 g, 1.377 mmol) was dissolved into DMF (5 mL) and added DIEA (0.481 mL, 2.75 mmol) and 1-(2-aminoethyl)-3-(1,3-dihydroxypropane-2-yl)urea hydrochloride (Compound 33) (294 mg, 1.377 mmol), and the mixture was stirred for 30 minutes. After powderization by adding diisopropyl ether, the resulted powder was purified by silica-gel column chromatography (chloroform/methanol/water=95/5/0.5 to 85/15/1.5) to give Compound 34 (450 mg, 26%). Compound 34 (450 mg, 0.355 mmol) was dissolved into DMF (2.51110 and added morpholine (0.31 mL, 3.55 mmol) and Pd(PPh$_3$)$_4$ (21 mg, 0.018 mmol), and the mixture was stirred for 40 minutes at room temperature. After powderization by adding diisopropyl ether, the resulted powder was purified by silica-gel column chromatography (chloroform/methanol/water=50/50/5 to 20/80/8). The obtained fractions was condensed and lyophilized to give Compound I-164 (120 mg, 28%).

LC/MS: m/z 1098.6 [M+H]+

Elementary analysis: C53H87N5O19(C3H7NO)0.5(H2O)2.4

Calculated value: C 55.56; H, 8.15; N, 6.54 (%).

Actual value: C 55.55; H, 8.07; N, 6.56 (%).

Example 20

Synthesis of Compound I-182

[Chemical Formula 63]

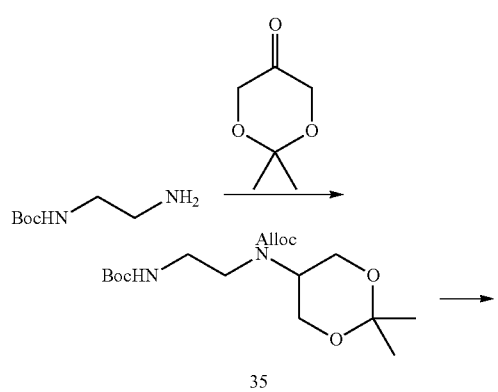

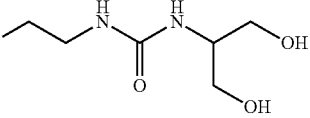

36

Step 1 Synthesis of Compound 35

2,2-dimethyl-1,3-dioxane-5-one (1 g, 7.68 mmol) was dissolved into dichloromethane (50 mL) and added tert-butyl 2-aminoethylcarbamate (1.354 g, 8.45 mmol) and sodium triacetoxyborohydride (2.117 g, 9.99 mmol), and the mixture was stirred for 2 hours 40 minutes at room temperature. N-(allyloxycarbonyloxy)succinimide (2.469 g, 12.4 mmol) and DIEA (6.71 mL, 38.4 mmol) was added, the mixture was stirred at room temperature. After water was added and the reaction was quenched, the mixture was extracted with dichloromethane. The resulted residue was purified by silica-gel column chromatography (hexane/ethyl acetate=50/50 to 10/90) to give Compound 35 (2.45 g, colorless liquid, 89%).

TLC: Rf=0.6 (chloroform/methanol=9/1)

1H-NMR(CDCl3, 300 MHz)δ:6.1-5.9 (m, 1H), 5.4-5.2 (m, 2H), 4.7-4.6 (m, 2H), 4.2-3.9 (m, 4H),3.7-3.5 (br, 2H), 3.4-3.3 (br, 2H), 1.5-1.3(m, 15H)

Step 2 Synthesis of Compound 36

Compound 35 (2.45 g, 6.84 mmol) was dissolved into dichloromethane (30 mL) and hydrochloric acid-dioxane (4 mol/L, 10.25 mL, 41 mmol) was added, and the mixture was stirred for 4 hours at room temperature. The mixture was condensed to give Compound 36 (1.7 g). Compound 36 was used to next reaction without purification.

[Chemical Formula 64]

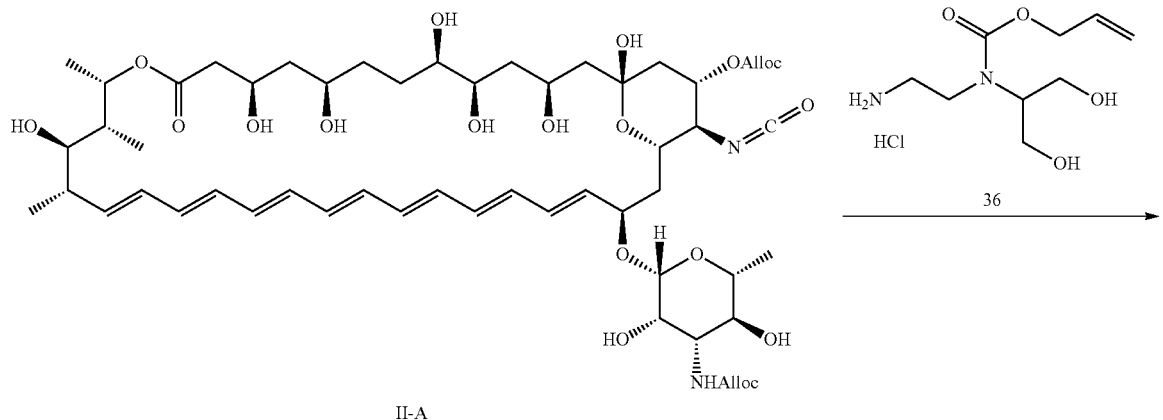

II-A

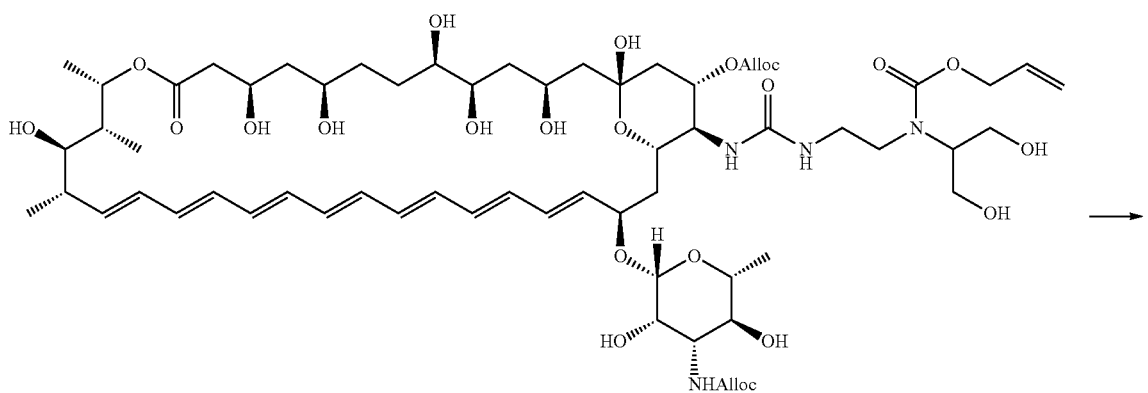

37

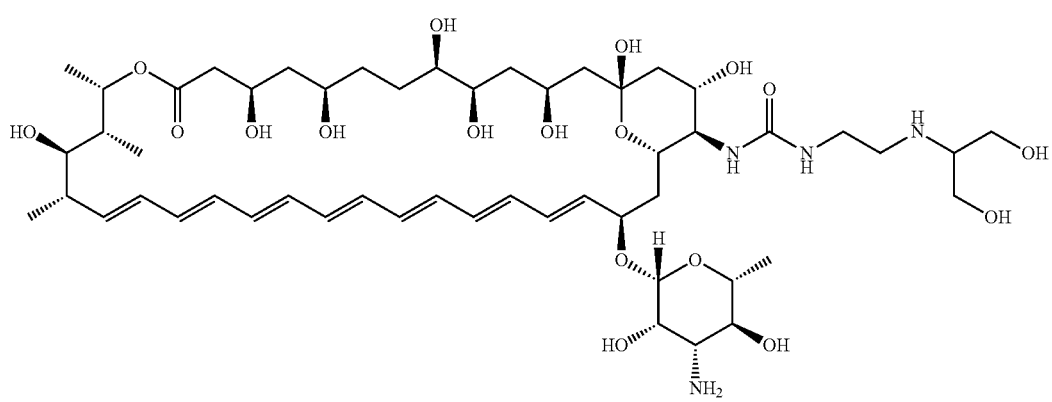

I-182

Compound II-A (1 g, 0.918 mmol) was dissolved into DMF (5 mL), and DIEA (0.64 mmol) and Compound 36 (234 mg, 0.918 mmol) were added. The mixture was stirred for an hour at room temperature. After powderization by adding diisopropyl ether, the resulted powder was purified by silica-gel column chromatography (chloroform/methanol/water=95/5/0.5) to give Compound 37 (240 mg, 10%). Compound 37 (240 mg, 0.184 mmol) was dissolved into DMF (3 mL) and added morpholine (0.24 mL, 2.75 mmol) and Pd(PPh$_3$)$_4$ (11 mg, 0.009 mmol), and the mixture was stirred for 20 minutes at room temperature. After powderization by adding diisopropyl ether, the resulted powder was purified by silica-gel column chromatography (chloroform/methanol/water=505/50/5 to 20/80/8). The obtained fractions were condensed and lyophilized to give Compound I-182 (67 mg, 26%).

LC/MS: m/z 1055.6 [M+H]+, 1077.6 [M+Na]+
Elementary analysis: C52H86N4O18(H2O)3.0
Calculated value: C 56.30; H, 8.36; N, 5.05 (%).
Actual value: C 56.35; H, 8.36; N, 4.84 (%).

Example 21

Synthesis of Compound I-208

[Chemical Formula 65]

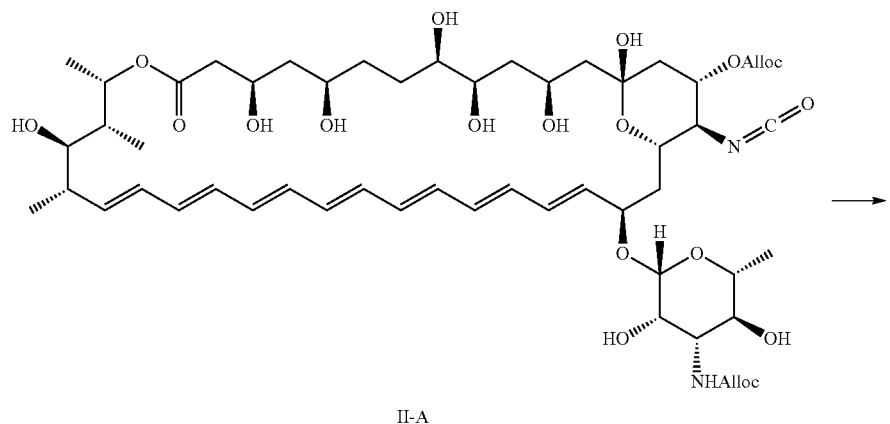

II-A

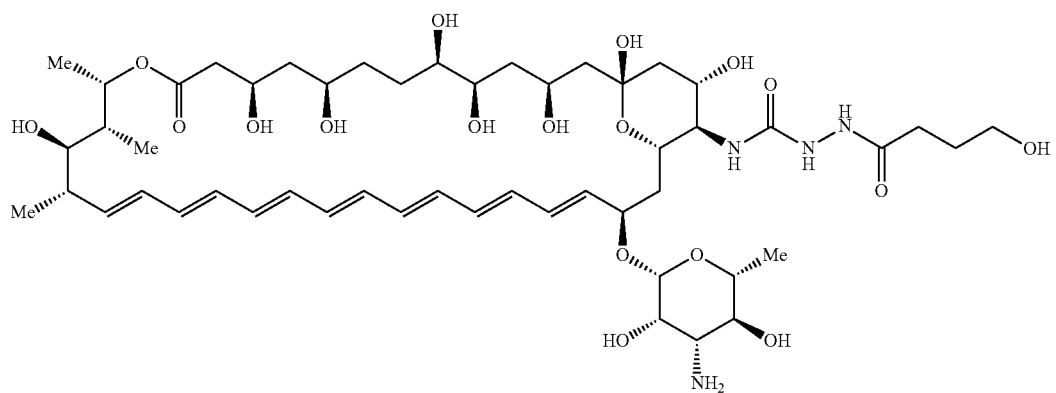

I-208

Compound II-A (1.32 g, 1.21 mmol) was dissolved into DMA (5 mL) and added DIEA (0.42 mL, 2.42 mmol) and 4-hydroxybutanehydrazide (143 mg, 1.21 mmol), and the mixture was stirred for an hour 20 minutes at room temperature. The mixture was purified by silica-gel column chromatography. The resulted solids (200 mg, 0.166 mmol) was dissolved into DMF (3 mL) and added morpholine (0.144 mL, 1.657 mmol) and Pd(PPh$_3$)$_4$ (9.5 mg, 0.0082 mmol), and the mixture was stirred for 15 minutes at room temperature. The mixture was purified by silica-gel column chromatography (amino silica-gel, chloroform/methanol/water=90/10/1 to 50/50/5) to give Compound I-208 (61 mg, 5%).

LC/MS: m/z 1039.56 [M+H]+, 1061.6 [M+Na]+

Elementary analysis: C51H82N4O18 (C3H7NO)0.3 (H2O)5.9

Calculated value: C 53.40; H, 8.28; N, 5.16 (%).

Actual value: C 53.43; H, 8.15; N, 5.21 (%).

Example 22

Synthesis of Compound I-219

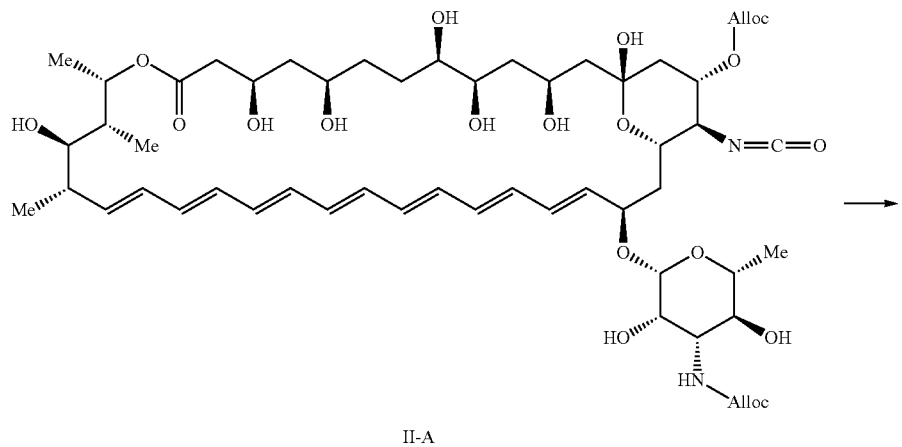

II-A

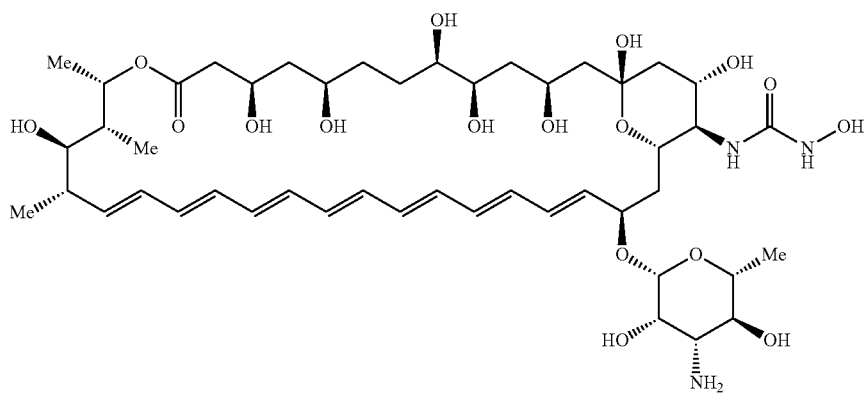

I-219

Compound II-A (10 g, 9.18 mmol) was dissolved into DMF (25 mL) and added DIEA (4.81 mmol) and hydroxylamine hydrochloride (766 mg, 11.02 mmol), and the mixture was stirred for 40 minutes at room temperature. After powderization by adding diisopropyl ether, the resulted powder was purified by silica-gel column chromatography (chloroform/methanol=70/30) to give yellow powder (2.1 g, 20%). The resulted powder was dissolved into DMF (10 mL) and added morpholine (1.63 mL, 18.71 mmol) and Pd(PPh$_3$)$_4$ (216 mg, 0.187 mmol), and the mixture was stirred for 40 minutes at room temperature. After powderization by adding diisopropyl ether, the powder was purified by silica-gel column chromatography (chloroform/methanol=40/60 to 5/95) to give Compound I-219 (530 mg, 30%).

LC/MS: m/z 954.4 [M+H]+, 976.5 [M+Na]+

Elementary analysis: C47H75N3O17(C3H7NO)0.5 (H2O)2.8

Calculated value: C 55.95 (−0.02%); H, 8.14 (−0.01%); N, 4.71 (−0.03%); O, 31.20 (%).

Actual value: C 55.93; H, 8.13; N, 4.68 (%).

Example 23

Synthesis of Compound I-25 1

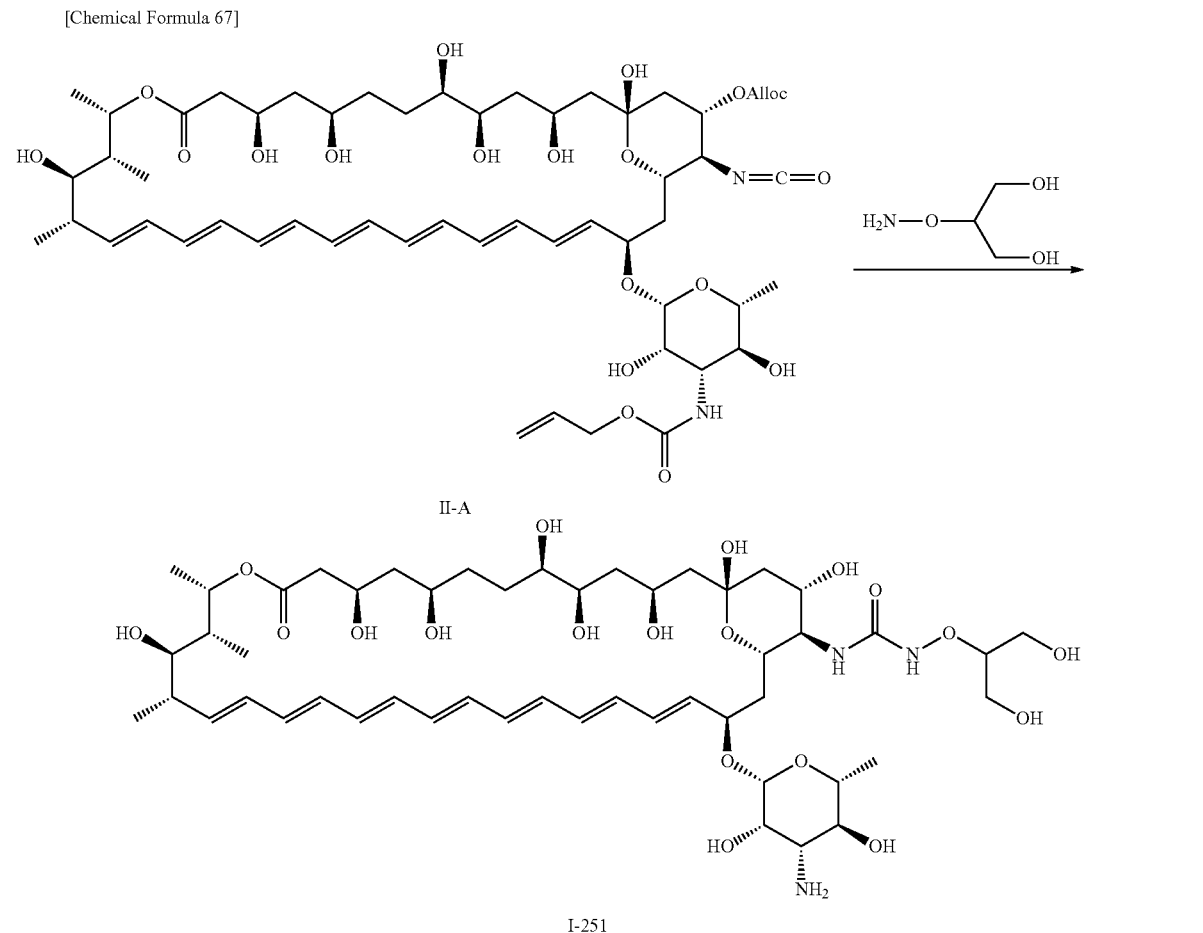

Compound II-A (2.6 g, 2.387 mmol) was dissolved into DMA (10 mL) and added 1-(hydroxymethyl)-2-hydroxyethyloxyamine (811 mg, 2.86 mmol) and tributyltin oxide (1.46 mL, 2.86 mmol), the mixture was stirred at room temperature. After powderization by adding diisopropyl ether, the resulted powder was purified by silica-gel column chromatography. The obtained powder (250 mg, 0.209 mmol) was dissolved into NMP (3 mL) and added morpholine (0.13 mL, 1.46 mmol) and Pd(PPh$_3$)$_4$ (24.1 mg, 0.021 mmol), and the mixture was stirred for 10 minutes at room temperature. After powderization by adding diisopropyl ether, the resulted powder was purified by silica-gel column chromatography (amino silica-gel, chloroform/methanol=90/10 to 70/30) to give Compound I-251 (114 mg, 5%).

LC/MS: m/z 1028.4 [M+H]+, 1050.4 [M+Na]+

Elementary analysis: C50H81N3O19(C3H7NO)2.9 (H2O)1.9

Calculated value: C 55.32; H, 8.31; N, 6.48 (%).

Actual value: C 55.30; H, 8.30; N, 6.90 (%).

Example 24

Synthesis of Compound I-303

[Chemical Formula 68]

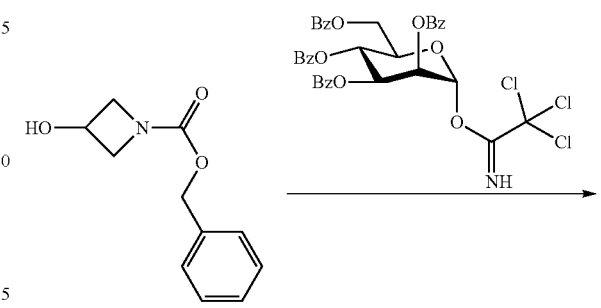

-continued

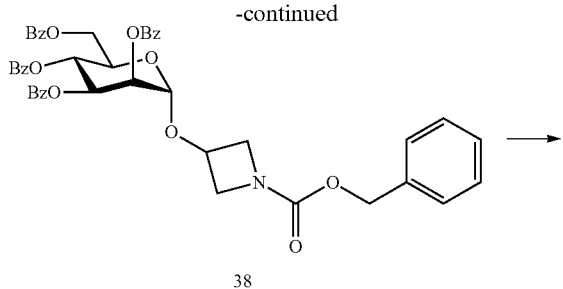

38

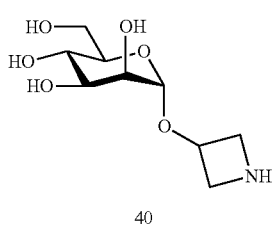

39

HO, OH
HO, -O
HO
O
NH

40

Step 1 Synthesis of Compound 38

2,3,4,6-tetra-O-benzoyl-mannose-1-O-trichloroacetimidate (4.19 g, 5.79 mmol) and benzyl 3-hydroxyazetidine-1-carboxylate (1 g, 4.83 mmol) were dissolved into dichloromethane (15 mL) and boron trifluoride diethyl ether complex (0.685 mL, 5.79 mmol) was added at −20° C., and the mixture was stirred for 2 hours in an ice-water bath. After heating to room temperature, the reaction was quenched with saturated sodium bicarbonate aqueous solution, and the mixture was extracted with ethyl acetate. The mixture was purified by silica-gel column chromatography to give Compound 38 (2.84 g, 74.9%).

TLC: Rf=0.2 (hexane/ethyl acetate=2/1)

LC-MS: 785 [M+H]+, 803 [M+Na]+

Step 2 Synthesis of Compound 39

Compound 38 (2.71 g, 3.45 mmol) was dissolved into methanol (20 mL) and tetrahydrofuran (20 mL) and added sodium methoxide (1 mol/L, 0.345 mL) in an ice-water bath, and the mixture was stirred for 16 hours at room temperature. After the reaction was quenched by adding Amberlite (H)IRA, the mixture was filtrated, and the obtained filtrate was condensed. The obtained gummy condensed residue was triturated to give Compound 39 (1.017 g, 79.8%) as white solid.

TLC: Rf=0.3 (chloroform/methanol=5/1)

1H-NMR(d2o)δ:7.37 (brs, 5H), 5.06 (s, 2H),4.82 (s, 1H), 4.57 (s, 1H), 4.20 (brs, 2H), 4.0-3.5 (br, 8H)

Step 3 Synthesis of Compound 40

Compound 39 (1.01 g, 2.73 mmol) was dissolved into methanol (20 mL) and added 10% Pd—C (200 mg, 0.188 mmol), and the mixture was stirred for 2 hours at room temperature under 1 atm hydrogen atmosphere. After confirmation of disappearance of material by TLC, the mixture was filtrated by Celit®. The obtained filtrate was condensed. The obtained residue was washed with hexane to give Compound 40 (597 mg, 92.8%) as white solid.

LC-MS: 236 [M+H]+

[Chemical Formula 69]

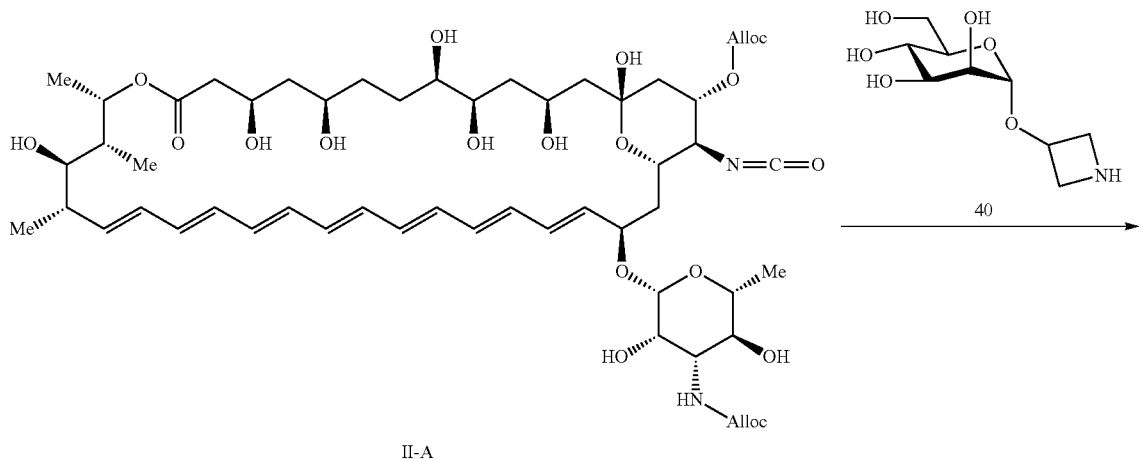

II-A

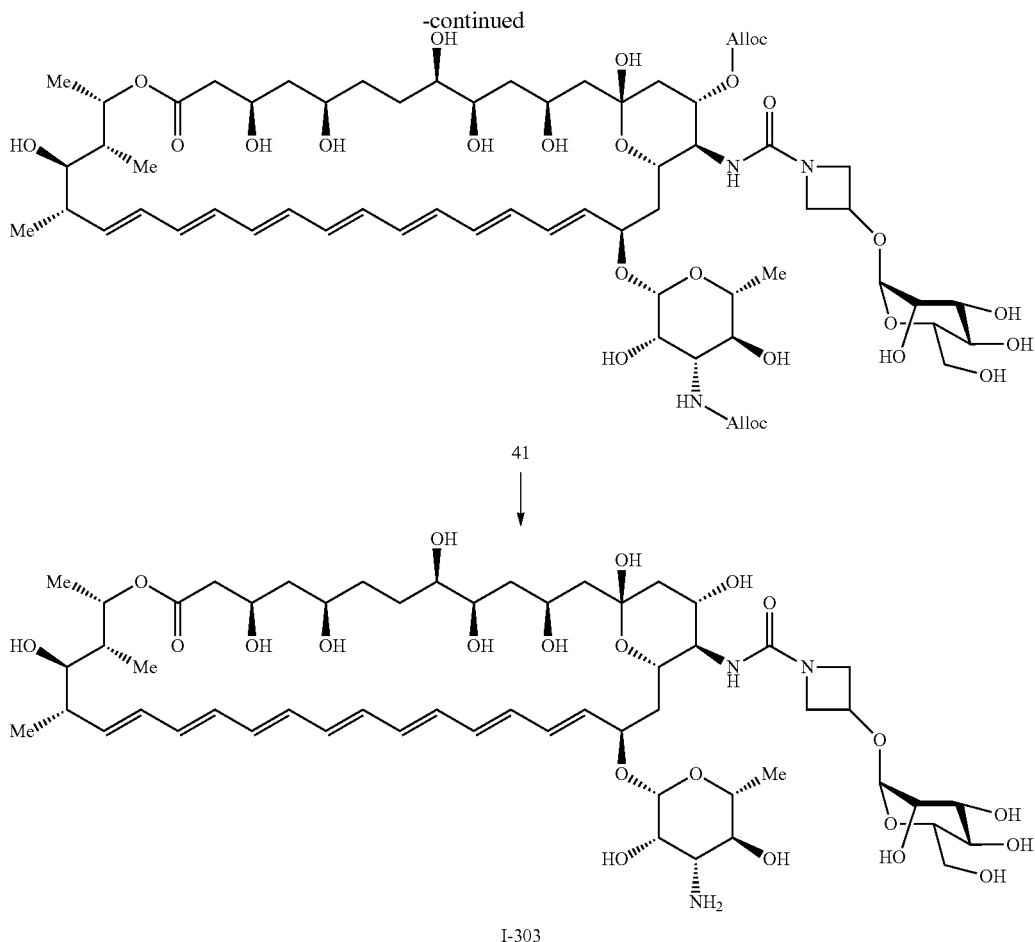

41

↓

I-303

Step 1 Synthesis of Compound 41

Compound II-A (2.284 g, 2.097 mmol) was dissolved into DMF (12 mL) and added side chain amine 40 (0.592 g, 2.52 mmol) and DIEA (1.1 mL, 6.29 mmol), and the mixture was stirred for 2 hours 40 minutes at room temperature. After the mixture was oil-outed with diisopropyl ether, the resulted residue was purified by silica-gel column chromatography (chloroform/methanol=90/10 to 70/30) to give Compound 41 (1.15 g, 41%).

LC/MS: m/z 1324 [M+H]+

Step 2 Synthesis of Compound I-303

Compound 41 (1.15 g, 0.865 mmol) was dissolved into DMF (10 mL) and added morpholine (1.05 mL, 12.1 mmol) and Pd(PPh$_3$)$_4$ (200 mg, 0.173 mmol), and the mixture was stirred for 4 hours at room temperature. After powderization by adding diisopropyl ether, the resulted powder was purified by silica-gel column chromatography to give Compound I-303 (187 mg, 18%).

LC-MS: 1156.5 [M+H]+, 1178.5 [M+Na]+.

Elementary analysis: (C56H89N3O22)(H2O)4(C3H7NO)0.3:

Calculated value: C 54.66; H, 7.99; N, 3.70 (%).

Actual value: C 54.63; H, 7.91; N, 3.94 (%).

Example 25

Synthesis of Compound I-310

[Chemical Formula 70]

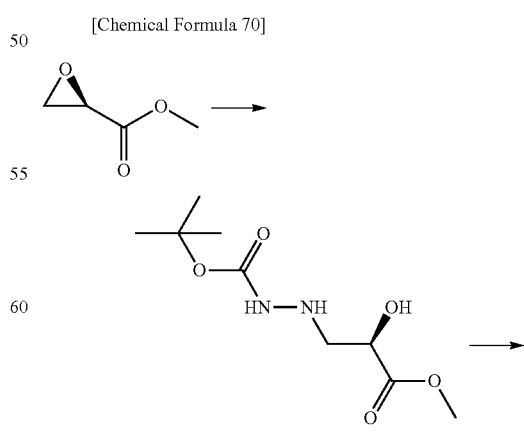

42

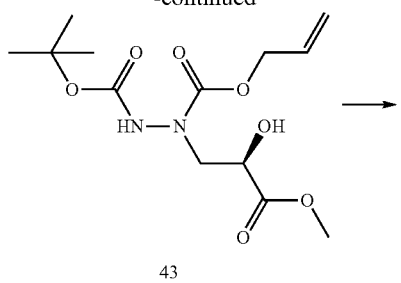

43

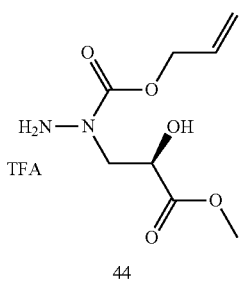

44

Step 1 Synthesis of Compound 42

To a solution of tert-butyloxycarbonylhydrazine (11.35 g, 86 mmol) in methanol (70 mL) was added (R)-methyl oxirane-2-carboxylate (25.4 g, 249 mmol). The mixture was stirred for 24 hours at room temperature. After the reaction mixture was concentrated, the residue was purified by silica-gel column chromatography (hexane/ethyl acetate=9/1 to 1/1) to give Compound 42 (7.84 g, white solid, 39%).

TLC: Rf=0.1 (hexane/ethyl acetate=1/1)
13C-NMR(CDCl3, 100 MHz)δ:173.82, 157.36, 81.17, 68.92, 54.89, 52.49, 28.36, 14.21;
1H-NMR(CDCl3, 400 MHz)δ:6.20 (brs, 1H), 4.30-4.20 (m, 1H),3.78 (s, 3H),3.25-3.10 (m, 2H), 1.48 (s, 9H).

Step 2 Synthesis of Compound 43

To a solution of Compound 42 (7.84 g, 33.5 mmol) in dichloromethane (80 mL) were added DIEA (7.6 mL, 43.5 mmol) and allyloxycarbonyl chloride (4.26 mL, 40.2 mmol). The mixture was stirred for an hour at room temperature. Water and ethyl acetate are added. After extracted with ethyl acetate, the organic phase was washed with water. The solution was dried with sodium sulfate anhydrous and filtrated and condensed. The resulted residue was purified by silica-gel column chromatography (hexane/ethyl acetate=1/1) to give Compound 43 (9.38 g, colorless liquid, 88%).

TLC: Rf=0.3 (hexane/ethyl acetate=1/1)
1H-NMR(CDCl3, 400 MHz)δ:6.50 (brs, 1H), 5.9 (brs, 1H), 5.4-5.2 (m, 2H), 4.63 (brs, 2H),4.43 (s, 1H), 4.40-3.8 (m, 3H), 3.79(s, 3H), 1.48(s, 9H). LC-MS: [M+H]+=341.15

Step 3 Synthesis of Compound 44

To a solution of Compound 43 (9.38 g, 29.5 mmol) in dichloromethane (100 mL) was added trifluoroacetic acid (22.7 mL, 295 mmol) in an ice-water bath. The mixture was stirred for 3 hours at room temperature. After condensed by rotatory evaporator, the mixture was condensed by adding toluene. The resulted residue was evaporated in vacuo to give Compound 44 (11.3 g, gummy colorless liquid).

TLC: Rf=0.1 (hexane/ethyl acetate=1/1)
1H-NMR(D2O, 400 MHz)δ:5.9-5.8 (m, 1H), 5.3-5.2 (m, 2H), 4.61 (m, 2H), 4.48 (m, 1H), 3.92(m, 2H),3.65(s, 3H).
13C-NMR (D2O, 100 MHz) δ: 173.6, 162.8, 162.4, 131.5, 131.1, 119.0, 117.6, 114.7, 68.6, 68.4, 53.0, 52.9, 50.6.

[Chemical Formula 71]

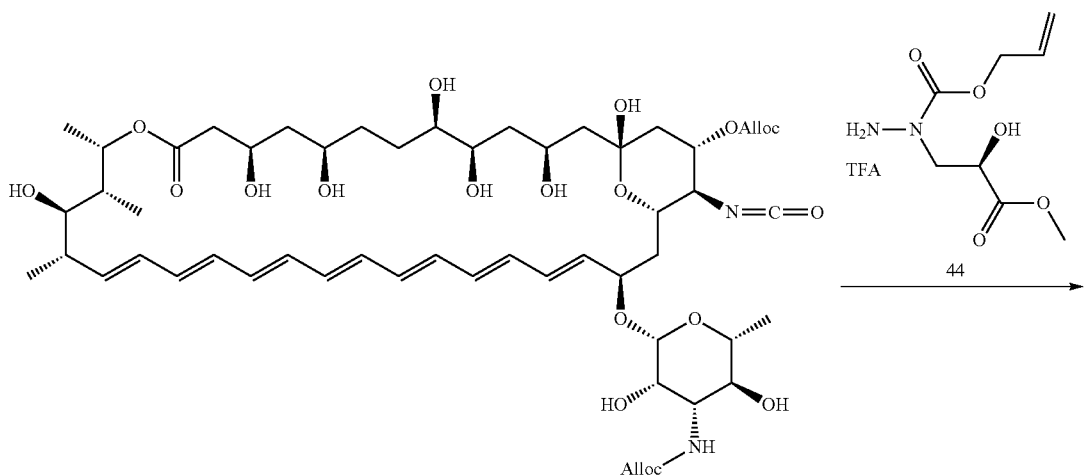

II-A

-continued

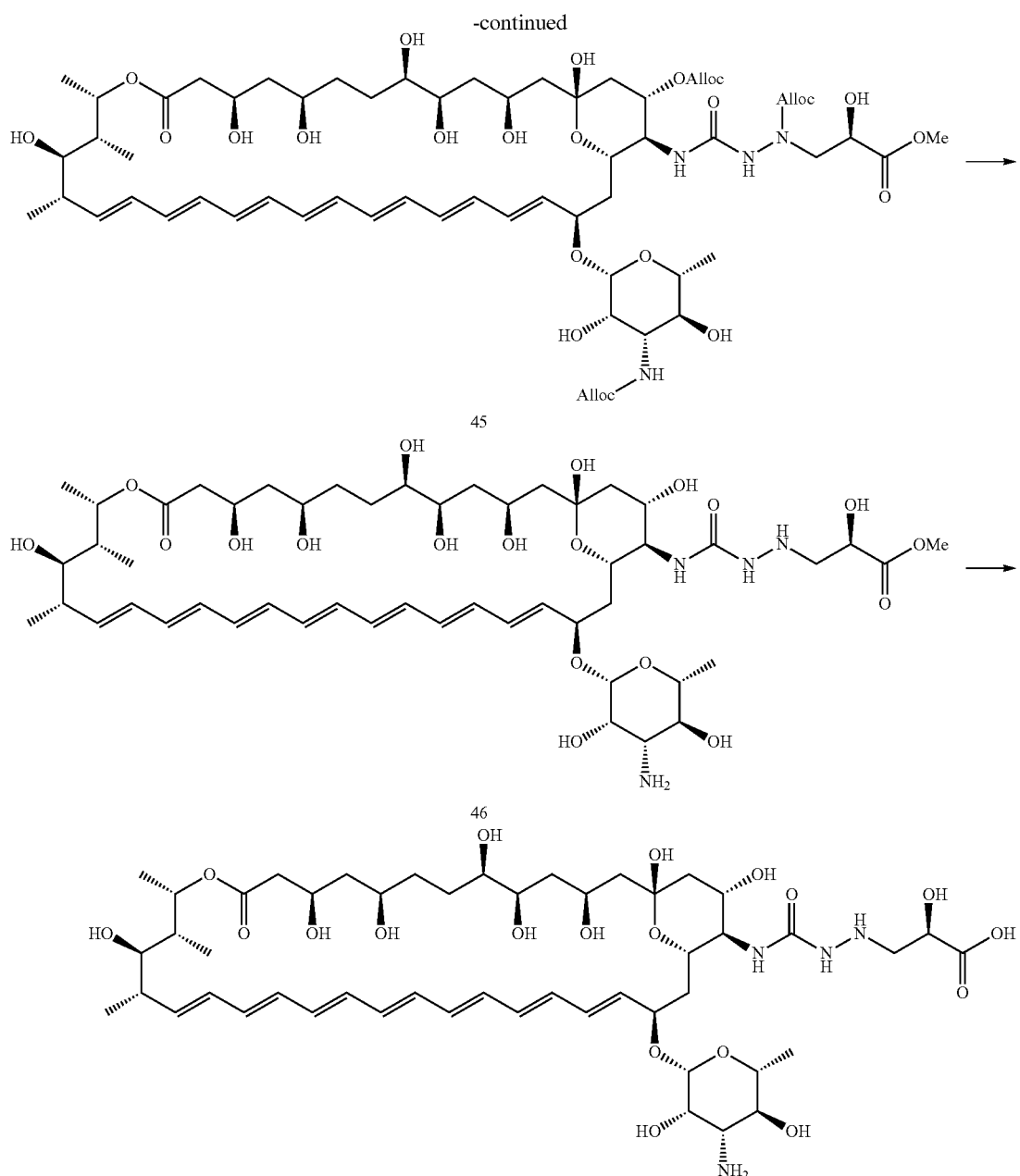

Step 1 Synthesis of Compound 45

To a solution of Compound II-A (9.27 g, 8.51 mmol) in DMF (40 mL) were added DIEA (10.4 mL, 59.6 mmol), side chain amide Compound 44 (5.35 g, 11.9 mmol) and bis tributyltin oxide (0.867 mmol, 1.70 mmol). The mixture was stirred for 2 hours at room temperature. After cooling to 4° C., the mixture was reacted for 4 days at 4° C. The reaction solution was suspended first, after 4 days, the solution became orange color. Diisopropyl ether (1 L)/methanol (30 mL) was added to the reaction mixture, and the mixture was stirred strongly. The obtained orange color solids were filtrated. The solids were purified by silica-gel column chromatography (chloroform/methanol/water=95/5/0.5 to 90/10/1). The obtained fractions were condensed to give Compound 45 (6.82 g, 5.22 mmol, 61%) as orange color powder. The retention time of Compound 17 by HPLC analysis was 11.8 minutes (methanol/distilled water containing 0.1% PIC-B7=gradient from 70/30 to 100/0, flow speed 1 ml/min, wavelength of detection=385 nm).

LC-MS: m/z 1308.6 [M+H]+

Step 2 Synthesis of Compound 46

To a solution of Compound 45 (10.03 g, 7.67 mmol) in DMF (55 mL) were added morpholine (4.68 mL, 53.7 mmol) and Pd(PPh$_3$)$_4$ (0.887 g, 0.767 mmol). The mixture was stirred for 40 minutes at room temperature under nitrogen atmosphere. The deposited solids by adding diisopropyl ether (900 mL) was filtrated. The solids were purified by silica-gel column chromatography (chloroform/methanol/water=70/30/3 to 5/95/5). The obtained fractions were condensed to give Compound 46 (4.45 g, yellow powder, 55%) as orange color powder. The retention time of Compound 46 by HPLC analysis was 6.37 minutes (methanol/distilled water containing 0.1% PIC-B7=gradient from 70/30 to 100/0, flow speed 1 ml/min, wavelength of detection=385 nm).

LC-MS: m/z 1055.6 [M+H]+

Actual value: C 50.41; H, 7.21; N, 4.75; Na, 3.05; Cl, 5.51 (%).

Example 26

Synthesis of Compound I-246

[Chemical Formula 72]

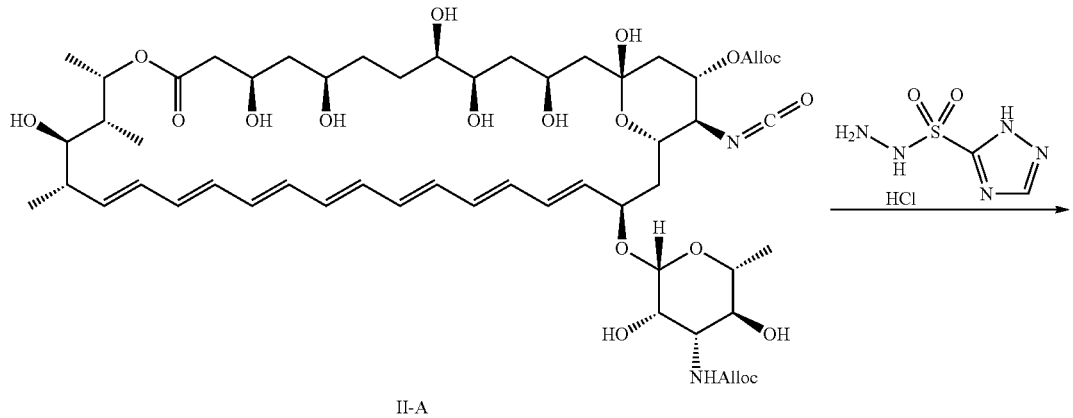

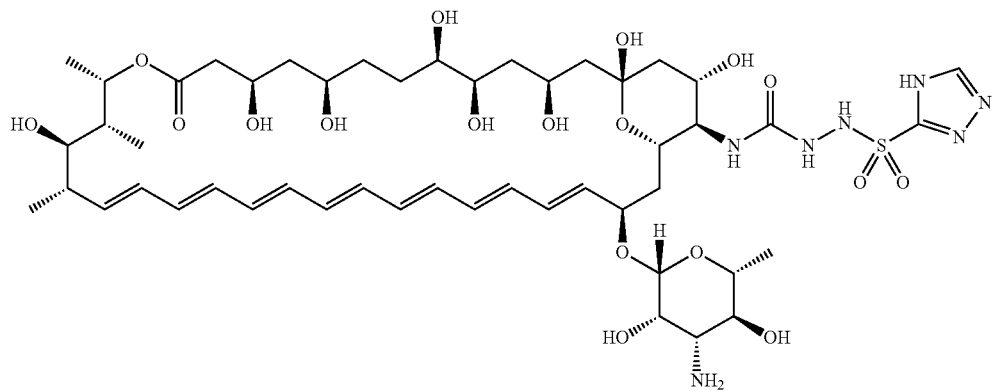

Step 3 Synthesis of Compound I-310

Tetrahydrofuran (210 mL) and water (11 mL) was added to Compound 46 (4.45 g, 4.22 mmol), and sodium hydroxide aqueous solution (0.5 mol/L, 12.65 mL, 6.33 mmol) was added in an ice-water bath. The mixture was stirred for an hour at 0° C. After the solution was neutralized by adding hydrochloric acid aqueous solution (0.5 mol/L, 12.65 mL, 6.33 mmol) dropwise, the mixture was condensed by rotatory evaporator. After all tetrahydrofuran were removed, water was condensed to 30 mL. The mixture was lyophilized to give Compound I-310 (5.87 g). The retention time by HPLC analysis was 7.39 minutes (methanol/distilled water containing 0.1% PIC-B7=gradient from 70/30 to 100/0, flow speed 1 ml/min, wavelength of detection=385 nm).

LC-MS: m/z 1041.6 [M+H]+

Elementary analysis: (C50H80N4O19)(NaCl)1.7(H2O)2.8

Calculated value: C 50.42; H, 7.24; N, 4.70; Na, 3.28; Cl, 5.06 (%).

Compound II-A (2 g, 1.836 mmol) was dissolved into DMF (10 mL), and DIEA (3.21 mL, 18.36 mmol) and 1H-1,2,4-triazole-5-sulfonylhydrazine hydrochloride (0.733 g, 3.67 mmol) were added. The mixture was stirred at 40° C. After powderization by adding diisopropyl ether, the obtained solids were purified by silica-gel column chromatography to give oily solids (200 mL). The solids were dissolved into DMF (2 mL), and morpholine (0.139 mL, 1.59 mmol) and Pd(PPh3)4 (9.2 mg, 0.008 mmol) were added. The mixture was stirred for an hour at room temperature. After powderization by adding diisopropyl ether, the obtained powder was purified by silica-gel column chromatography to give Compound I-246 (21 mg, 10%).

LC/MS: m/z 1084.4 [M+H]+

Example 27

Synthesis of Compound I-254

[Chemical Formula 73]

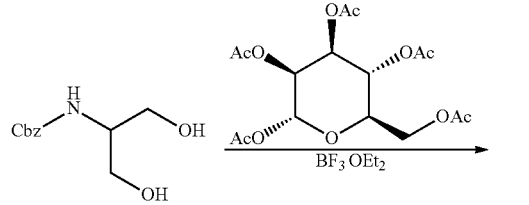

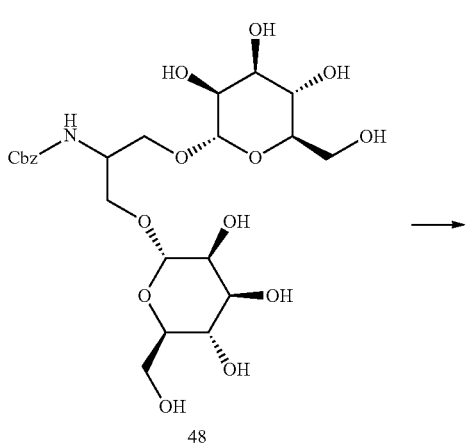

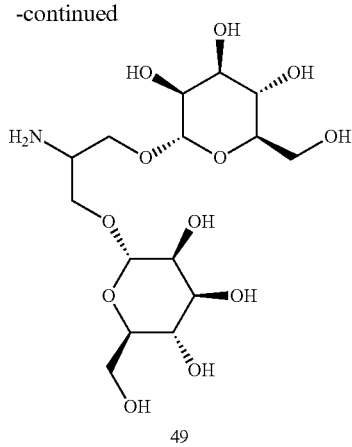

Step 1

Benzyl 1,3-hydroxypropane-2-yl carbamate (4.72 g, 21 mmol) was dissolved into dichloromethane (310 mL), and 6-D-mannopyranose 1,2,3,4,6-pentaacetate (24.5 g, 62.9 mmol) was added and was cooled in an ice-water bath. Boron trifluoride diethyl ether complex (8 mL, 62.9 mmol) was added dropwise. After the mixture was stirred for an hour, boron trifluoride diethyl ether complex (0.8 mL, 6.29 mmol) was added. The mixture was stirred at room temperature over night. After the reaction was quenched by saturated sodium bicarbonate aqueous solution, the mixture was extracted with chloroform (200 mL) twice. The organic phase was washed with brine and dried up with sodium sulfate anhydrous and filtrated and condensed. The residue was purified by silica-gel column chromatography (hexane/ethyl acetate) to give Compound 47 (3.45 g, 18%).

TLC: Rf=0.4 (hexane/ethyl acetate=1/2)

LC-MS: 886.5 [M+H]+

Step 2

Compound 47 (3.36 g, 3.79 mmol) was dissolved into methanol (30 mL), and sodium methoxide (1 mol/L, 3.79 mL) was added in an ice-water bath. The mixture was stirred for an hour at 0° C., further stirred for an hour at room temperature. The mixture was neutralized by adding ion exchange resin of Amberlite IR-120B (H+ form) and filtrated and condensed to give Compound 48 (2.05 g, 98%).

TLC: Rf=0.1 (chloroform/methanol=4/1)

Step 3

Compound 48 (2.05 g, 3.73 mmol) was dissolved into methanol (50 mL), and 10% Pd—C (200 mg, 0.188 mmol) was added. The mixture was stirred under hydrogen atmosphere (1 atm). The reaction mixture was filtrated and condensed to give Compound 49 (1.62 g). Compound 49 was used to next reaction without purification.

LC-MS: 416.1 [M+H]+

[Chemical Formula 74]
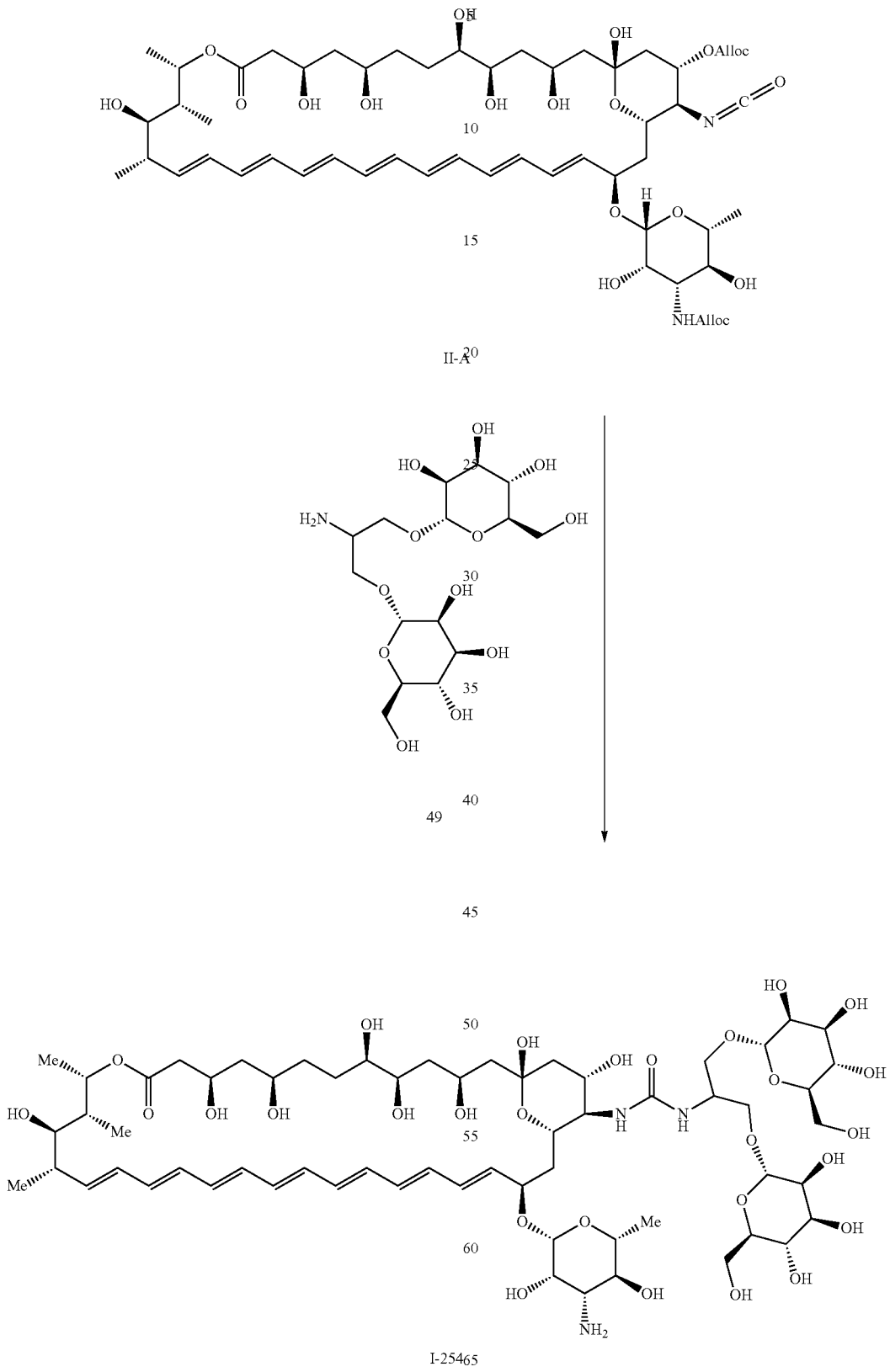

Compound II-A (500 mg, 0.459 mmol) was dissolved into DMF (2 mL), and DIEA (0.241 mL, 1.38 mmol) and 2-amino-1,3-propanediyl bis-α-D-mannopyranoside (Compound 49: 286 mg, 0.689 mmol) were added. The mixture was stirred for an hour at 40° C. After powderization by adding diisopropyl ether, the obtained solids were purified by silica-gel column chromatography to give solids (220 mg, 0.146 mmol). The solids were dissolved into DMF (2 mL), and morpholine (0.127 mL, 1.462 mmol) and Pd(PPh$_3$)$_4$ (51 mg, 0.044 mmol) were added. The mixture was stirred for an hour at room temperature. After powderization by adding diisopropyl ether, the obtained solids were purified by silica-gel column chromatography (amino silica-gel, chloroform/methanol/water=70/30/3 to 10/90/9) to give Compound I-254 (70 mg, 12%).

LC/MS: m/z 1336.6 [M+H]+

Elementary analysis: (C62H101N3O28)(H2O)9.5

Calculated value: C 49.39; H, 8.02; N, 2.79 (%).

Actual value: C 49.29; H, 7.55; N, 4.75; Na, 3.14 (%).

Example 27

Synthesis of Compound I-248

[Chemical Formula 75]

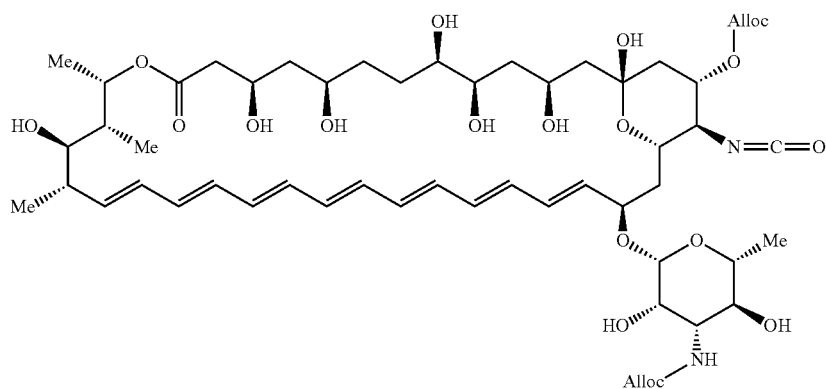

II-A

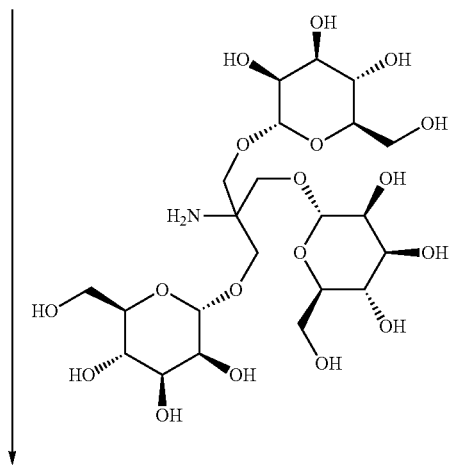

-continued

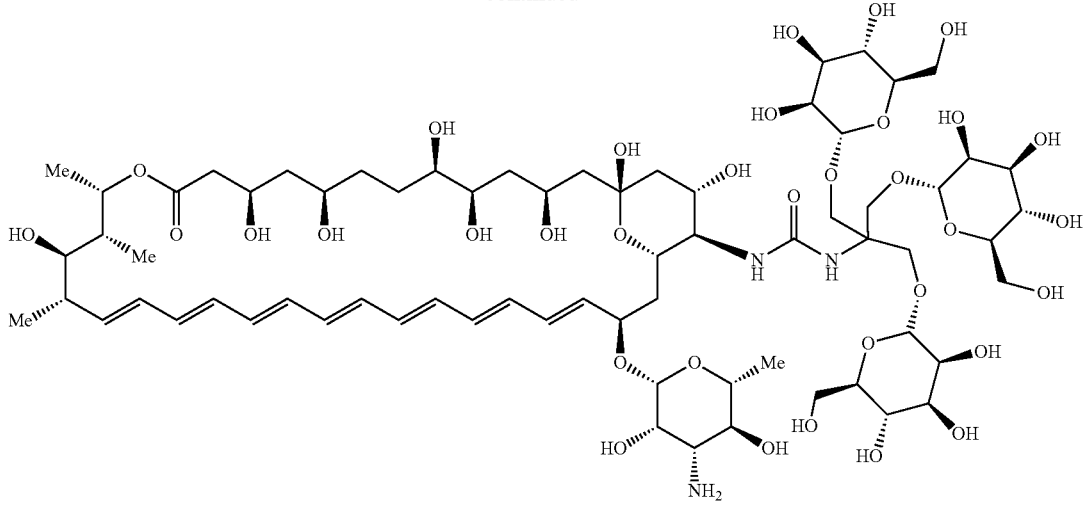

I-248

Compound II-A (240 mg, 0.220 mmol) was dissolved into DMF (2 mL), and DIEA (0.115 mL, 0.661 mmol) and α-D-mannopyranoside, 2-amino-2-[(α-D-mannopyranosyloxy)methyl]-1,3-propanediyl, bis-(Compound 50: 201 mg, 0.331 mmol) were added. The mixture was stirred for 20 hours at room temperature. After powderization by adding diisopropyl ether, the obtained solids were purified by silica-gel column chromatography to give solids (30 mg, 0.018 mmol). The solids were dissolved into DMF (1 mL), and morpholine (0.015 mL, 0.177 mmol) and Pd(PPh$_3$)$_4$ (10 mg, 0.009 mmol) were added. The mixture was stirred for an hour 15 minutes at room temperature. After powderization by adding diisopropyl ether, the powder was purified by silica-gel column chromatography (amino silica-gel, chloroform/methanol/water=50/50/5 to 10/90/9) to give Compound I-248 (16 mg, 5%).

LC/MS: m/z 1529.3 [M+H]+

Example 28

Synthesis of Compound I-260

[Chemical Formula 76]

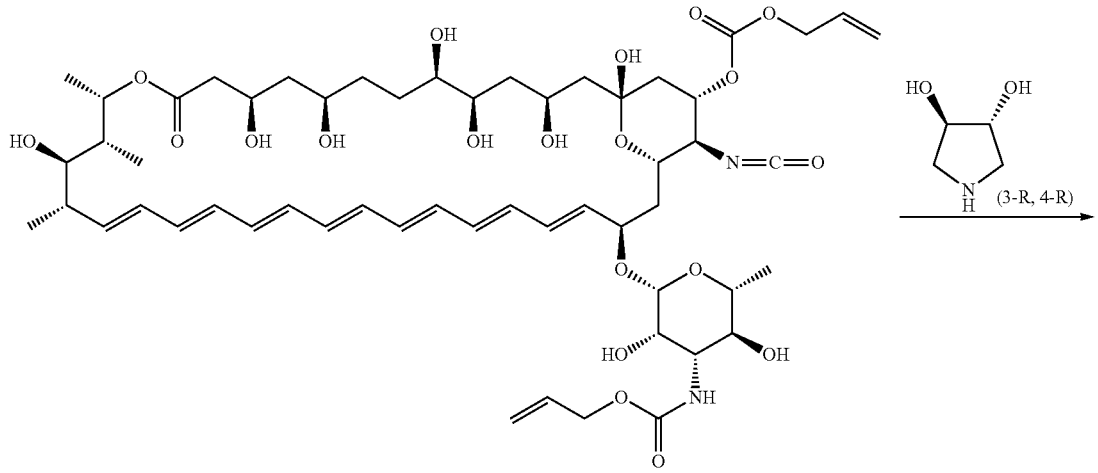

II-A

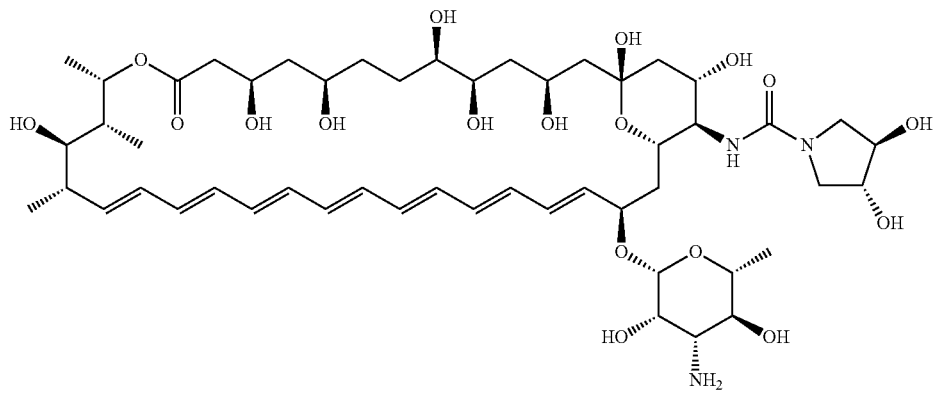

I-260

Compound II-A (2 g, 1.836 mmol) was dissolved into DMF (10 mL), and DIEA (1.28 mL, 7.34 mmol) and (3R,4R)-pyrrolidine-3,4-diol (227 mg, 2.203 mmol) were added. The mixture was stirred for 3 hours at room temperature. After powderization by adding diisopropyl ether, the obtained solids were purified by silica-gel column chromatography (chloroform/methanol/water=85/15/1.5) to give Compound 19 (379 mg, 17%) as brown solids. Compound 19 (379 mg, 0.318 mmol) was dissolved into DMF (5 mL), and morpholine (0.277 mL, 3.18 mmol) and Pd(PPh$_3$)$_4$ (18.4 mg, 0.016 mmol) were added. The mixture was stirred for an hour at room temperature. After powderization by adding diisopropyl ether, the obtained powder was purified by silica-gel column chromatography (chloroform/methanol/water=70/30/3 to 10/90/9) to give Compound I-260 (195 mg, 10%).

LC/MS: m/z 1024.5 [M+H]+, 1046.6, [M+Na]+

Elementary analysis: (C51H81N3O18)(H2O)3.9

Calculated value: C 55.97; H, 8.18; N, 3.84 (%).

Actual value: C 55.98; H, 8.25; N, 3.97 (%).

Example 29

Synthesis of Compound I-263

[Chemical Formula 77]

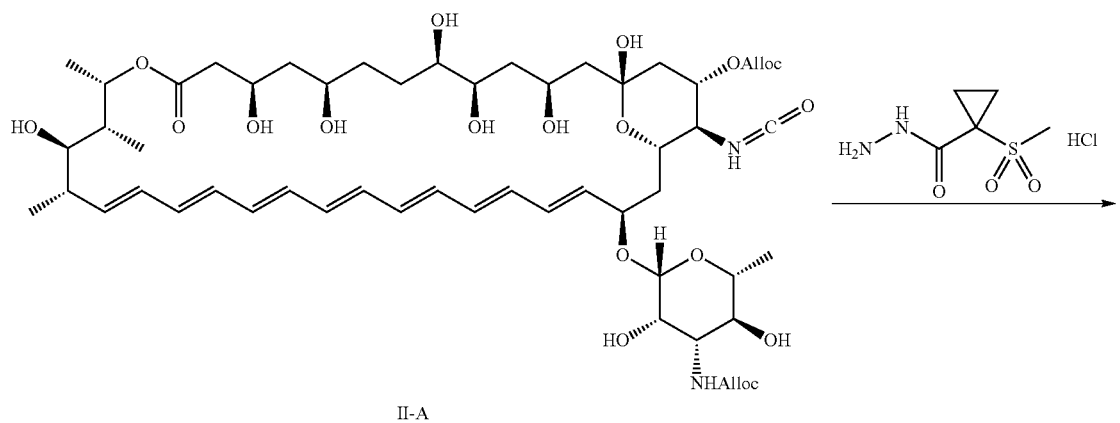

II-A

-continued

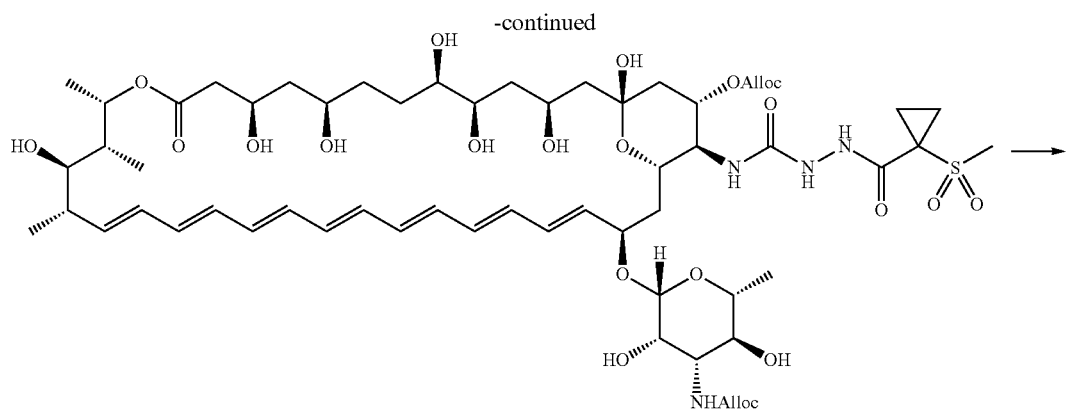

20

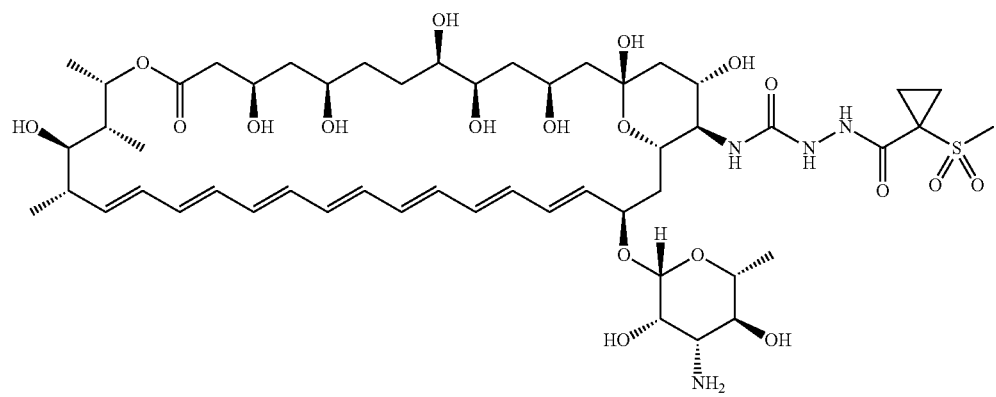

I-263

Compound II-A (2 g, 1.836 mmol) was dissolved into DMF (10 mL), and DIEA (1.6 mL, 9.18 mmol) and 1-(methylsulfonyl)cyclopropanecarbonylhydrazine hydrochloride (394 mg, 1.836 mmol) were added. The mixture was stirred at 40° C. After powderization by adding diisopropyl ether, the obtained solids were purified by silica-gel column chromatography to give Compound 20 (576 mg, 25%) as brown solids. Compound 20 was dissolved into DMF (5 mL), and morpholine (0.396 mL, 4.54 mmol) and Pd(PPh$_3$)$_4$ (26 mg, 0.023 mmol) were added. The mixture was stirred for an hour at room temperature. After powderization by adding diisopropyl ether, the obtained powder was purified by silica-gel column chromatography to give Compound I-263 (307 mg, 58%).

LC/MS: m/z 1099.4 [M+H]+, 1121.5, [M+Na]+

Elementary analysis: C52H82N4O19S(C3H7NO)0.4 (H2O)2.8

Calculated value: C 54.20; H, 7.73; N, 5.23; S, 2.72 (%).

Actual value: C 54.22; H, 7.68; N, 5.23; S, 2.76 (%).

Example 30

Synthesis of Compound I-272

[Chemical Formula 78]

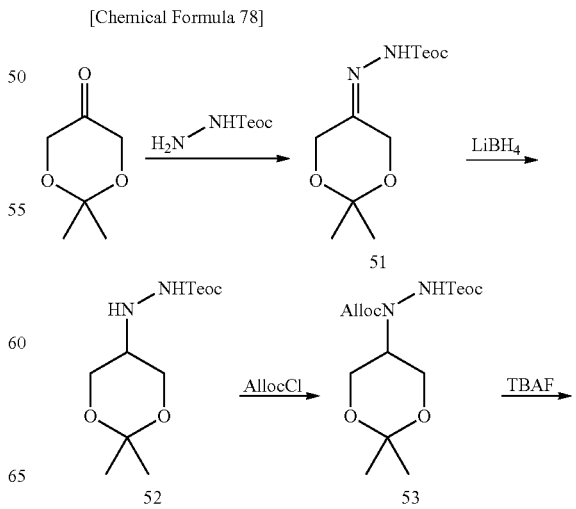

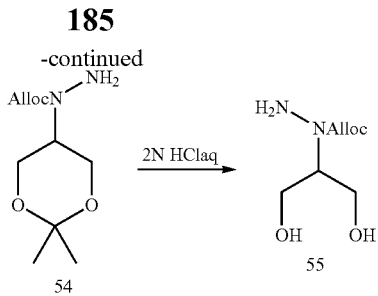

Step 1

2-Trimethylsilylethyloxycarbonylhydrazine (3.27 g, 18.55 mmol) and 2,2-dimethyl-1,3-dioxane-5-one (2.414 g, 18.55 mmol) were dissolved into methanol (20 mL). After the mixture was stirred at room temperature, the mixture was condensed. The mixture was purified by silica-gel column chromatography (hexane/ethyl acetate=9/1) to give Compound 51 (4.46 g, 83%) as white solids.

1H-NMR (CDCl3, 400 MHz) δ: 4.19 (m, 4H), 4.29 (t, 2H, J=12 Hz), 1.26 (s, 6H), 1.05 (t, 2H, J=12 Hz), 0.04 (s, 9H)

Step 2

Compound 51 (4.46 g, 15.5 mmol) was dissolved into tetrahydrofuran (100 mL), and LiBH$_4$ (1.013 g, 46.5 mmol) and methanol (10 mL) were added. After the mixture was stirred for 40 minutes at 0° C., LiBH$_4$ (1.013 g, 46.5 mmol) was added and further the mixture was stirred at room temperature. The reaction was quenched by water. After the mixture was extracted with ethyl acetate, the mixture was purified by silica-gel column chromatography to give Compound 52 (3.91 g, 87%).

Step 3

Compound 52 (3.91 g, 13.46 mmol) was dissolved into DMF (20 mL), and DIEA (3.29 mL, 18.85 mmol) was added, and further allyl chloroformate (1.72 mL, 16.16 mmol) was added in an ice-water bath. The mixture was stirred at room temperature. The reaction was quenched by adding saturated sodium bicarbonate aqueous solution, and the mixture was extracted with ethyl acetate. The organic phase was washed with water five times and dried up with magnesium sulfate. The obtained residue was purified by silica-gel column chromatography (hexane/ethyl acetate=4/1 to 3/2).

1H-NMR(CDCl3, 400 MHz)δ:5.88 (m, 1H), 5.30 (d, 1H, J=16 Hz), 5.27(m, 1H), 4.62 (s, 2H),4.23 (m, 3H), 3.97 (br, 4H),1.41(s, 3H), 1.40(s, 3H), 1.01 (t, 2H, J=8 Hz), 0.03 (s, 9H)

Step 4

Compound 53 (1.73 g, 4.62 mmol) was dissolved into tetrahydrofuran (20 mL), and tetrabutylammonium fluoride (1 mol/L, 9.2 mL, 9.2 mmol) was added. The mixture was stirred for an hour at room temperature. The reaction was quenched with water, and the mixture was extracted with ethyl acetate. The organic phase was washed with water and brine and dried up with sodium sulfate anhydrous. The residue was condensed to give crude Compound 54 (1.17 g).

δ:6.00-5.90 (m, 1H), 5.32 (d, 1H, J=16 Hz), 5.25(d, 1H, J=8 Hz), 4.62 (d, 2H, J=4 Hz),4.23 (m, 1H), 4.13 (br, 2H),3.84 (br, 4H), 1.51(s, 3H), 1.41 (s, 3H).

Step 5

Compound 54 (1.17 g, 5.08 mmol) was dissolved into tetrahydrofuran (10 mL), and 2 mol/L hydrochloric acid aqueous solution (5.08 mL, 10.16 mmol) was added. After the mixture was stirred at room temperature, the mixture was condensed. The resulted residue was dissolved into methanol and purified by silica-gel column chromatography (chloroform/methanol=1/1) to give Compound 55 (1.02 g).

[Chemical Formula 79]

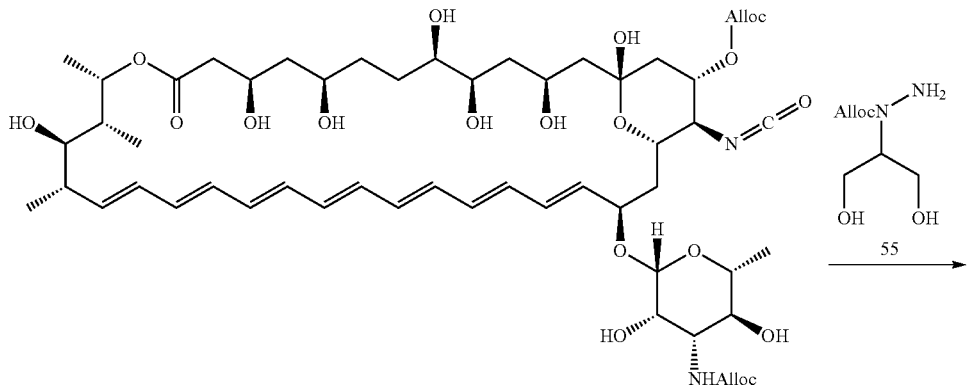

II-A

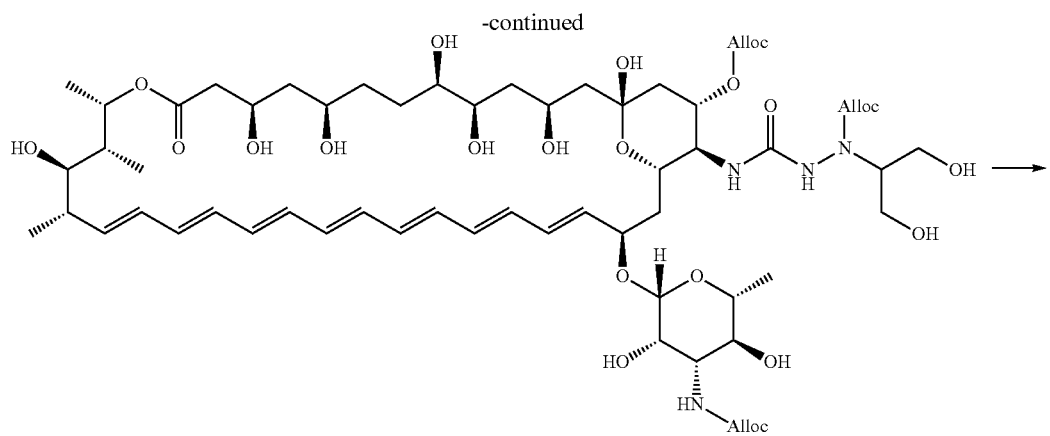

56

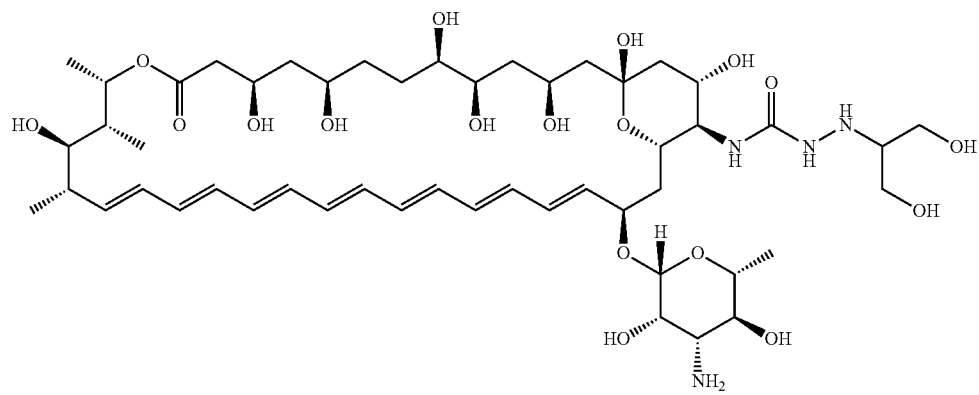

I-272

Compound II-A (3 g, 2.75 mmol) was dissolved into DMF (15 mL), and Compound 55 (524 mg, 2.75 mmol) and DIEA (1.92 mL, 11.02 mmol) were added. The mixture was stirred at room temperature. After powderization by adding diisopropyl ether, the obtained residue was purified crudely by silica-gel column chromatography. The obtained powder (Compound 56: 887 mg) was dissolved into DMF (5 mL), and morpholine (0.6 mL, 6.93 mmol) and Pd(PPh$_3$)$_4$ (40 mg, 0.035 mmol) were added. The mixture was stirred at room temperature under nitrogen atmosphere. The obtained solids by adding diisopropyl ether (900 mL) were filtrated. The resulted residue was purified by silica-gel column chromatography (chloroform/methanol/water=70/30/3 to 10/90/9). The obtained fractions were condensed to give Compound I-272 (213 mg, 0.176 mmol, yellow powder, 6%) as orange color powder.

LC/MS: m/z 1027.4 [M+H]+

Elementary analysis: C50H82N4O18(C3H7NO)0.5 (H2O)2.4

Calculated value: C 55.88 (0.02%); H, 8.22 (−0.05%); N, 5.69 (−0.02 %) (%).

Actual value: C 55.90; H, 8.17; N, 5.67 (%).

Example 31

Synthesis of Compound I-273

[Chemical Formula 80]

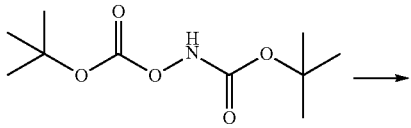

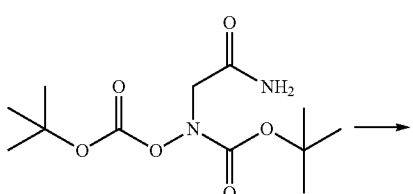

57

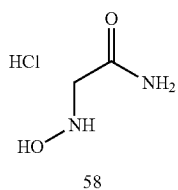

Tert-butyl tert-butyloxycarbonyloxycarbamate (1.91 g, 8.19 mmol) was dissolved into DMF (10 mL), and 2-bromoacetamide (1.243 g, 9.01 mmol) and potassium carbonate (1.471 g, 10.64 mmol) were added. The mixture was stirred at room temperature. After the reaction was quenched with ethyl acetate, the mixture was purified by silica-gel column chromatography to give Compound 57 (898 mg, 38%). Compound 57 was dissolved into dichloromethane (20 mL), and hydrochloric acid-dioxane (4 mol/L, 6.19 mL, 24.75 mmol) was added. After the mixture was stirred at room temperature, the mixture was condensed to give Compound 58 (391 mg). Compound 58 was used to next reaction without purification.

2-Hydroxyamino acetate amide (Compound 58: 0.391 g, 3.08 mmol) was dissolved into DMF (15 mL), and DIEA (1.924 mL, 11.02 mmol) was added. After the mixture was stirred at room temperature, Compound II-A (3 g, 2.75 mmol) was added. The mixture was stirred for 20 minutes at room temperature. After powderization by adding diisopropyl ether, the obtained residue was purified crudely by silica-gel column chromatography. The obtained solids (2.23 g, 1.891 mmol) were dissolved into DMF (4 mL), morpholine (1.65 mL, 18.91 mmol) and Pd(PPh$_3$)$_4$ (109 mg, 0.095 mmol) were added. The mixture was stirred at room temperature under nitrogen atmosphere. After the resulting solids by adding diisopropyl ether were filtered, the solids were purified by silica-gel column chromatography (chloroform/methanol/water=70/30/3 to 10/90/9) to give Compound I-273 (341 mg, 16%) as yellow powder.

LC/MS: m/z 1011.4 [M+H]+

Elementary analysis: C49H78N4O18(C3H7NO)1.3 (H2O)1.9

Calculated value: C 55.71 (0.02%); H, 8.03 (−0.05%); N, 6.51 (−0.02 %) (%).

Actual value: C 55.73; H, 7.98; N, 6.49 (%).

[Chemical Formula 81]

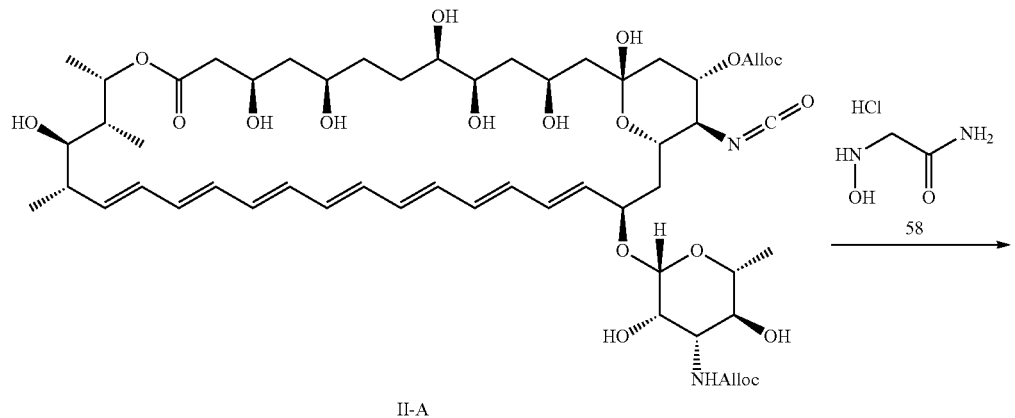

II-A

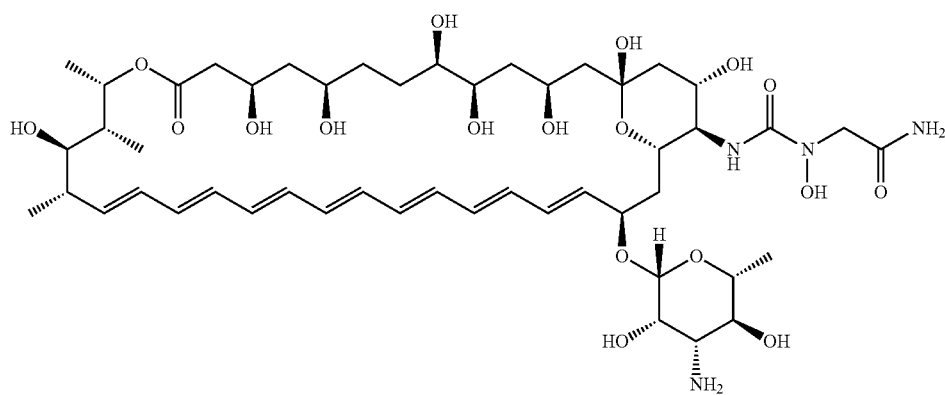

I-273

Example 32

Synthesis of Compound I-281

[Chemical Formula 82]

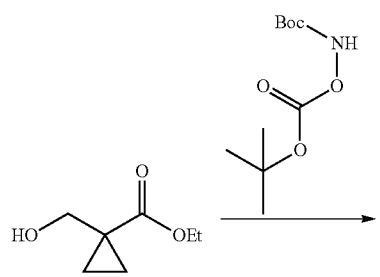

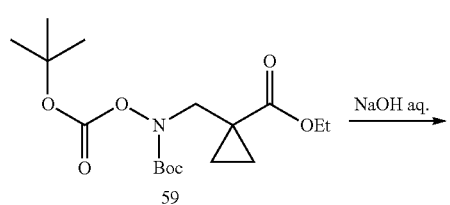

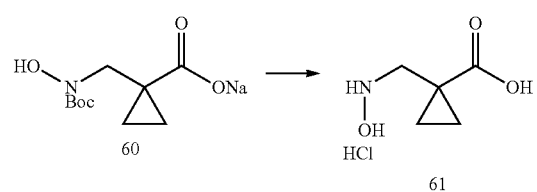

Step 1

Ethyl 1-(hydroxymethyl)cyclopropanecarboxylate (500 mg, 3.47 mmol) was dissolved into tetrahydrofuran (20 mL), and tert-butyl tert-butyloxycarbonyloxycarbamate (0.971 g, 4.16 mmol) was added, and triphenylphosphine (1.364 g, 5.20 mmol) and DIAD (2.74 mmol) were added in an ice-water bath. The mixture was stirred. After silica-gel was added, and the mixture was condensed, the residue was purified by silica-gel column chromatography to give Compound 59 (1.29 g, 99%).

Step 2

Compound 59 (1.29 g, 3.61 mmol) was dissolved into tetrahydrofuran (10 mL), and 2 mol/L sodium hydroxide aqueous solution (1.8 mL, 3.61 mmol) was added. The mixture was stirred under heat reflux. The mixture was reacted not only hydrolysis but also leaving carbonate reaction by cooling to room temperature. Ethanol was added, and the mixture was condensed and solidified to give Compound 60 (914 mg). Compound 60 was used to next reaction without purification.

Step 3

Compound 60 (914 mg, 3.61 mmol) was dissolved into dichloromethane (20 mL), and hydrochloric acid-dioxane (4 mol/L, 7.2 mL) was added. After the mixture was stirred at room temperature, the mixture was condensed to give Compound 61 (615 mg).

LC-MS: 132 [M+1]

[Chemical Formula 83]

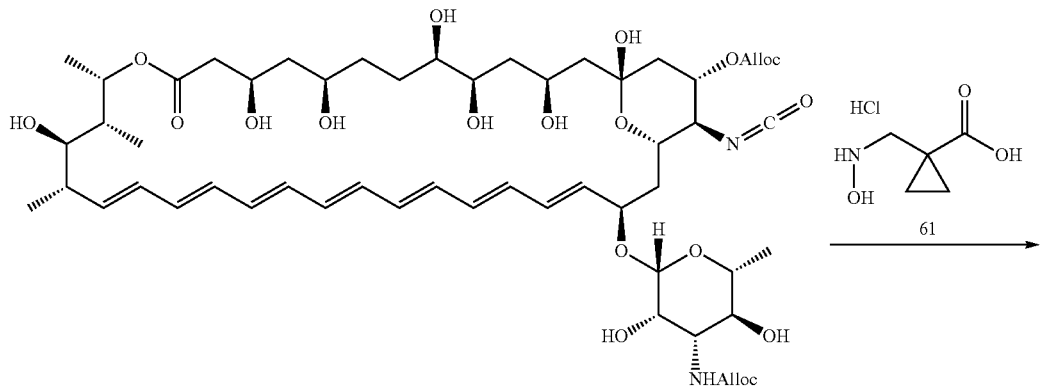

II-A

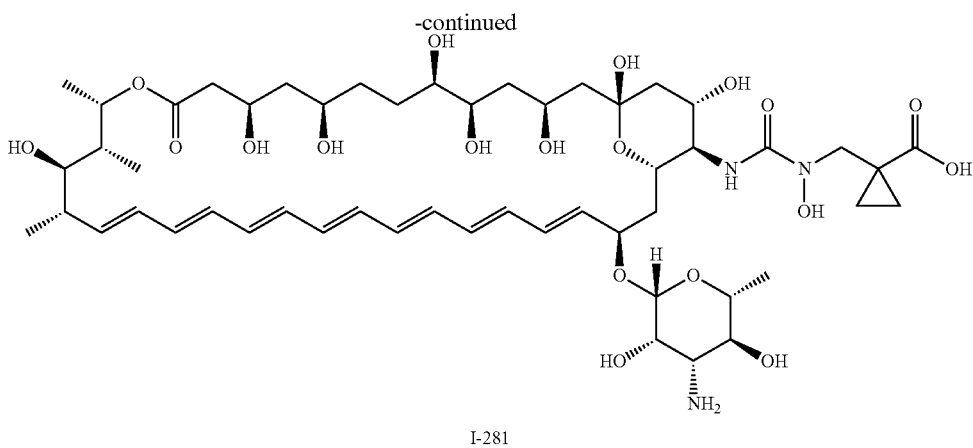

I-281

Compound II-A (2 g, 1.84 mmol) was dissolved into DMF (10 mL), and Compound 61 (615 mg, 3.67 mmol) and DIEA (1.6 mL, 9.18 mmol) were added. The mixture was stirred at room temperature. After powderization by adding diisopropyl ether, the obtained residue was purified crudely by silica-gel column chromatography. The obtained solids (753 mg) were dissolved into DMF (5 mL), and morpholine (0.54 mL, 6.17 mmol) and Pd(PPh$_3$)$_4$ (36 mg, 0.031 mmol) were added. The mixture was stirred at room temperature under nitrogen atmosphere. The resulted solids by adding diisopropyl ether were filtered. The resulted solids were purified by silica-gel column chromatography (chloroform/methanol/water=70/30/3 to 10/90/9). The obtained fractions were condensed to give Compound I-281 (199 mg, 28%) as orange color powder.

LC/MS: m/z 1052.4 [M+H]+

Elementary analysis: C52H81N3O19(C3H7NO)1.3 (H2O)1.7

Calculated value: C 57.00; H, 8.00; N, 5.11 (%).
Actual value: C 57.01; H, 8.01; N, 5.17 (%).

Example 33

Synthesis of Compound I-292

[Chemical Formula 84]

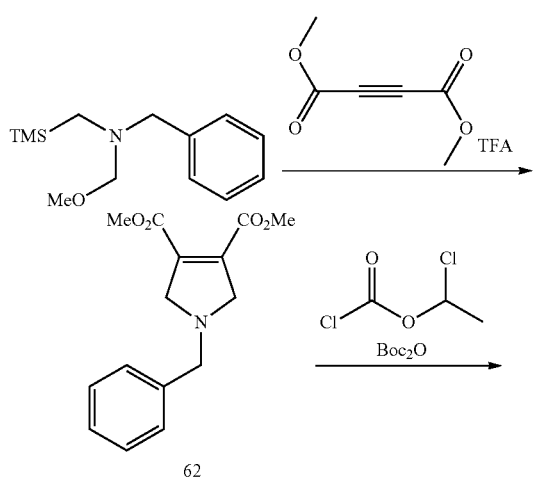

Step 1

N-Benzyl-N-(methoxymethyl)-N-trimethylsilylmethyl-amine (10 g, 42.1 mmol) was dissolved into dichloromethane (150 mL), and Dimethyl acetylenedicarboxylate (7.18 g, 50.5 mmol) was added in an ice-water bath. The mixture was stirred. After trifluoroacetic acid (16.2 mL, 211 mmol) was added and stirred, the reaction was quenched with saturated sodium bicarbonate aqueous solution. After the mixture was extracted with dichloromethane, the organic phase was washed with brine and dried up with sodium sulfate anhydrous. The resulted residue was purified by silica-gel column chromatography (hexane/ethyl acetate=9/1 to 1/1) to give Compound 62 (5.87 g, 51%) as yellow oil.

1H-NMR(CDCl3, 400 MHz)δ:7.33-7.27 (m, 5H), 3.94(s, 2H), 3.82(s, 4H), 3.77 (s, 6H).

Step 2

Compound 62 (5.36 g, 19.5 mmol) was dissolved into toluene (76 mL), and 1-chloroethyl chloroformate (2.94 mL, 27.3 mmol) was added in an ice-water bath. The mixture was stirred under heat reflux. After confirmation of disappearance of materials by TLC, the obtained gel solid by evaporating was dissolved into methanol (7 mL). The mixture was stirred under heat reflux to remove benzyl group. After cooling to room temperature, Boc$_2$O (9.04 mL, 38.9 mmol) and DIEA (6.8 mL, 38.9 mmol) were added. Methanol was removed by evaporating, and the mixture was extracted with ethyl acetate. The organic phase was washed with 0.2 mol/L hydrochloric acid aqueous solution and brine and dried up with sodium sulfate anhydrous. The residue was purified by silica-gel column chromatography (hexane/ethyl acetate=7/3) to give Compound 63 (4.17 g, 75%) as colorless oil.

1H-NMR(CDCl3, 400 MHz) δ: 4.44 (d, 4H, J=12 Hz), 3.82 (s, 6H), 1.48 (s, 9H).

Step 3

Compound 63 (917 mg, 3.21 mmol) was dissolved into tetrahydrofuran (10 mL), and 2 mol/L sodium hydroxide aqueous solution (4.82 mL) was added. The mixture was stirred for 2 hours at room temperature. After the mixture was neutralized with 2 mol/L hydrochloric acid aqueous solution (4.82 mL) and condensed, the mixture was dissolved into dichloromethane (15 mL). After hydrochloric acid-dioxane (4 mol/L, 3.2 mL) was added, and the mixture was stirred at room temperature, the mixture was condensed to give Compound 64 (600 mg). Compound 64 was used to next reaction without purification.

tography. The obtained solids (1.47 g) were dissolved into DMF (5 mL), and morpholine (1.03 mL, 11.8 mmol) and Pd(PPh$_3$)$_4$ (68 mg, 0.059 mmol) were added. The mixture was stirred at room temperature under nitrogen atmosphere. The resulted solids by adding diisopropyl ether were filtrated. The solids were purified by silica-gel column chromatography (chloroform/methanol/water=70/30/3 to 10/90/

[Chemical Formula 85]

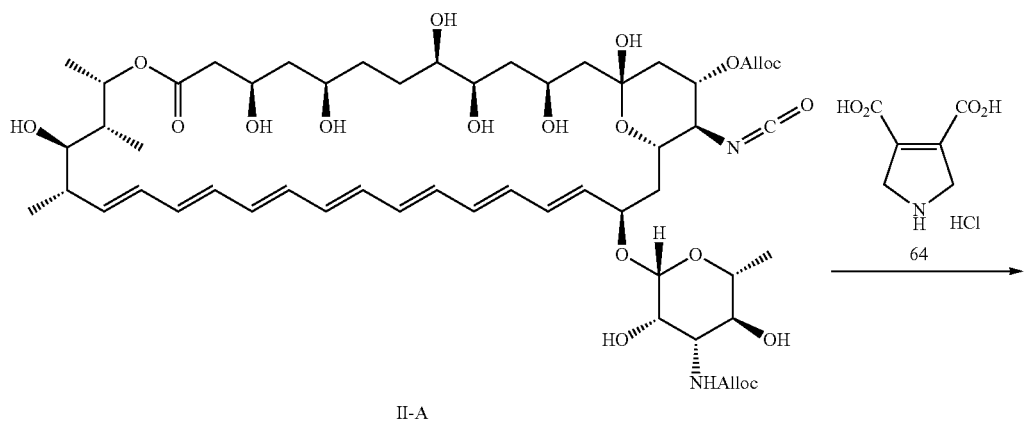

II-A

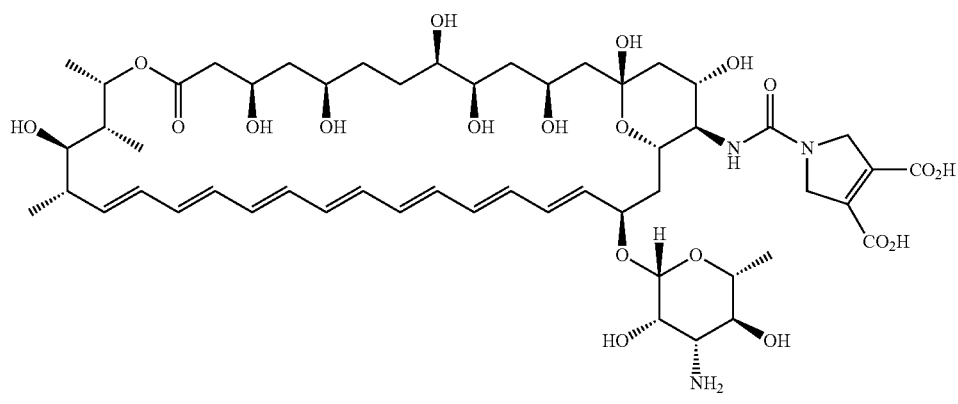

I-292

Compound 64 (355 mg, 1.83 mmol) was dissolved into DMF (10 mL), and DIEA (0.321 mL, 1.83 mmol) and Compound II-A (2 g, 1.84 mmol) were added. The mixture was stirred for a few hours at room temperature. After powderization by adding diisopropyl ether, the obtained residue was purified crudely by silica-gel column chroma- 9). The obtained fractions were condensed to give Compound I-292 (13 mg, yellow powder, 0.9%).

LC/MS: m/z 1078.5 [M+H]+

Elementary analysis: C53H79N3O20(C3H7NO)0.3 (H2O)4.4

Calculated value: C 54.89; H, 7.68; N, 3.97 (%).

Actual value: C 54.90; H, 7.49; N, 3.97 (%).

Example 34

Synthesis of Compound I-309

[Chemical Formula 86]

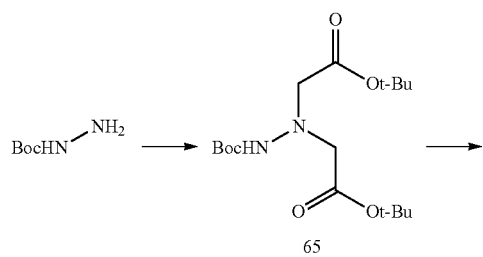

Step 1

Tert-butyl 2-bromoacetate (2.2 mL, 15.1 mmol) was dissolved into DMF (10 mL), and DIEA (2.64 mL, 15.1 mmol) and tert-butyl hydrazine carboxylate (1 g, 7.57 mmol) were added. The mixture was stirred at room temperature. After water was added, the mixture was extracted with ethyl acetate. The organic phase was washed with water and brine and dried up with sodium sulfate anhydrous. The residue was purified by silica-gel column chromatography (hexane/ethyl acetate=1/1) to give Compound 65 (1.8 g, 66%) as white solids.

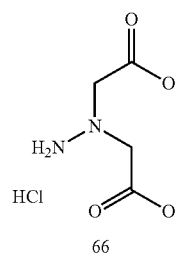

Step 2

Compound 1 (1.8 g, 4.99 mmol) was dissolved into dichloromethane (20 mL), and hydrochloric acid-dioxane (4 mol/L, 5 mL) was added. The mixture was stirred at room temperature and condensed to give Compound 66 (1.01 g) as gummy solids. Compound 66 was used to next reaction without purification.

[Chemical Formula 87]

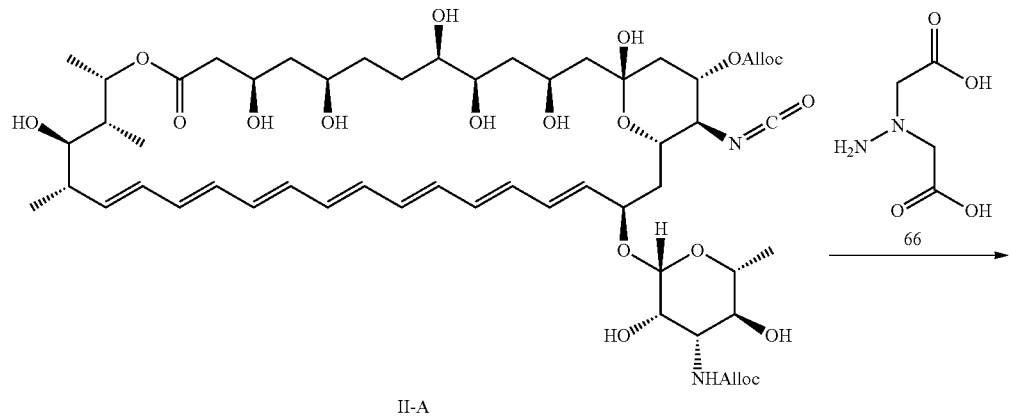

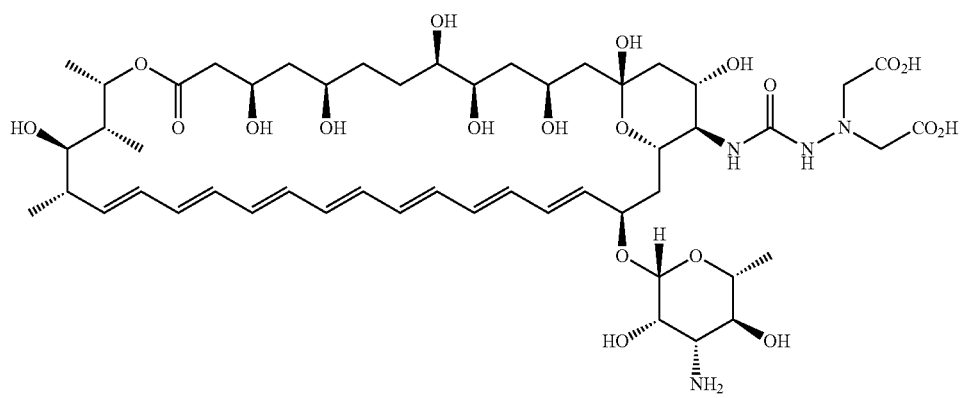

Compound II-A (2 g, 1.84 mmol) was dissolved into DMF (10 mL), and DIEA (0.321 mL, 1.84 mmol) and Compound 66 (0.339 g, 1.836 mmol) were added. The mixture was stirred for 40 minutes at room temperature. After powderization by adding diisopropyl ether, the obtained residue was purified crudely by silica-gel column chromatography. The obtained solids (1.51 g) were dissolved into DMF (6 mL), and morpholine (1.06 mL, 12.2 mmol) and Pd(PPh$_3$)$_4$ (71 mg, 0.061 mmol) were added. The mixture was stirred for 20 minutes at room temperature under nitrogen atmosphere. The resulting solids by adding diisopropyl ether were filtered. The solids were purified by silica-gel column chromatography (chloroform/methanol/water=70/30/3 to 10/90/9). The obtained fractions were condensed to give Compound I-309 (174 mg, 7%) as orange powder.

LC/MS: m/z 1069.4 [M+H]+

Elementary analysis: C51H80N4O20(C3H7NO)1.1(H2O)0.4(MeOH)1.7

Calculated value: C 55.53 (−0.01%); H, 7.93 (0.01%); N, 5.90 (0.02%) (%).

Actual value: C 55.52; H, 7.94; N, 5.92 (%).

Example 35

Synthesis of Compound I-278

[Chemical Formula 88]

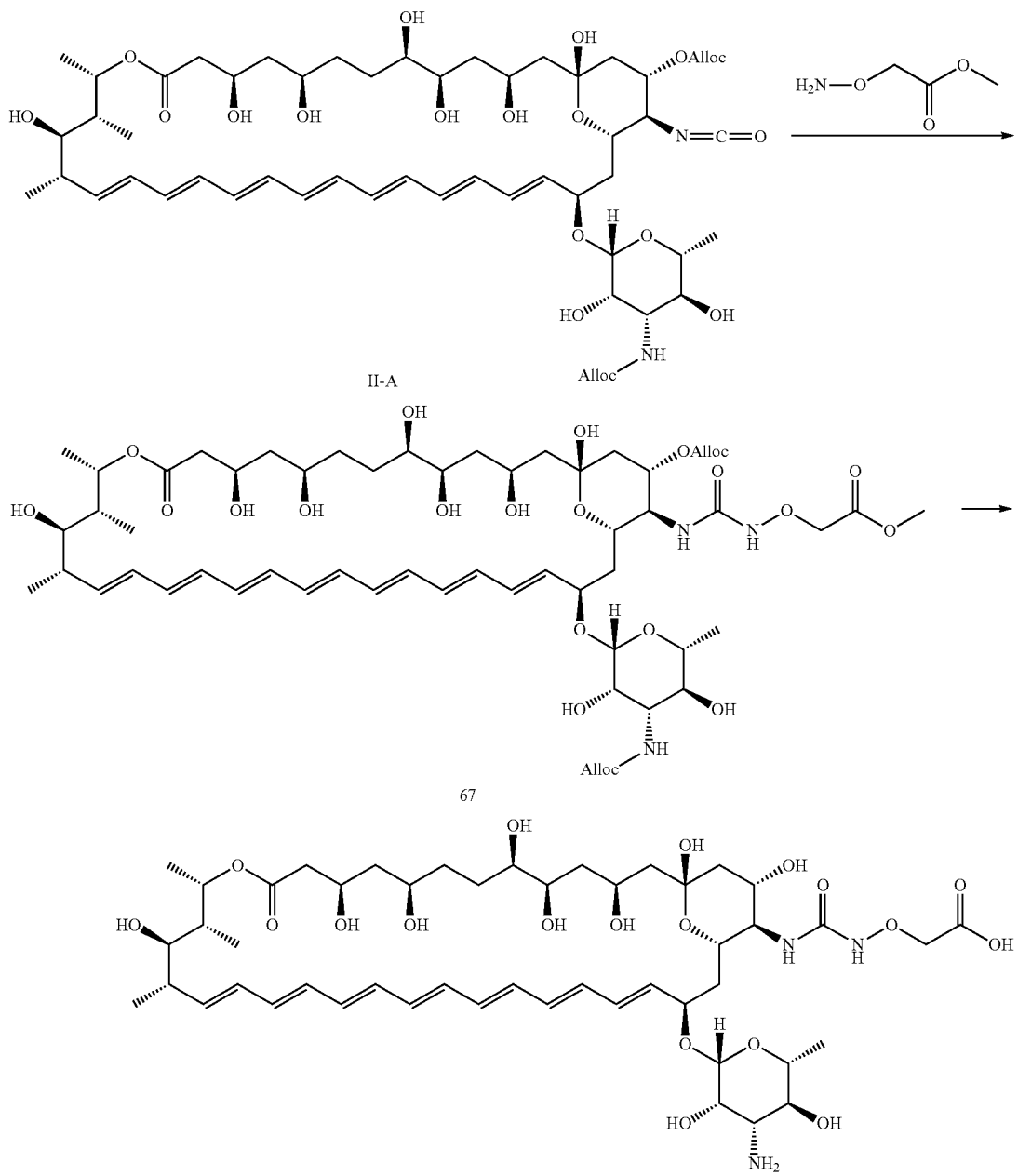

Step 1

Compound II-A (2 g, 1.84 mmol) was dissolved into DMF (10 mL), and DIEA (1.6 mL, 9.18 mmol) and methylaminooxy acetate (347 mg, 3.31 mmol) were added. The mixture was stirred for an hour 20 minutes at room temperature. After water was added, the mixture was stirred for an hour 30 minutes at room temperature. After powderization by adding diisopropyl ether, the powder was purified by silica-gel column chromatography (chloroform/methanol/water=95/5/0.5-85/15/1.5) to give yellow powder (Compound 67: 300 mg, 13%). The retention time was 11.4 minutes by HPLC analysis (methanol/distilled water containing 0.1% PIC-B7=gradient 70/30 to 100/0, flow speed 1 ml/min, wavelength of detection=385 nm).

Step 2

Compound 67 (300 mg, 0.251 mmol) was dissolved into DMF (5 mL), and morpholine (0.22 mL, 2.51 mmol) and Pd(PPh$_3$)$_4$ (14.5 mg, 0.013 mmol) were added. The mixture was stirred for 45 minutes at room temperature under nitrogen atmosphere. The resulting solids by adding diisopropyl ether were filtered. The solids were purified by silica-gel column chromatography (chloroform/methanol/water=50/50/3 to 10/90/9). The obtained fractions were condensed to give orange powder (141 mg, 0.137 mmol). The powder was dissolved into tetrahydrofuran (12 mL) and methanol (6 mL), and 2 mol/L sodium hydroxide aqueous solution (0.21 mL, 0.412 mmol) was added. The mixture was stirred for an hour at room temperature. The mixture was neutralized with 2 mol/L hydrochloric acid aqueous solution and diluted with water. After organic solvent was condensed, the residue was lyophilized to give Compound I-278 (190 mg, 55%). The retention time was 7.7 minutes by HPLC analysis (methanol/distilled water containing 0.1% PIC-B7=gradient 70/30 to 100/0, flow speed 1 ml/min, wavelength of detection=385 nm).

LC/MS: 1012.3 [M+H]+

Elementary analysis: C49H77N3O19(H2O)6.1(NaCl)5

Calculated value: C 41.61; H, 6.36; N, 2.97 (%).

Actual value: C 41.64; H, 6.65; N, 3.34 (%).

Example 36

Synthesis of Compound I-223

[Chemical Formula 89]

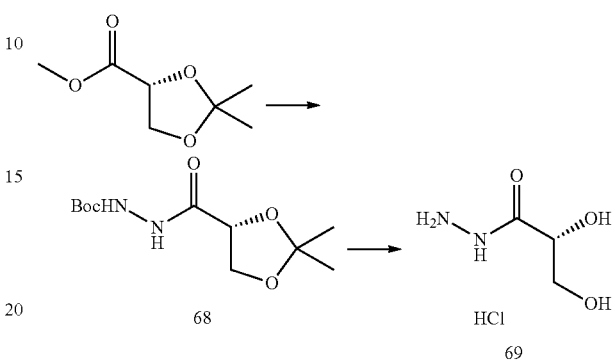

(R)-methyl 2,2-dimethyl-1,3-dioxolane-4-carboxylate (1 g, 6.24 mmol) was dissolved into methanol (10 mL), and hydrazine monohydrate (0.303 mL, 6.24 mmol) was added. The mixture was stirred for 4 hours at room temperature. Boc$_2$O (1.45 mL, 6.24 mmol) was added, and the mixture was stirred. After concentration, the mixture was purified by silica-gel column chromatography to give (R)-tert-butyl 2-(2,2-dimethyl-1,3-dioxolane-4-carbonyl)hydrazine carboxylate (Compound 68: 490 mg, 30%).

H-NMR (CDCl3, 400 MHz) δ: 8.13 (s, 1H), 6.44 (br, 1H), 4.59 (m, 1H), 4.30 (m, 1H), 4.18 (m, 1H), 1.58 (s, 3H), 1.48 (s, 9H), 1.40 (s, 3H)

Compound 68 was dissolved into dichloromethane (10 mL), hydrochloric acid-dioxane (4 mol/L, 1.883 mL, 7.53 mmol) was added. The mixture was stirred and condensed to give Compound 69. Compound 69 was used to next reaction without purification.

[Chemical Formula 90]

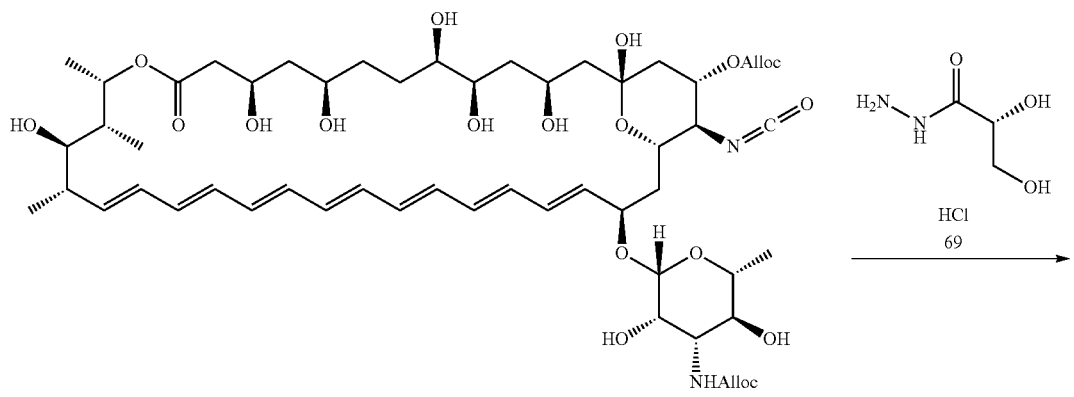

II-A

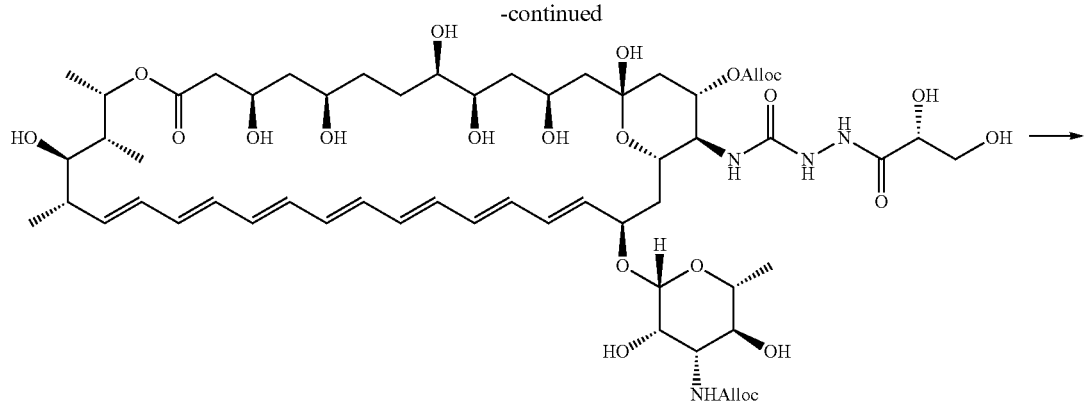

70

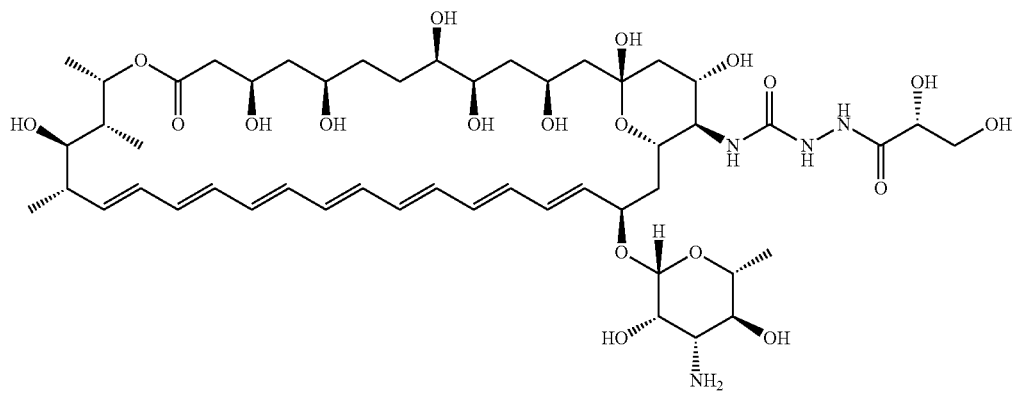

I-223

Compound II-A (1.961 g, 1.8 mmol) was dissolved into DMF, and DIEA (1.57 mL, 9.00 mmol) and Compound 69 (282 mg, 1.8 mmol) were added. The mixture was stirred at room temperature. After powderization by adding diisopropyl ether, the powder was purified by silica-gel column chromatography (chloroform/methanol/water=95/5/0.5 to 85/15/1.5) to give Compound 70 (750 mg, 34%). Compound 70 (750 mg, 0.62 mmol) was dissolved into DMF (4 mL), and morpholine (0.54 mL, 6.2 mmol) and Pd(PPh$_3$)$_4$ (35.8 mg, 0.031 mmol) were added. The mixture was stirred for an hour at room temperature under nitrogen atmosphere. The resulting solids by adding diisopropyl ether were filtered and purified by silica-gel column chromatography (chloroform/methanol/water=50/50/3 to 10/90/9) to give Compound I-223 (104 mg, 14%).

LC/MS: 1041.4 [M+H]+, 1063.5 [M+Na]+
Elementary analysis: C50H80N4O19(H2O)4.5
Calculated value: C 53.51; H, 7.99; N, 4.99 (%).
Actual value: C 53.53; H, 7.73; N, 4.86 (%).

Example 37

Synthesis of Compound I-298

[Chemical Formula 91]

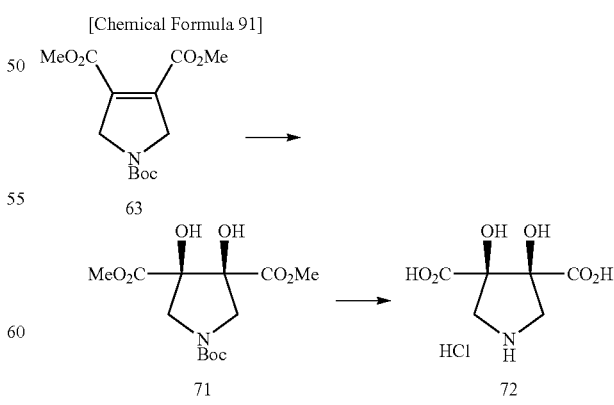

Step 1

1-Tert-butyl 3,4-dimethyl 1H-pyrrole-1,3,4(2H,5H)-tricarboxylate (Compound 63: 1 g, 3.51 mmol) synthesized at Example 33 was dissolved into dioxane (10 mL), and water (10 mL) and Potassium Osmate(VI) Dihydrate (65 mg, 0.175 mmol) were added. The mixture was stirred in an ice-water bath. N-methylmorpholine N-oxide (616 mg, 5.26 mmol) was added, and the mixture was stirred. The reaction was quenched with 10% sodium hydrogen sulfite aqueous solution, and the mixture was extracted with ethyl acetate. The organic phase was washed with brine and dried up with sodium sulfate anhydrous, and the resulted residue was purified by silica-gel column chromatography (hexane/ethyl acetate=1/1) to give Compound 71 (843 mg, 75%).

1H-NMR(CDCl3, 400 MHz)δ:3.97 (d, 1H, J=8 Hz), 3.90(d, 1H, J=8 Hz), 3.79 (s, 6H).3.72(d, 2H, J=8 Hz), 3.62(d, 2H, J=12 Hz), 1.49(s, 9H)

Step 2

Compound 71 (743 mg, 2.327 mmol) was dissolved into tetrahydrofuran (10 mL) and water (5 mL), and 2 mol/L sodium hydroxide aqueous solution (3.49 mL, 6.98 mmol) was added. The mixture was stirred for 2 hours at room temperature. The mixture was neutralized with 2 mol/L hydrochloric acid aqueous solution and condensed. Dichloromethane (20 mL) was added to the obtained residue, and hydrochloric acid-dioxane (4 mol/L, 2.3 mL) was added. After the mixture was stirred for at room temperature, the mixture was condensed to give Compound 72 (530 mg) as gummy solids. Compound 72 was used to next reaction without purification.

[Chemical Formula 92]

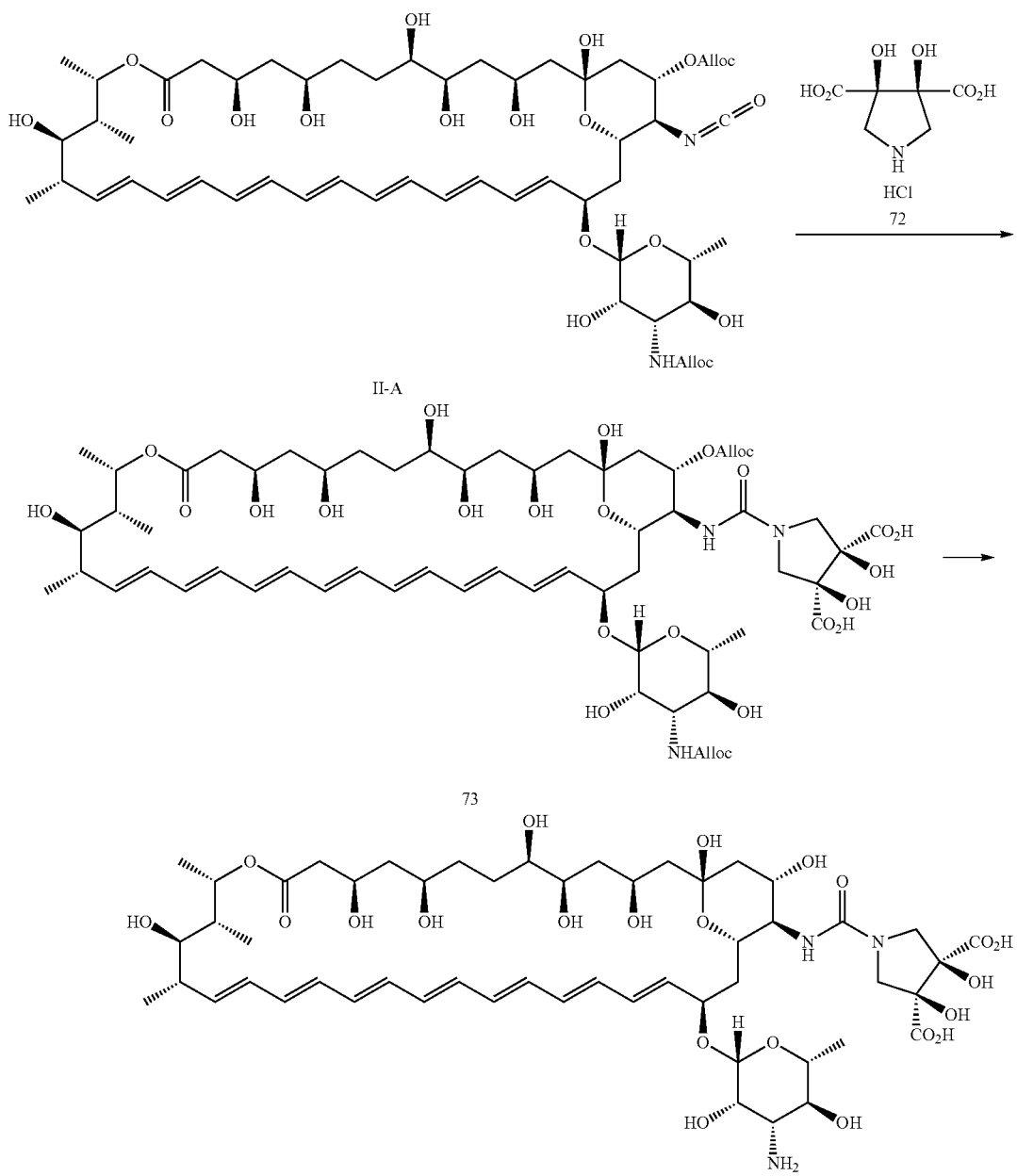

Compound 72 (530 mg, 2.33 mmol) was dissolved into DMF (10 mL), and DIEA (1.28 mL, 7.34 mmol) and Compound II-A (2 g, 1.84 mmol) were added. The mixture was stirred at room temperature. After powderization by adding diisopropyl ether, the resulted powder was purified by silica-gel column chromatography (chloroform/methanol/water=95/5/0.5 to 85/15/1.5). The obtained powder 73 (706 mg, 0.551 mmol) was dissolved into DMF (3 mL), and morpholine (0.48 mL, 5.51 mmol) and Pd(PPh$_3$)$_4$ (32 mg, 0.028 mmol) were added. The mixture was stirred at room temperature. The resulting solids by adding diisopropyl ether were filtered. The solids were purified by silica-gel column chromatography (chloroform/methanol/water=50/50/3 to 10/90/9) to give Compound I-298 (43 mg, 7%).

LC/MS: 1112.4 [M+H]+

Elementary analysis: C53H81N3O22(C3H7NO)0.2(H2O)4.2

Calculated value: C 53.54; H, 7.61; N, 3.73 (%).
Actual value: C 53.55; H, 7.54; N, 3.80 (%).

Example 38

Synthesis of Compound I-252

Compound II-A (2 g, 1.836 mmol) was dissolved into DMF (10 mL), and DIEA (1.6 mL, 9.18 mmol) and 3-aminooxetan-3-carboxylic acid (215 mg, 1.836 mmol) were added. The mixture was stirred at 40° C. over night. After powderization by adding diisopropyl ether, the resulted powder was purified by silica-gel column chromatography. The obtained powder (695 mg, 31%) was dissolved into DMF (5 mL), and morpholine (0.50 mL, 5.76 mmol) and Pd(PPh$_3$)$_4$ (33 mg, 0.029 mmol) were added. The mixture was stirred for 15 minutes at room temperature under nitrogen atmosphere. The resulting solids by adding diisopropyl ether were filtered. The resulted solids were purified by silica-gel column chromatography (chloroform/methanol/water=70/30/3 to 10/90/9) to give Compound I-252 (58.4 mg, 8%).

LC/MS: 1038.4[M+H]+

Elementary analysis: C51H79N3O19(C3H7NO)0.7(H2O)2.0(MeOH)1.8

Calculated value: C 55.74; H, 8.10; N, 4.38 (%).
Actual value: C 55.72; H, 8.04; N, 4.36 (%).

[Chemical Formula 93]

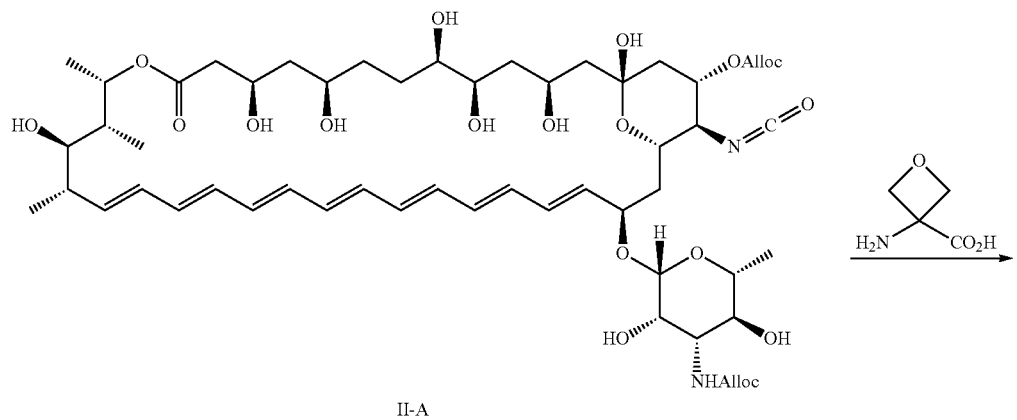

II-A

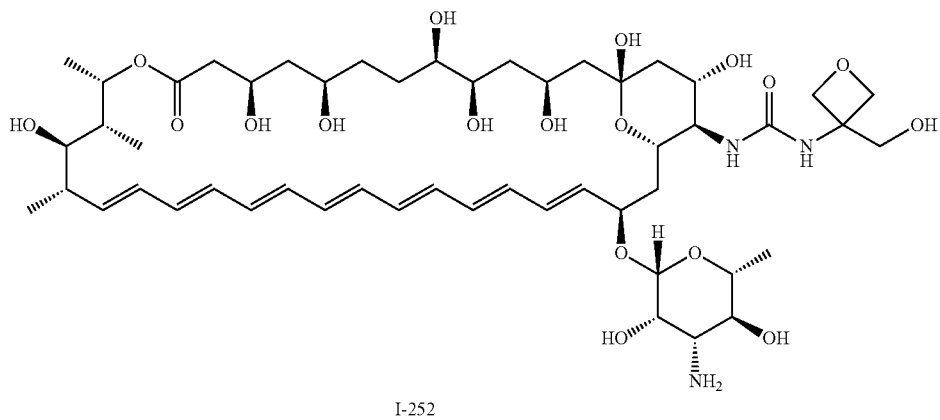

I-252

Example 39

Synthesis of Compound I-307

[Chemical Formula 94]

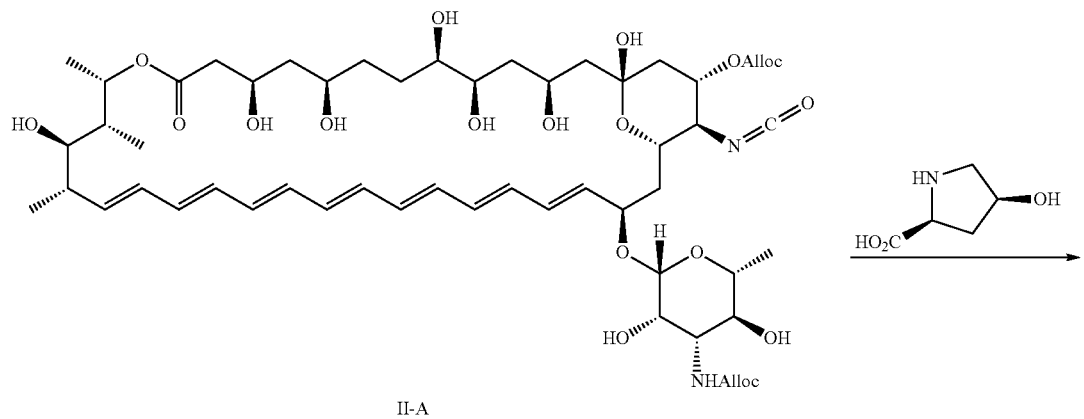

II-A

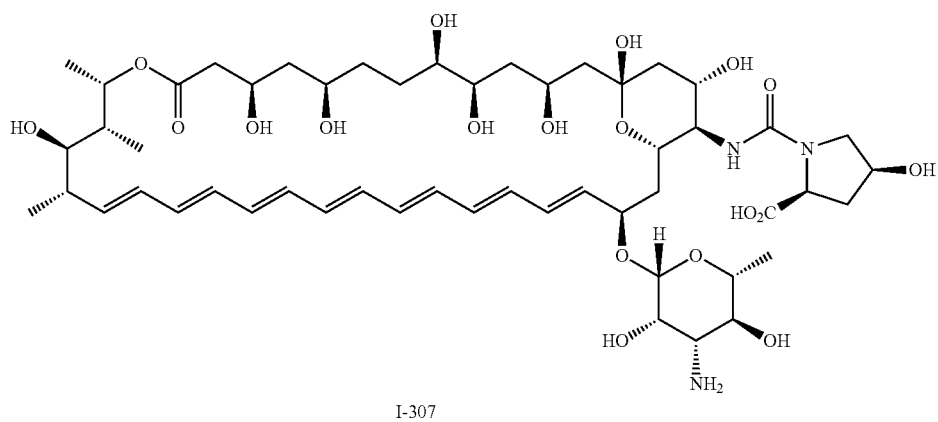

I-307

Compound II-A (2 g, 1.836 mmol) was dissolved into DMF (10 mL), and DIEA (1.283 mL, 7.34 mmol) and (2S,4S)-4-Hydroxypyrrolidine-2-carboxylic acid (241 mg, 1.836 mmol) were added. The mixture was stirred at 40° C. over night. After powderization by adding diisopropyl ether, the obtained powder was purified by silica-gel column chromatography. The obtained powder (1 g, 0.819 mmol, 45%) was dissolved into DMF (5 mL), and morpholine (0.71 mL, 8.19 mmol) and Pd(PPh$_3$)$_4$ (47 mg, 0.041 mmol) were added. The mixture was stirred for 15 minutes at room temperature. The resulting solids by adding diisopropyl ether were filtered. The resulted solids were purified by silica-gel column chromatography (chloroform/methanol/water=70/30/3 to 10/90/9) to give Compound I-307 (124 mg, 13%).

LC/MS: 1052.5 [M+H]+, 1074.5 [M+Na]+

Elementary analysis: C52H81N3O19(C3H7NO)0.8(H2O)1.8(MeOH)0.2

Calculated value: C 57.05; H, 7.98; N, 4.63 (%).

Actual value: C 57.06; H, 7.97; N, 4.60 (%).

Example 40
Synthesis of Compound I-329
[Chemical Formula 95]
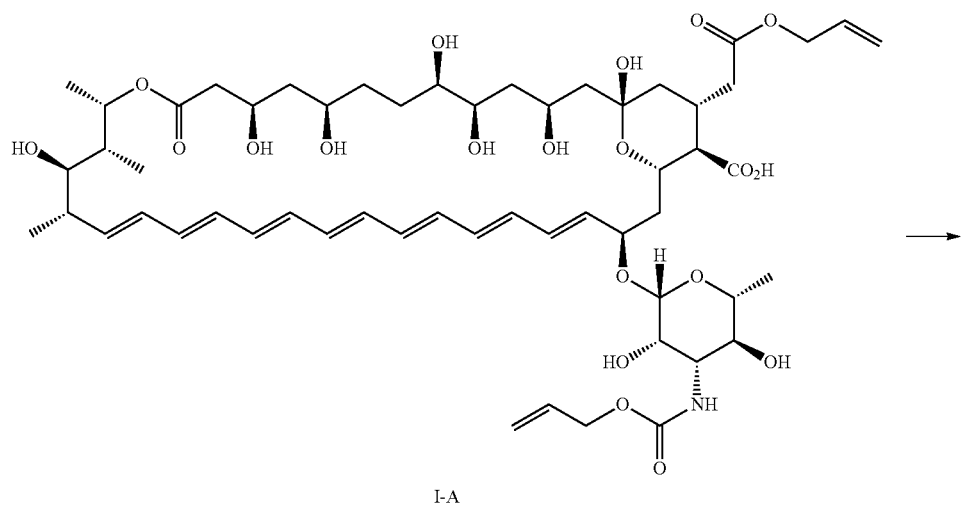
I-A
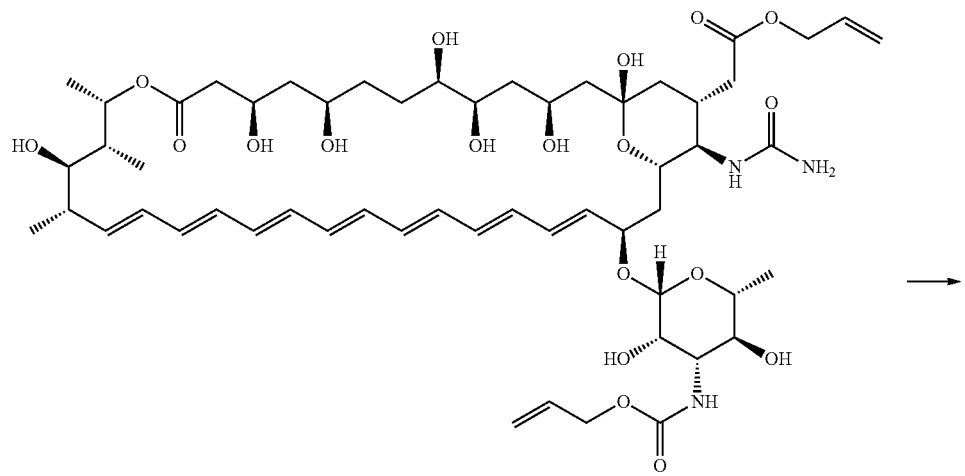
74
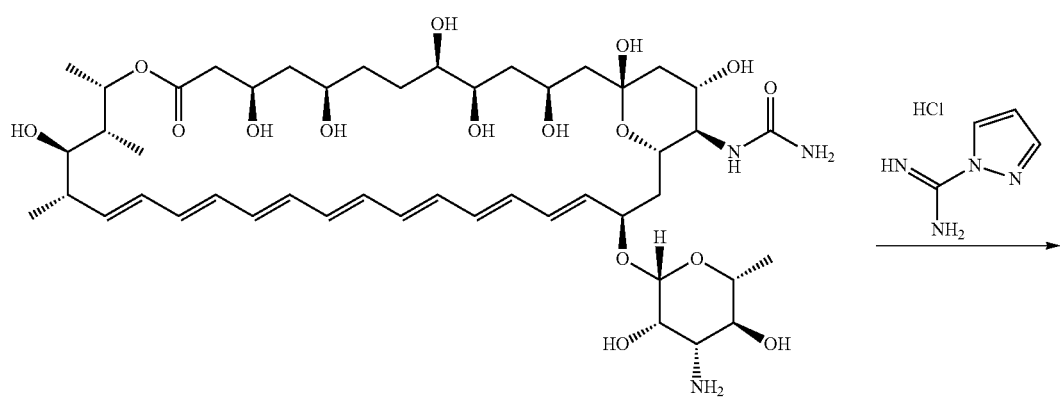
36

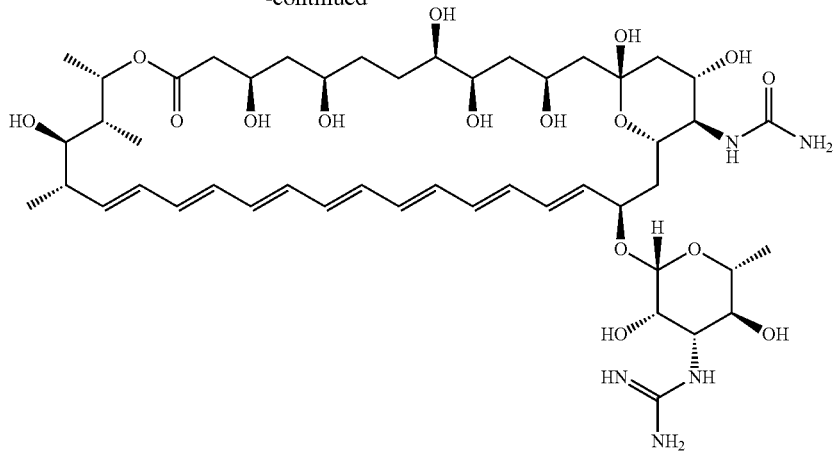

I-329

Step 1

Compound I-A (10.3 g, 9.43 mmol) was dissolved into DMF (50 mL) and DIEA (2.47 mmol) and diphenylphosphoryl azide (3.04 mL, 14.1 mmol) were added. The mixture was stirred for 2 hours 30 minutes at room temperature further 90 minutes 50° C. Ammonia (7 mol/L, methanol solution, 4 mL) was added, and the mixture was stirred for 35 minutes at room temperature. After powderization by adding diisopropyl ether (600 mL), the resulted powder was purified by silica-gel column chromatography (chloroform/methanol/water=10/1/0.1) to give Compound 74 (3.14 g, 30%).

Step 2

Compound 74 (3.14 g) was dissolved into DMF (15 mL), and morpholine (1.73 mL, 19.8 mmol) and Pd(PPh$_3$)$_4$ (328 mg, 0.284 mmol) were added. The mixture was stirred for 90 minutes at room temperature under nitrogen atmosphere. The resulting solids by adding diisopropyl ether were filtered. The resulted residue was purified by silica-gel column chromatography (amino silica-gel, chloroform/methanol/water=70/30/3 to 50/50/9) to give Compound I-36 (615 mg, 23%).

LC-MS: 938.9 [M+H]+

Step 3

Compound I-36 (614 mg, 0.656 mmol) was dissolved into DMF (10 mL), and DIEA (0.572 mL, 3.28 mmol) and 1H-pyrazole-1-carboxyimidamide hydrochloride (480 mg, 3.28 mmol) were added. The mixture was stirred for 22 hours at room temperature. After powderization by adding diisopropyl ether, the obtained powder was purified by silica-gel column chromatography (amino silica-gel, chloroform/methanol/water=70/30/3 to 30/70/7) to give Compound I-329 (262 mg, 41%).

LC-MS: 980.5[M+H]+

Elementary analysis: (C48H77N5O16)(C3H7NO)0.5 (H2O)4.4

Calculated value: C 54.25; H, 8.21; N, 7.03 (%).

Actual value: C 54.26; H, 7.97; N, 7.32 (%).

Example 41

Synthesis of Compound I-330

[Chemical Formula 96]

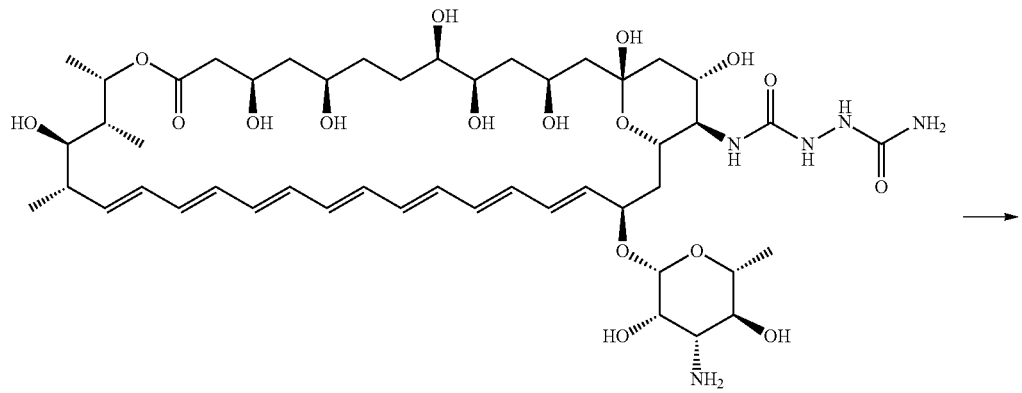

I-60

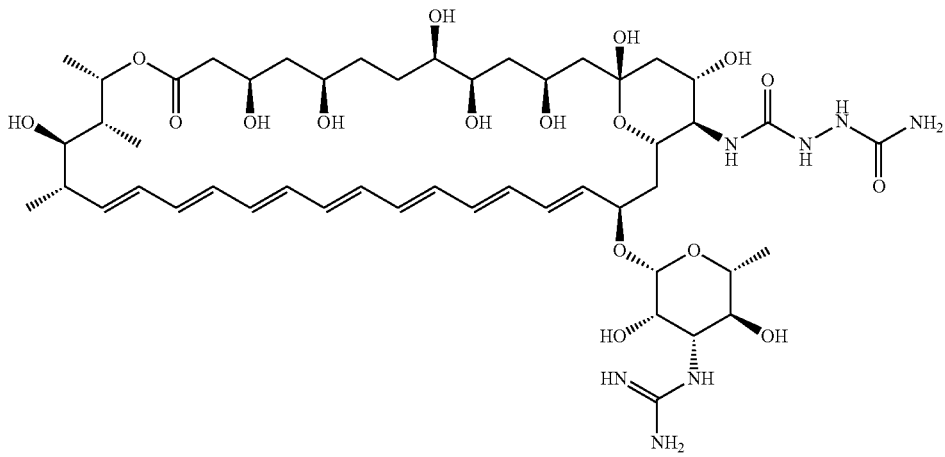

I-330

Compound I-60 (200 mg, 0.201 mmol) was dissolved into DMF (1 mL), and DIEA (0.245 mL, 1.41 mmol) and 1H-pyrazole-1-carboxyimidamide hydrochloride (206 mg, 1.41 mmol) were added. The mixture was stirred for 24 hours at room temperature. After powderization by adding diisopropyl ether, the powder was purified by reverse-phase chromatography (HP20ss, 0.05% formic acid aqueous solution/acetonitrile=90/10 to 70/30). The obtained fractions were condensed and lyophilized to give Compound I-330 (119 mg, 58%).

LC-MS: 1038.5[M+H]+

Elementary analysis: (C49H78N7O17)(HCO2H)0.5 (C12H11O4P)0.3(H2O)7(HCl)0.1

Calculated value: C 50.42; H, 7.68; N, 7.75 (%).

Actual value: C 50.58; H, 7.51; N, 7.55 (%).

Example 42

Synthesis of Compound I-365

[Chemical Formula 97]

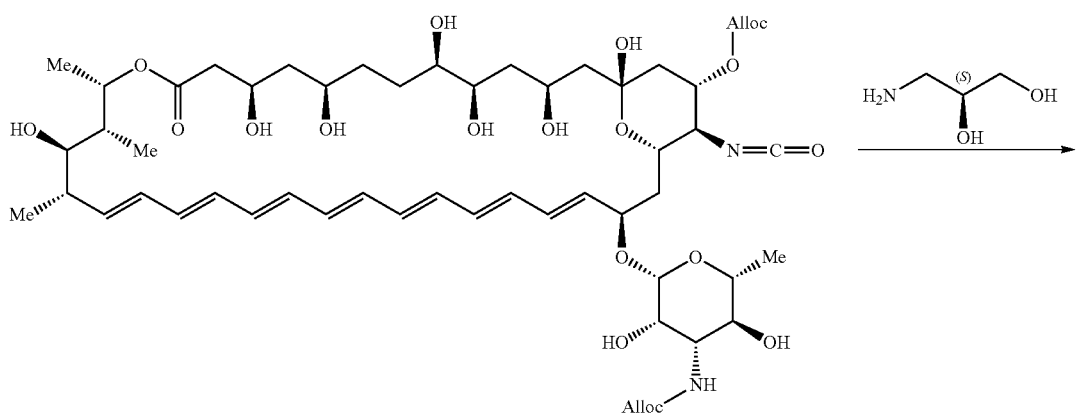

II-A

-continued

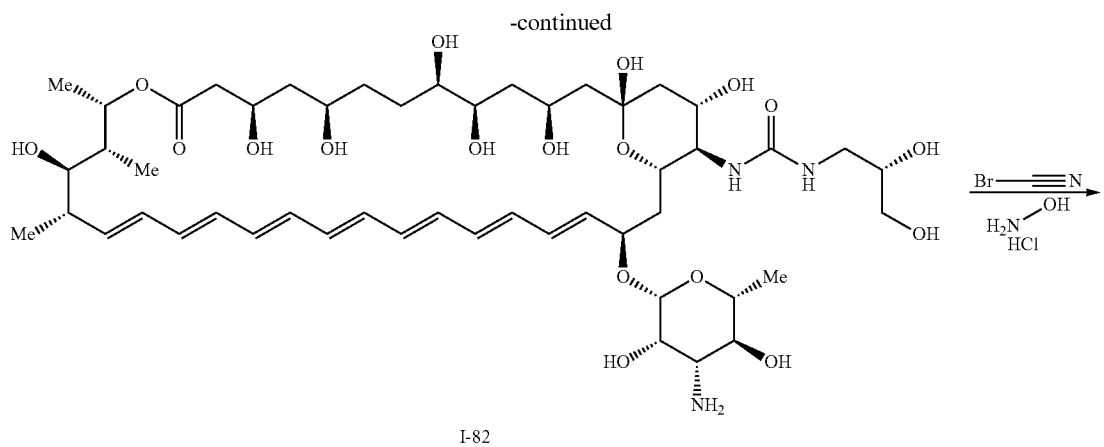

I-82

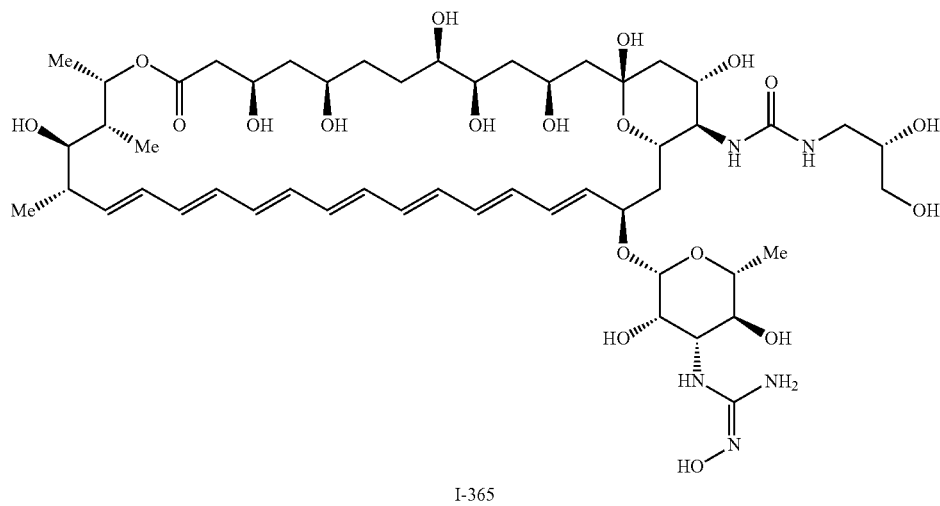

I-365

Step 1

Compound II-A (15.7 g, 14.41 mmol) was dissolved into DMF (75 mL), and DIEA (7.55 mL, 43.2 mmol) and (S)-3-aminopropane-1,2-diol (1.97 g, 21.62 mmol) were added. The mixture was stirred for 2 hours 30 minutes at room temperature. After powderization by adding diisopropyl ether, the resulted powder was purified by silica-gel column chromatography to give powder (1.07 g, 6%). The obtained powder was dissolved into DMF (10 mL), and morpholine (0.553 mL, 6.35 mmol) and Pd(PPh$_3$)$_4$ (52.4 mg, 0.045 mmol) were added. The mixture was stirred for 2 hours 30 minutes at room temperature under nitrogen atmosphere. The resulting solids by adding diisopropyl ether were filtered. The solids were purified by silica-gel column chromatography to give Compound I-82 (882 mg, 6%).

LC-MS: 1012.4[M+H]+, 1034.4[M+Na]+

Step 2

Compound I-82 (365 mg, 0.361 mg) was dissolved into DMF (3.6 mL), and DIEA (0.157 mL, 0.902 mmol) and cyanicbromide (76 mg, 0.721 mmol) were added. The mixture was stirred for an hour 40 minutes at room temperature. DIEA (0.189 mL, 1.082 mmol) and hydroxylamine hydrochloride (75 mg, 1.08 mmol) were added, and the mixture was stirred for an hour 40 minutes. After powderization by adding diisopropyl ether, the powder was purified by silica-gel column chromatography (amino silica-gel, chloroform/methanol/water=90/10/3 to 50/50/5) to give Compound I-365 (93 mg, 24%).

LC-MS: 1071 [M+H]+

Elementary analysis: (C51H83N5O19)(C3H7NO)1.2 (H2O)4

Calculated value: C 53.32; H, 8.15; N, 7.06 (%).

Actual value: C 53.59; H, 7.94; N, 7.40 (%).

Example 43

Synthesis of Compound I-368

[Chemical Formula 98]

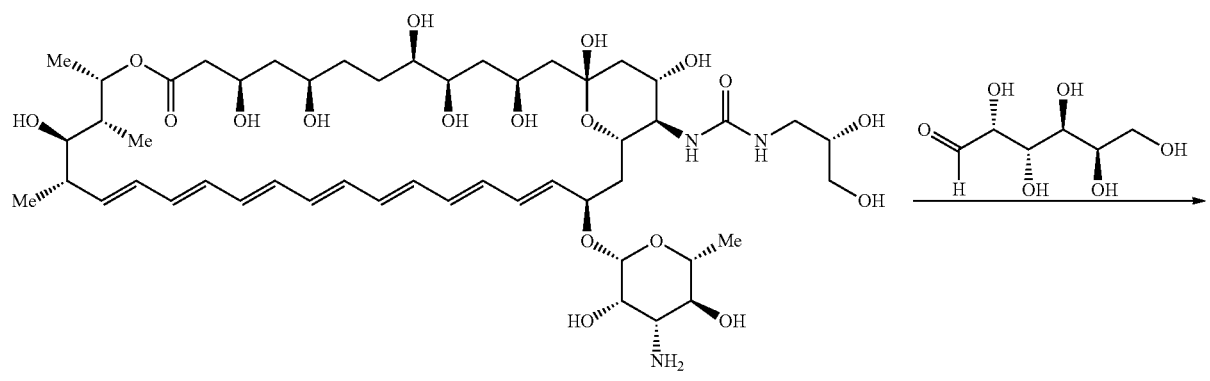

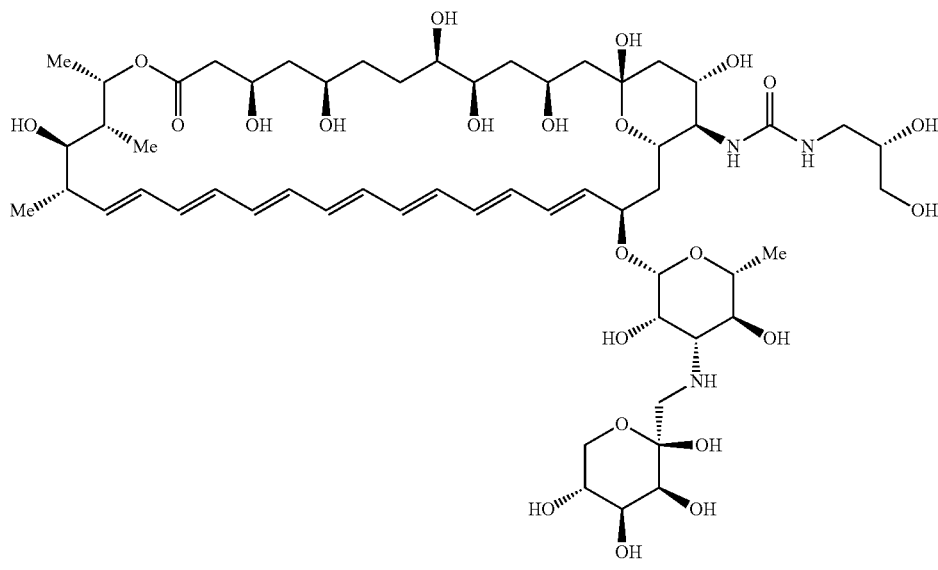

Compound I-82 (200 mg, 0.198 mmol) was dissolved into DMF (1 mL), and d-galactose (71 mg, 0.395 mmol) and acetic acid (0.113 mL, 1.976 mmol) were added. The mixture was stirred for 2 hours 30 minutes at room temperature, further for 3 hours at 40° C. After powderization by adding diisopropyl ether, the powder was purified by silica-gel column chromatography (amino silica-gel, chloroform/methanol/water=70/30/3) to give Compound I-368 (11 mg, 5%).

LC-MS: 1174 [M+H]+

Example 44

Synthesis of Compound I-361

[Chemical Formula 99]

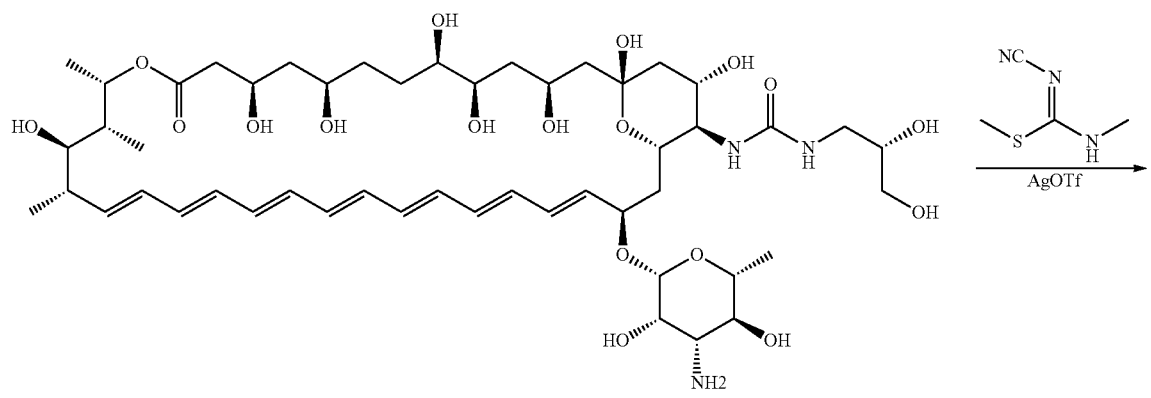

I-82

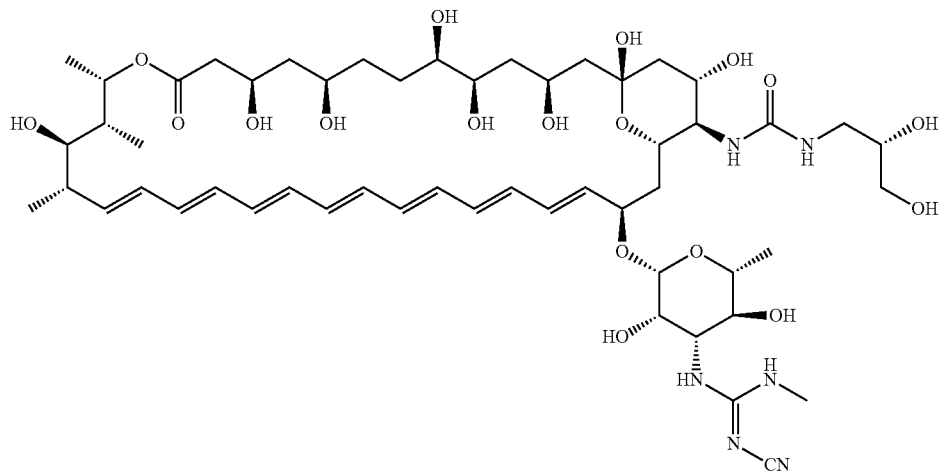

I-361

Compound I-82 (100 mg, 0.099 mmol) was dissolved into DMF (1 mL), and (Z)-methyl N'-cyano-N-methylcarbamidethioate (15.32 mg, 0.119 mmol), DIEA (0.052 mL, 0.296 mmol) and Silver Trifluoromethanesulfonate (30 mg, 0.119 mmol) were added. The mixture was stirred for 2 hours at 0° C. (Z)-methyl N'-cyano-N-methylcarbamidethioate (15.32 mg, 0.119 mmol), Silver Trifluoromethanesulfonate (30 mg, 0.119 mmol) and DIEA (0.052 mL, 0.296 mmol) were added. The mixture was stirred for an hour 30 minutes at 0° C., further 3 hours at room temperature. After powderization by adding diisopropyl ether, the powder was purified by silica-gel column chromatography (amino silica-gel, chloroform/methanol/water=95/5/0.5 to 50/50/5) to give Compound I-361 (27 mg, 25%).

LC-MS: 1093.5 [M+H]+, 1115.5 [M+Na]+

Elementary analysis: C53H84N6O18(H2O)6.5(C6H14O)0.5

Calculated value: C 53.32; H, 8.31; N, 6.66 (%).

Actual value: C 53.45; H, 7.86; N, 6.36 (%).

Example 45

Synthesis of Compound I-362

[Chemical Formula 100]

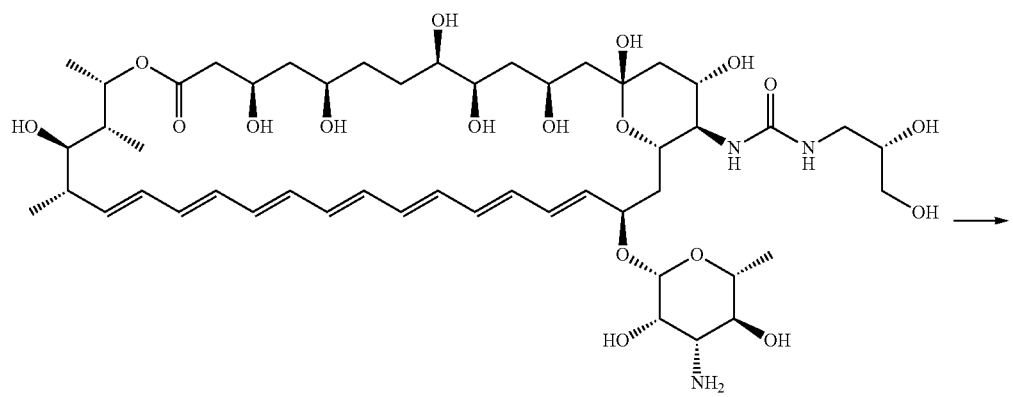

I-82

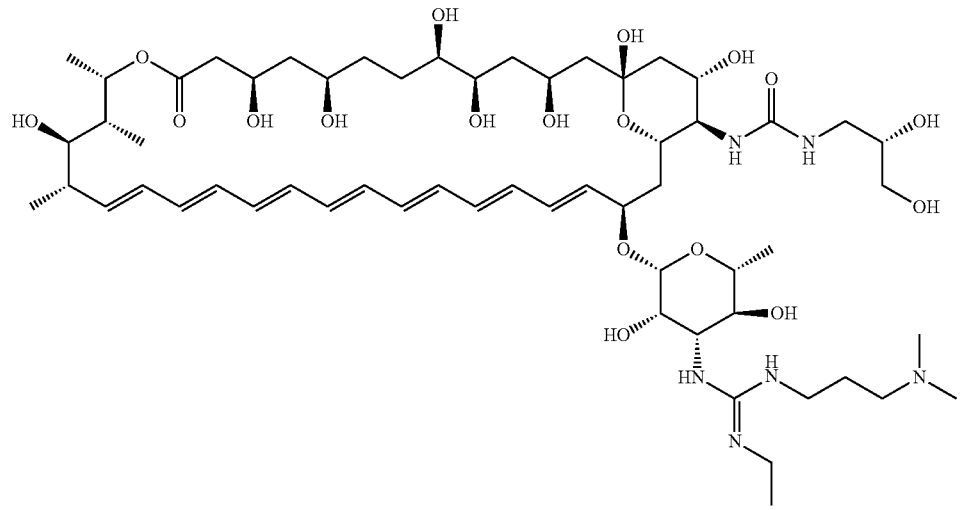

I-362

Compound I-82 (98 mg, 0.097 mmol) was dissolved into DMF (1 mL), and EDC HCl (27.8 mg, 0.145 mmol) and DMAP (1.183 mg, 0.009 mmol) were added. The mixture was stirred for 4 hours at room temperature. DMAP (5.3 mg, 0.044 mmol) was added, and the mixture was stirred for 19 hours at room temperature. DIEA (0.034 mL, 0.194 mmol), EDC HCl (37.1 mg, 0.194 mmol) and DIEA (0.034 mL, 0.194 mmol) were added, and the mixture was stirred for 23 hours at room temperature. After powderization by adding diisopropyl ether, the powder was purified by silica-gel column chromatography (amino silica-gel, chloroform/methanol/water=50/50/5) to give Compound I-362 (45 mg, 39%).

LC-MS: 1167.6 [M+H]+

Elementary analysis: $C_{58}H_{98}N_6O_{18}(H_2O)_6$

Calculated value: C 54.62; H, 8.69; N, 6.59 (%).

Actual value: C 54.79; H, 8.16; N, 6.31 (%).

Example 46

Synthesis of Compound I-380

[Chemical Formula 101]

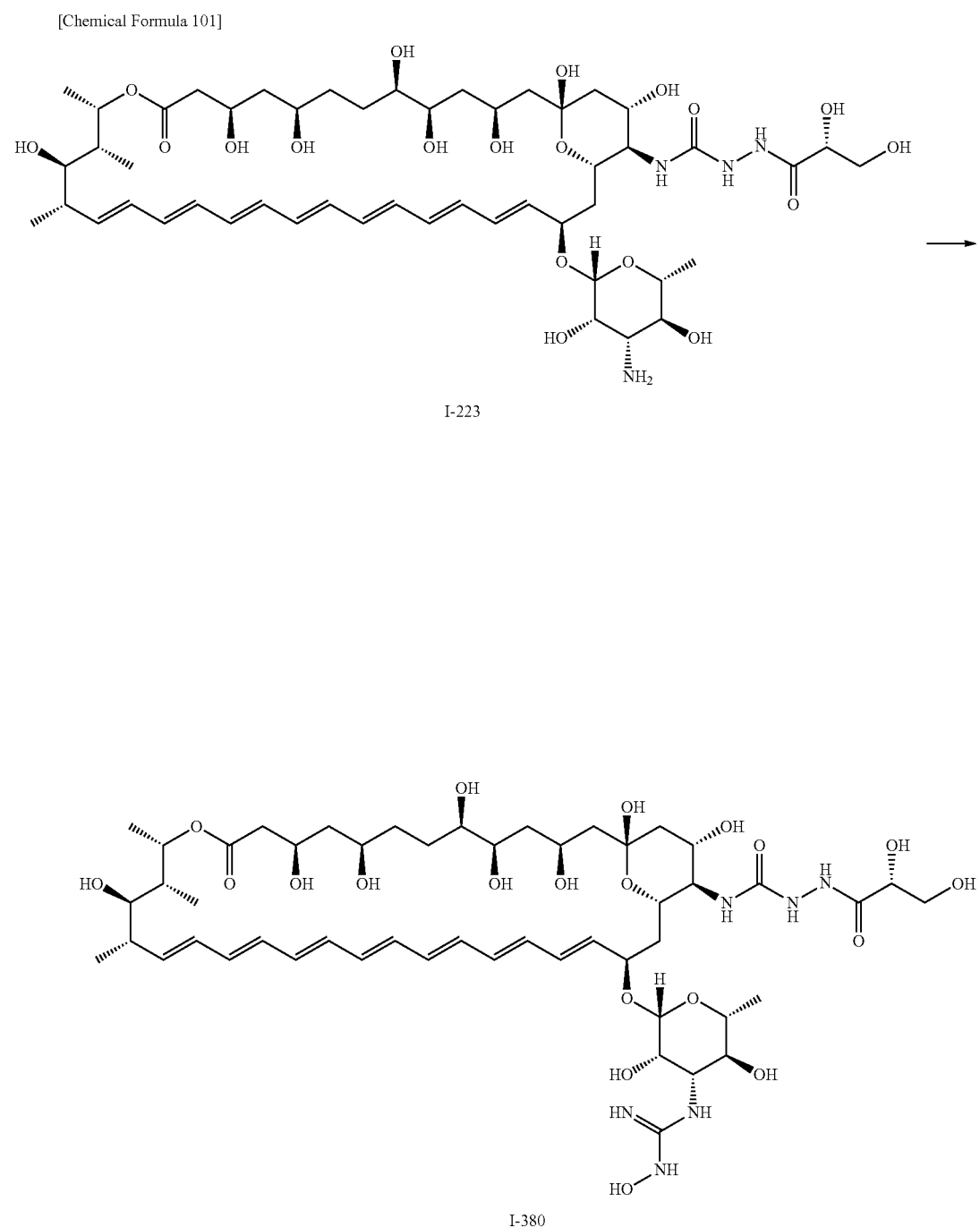

Compound I-223 (121 mg, 0.116 mmol) was dissolved into DMF (3 mL), and DIEA (0.20 mL, 1.162 mmol) and cyanicbromide (42 mg, 0.397 mmol) were added. The mixture was stirred for 50 minutes at room temperature. Hydroxylamine hydrochloride (41 mg, 0.58 mmol) was added, and the mixture was stirred for an hour. After powderization by adding diisopropyl ether, the powder was purified by silica-gel column chromatography (amino silica-gel, chloroform/methanol/water=90/10/3 to 50/50/5) to give Compound I-380 (80 mg, 54%).

LC-MS: 1099.5 [M+H]+, 1121.6 [M+Na]+analysis: $C_{51}H_{82}N_6O_{20}(C_3H_7NO)0.8(H_2O)3.9$ Calculated value: C 52.23; H, 7.83; N, 7.76 (%).

Actual value: C, 52.17; H, 7.55; N, 7.76 (%).

Example 47

Synthesis of Compound I-367

[Chemical Formula 102]

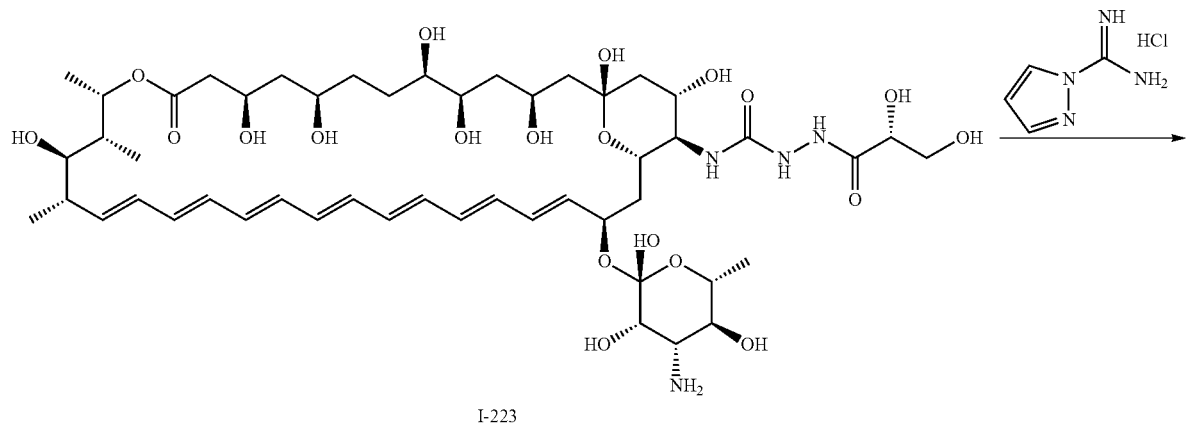

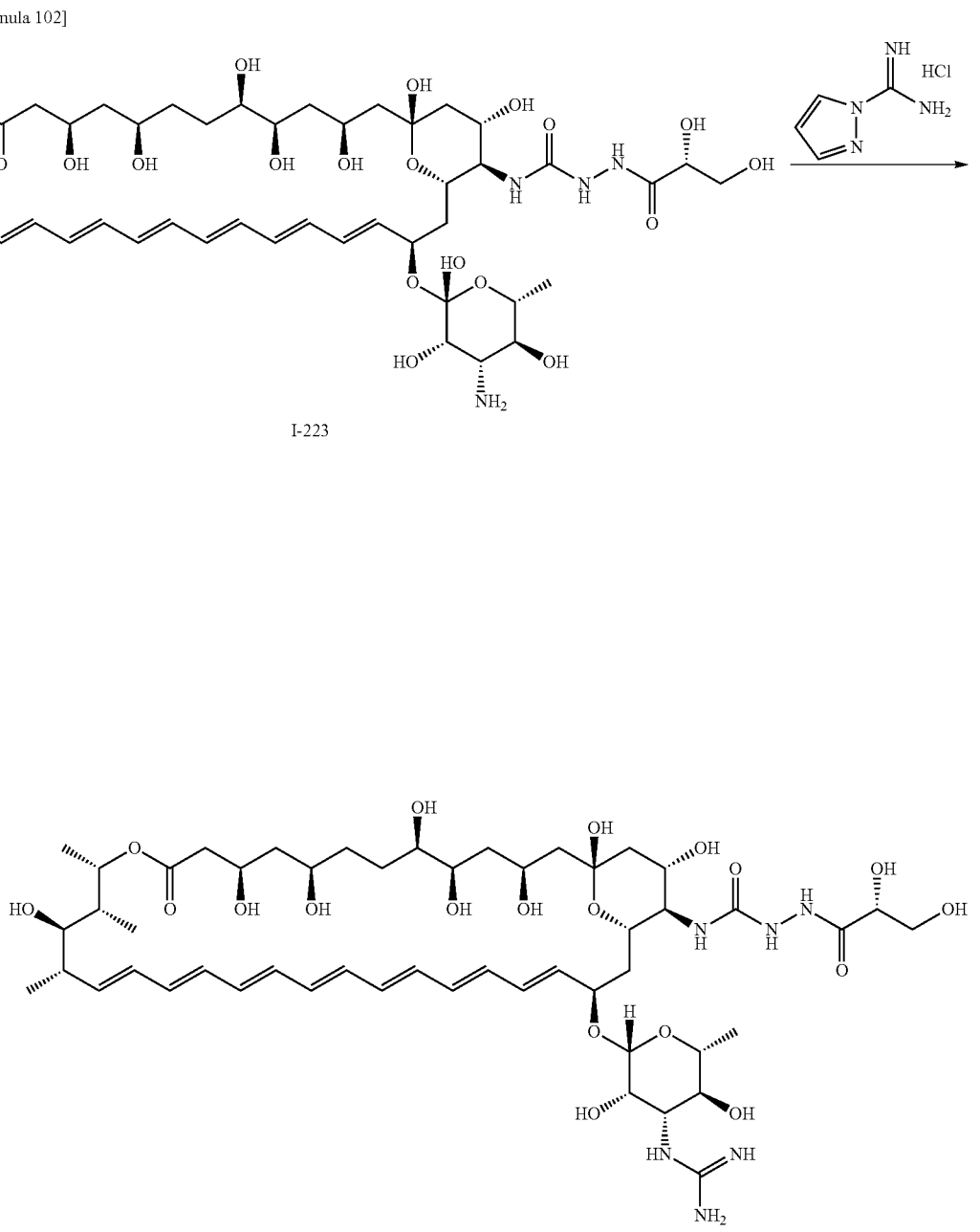

Compound I-223 (108 mg, 0.104 mmol) was dissolved into DMF (2 mL), and DIEA (0.127 mL, 0.726 mmol) and 1H-pyrazole-1-carboxyimidamide hydrochloride (106 mg, 0.726 mmol) were added. The mixture was stirred for 24 hours at room temperature. 1H-pyrazole-1-carboxyimidamide hydrochloride (106 mg, 0.726 mmol) was added, and the mixture was stirred for 24 hours at room temperature. After powderization by adding diisopropyl ether, the powder was purified by silica-gel column chromatography (amino silica-gel, chloroform/methanol/water=70/30/3). The obtained fractions were condensed and lyophilized to give Compound I-367 (74 mg, 59%).

LC-MS: 1083.3 [M+H]+

Elementary analysis: $C_{51}H_{82}N_6O_{19}(C_3H_7NO)0.7(H_2O)3.4(CHCl_3)0.4$

Calculated value: C 51.68; H, 7.63; N, 7.55 (%).

Actual value: C 51.64; H, 7.60; N, 7.61 (%).

Example 48

Synthesis of Compound I-385

[Chemical Formula 103]

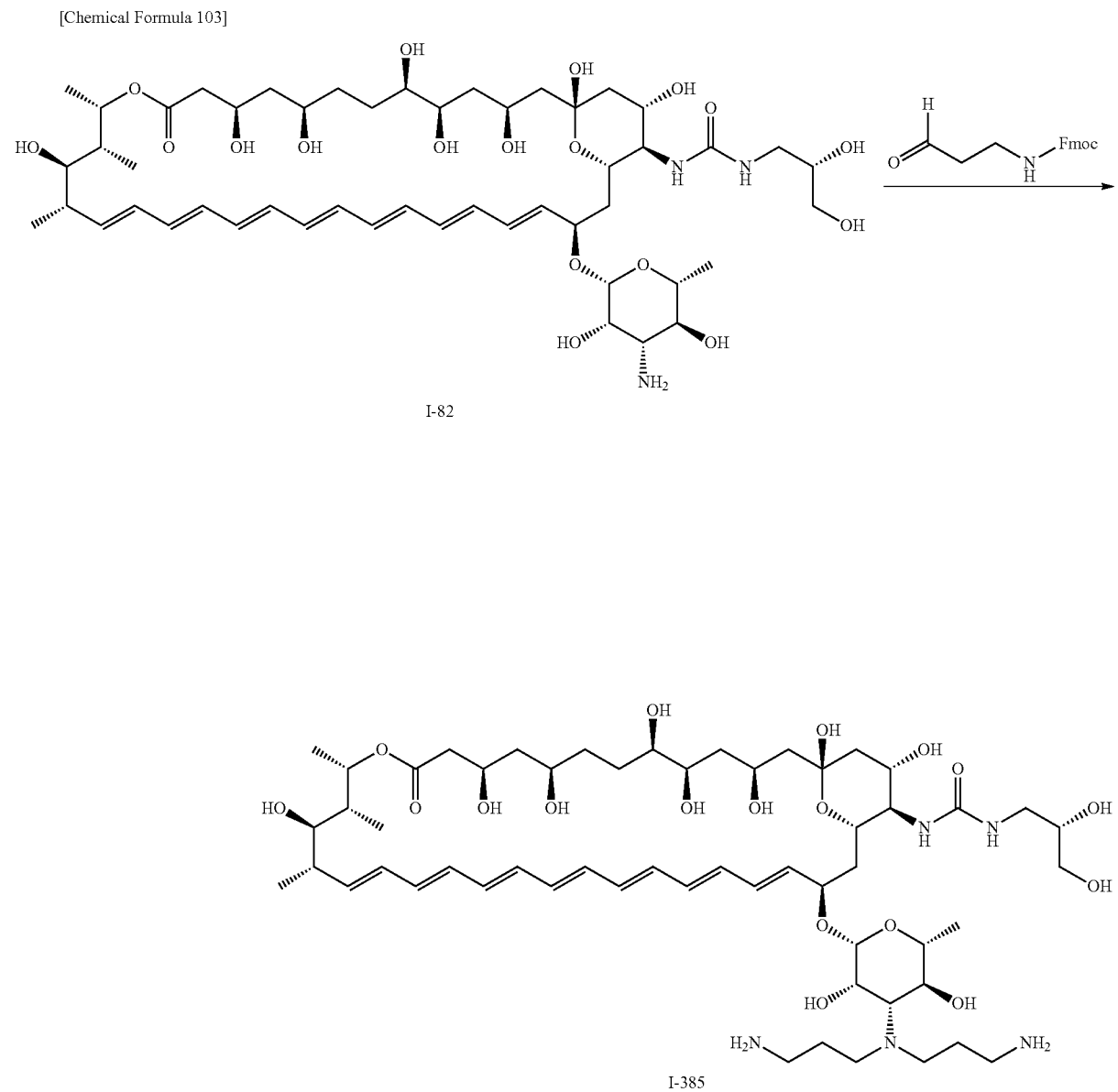

Compound I-82 (1 g, 0.998 mmol) was dissolved into DMF (10 mL), and 3-N-(fluorenylmethyloxycarbonyl)-3-aminopropionaldehyde (875 mg, 2.96 mmol) was added. After the mixture was stirred for 5 minutes at room temperature, sodium cyanoborohydride (186 mg, 2.96 mmol) and concentrated hydrochloric acid (0.165 mL, 1.976 mmol) were added. The mixture was stirred for 24 hours at room temperature. 3-N-(fluorenylmethyloxycarbonyl)-3-aminopropionaldehyde (292 mg, 0.988 mmol), sodium cyanoborohydride (93 mg, 1.48 mmol) and concentrated hydrochloric acid (0.041 mL, 0.494 mmol) were added, and the mixture was stirred for 24 hours. After powderization by adding diisopropyl ether, the powder was purified by silica-gel column chromatography (chloroform/methanol/water=95/5/ 0.5 to 70/30/3). The obtained solids (261 mg, 0.166 mmol) were dissolved into DMF (2.5 mL), and piperidine (0.082 mL, 0831 mmol) was added. The mixture was stirred for 3 hours 50 minutes at room temperature. diisopropyl ether was added and filtrated, and the mixture was washed with diisopropyl ether to give Compound I-385 (178 mg, 0.158 mmol, 16%) as yellow solids. The retention time was 5.1 minutes by HPLC analysis (methanol/distilled water containing 0.1% PIC-B7=gradient 70/30 to 100/0, flow speed 1 ml/min, wavelength of detection=385 nm).

LC-MS: 1126.6[M+H]+

Elementary analysis: $C_{56}H_{95}N_5O_{18}$ $(H_2O)_{3.5}$

Calculated value: C 56.55; H, 8.64; N, 5.89 (%).

Actual value: C 56.76; H, 8.31; N, 5.75 (%).

Example 49

Synthesis of Compound I-388

[Chemical Formula 104]

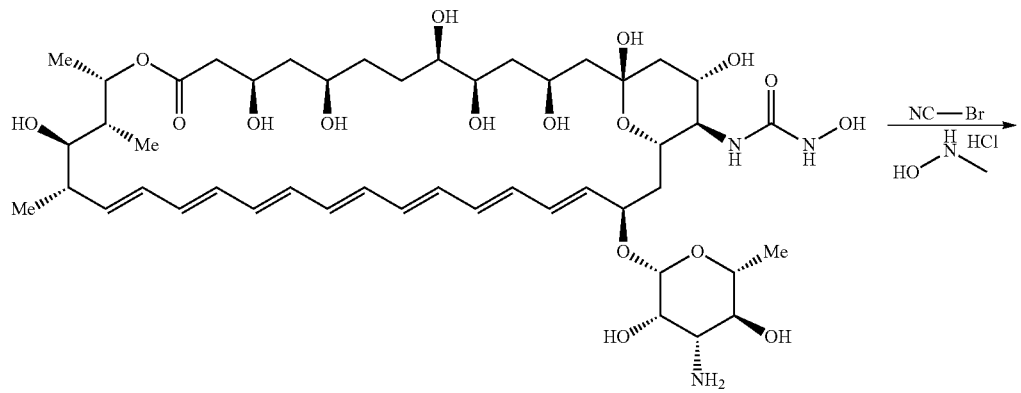

Compound I-219 (150 mg, 0.157 mmol) was dissolved into DMF (5 mL), and DIEA (0.165 mM, 0.943 mmol) and cyanicbromide (33 mg, 0.31 mmol) were added. The mixture was stirred for 55 minutes at room temperature. N-Methylhydroxylamine hydrochloride (26 mg, 0.31 mmol) was added, and the mixture was stirred for 21 hours at room temperature. After powderization by adding diisopropyl ether, the obtained powder was purified by silica-gel column chromatography (chloroform/methanol/water=70/30/3 to 30/70/7) to give Compound I-388 (23 mg, 27%).

LC-MS: 1026.5 [M+H]+, 1048.5 [M+Na]+

Elementary analysis: C49H79N5O18(C3H7NO)2(H2O)9.5

Calculated value: C 49.17; H, 8.40; N, 7.30 (%).

Actual value: C 49.00; H, 7.30; N, 7.49 (%).

Example 50

Synthesis of Compound I-387

[Chemical Formula 105]

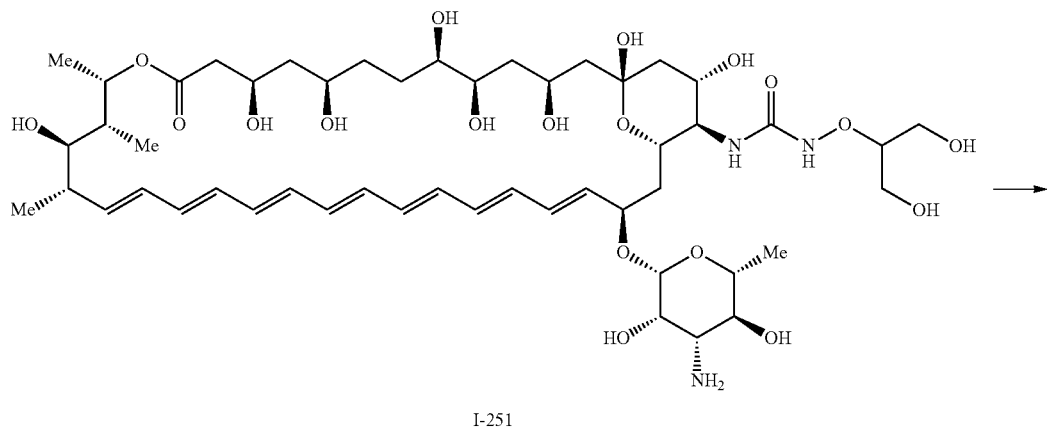

I-251

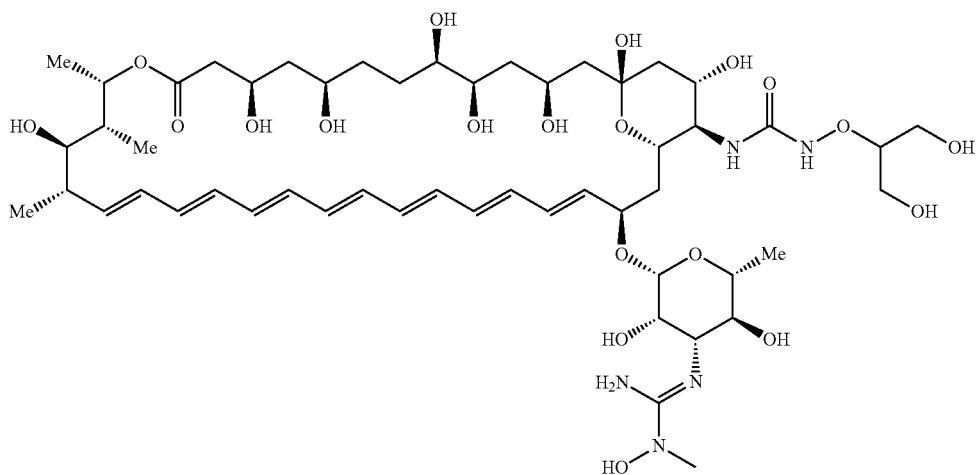

I-387

Compound I-251 (110 mg, 0.107 mmol) was dissolved into DMF (5 mL), and DIEA (0.112 mL, 0.642 mmol) and cyanicbromide (17 mg, 0.16 mmol) were added. The mixture was stirred for an hour 15 minutes at room temperature. N-Methylhydroxylamine hydrochloride (26.8 mg, 0.32 mmol) was added, and the mixture was stirred at room temperature overnight. After powderization by adding diisopropyl ether, the obtained powder was purified by silica-gel column chromatography (chloroform/methanol/water=70/30/3 to 30/70/7) to give Compound I-387 (40 mg, 34%).

LC-MS: 1100.5 [M+H]+, 1122.5 [M+Na]+

Elementary analysis: C52H85N5O20 (C3H7NO)0.3 (H2O)3.5

Calculated value: C 53.61; H, 8.00; N, 6.26 (%).

Actual value: C 53.65; H, 7.94; N, 6.24 (%).

Example 51

Synthesis of Compound I-331

[Chemical Formula 106]

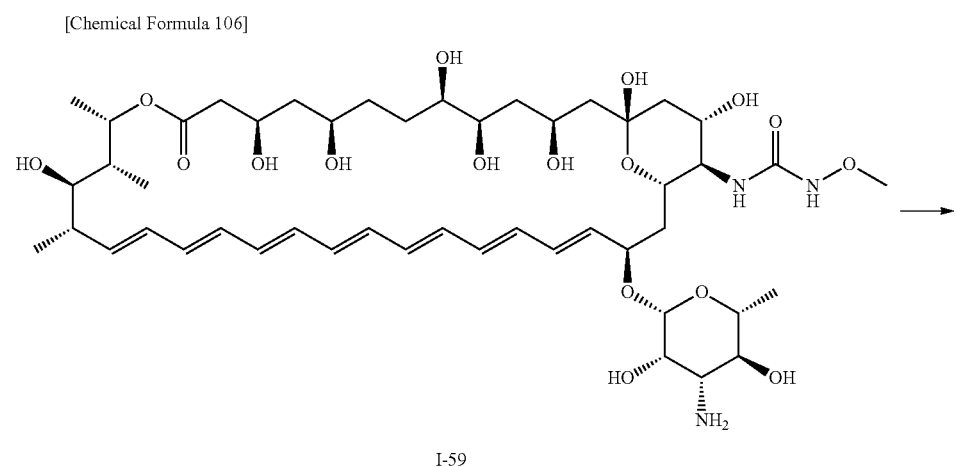

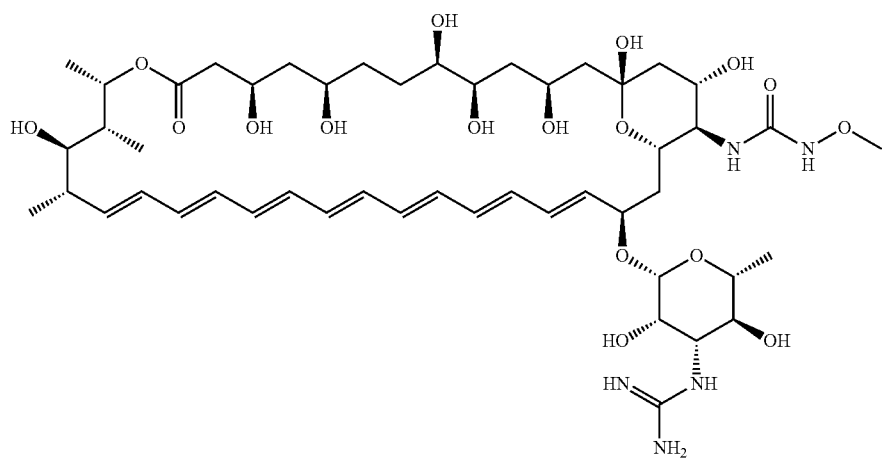

Compound I-59 (250 mg, 0.258 mmol) and 1H-pyrazole-1-carboxyimidamide hydrochloride (265 mg, 1.81 mmol) were dissolved into DMF (1 mL), and DIEA (0.316 mL, 1.81 mmol) was added. The mixture was stirred for 25 hours at room temperature. After powderization by adding diisopropyl ether, the obtained powder was purified by reverse-phase chromatography (HP20ss, acetonitrile/aqueous solution containing 0.05% formic acid=10/90 to 30/70). The obtained fractions were condensed and lyophilized to give Compound I-331 (154 mg, 51%).

LC-MS: 1011.1 [M+H]+

Elementary analysis: (C49H79N5O17) (HCO2H)0.4 (H2O)7.3

Calculated value: C 51.14; H, 8.20; N, 6.04 (%).

Actual value: C 51.10; H, 7.81; N, 6.13 (%).

Example 52
Synthesis of Compound I-313
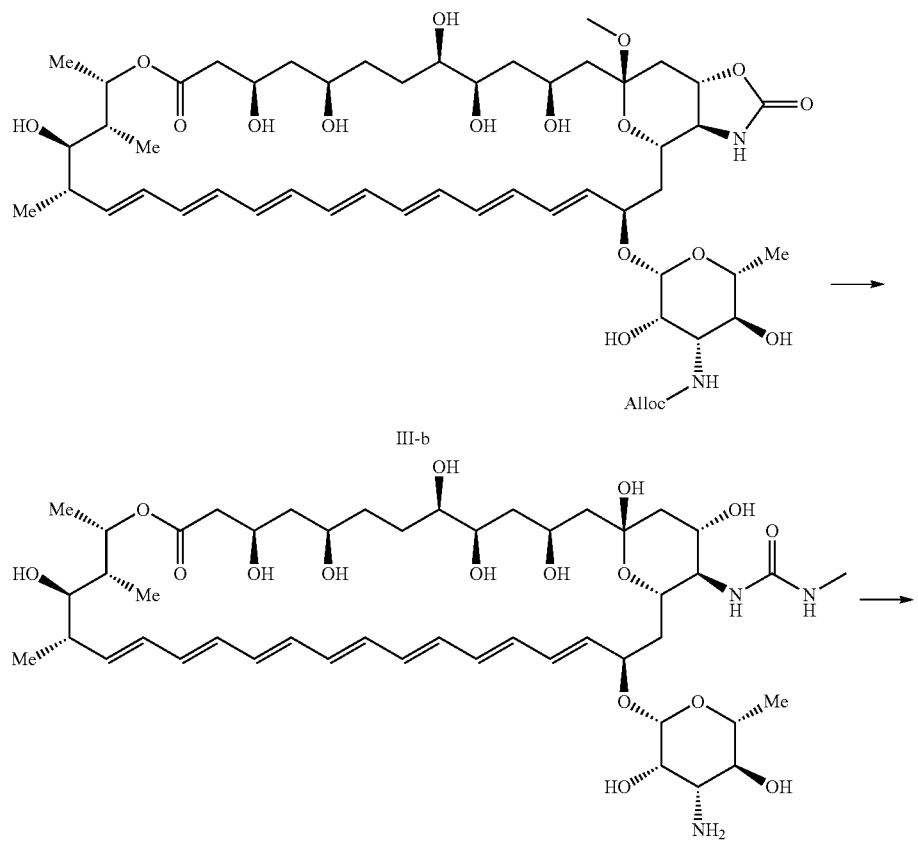
III-b
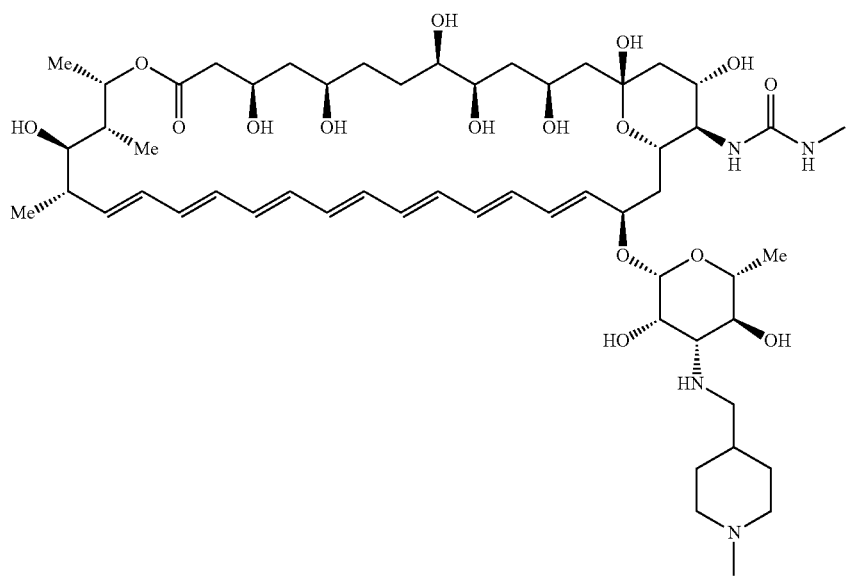
I-313

Step 1

Compound III-b (10 g, 9.81 mmol) was dissolved into DMA (30 mL), and methylamine (30% ethanol solution, 2 g, 19.6 mmol) was added. The mixture was stirred for 2 hours at room temperature. After powderization by adding diisopropyl ether/methanol, the crude purified powder (8.8 g) was obtained. Without purification, the crude powder was dissolved into DMF (4 mL), tetrahydrofuran (16 mL), water (2 mL), and PPTS (8.42 g, 33.5 mmol) was added. The mixture was stirred for 3 hours at room temperature. Further, water (2 mL) and PPTS (2.1 mmol, 8.38 mmol) were added, and the mixture was stirred for an hour. The reaction was quenched by adding triethylamine (11.6 mL, 84 mmol). After the mixture was condensed and oil-outed with diisopropyl ether, the obtained residue was purified by silica-gel column chromatography (chloroform/methanol/water=70/30/3) to give the objective substance (3.85 g, 3.71 mmol, 44%). The objective substance was dissolved into DMF (20 mL), and morpholine (3.2 mL, 37.2 mmol) was added. The mixture was degassed and replaced by nitrogen gas. Pd(PPh$_3$)$_4$ (429 mg, 0.37 mmol) was added, and the mixture was stirred for 10 minutes at room temperature. After powderization by adding diisopropyl ether, the obtained powder was purified by silica-gel column chromatography (amino silica-gel, chloroform/methanol/water=65/35/3.5) to give Compound 75 (1.1 g, 31%).

LC-MS: 952.5 [M+H]+, 974.6 [M+Na]+

Elementary analysis: C48H77N3O16(C3H7NO)(H2O)2.4

Calculated value: C 57.33; H, 8.38; N, 5.24 (%).

Actual value: C 57.35; H, 8.37; N, 5.27 (%).

Step 2

Compound 75 (230 mg, 0.242 mmol) and 4-formyl-1-methylpiperidine hydrochloride (119 mg, 0.725 mmol) were added to DMF (2.4 mL), and methanol (0.7 mL), acetic acid (0.4 mL) and NaBH$_3$CN (76 mg, 1.21 mmol) were added. The mixture was stirred at room temperature overnight. The reaction was quenched by adding Amberlite IRA-743 (630 mg). After the reaction mixture was filtrated, the mixture was powdered by adding diisopropyl ether. The powder was purified by silica-gel column chromatography to give Compound I-313 (143 mg, 55%).

LC-MS: 1064.2 [M+H]+

Elementary analysis: C55H90N4O16(H2O)6.2

Calculated value: C 56.22; H, 8.78; N, 4.77 (%).

Actual value: C 56.03; H, 8.48; N, 5.02 (%).

Example 53

Synthesis of Compound I-12

[Chemical Formula 108]

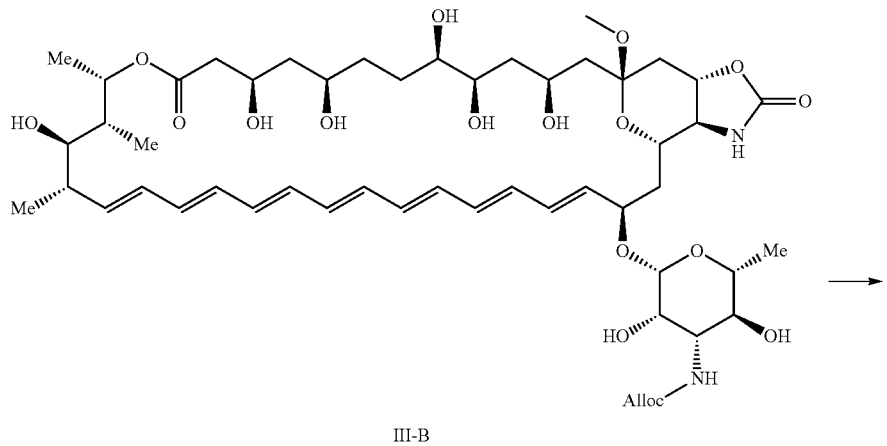

III-B

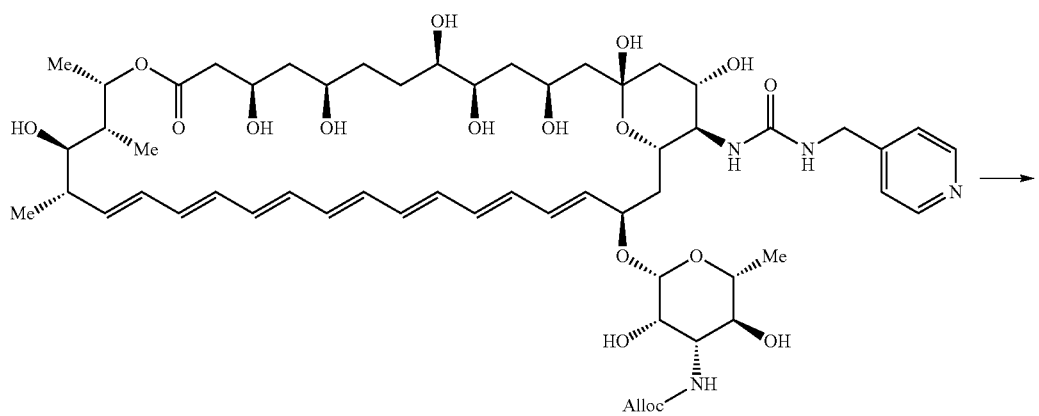

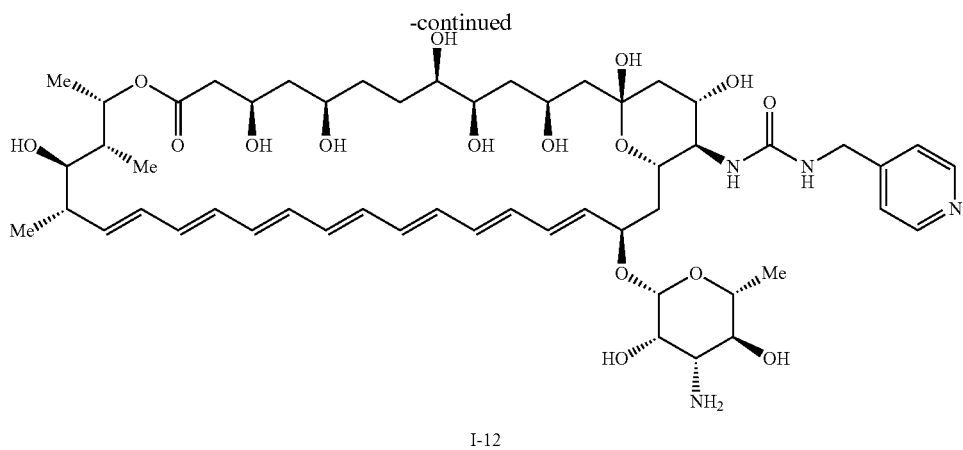

I-12

Step 1 Synthesis of Compound 76

Compound III-b (1 g, 0.981 mmol) was dissolved into DMF (10 mL), and 2-(4-pyridyl)methylamine (0.299 mL, 2.94 mmol) was added. The mixture was stirred for 3.5 hours at room temperature. 2-(4-pyridyl)methylamine (0.299 mL, 2.94 mmol) was added, and the mixture was stirred for 23.5 hours at room temperature. Further, 2-(4-pyridyl)methylamine (0.299 mL, 2.94 mmol) was added, and the mixture was stirred for 3 hours at room temperature. After powderization by adding diisopropyl ether/acetonitrile, the solids were filtrated. The obtained solids (1.09 g) were dissolved to tetrahydrofuran (4 mL) and water (1 mL). PPTS (740 mg, 2.94 mmol) was added, and the mixture was stirred for 5 hours at room temperature. After the mixture incubated at 4° C. overnight, the mixture was stirred for 3 hours at room temperature. After the reaction was quenched by adding triethylamine (0.408 mL, 2.94 mmol), the mixture was condensed and oil-outed with diisopropyl ether/acetonitrile. After decantation of the obtained oil, the obtained oil was dissolved into chloroform/methanol. After the solvent was removed, the residue was dissolved into DMF. After powderization with diisopropyl ether/acetonitrile, the obtained solids were filtrated and washed with diisopropyl ether to give crude Compound 76 (0.84 g).

Step 2 Synthesis of Compound I-12

Crude product of Compound 2 (0.84 g) was dissolved into DMF (8 mL), morpholine (0.131 mL, 1.509 mmol) and Pd(PPh$_3$)$_4$ (61 mg, 0.053 mmol) were added. After degassing and nitrogen purge, the mixture was stirred for 2 hours at room temperature. After the reaction mixture was powdered with diisopropyl ether/acetonitrile, the mixture was purified by reverse-phase chromatography (HP20ss, acetonitrile/0.5 mmol/L hydrochloric acid aq) to give Compound I-12 (52.9 mg, 6.8%).

Elementary analysis: C53H80N4O16(HCl)0.17(H2O)3.4 (H2SO4)0.27

Calculated value: C 56.68; H, 7.85; N, 4.99; Cl, 0.54; S, 0.77 (%).

Actual value: C 56.73; H, 7.51; N, 4.85; Cl, 0.54; S, 0.78 (%).

MS(ESI) m/z: 1029.6(M+H+), 1051.6(M+Na+)

Example 54

Synthesis of Compound I-13

[Chemical Formula 109]

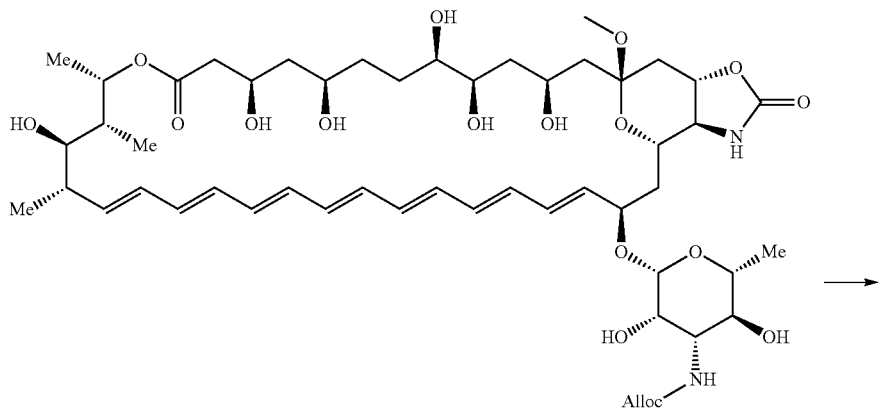

III-b

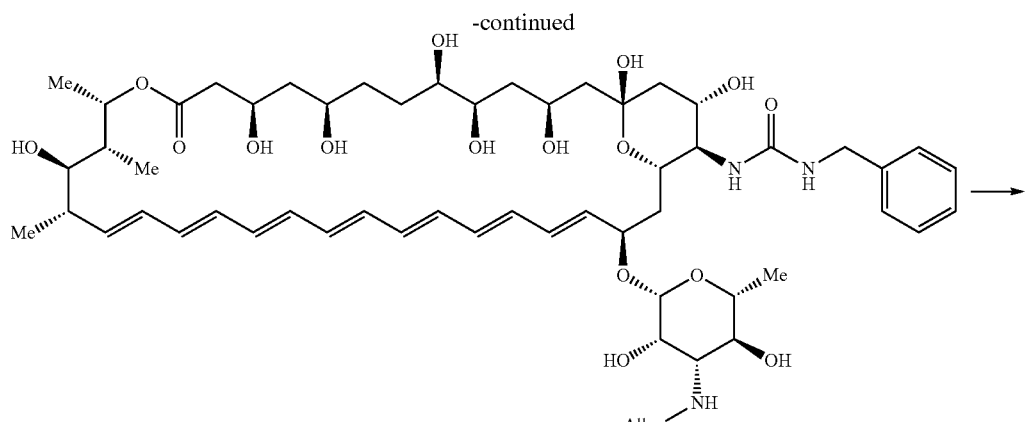

77

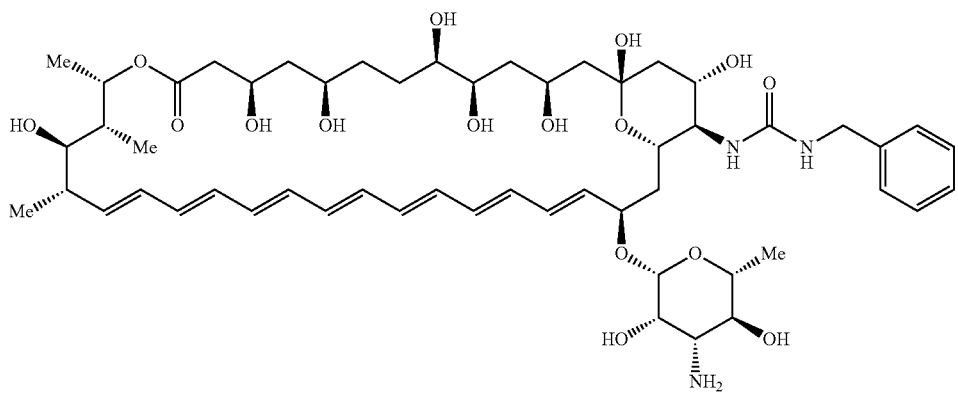

I-13

Step 1 Synthesis of Compound 77

Compound III-b (1 g, 0.981 mmol) was dissolved into DMF (10 mL), and benzylamine (0.322 mL, 2.94 mmol) was added. The mixture was stirred for 27 hours at room temperature. Benzylamine (0.215 mL, 1.96 mmol) was added, and the mixture was stirred for 3 hours at room temperature. After the reaction mixture was powdered with diisopropyl ether/acetonitrile, the mixture was purified by silica-gel column chromatography to give crude product (203 mg). The obtained crude product (200 mg) was dissolved into tetrahydrofuran (3 mL) and water (0.75 mL), and PPTS (66.9 mg, 0.266 mmol) was added. After the mixture was stirred for 2.5 hours at room temperature, the mixture was incubated at 4° C. overnight. After that, the mixture was stirred for 3 hours at room temperature. After the reaction was quenched with triethylamine (0.039 mL, 0.284 mmol), the mixture was incubated at 4° C. overnight. After powderization by adding diisopropyl ether/acetonitrile, the obtained solids were filtrated and wished with diisopropyl ether to give crude Compound 77 (0.195 mg).

Step 2

Crude product of Compound 77 (193 mg) was dissolved into N-methylpyrrolidone (10 mL), the mixture was degassed and replaced by nitrogen gas. Morpholine (0.030 mL, 0.347 mmol) and Pd(PPh$_3$)$_4$ (14 mg, 0.012 mmol) were added, and the mixture was stirred for 1.5 hours at room temperature. After the reaction mixture was powdered with diisopropyl ether/acetonitrile, the powder was purified by silica-gel column chromatography (CHCl$_3$/MeOH/H$_2$O) to give Compound I-13 (87.8 mg, 49.2%).

Elementary analysis; C54H81N3O16(H2O)2.6(CHCl3)0.47(H2SO4)0.42

Calculated value; C 55.77; H, 7.32; N, 3.51; Cl, 4.27; S, 1.08 (%).

Actual value: C 55.80; H, 7.52; N, 3.58; Cl, 4.26; S, 1.15 (%).

MS(ESI) m/z;1028.6(M+H+), 1050.6(M+Na+)

Example 55
Synthesis of Compound I-390
[Chemical Formula 110]
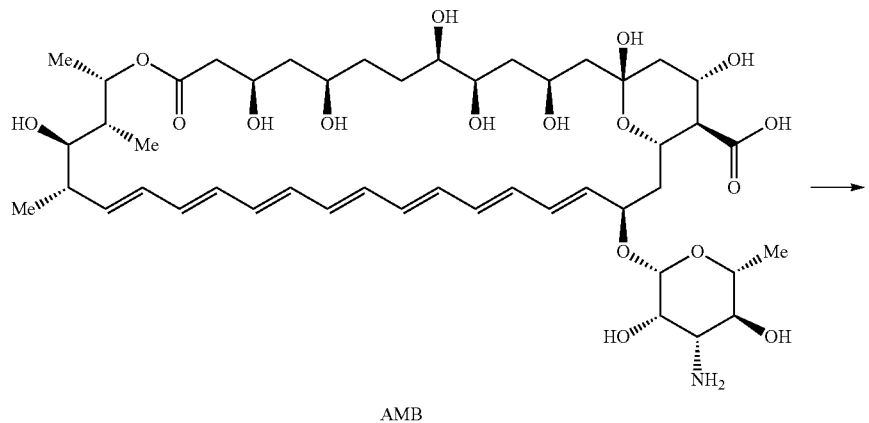
AMB
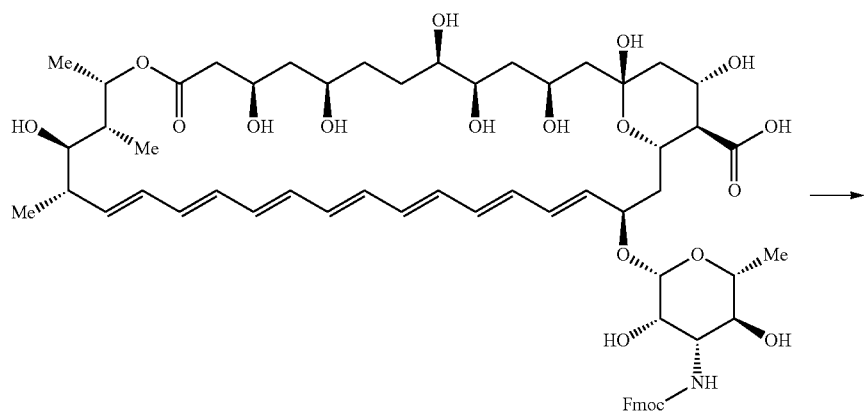
78
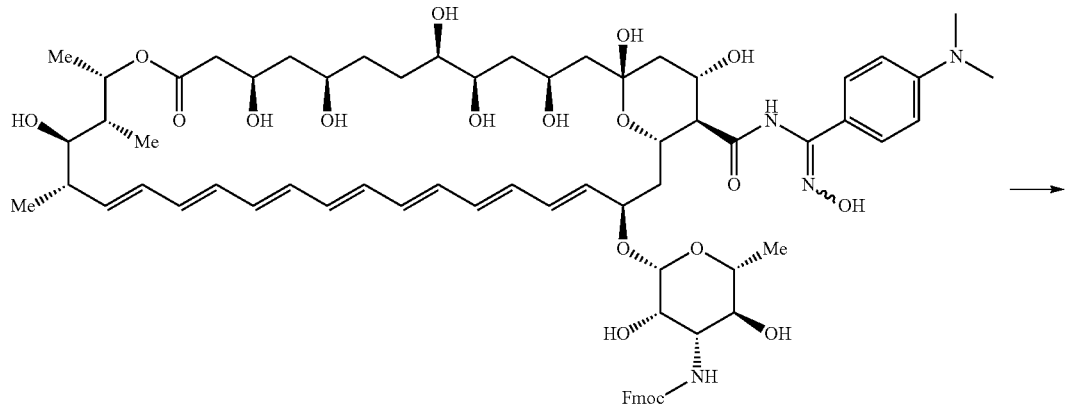
79

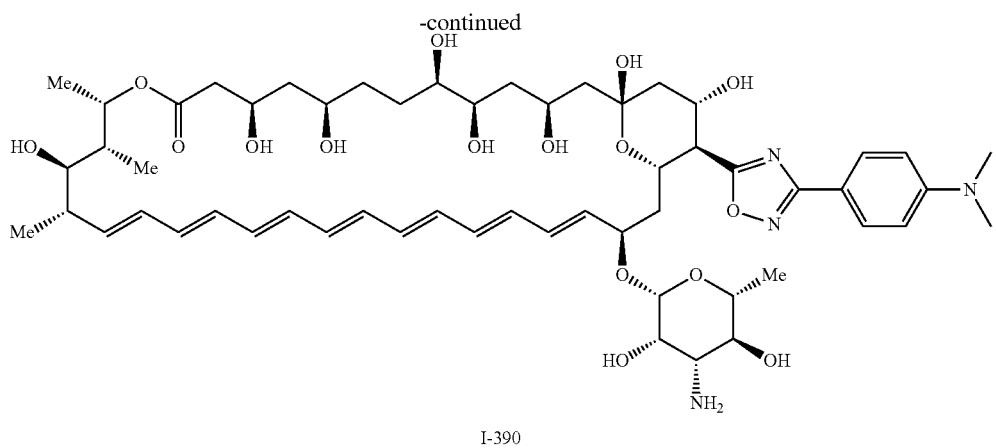

I-390

Step 1 Synthesis of Compound 78

Amphotericin B (5 g, 5.41 mmol) was dissolved into DMF (100 mL), and pyridine (1.31 mL, 16.23 mmol) and N-(9-Fluorenylmethoxycarbonyloxy)succinimide (3.65 g, 10.82 mmol) were added. The mixture was stirred for 3 hours at room temperature. After that, pyridine (0.873 mL, 10.82 mmol) and N-(9-Fluorenylmethoxycarbonyloxy)succinimide (1.83 g, 5.41 mmol) were added, and the mixture was stirred for 2 hours at room temperature. After powderization by adding diisopropyl ether, the obtained solids were filtrated to give crude product of Compound 78 (6.42 g).

Step 2 Synthesis of Compound I-390

Compound 78 (500 mg) was dissolved into DMF (5 mL), and PyBOP (681 mg, 1.309 mmol) and ethylisopropylamine (0.229 mL, 1.309 mmol) were added. The mixture was stirred for an hour at room temperature. (Z)-4-dimethylaminobenzamido oxime (313 mg, 1.745 mmol) was added, and the mixture was stirred for 5 hours at room temperature. After powderization by adding diisopropyl ether/acetonitrile, the obtained solids were filtrated and washed with diisopropyl ether to give crude Compound (545.6 mg). The obtained crude Compound 79 (545.6 mg) was dissolved into DMF (6 mL), and molecular sieve 3 Å was added. 1 mol/L Tetrabutylammonium Fluoride tetrahydrofuran solution (0.625 mL, 0.625 mmol) was added, and the mixture was stirred for 8 hours at 45° C. After the reaction mixture was filtrated and dissolved materials were removed, the mixture was condensed. After powderization by adding diisopropyl ether/acetonitrile (6/1), the powder was purified by silica-gel column chromatography ($CHCl_3$/MeOH/$H_2O$) to give Compound I-390 (94.2 mg, 27.2%).

Elementary analysis: C56H82N4O16(H2O)3.2
Calculated value: C 59.79; H, 7.92; N, 4.98 (%).
Actual value: C 59.75; H, 7.73; N, 4.90 (%).
MS(ESI) m/z: 1067.5(M+H+)

Example 56

Synthesis of Compound I-391

[Chemical Formula 111]

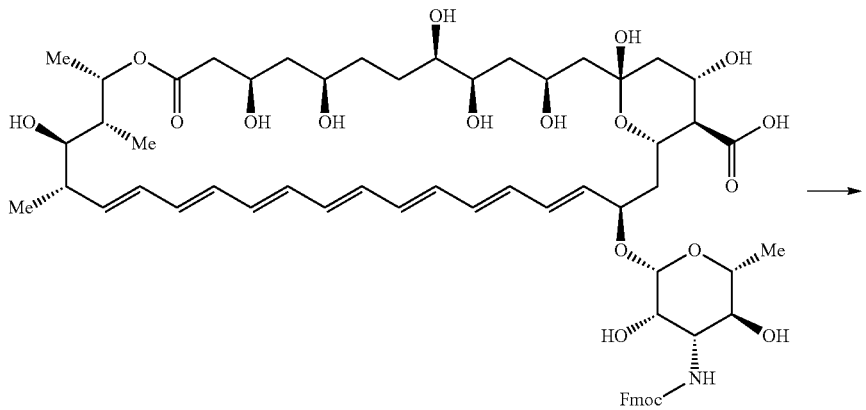

78

-continued

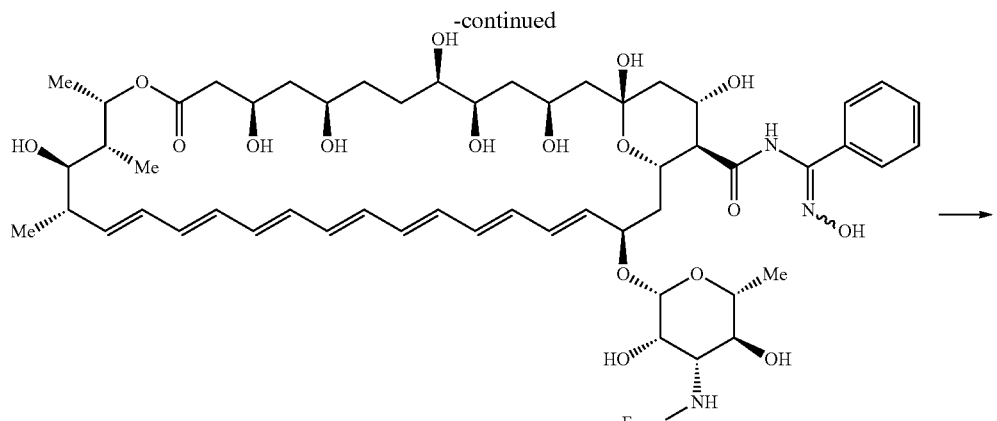

80

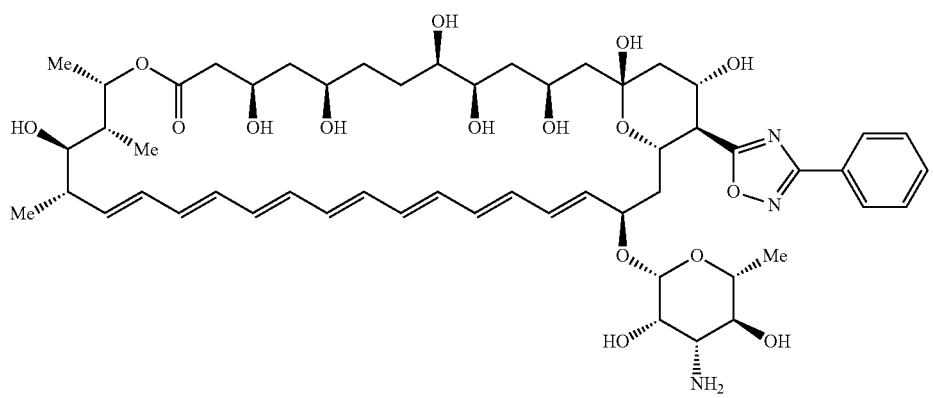

I-391

Compound 78 (500 mg) synthesized as reference to Step 1 of Example 55 was DMF (5 mL), and PyBOP (681 mg, 1.309 mmol) and ethylisopropylamine (0.229 mL, 1.309 mmol) were added. The mixture was stirred for an hour at room temperature. (Z)-Benzamido oxime (178 mg, 1.309 mmol) was added, and the mixture was stirred for 5 hours at room temperature. After powderization by adding diisopropyl ether/acetonitrile, the obtained solids were filtrated and washed with diisopropyl ether to give crude Compound 80 (485.9 mg). The crude Compound 80 (485.9 mg) was dissolved into DMF (7 mL), and molecular sieve 3 Å was added. 1 mol/L Tetrabutylammonium Fluoride tetrahydrofuran solution (0.460 mL, 0.460 mmol) was added, and the mixture was stirred for 8 hours at 45° C. After that, 1 mol/L Tetrabutylammonium Fluoride tetrahydrofuran solution (0.115 mL, 0.115 mmol) was added, and the mixture was stirred for 8 hours at 40° C. After the reaction mixture was filtrated and dissolved materials were removed, the mixture was condensed. After powderization by adding diisopropyl ether/acetonitrile (6/1), the powder was purified by silica-gel column chromatography ($CHCl_3$/MeOH/$H_2O$) to give Compound I-391 (85.6 mg, 19.3%).

Elementary analysis: C54H77N3O16(H2O)2.3(CHCl3)0.4

Calculated value: C 58.68; H, 7.42; N, 3.77 (%).
Actual value: C 58.67; H, 7.42; N, 3.85 (%).
MS(ESI) m/z: 1024.5(M+H+)

Example 57

Synthesis of Compound I-392

[Chemical Formula 112]

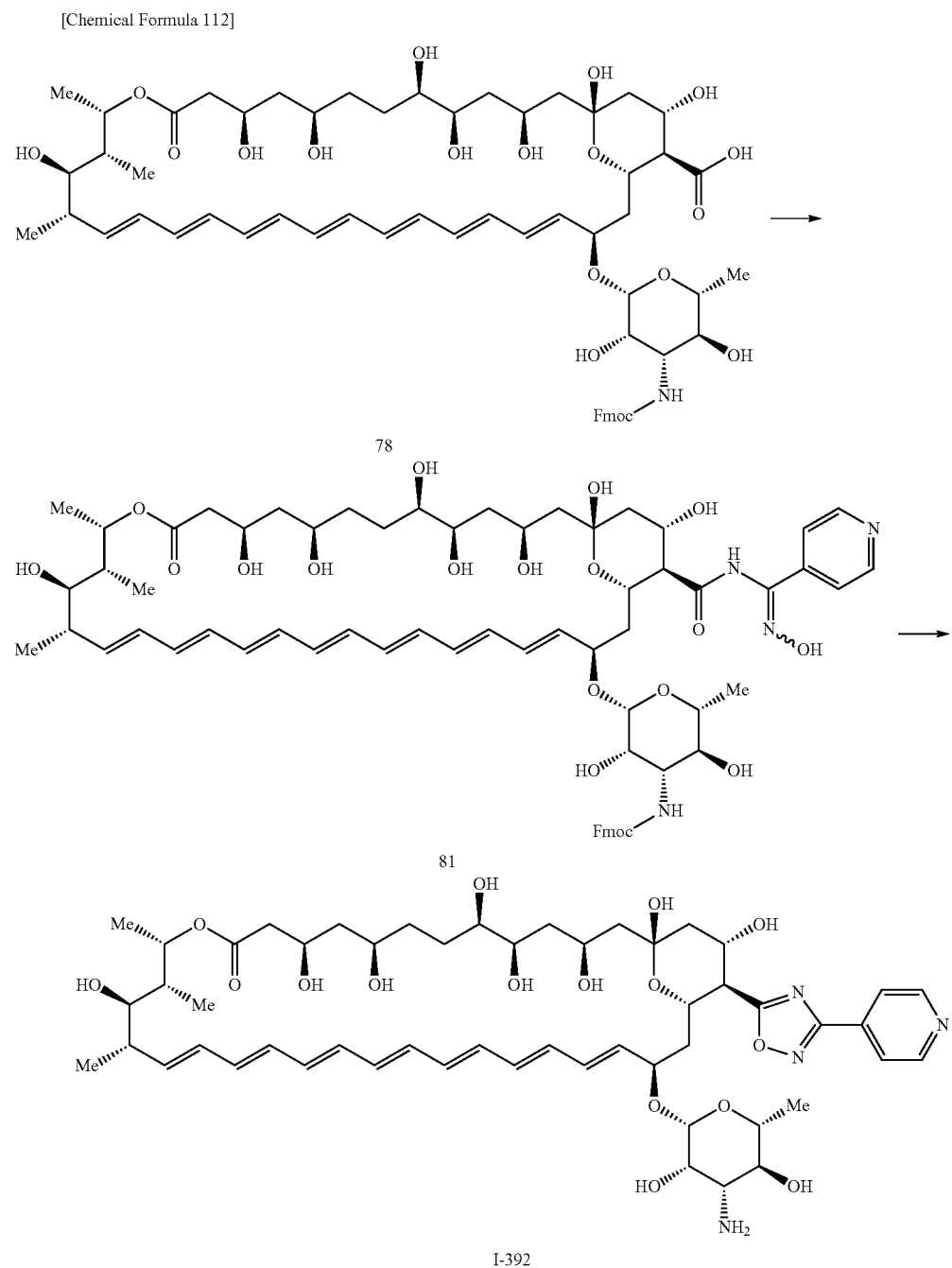

I-392

The crude Compound 78 (1 g) synthesized as reference to Step 1 of Example 55 was DMF (10 mL), and PyBOP (1.36 g, 2.62 mmol) and ethylisopropylamine (0.457 mL, 2.62 mmol) were added. The mixture was stirred for 4.5 hours at room temperature. After that, (Z)-4-pyridilamideoxime (479 mg, 3.49 mmol) was added, and the mixture was stirred for 3 days at room temperature. PyBOP (227 mg, 0.436 mmol) and ethylisopropylamine (0.076 mL, 0.436 mmol) were added, and the mixture was stirred for 3 hours at room temperature. After powderization by adding diisopropyl ether/acetonitrile, the obtained solids were filtrated and washed with diisopropyl ether to give crude Compound 81 (966.4 mg). The crude Compound 81 (966 mg) was dissolved into DMF (10 mL), and molecular sieve 3 Å was added. 1 mol/L Tetrabutylammonium Fluoride tetrahydrofuran solution (1.145 mL, 1.145 mmol) was added, and the mixture was stirred for 8 hours at 45° C. After the reaction mixture was filtrated and dissolved materials were removed, the mixture was condensed. After powderization by adding diisopropyl ether/acetonitrile (6/1), the powder was purified by silica-gel column chromatography (CHCl₃/MeOH/H₂O) to give Compound I-392 (200.6 mg, 23.4%).
Elementary analysis: C54H77N3O16(H2O)2.3(CHCl3)0.4
Calculated value: C 56.32; H, 7.51; N, 4.93; Cl, 2.81 (%).
Actual value: C 56.28; H, 7.51; N, 5.07; Cl, 2.75 (%).
MS(ESI) m/z: 1025.5(M+H+)
Example 58
Synthesis of Compound I-393
[Chemical Formula 113]
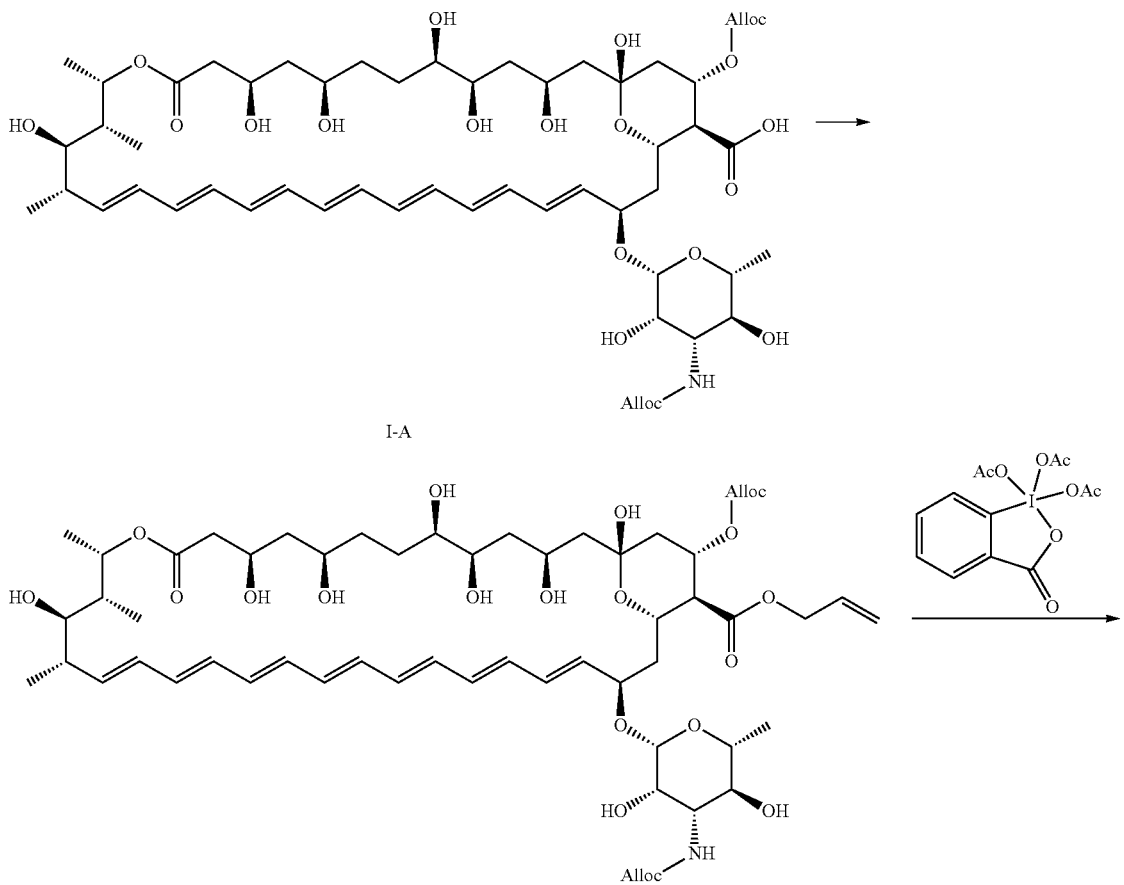
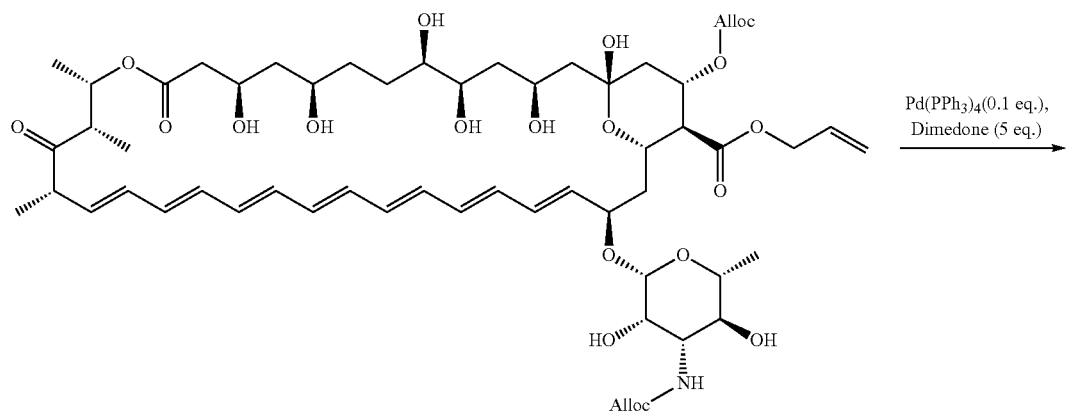

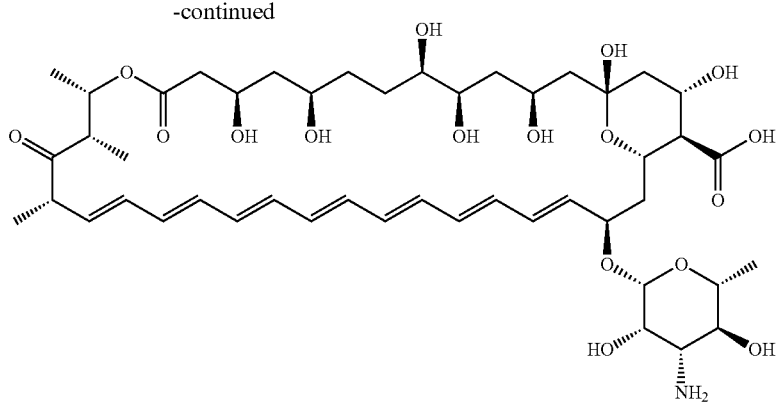

I-393

Step 1 Synthesis of Compound 82

Compound I-A (1 g, 0.916 mmol) was dissolved into DMF (10 mL), and DIEA (1.12 mL, 6.41 mmol) and Allyl Bromide (0.396 mL, 4.58 mmol) were added. After the mixture was stirred for 6 hours at room temperature, and DIEA (0.32 mL, 1.83 mmol) and Allyl Bromide (0.079 mL, 0.916 mmol) were added. The mixture was stirred for 2 hours at room temperature. The reaction mixture was added to diisopropyl ether/acetonitrile (6/1, 200 mL) and stirred to give solids by filtration. The obtained solids were purified by silica-gel column chromatography (chloroform/methanol/water=96/4/0.4) to give Compound 82 (277 mg, 27%).

LC-MS: 1133.8 [M+H]+, 1114.9 [M+H—H2O]+

Step 2 Synthesis of Compound 83

Compound 82 (277 mg, 0.245 mmol) was dissolved into dichloromethane (8 mL), and Dess-Martin Periodinane (Dess-Martin Reagent: 114 mg, 0.269 mmol) was added. The mixture was stirred for 1.5 hours at 0° C. Dess-Martin Periodinane (Dess-Martin Reagent: 21 mg, 0.049 mmol) was added, and the mixture was stirred for 2 hours at 0° C. The reaction mixture was diluted with saturated sodium bicarbonate aqueous solution, and extracted with dichloromethane (20 mL) three times. After the organic phase was washed with water and brine, the organic phase was dried with sodium sulfate anhydrous. After the mixture was filtrated and condensed, the residue was purified by silica-gel column chromatography (chloroform/methanol/water=95/5/0.5) to give Compound 83 (91 mg, 33%).

LC-MS: 1112.8 [M+H—H2O]+

Step 3 Synthesis of Compound I-393

Compound 83 (90 mg, 0.080 mmol) was dissolved into tetrahydrofuran (1 mL) and water (0.1 mL), and dimedone (56 mg, 0.398 mmol) and Tetrakis (triphenylphosphine) palladium (0) (9.2 mg, 0.008 mmol) were added. The mixture was stirred for an hour at room temperature under nitrogen atmosphere. After the reaction mixture was filtrated and washed with tetrahydrofuran, corrected filtrate was condensed in vacuo. The residue was purified by reverse-phase chromatography (HP20ss, acetonitrile/water=95/5) to give 35-position ketone Compound I-393 (12 mg, 17%)

LC-MS: m/z=922.9 [M+H]+

Elementary analysis: (C47H71NO17)(H2O)3.8(CH3CN)0.2

Calculated value: C 57.00; H, 7.99; N, 1.68 (%).

Actual value: C 57.06; H, 7.85; N, 2.00 (%).

Example 59

Synthesis of Compound I-393

[Chemical Formula 114]

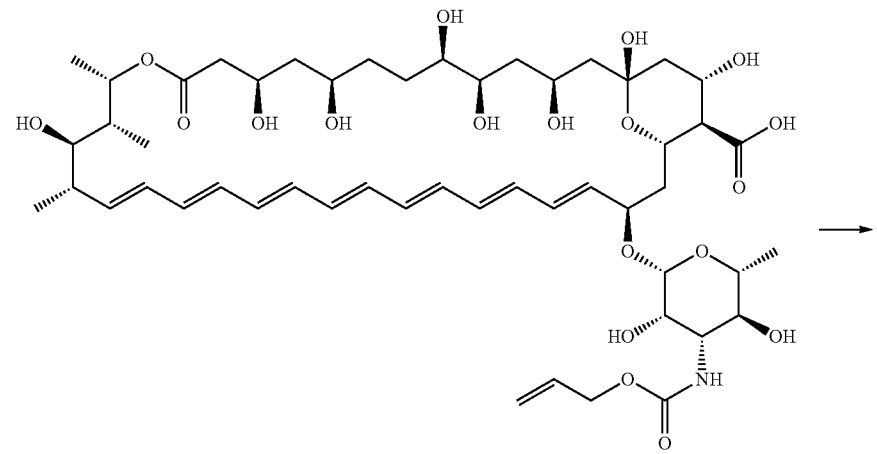

I-b 257 258
-continued
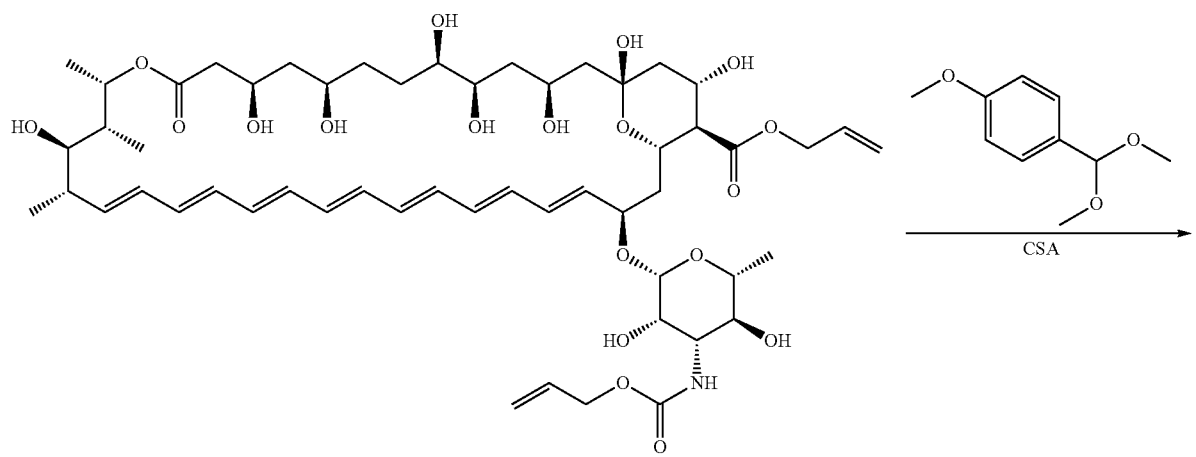
84
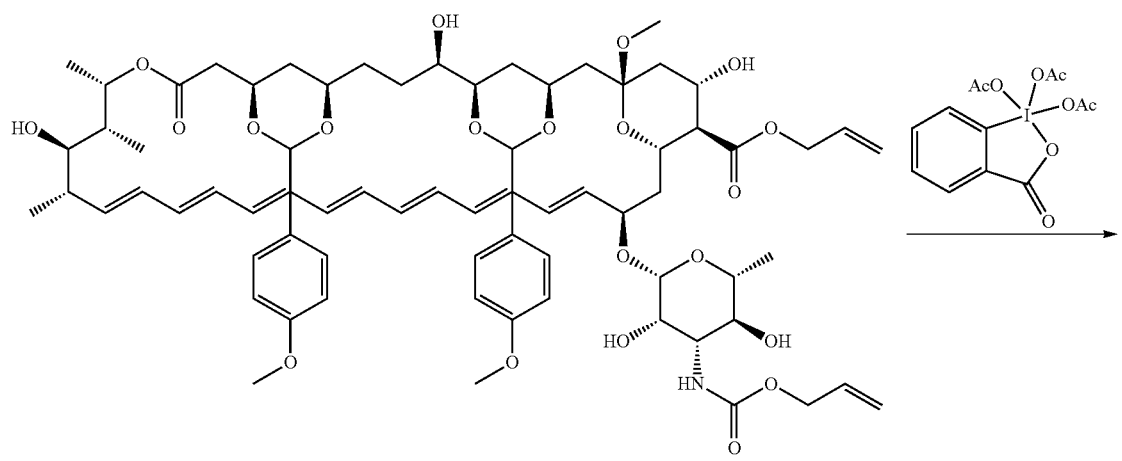
85
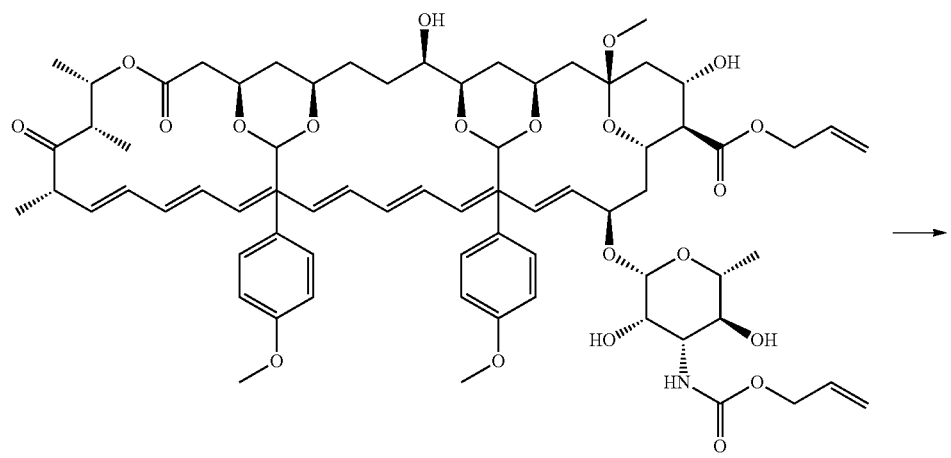
86

-continued
[Chemical Formula 115]
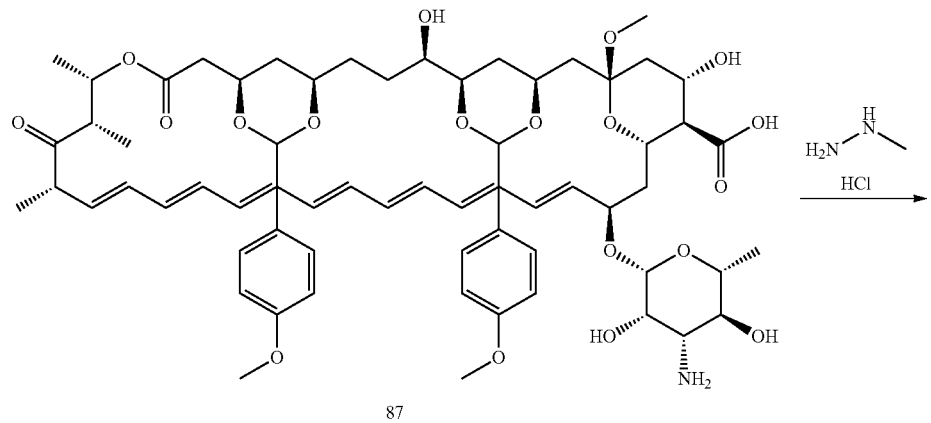
87
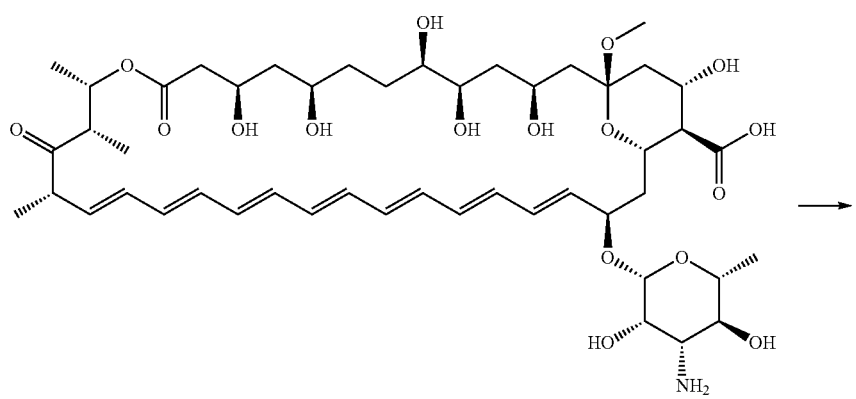
88
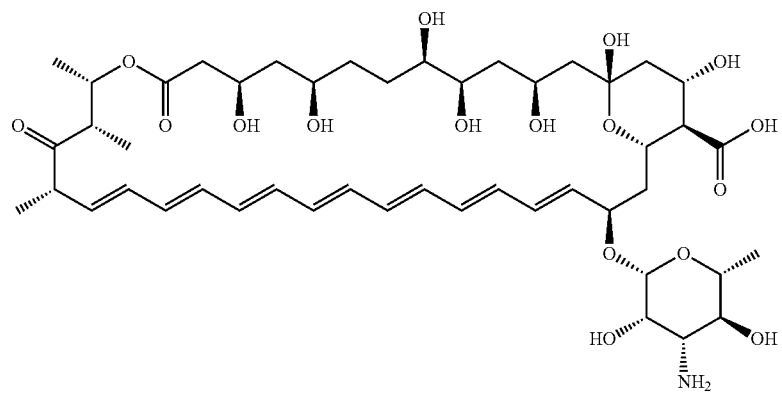
I-393

Step 1

The intermediate I-b (16.3 g, 16.23 mmol) was dissolved into DMF (100 mL), and allyl bromide (4.2 mL, 48 mmol) and DIEA (14 mL, 81 mmol) were added. The mixture was stirred for 5.5 hours at room temperature. allyl bromide (2.8 mL, 32.5 mmol) and DIEA (5.7 mL, 32.5 mmol) were added, and the mixture was stirred overnight. The reaction solution was powderized with diisopropyl ether (1.5 L) to give Compound 85 (20.84 g).

Step 2

Compound 84 (10.48 g, 10 mmol) was suspended in methanol (100 mL), and 1-(Dimethoxymethyl)-4-Methoxybenzene (9.2 mL, 54 mmol) and CSA (1.533 g, 6.6 mmol) were added. After The mixture was stirred for 1.5 hours at 0° C., the reaction was quenched with triethylamine (0.97 mL, 7 mmol). After concentration, the reaction mixture was diluted with ethyl acetate and filtrated. The obtained organic phase was washed with water. After the organic phase was dried up with magnesium sulfate anhydrous, the organic phase was condensed. The obtained residue was purified by silica-gel column chromatography (chloroform/methanol/water=99/1/0.1) to give yellow caramel-solids Compound 85 (5.14 g, 39%).

LC-MS: 1299.2 [M+H]+

Step 3

Compound 85 (5.1 g, 3.93 mmol) was dissolved into dichloromethane (70 mL), and Dess-Martin Periodinane (1.89 g, 4.32 mmol) was added in an ice-water bath. The mixture was stirred for an hour 30 minutes. The reaction mixture was diluted with saturated sodium bicarbonate aqueous solution and extracted with dichloromethane. The organic phase was washed with brine and dried up with sodium sulfate anhydrous. The residue was purified by silica-gel column chromatography to give orange caramel-solids Compound 86 (2.16 g, 42%). The presence of 35-position ketone was identified by $^{13}$CNMR and HMBC.

$^{13}$C NMR (DMSO-d6) δ 211.90 (35-C).

LC-MS: 1265.9 [M-CH$_2$O+H]+, 1296.9 {M+H}+

Step 4

Compound 86 (0.96 g, 0.74 mmol) was dissolved into tetrahydrofuran (15 mL), and dimedone (519 mg, 3.7 mmol) and Pd(PPh$_3$)$_4$ (60 mg, 0.052 mmol) were added. The mixture was stirred for 90 minutes at room temperature under nitrogen atmosphere. The reaction mixture was condensed, and dissolved into DMF (5 mL). The mixture was added dropwise to diisopropyl ether. The obtained solids were filtrated to give Compound 87 (887 mg).

LC-MS: 1173.1 [M+H]+

Step 5

Compound 87 (887 mg, 0.757 mmol) was dissolved into DMF (3 mL), and hydrochloric acid-methanol (3.5 mol/L, 2.6 mL, 9 mmol) was added. The mixture was stirred for an hour at 0° C. hydrochloric acid-methanol (3.5 mol/L, 0.857 mL, 3 mmol) and methylhydrazine (0.128 mL, 2.24 mmol) were added, and the mixture was stirred for an hour at 0° C. The reaction was quenched with triethylamine (1.67 mL, 12.1 mmol) and added dropwise to diisopropyl ether to give Compound 88 (1.95 g).

Step 6

Compound 88 (709 mg, 0.75 mmol) was dissolved into DMF (8 mL), and water (5 mL) was added. The mixture was cooled. Concentrated hydrochloric acid (0.667 mL, 8 mmol) was added in an ice-water bath, and the mixture was stirred for 2 hours at 0° C. The reaction mixture was neutralized by adding triethylamine (1.15 mL, 8.33 mmol). After tetrahydrofuran was removed by concentration in vacuo, the mixture was poured to diisopropyl ether-methanol (800 mL/30 mL). The mixture was stirred for 10 minutes at room temperature. After filtration, the obtained solids were purified by reverse-phase chromatography (HP20ss, acetonitrile:water=20:80 to 35:65) to give Compound I-393 (46 mg, 7%).

LC-MS: 922.9 [M+H]+

Example 60

Synthesis of Compound I-394

[Chemical Formula 116]

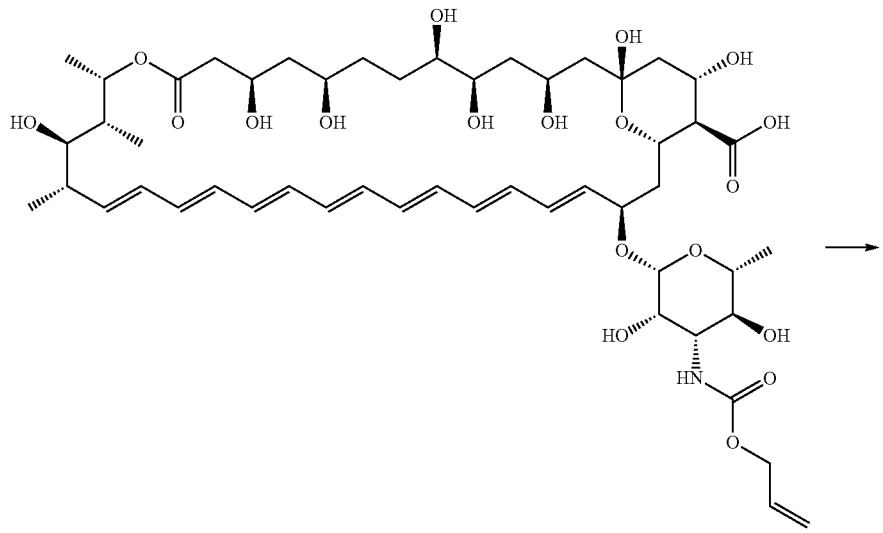

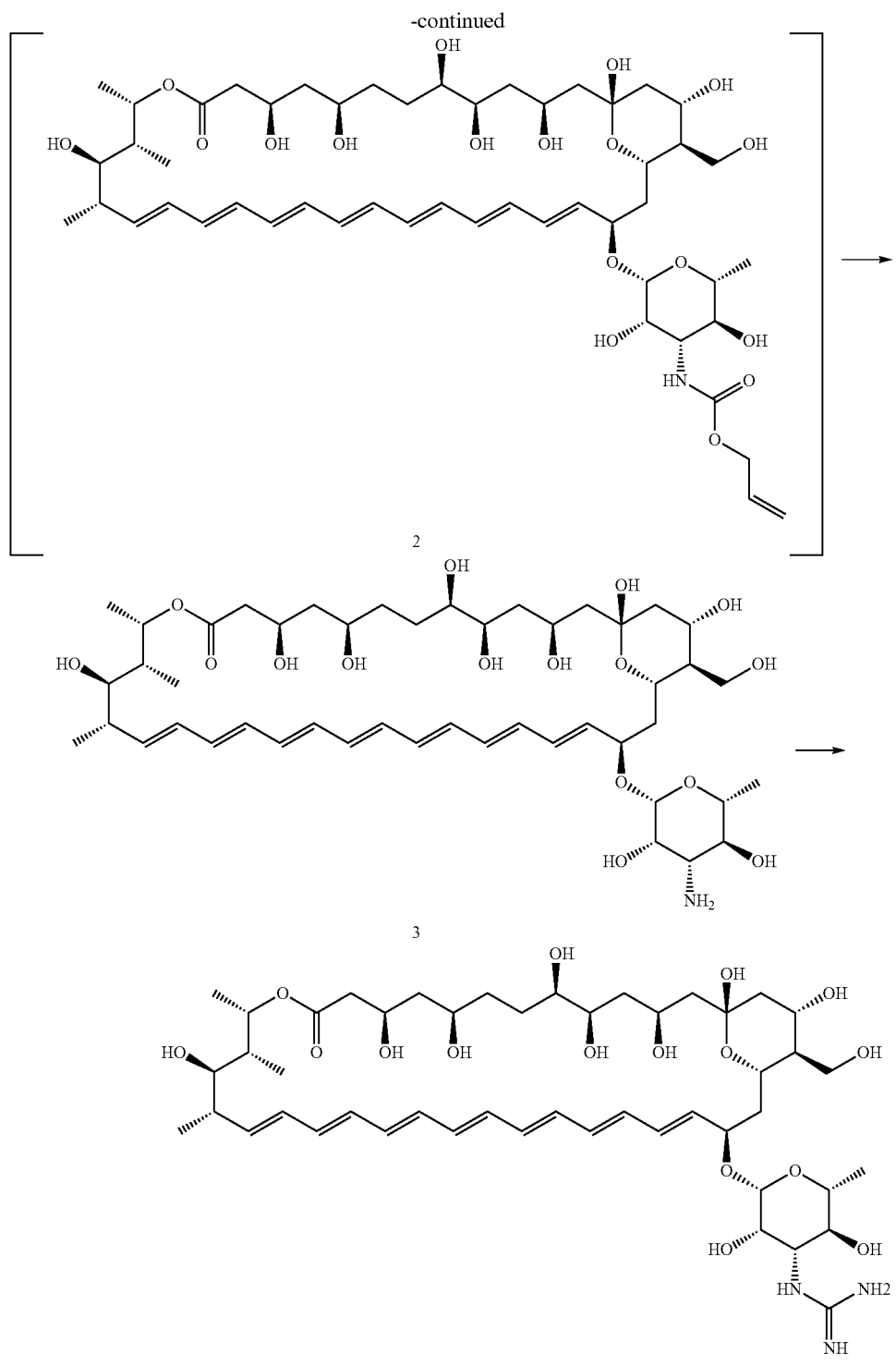

I-394

Step 1 Synthesis of Compound 3

Compound 1 (1 g, 0.992 mmol) was dissolved into NMP (7 mL), and the mixture was cooled to 0° C. (7-Azabenzotriazol-1-yloxy)tripyrrolidinophosphonium Hexafluorophosphate (542 mg, 1.042 mmol) and DIEA (0.26 mL, 1.49 mmol) were added, and the mixture was stirred for 30 minutes at room temperature. Sodium borohydride (113 mg, 2.98 mmol) was added, and the mixture was stirred for an hour at room temperature. Further, sodium borohydride (75 mg, 1.98 mmol) was added, and the mixture was stirred for an hour at room temperature. Acetone and IRA743 resin (1 g) were added, the mixture was stirred for an hour at room temperature. The mixture was filtrated by Celite®. The mixture was oil-outed by adding diisopropyl ether, and the residue was purified by silica-gel column chromatography (chloroform/methanol/water=95/5/0.5 to 80/20/2) to give Compound 2 (232 mg, 24%). Compound 2 (232 mg, 0.233 mmol) was dissolved into NMP (3 mL), and morpholine (0.142 mL, 1.63 mmol) and Pd(PPh$_3$)$_4$ (27 mg, 0.023 mmol) were added. The mixture was stirred for an hour at room temperature. After powderization by adding diisopropyl ether, the powder was purified by silica-gel column chromatography (amino silica-gel, chloroform/methanol/water=70/30/3-70/30/5) to give Compound 3 (81 mg, 38%).

LC-MS: m/z 910.5 [M+H]+, 932.5[M+Na]+

Step 2 Synthesis of Compound I-394

Compound 3 (200 mg, 0.220 mmol) was dissolved into DMF (2 mL), and 1H-pyrazole-1-carboxyimidamide hydrochloride (169 mg, 1.15 mmol) and DIEA (0.269 mL, 1.54 mmol) were added. The mixture was stirred for 12 hours at room temperature. After powderization by adding diisopropyl ether, the obtained powder was purified by silica-gel column chromatography (amino silica-gel, chloroform/methanol/water=70/30/3-50/50/5) to give Compound I-394 (110 mg, 53%).

LC-MS: m/z 952.8 [M+H]+

Example 61

Synthesis of Compound I-395

[Chemical Formula 117]

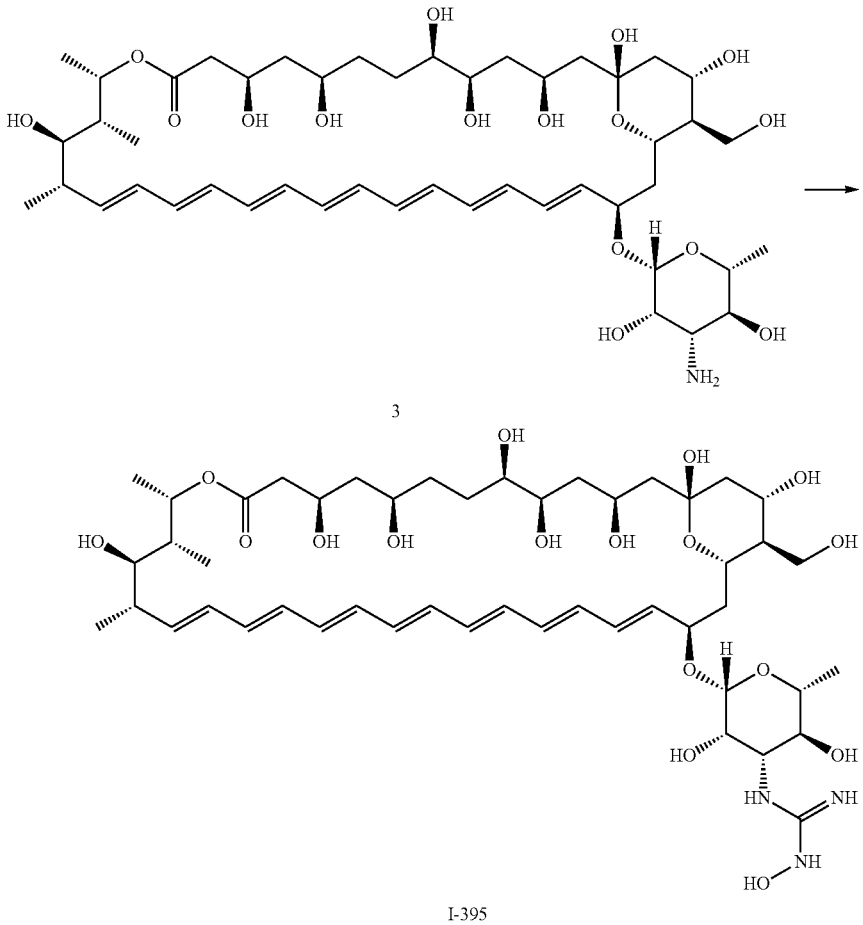

I-395

Synthesis of Compound I-395

Compound 3 (100 mg, 0.11 mmol) was dissolved into DMF (1 mL), and DIEA (0.096 ml, 0.55 mmol), cyanogen bromide (11.6 mg, 0.11 mmol) and Hydroxylamine Hydrochloride (7.64 mg, 0.11 mmol) were added at room temperature. After the mixture was stirred for 5 hours at room temperature, Hydroxylamine Hydrochloride (1.53 mg, 0.022 mmol) was added. After the mixture was stirred for 15 hours at room temperature, isopropyl ether was added to give solids. the obtained solids were purified by silica-gel column chromatography (chloroform/methanol/water=50/45/5) to give Compound I-395 (36 mg, 27%).

LC-MS: m/z 968.5 [M+H]+

Example 62
Synthesis of Compound I-396
[Chemical Formula 118]
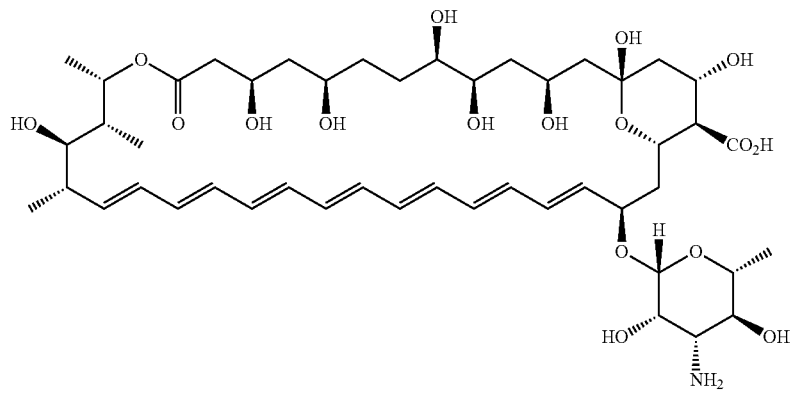
Amphotericin B ↓
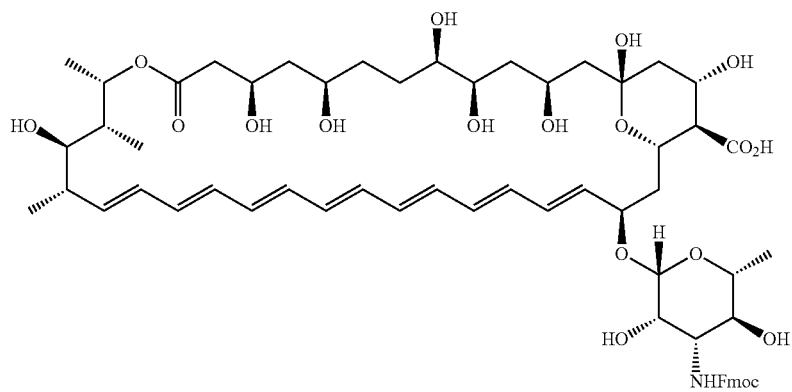
I-c
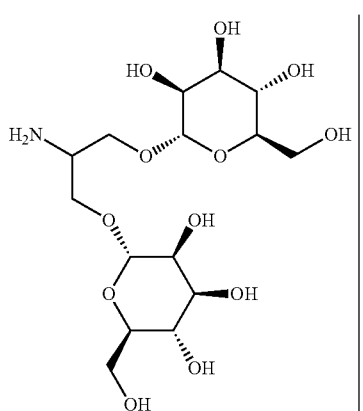
49
↓

-continued

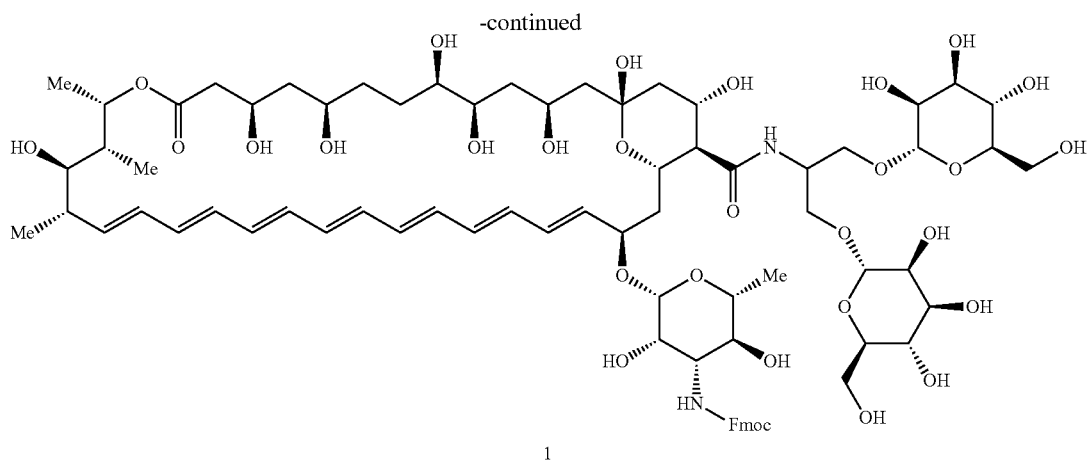

1

↓

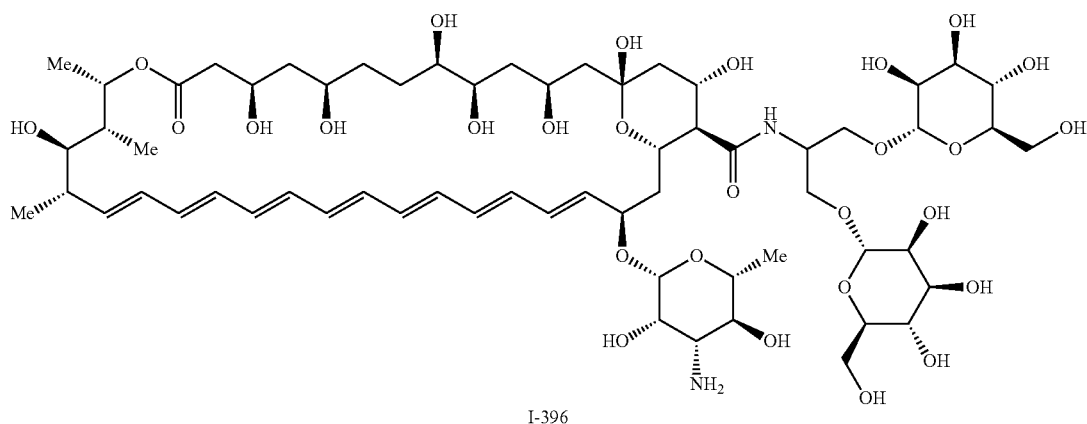

I-396

Step 1 Synthesis of Compound I-c

Amphotericin B (10 g, 9.74 mmol) was dissolved into dimethylformamide (25 mL) and methanol (25 mL), and pyridine (9 mL, 112 mmol) and Fmoc-OSu (9.20 g, 27.3 mmol) were added. The mixture was stirred for 12 hours at room temperature. The reaction solution was poured to isopropyl ether (1000 mL) and stirred strongly. The obtained powder was filtrated. The obtained solids were washed with isopropyl ether and dried up in vacuo to give crude Compound I-c (14.27 g). The retention time of Compound I-c was 13 minutes by HPLC analysis (methanol/distilled water containing 0.1% PIC-B7=gradient 70/30 to 100/0, flow speed 1 ml/min, wavelength of detection=385 nm). The retention time of raw material amphotericin B was 8.6 minutes under the same condition.

Step 2 Synthesis of Compound I-396

Compound I-c (2 g, 1.745 mmol) was dissolved into N,N-dimethylformamide (18 mL), and PyBOP (2.72 g, 5.23 mmol) and N,N-diisopropylethylamine (1.52 mL, 8.72 mmol) were added. Compound 49 (1.087 g, 2.62 mmol) synthesized at example 27 was added, and the mixture was stirred for 5 hours at room temperature. The reaction mixture was poured to diisopropyl ether (300 mL) and stirred strongly. The obtained powder was filtrated and purified by silica-gel column chromatography (chloroform:methanol containing 10% water=9:1-1:1-3:7) to give Compound 1 (1.95 g, 72%). The retention time of Compound 1 was 9.5 minutes by HPLC analysis (methanol/distilled water containing 0.1% PIC-B7=gradient 70/30 to 100/0, flow speed 1 ml/min, wavelength of detection=385 nm).

Step 3

Compound 1 (1.84 g, 1.192 mmol) was dissolved into N,N-dimethylformamide (10 mL), and piperidine (1.18 mL, 11.92 mmol) was added. The mixture was stirred for an hour in an ice-water bath. The reaction mixture was poured to diisopropyl ether (300 mL) and stirred strongly. The obtained powder was filtrated to give crude gummy solids (1.98 g). The obtained solids were purified by reverse-phase chromatography (HP20ss, acetonitrile-water). The obtained fractions were condensed and lyophilized to give Compound I-396 (350 mg, 23%).

m/z 1321.7 [M+H]+.

Elementary analysis: (C62H100N2O28)(H2O)8.9

Calculated value: C 50.25; H, 8.01; N, 1.89 (%).

Actual value: C 50.21; H, 7.91; N, 2.53 (%).

The synthesis example of the side chain is shown as follow.

Reference Example 4

Synthesis of Compound 2 (the Side Chain of Compound I-162)

[Chemical Formula 119]

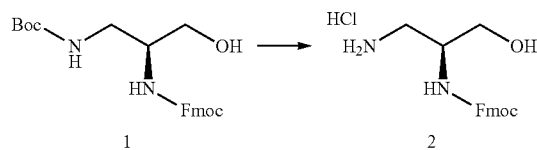

Step 1 Synthesis of Compound 2

Compound 1 (5.0 g, 12.1 mmol) was suspended in dichloromethane (50 mL), and hydrochloric acid (4 mol/L, dioxane solution, 6 mL) was added. The mixture was stirred for an hour at room temperature. The resulted solids were filtrated and dried up to give Compound 2. Compound 2 was used to synthesis of Compound I-162 without purification.

Reference Example 5

Synthesis of Compound 4 (the Side Chain of Compound I-169)

[Chemical Formula 120]

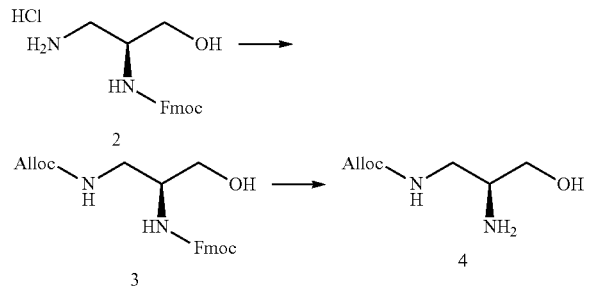

Step 1 Synthesis of Compound 3

Compound 2 obtained at Step 1 of example 1 and Compound 1 (1.0 g, 2.87 mmol) were dissolved into dichloromethane (10 mL) and triethylamine (795 mL, 5.73 mmol), and Alloc-OSu (1.0 g, 2.87 mmol) was added. The mixture was stirred for 2.5 hours at room temperature. The solvent was removed by evaporating in vacuo and extracted by adding water to residue. After the organic phase was washed with saturated ammonium chloride aqueous solution and brine, the organic phase was dried up with magnesium sulfate anhydrous. The solvent was evaporated in vacuo, and the obtained residue was purified by silica-gel column chromatography (hexane/ethyl acetate) to give Compound 3 (760 mg, 67%).

1H-NMR (CDCl3)

δ: 3.26-3.46 (m, 3H), 3.53-3.70 (m, 3H), 4.20 (t, J=6.9 Hz, 1H), 4.40 (d, J=6.9 Hz, 2H), 4.58 (d, J=6.0 Hz, 2H), 5.05-5.09 (m, 1H), 5.10-5.34 (m, 3H), 5.90 (ddt, J=17.0, 10.7, 5.8 Hz, 1H), 7.31 (t, J=7.3 Hz, 2H), 7.40 (t, J=7.3 Hz, 2H), 7.58 (d, J=7.3 Hz, 2H), 7.76 (d, J=7.3 Hz, 2H).

Step 2 Synthesis of Compound 4

Compound 3 (790 mg, 1.99 mmol) was dissolved into dichloromethane (10 mL), and piperidine (395 mL, 3.99 mmol) was added. The mixture was stirred for 3.5 hours at room temperature. After the solvent was evaporated in vacuo and dissolved into methanol, the solvent was oil-outed by adding isopropyl ether to remove solvent. This operation was repeated twice. Compound 4 was used to synthesis of Compound I-169 without purification.

Reference Example 6

Synthesis of Compound 12 (the Side Chain of Compound I-163)

[Chemical Formula 121]

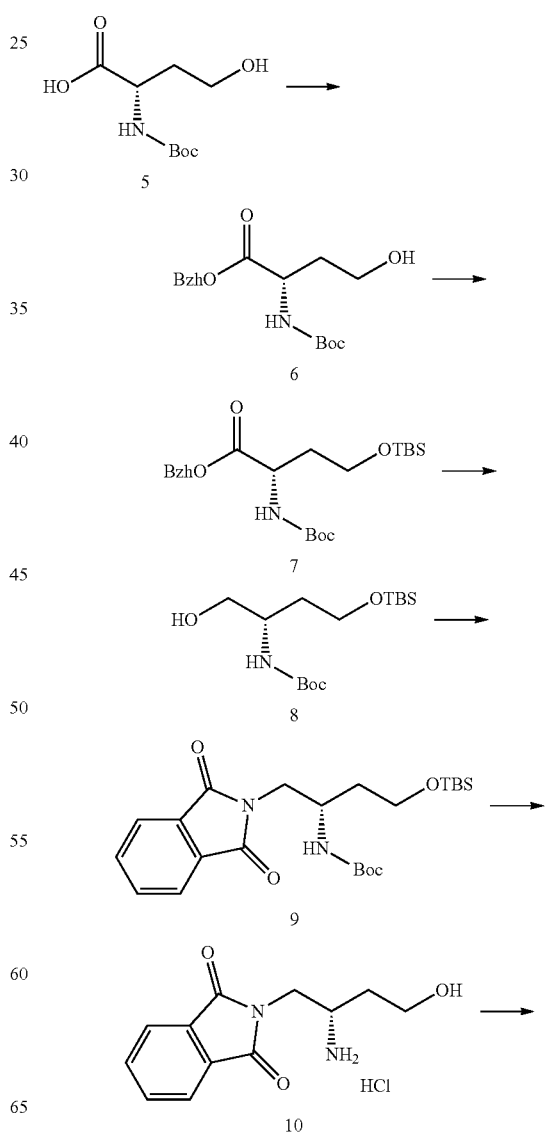

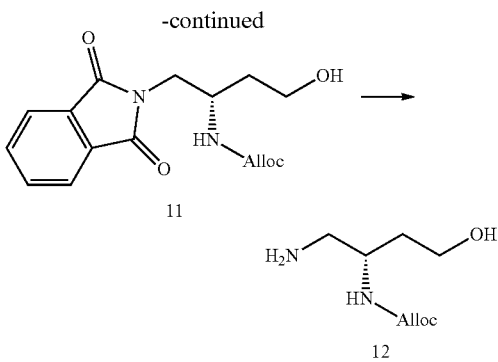

11

12

Step 1 Synthesis of Compound 6

Compound 5 (3.27 g, 14.9 mmol) was dissolved into tetrahydrofuran (15 mL), and diphenyldiazomethane (3.48 g, 17.9 mmol) was added. The mixture was stirred at room temperature. The reaction mixture was condensed, and the obtained residue was purified by silica-gel column chromatography (hexane/ethyl acetate) to give Compound 6 (5.17 g, 90%).

1H-NMR (CDCl3)

δ: 1.44 (s, 9H), 1.56-1.60 (m, 2H), 2.22-2.28 (m, 1H), 3.27-3.30 (m, 1H), 3.62-3.70 (m, 2H), 4.58-4.65 (m, 1H), 5.38 (d, J=7.5 Hz, 1H), 6.90 (s, 1H), 7.27-7.36 (m, 10H).

Step 2 Synthesis of Compound 7

Compound 6 (2.1 g, 5.45 mmol) was dissolved into N,N-dimethylformamide (5 mL) and tetrahydrofuran (5 mL), and imidazole (816 mg, 12 mmol) and TBS chloride (985 mg, 6.54 mmol) were added. The mixture was stirred for an hour at room temperature. Water was added to the reaction mixture, and the mixture was extracted with ethyl acetate. After the organic phase was washed with water and brine, the organic phase was dried up with magnesium sulfate anhydrous and evaporated in vacuo. The obtained residue was purified by silica-gel column chromatography (hexane/ethyl acetate) to give Compound 7 (2.4 g, 88%).

1H-NMR (CDCl3)

δ: 0.03 (s, 3H), 0.05 (s, 3H), 0.90 (s, 9H), 1.49 (s, 9H), 1.95-2.19 (m, 2H), 3.55-3.64 (m, 1H), 3.66-3.74 (m, 1H), 4.52-4.60 (m, 1H), 5.84 (d, J=7.0 Hz, 1H), 6.95 (s, 1H), 7.32-7.41 (m, 10H).

Step 3 Synthesis of Compound 8

Compound 7 (2.45 g, 4.9 mmol) was dissolved into tetrahydrofuran (20 mL) and methanol (10 mL), and the mixture was cooled to 0° C. Lithium triethylborohydride (12 mL, 2 mol/L solution, 23.9 mmol) was added dropwise, and the mixture was stirred for 30 minutes at room temperature. Water was added to the mixture, and the mixture was extracted with ethyl acetate. After the organic phase was washed with water and brine, the organic phase was dried up with magnesium sulfate anhydrous and evaporated in vacuo. The obtained residue was purified by silica-gel column chromatography (hexane/ethyl acetate) to give Compound 8 (2.4 g, 88%).

1H-NMR (CDCl3)

δ: 0.08 (s, 6H), 0.91 (s, 9H), 1.44 (s, 9H), 1.63-1.76 (m, 1H), 1.79-1.89 (m, 1H), 3.40-3.48 (m, 1H), 3.58-3.69 (m, 2H), 3.70-3.81 (m, 3H), 5.40-5.50 (m, 1H).

Step 4 Synthesis of Compound 9

Compound 8 (3.71 g, 11.6 mmol) was dissolved into tetrahydrofuran (20 mL), and phthalimide (2.05 g, 13.9 mmol), triphenylphosphine (3.65 g, 13.9 mmol) and DMAD (5.16 mL, 13.9 mmol, 2.7 mol/L solution) were added. The mixture was stirred at room temperature. Saturated sodium bicarbonate aqueous solution was added to the reaction mixture, and the mixture was extracted with ethyl acetate. After the organic phase was washed with water and brine, the organic phase was dried up with magnesium sulfate anhydrous and evaporated in vacuo. The obtained residue was purified by silica-gel column chromatography (hexane/ethyl acetate) to give Compound 9 (4.68 g, 90%).

1H-NMR (CDCl3)

δ: 0.07 (s, 3H), 0.09 (s, 3H), 0.91 (s, 9H), 1.22 (s, 9H), 1.63-1.71 (m, 1H), 1.80-1.93 (m, 1H), 3.70-3.86 (m, 4H), 4.08-4.17 (m, 1H), 5.12 (d, J=8.0 Hz, 1H), 7.66-7.72 (m, 2H), 7.80-7.86 (m, 2H).

Step 5 Synthesis of Compound 11

Compound 9 (2.23 g, 4.97 mmol) was dissolved into dichloromethane (15 mL) and methanol (1 mL), and hydrochloric acid (4 mol/L dioxane solution, 5 mL) was added. The mixture was stirred for 2 hours at room temperature. The resulted solids were filtrated to give Compound 10. Compound 10 was used to next reaction without purification. Compound 10 was dissolved into dichloromethane (10 mL), and Alloc-OSu (1.11 g, 5.6 mmol) and triethylamine (1.55 mL, 11.1 mmol) were added. The mixture was stirred for 30 minutes at room temperature. Water was added to the reaction mixture, and the mixture was extracted with ethyl acetate. After the organic phase was washed with water and brine, the organic phase was dried up with magnesium sulfate anhydrous and evaporated in vacuo. The obtained residue was purified by silica-gel column chromatography (hexane/ethyl acetate) to give Compound 11 (1.47 g, 99%).

1H-NMR (DMSO-d6)

δ: 1.50-1.70 (m, 2H), 3.34-3.50 (m, 2H), 3.52-3.66 (m, 2H), 3.86-3.97 (m, 1H), 4.20-4.37 (m, 2H), 4.44 (t, J=5.0 Hz, 1H), 5.03 (dq, J=10.4, 1.5 Hz, 1H), 5.14 (dd, J=17.3, 1.5 Hz, 1H), 5.71 (ddt, J=17.3, 10.4, 5.5 Hz, 1H), 7.08 (d, J=8.9 Hz, 1H), 7.80-7.88 (m, 4H).

Step 6 Synthesis of Compound 12

Compound 11 (1.47 g, 4.62 mmol) was dissolved into ethanol (10 mL), and hydrazine hydrate (337 mL, 6.93 mmol) was added. The mixture was stirred for 6 hours at 80° C. The reaction mixture was filtrated and condensed to give Compound 12. Compound 12 was used to synthesis of Compound I-163 without purification.

Reference Example 7

Synthesis of Compound 15 (the Side Chain of Compound I-168)

[Chemical Formula 122]

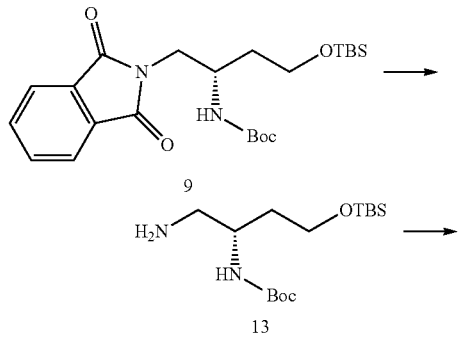

9

13

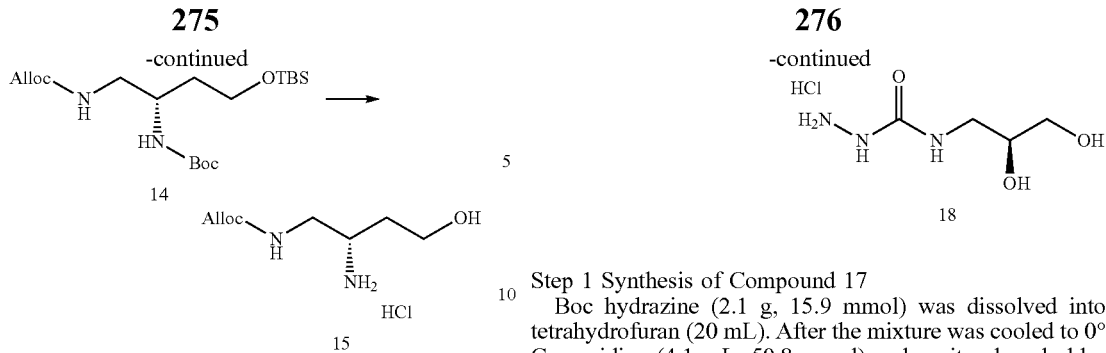

Step 1 Synthesis of Compound 14

Compound 9 (2.46 g, 5.48 mmol) was dissolved into ethanol (20 mL), and hydrazine hydrate (533 mL, 11 mmol) was added. The mixture was stirred for 4 hours at 80° C. The reaction mixture was filtrated and condensed to give Compound 13. The obtained Compound 13 was dissolved into dichloromethane (10 mL), and Alloc-OSu (1.68 g, 8.4 mmol) and DIEA (0.98 mL, 5.62 mmol) were added. The mixture was stirred for 20 hours at room temperature. The reaction mixture was condensed. Water was added to the mixture, and the mixture was extracted with ethyl acetate. After the organic phase was washed with water and brine, the organic phase was dried up with magnesium sulfate anhydrous and evaporated in vacuo. The obtained residue was purified by silica-gel column chromatography (hexane/ethyl acetate) to give Compound 14 (1.75 g, 77%).

1H-NMR (CDCl3)

δ: 0.06 (s, 6H), 0.90 (s, 9H), 1.43 (s, 9H), 1.59-1.70 (m, 1H), 1.72-1.85 (m, 1H), 3.20-3.31 (m, 1H), 3.31-3.41 (m, 1H), 3.65-3.83 (m, 4H), 4.55 (d, J=5.5 Hz, 2H), 5.19 (dd, J=10.4, 1.0 Hz, 1H), 5.29 (dd, J=17.2, 1.0 Hz, 1H), 5.35-5.43 (m, 1H), 5.90 (ddt, J=17.2, 10.4, 5.5 Hz, 1H).

Step 2 Synthesis of Compound 15

Compound 14 (1.75 g, 4.35 mmol) was dissolved into dichloromethane (10 mL) and methanol (1 mL), and hydrochloric acid (4 mol/L dioxane solution, 2.2 mL) was added. The mixture was stirred for an hour at room temperature. The reaction mixture was condensed to give Compound 15. Compound 15 was used to synthesis of Compound I-168 without purification.

Reference Example 8

Synthesis of Compound 18 (the Side Chain of Compound I-225)

[Chemical Formula 123]

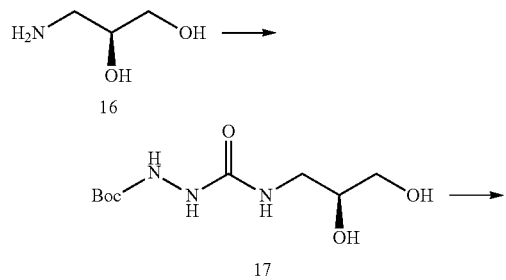

Step 1 Synthesis of Compound 17

Boc hydrazine (2.1 g, 15.9 mmol) was dissolved into tetrahydrofuran (20 mL). After the mixture was cooled to 0° C., pyridine (4.1 mL, 50.8 mmol) and p-nitrophenyl chloroformate (3.52 g, 1.7.5 mmol) were added. The mixture was stirred for 1.5 hours at 0° C. After that, Compound 16 (1.88 g, 20.7 mmol) and DIEA (3.61 mL, 20.7 mmol) were added, and the mixture was stirred for an hour at room temperature. The solvent was removed in vacuo, and the obtained residue was purified by silica-gel column chromatography (chloroform/methanol) to give Compound 17 (2.9 g, 73%).

1H-NMR (DMSO-d6)

δ: 1.38 (s, 9H), 2.90-2.98 (m, 1H), 3.10-3.51 (m, 4H), 4.54 (t, J=5.7 Hz, 1H), 4.77 (d, J=4.5 Hz, 1H), 6.14-6.19 (m, 1H), 7.72 (s, 1H), 8.51 (s, 1H).

Step 2 Synthesis of Compound 18

Compound 17 (2.9 g, 11.6 mmol) was dissolved into dichloromethane (30 mL), and hydrochloric acid (4 mol/L, dioxane solution, 6 mL) was added. The mixture was stirred for an hour at room temperature. The reaction mixture was condensed to give Compound 18. Compound 18 was used to synthesis of Compound I-225 without purification.

Reference Example 9

Synthesis of Compound 21 (the Side Chain of Compound I-233)

[Chemical Formula 124]

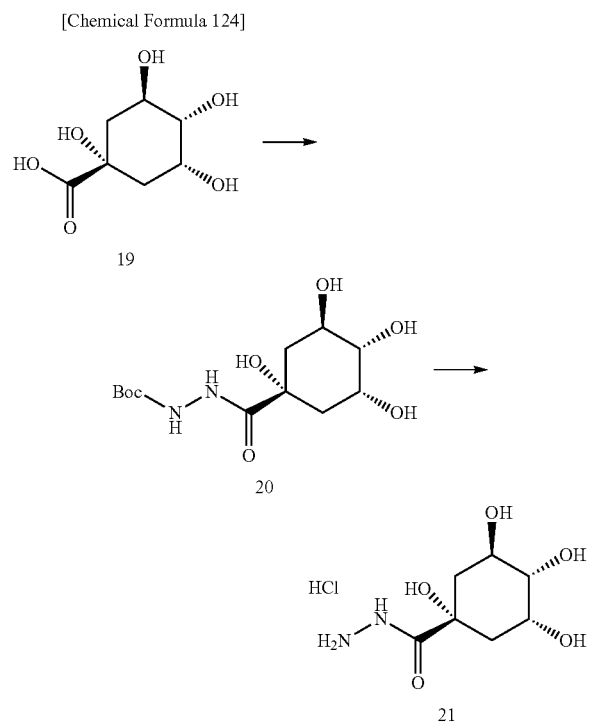

Step 1 Synthesis of Compound 21

Compound 19 (1 g, 5.2 mmol) was dissolved into N,N-dimethylformamide (5 mL), and Boc hydrazine (688 mg, 5.2 mmol), DIEA (1.8 mL, 10.4 mmol) and HATU (1.98 g, 5.2 mmol) were added. The mixture was stirred for 17 hours at room temperature. The mixture was oil-outed by adding diisopropyl ether (50 mL), and the solvent was removed to give Compound 20. The obtained Compound 20 was suspended in dichloromethane (15 mL), and hydrochloric acid (4 mol/L, dioxane solution, 6 mL) was added. The mixture was stirred for 2 hours at room temperature. The reaction mixture was filtrated and dried up to give Compound 21. Compound 21 was used to synthesis of Compound I-233 without purification.

Reference Example 10

Synthesis of Compound 24 (the Side Chain of Compound I-240)

[Chemical Formula 125]

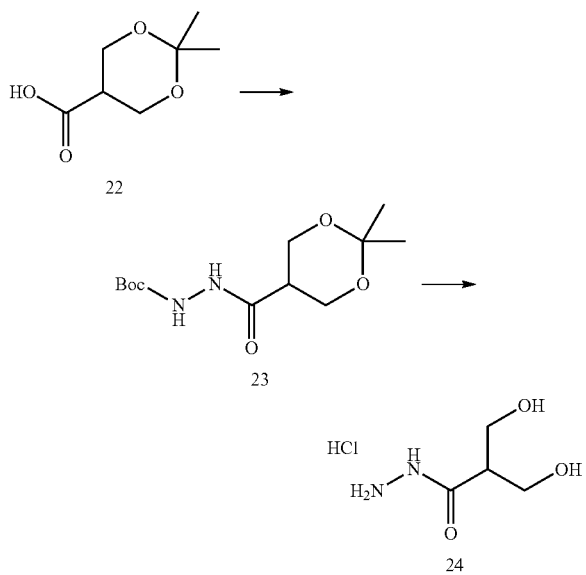

Step 1 Synthesis of Compound 24

Compound 22 (2.75 g, 17.2 mmol) was dissolved into N,N-dimethylformamide (10 mL), and Boc-hydrazine (2.27 g, 17.2 mmol), DIEA (6.0 mL, 34.3 mmol) and HATU (6.53 g, 17.2 mmol) were added. The mixture was stirred for 3 hours at room temperature. Saturated ammonium chloride aqueous solution was added, and the mixture was extracted with chloroform. After the organic phase was washed with brine, the organic phase was dried up with magnesium sulfate anhydrous. The solvent was removed in vacuo to give Compound 23. The obtained residue was suspended in dichloromethane (15 mL), and hydrochloric acid (4 mol/L, dioxane solution, 14 mL) was added. The mixture was stirred for 3.5 hours at room temperature. The reaction mixture was filtrated and dried up to give Compound 24. Compound 24 was used to synthesis of Compound I-240 without purification.

Reference Example 11

Synthesis of Compound 27 (the Side Chain of Compound I-247)

[Chemical Formula 126]

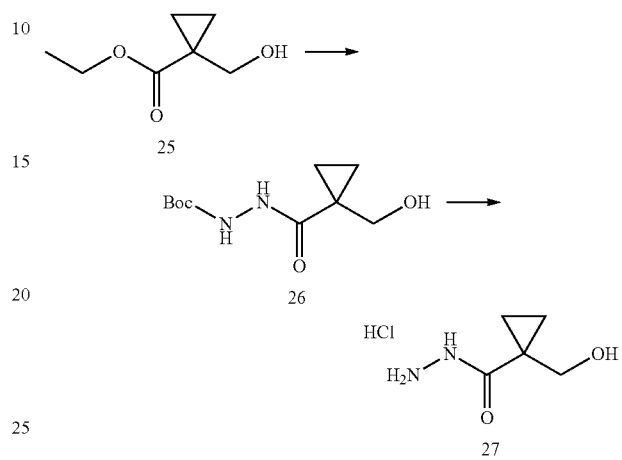

Step 1 Synthesis of Compound 26

Compound 25 (1 g, 6.94 mmol) was dissolved into ethanol (1 mL), and hydrazine monohydrate (0.371 mL, 7.63 mmol) was added. The mixture was stirred for 6 days under heat reflux. After the mixture was cooled to room temperature, Boc₂O (3.54 mL, 15.3 mmol) was added, and the mixture was stirred for 2 hours at room temperature. The obtained by evaporating solvent was purified by silica-gel column chromatography (hexane/ethyl acetate) to give Compound 26 (560 mg, 35%).

1H-NMR (CDCl3)

δ: 0.72-0.76 (m, 2H), 1.26-1.31 (m, 2H), 1.47 (s, 9H), 3.23 (s, 1H), 3.71 (s, 2H), 6.66 (s, 1H), 8.84 (s, 1H).

Step 2 Synthesis of Compound 27

Compound 26 (500 mg, 2.17 mmol) was suspended in dichloromethane (10 mL), and hydrochloric acid (4 mol/L, dioxane solution, 1 mL) was added. The mixture was stirred for an hour at room temperature. The reaction mixture was filtrated, and the obtained solids were dried up to give Compound 27. Compound 27 was used to synthesis of Compound I-247 without purification.

Reference Example 12

Synthesis of Compound 30 (the Side Chain of Compound I-256)

[Chemical Formula 127]

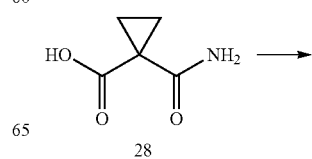

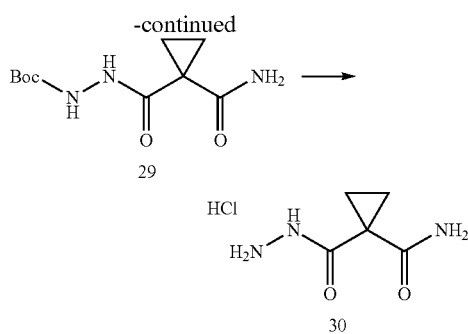

Step 1 Synthesis of Compound 29

Compound 28 (2 g, 15.5 mmol) was dissolved into N,N-dimethylformamide (10 mL), and Boc-hydrazine (2.05 g, 15.5 mmol), HATU (5.89 g, 15.5 mmol) and DIEA (5.41 mL, 31 mmol) were added. The mixture was stirred for 16 hours at room temperature. Water was added to the reaction mixture, and the mixture was extracted with ethyl acetate. The organic phase was washed with brine and dried up with magnesium sulfate anhydrous, and the solvent was removed in vacuo. The obtained residue was purified by silica-gel column chromatography (hexane/ethyl acetate) to give residue including Compound 29. Compound 29 was used to next reaction without purification. The obtained Compound 29 was dissolved into dichloromethane (10 mL), and hydrochloric acid (4 mol/L, dioxane solution, 15 mL) was added. The mixture was stirred for 7 hours at room temperature. The reaction mixture was filtrated, and the obtained solids were dried up to give Compound 30. Compound 30 was used to synthesis of Compound I-256 without purification.

Reference Example 13

Synthesis of Compound 33 (the Side Chain of Compound I-257)

[Chemical Formula 128]

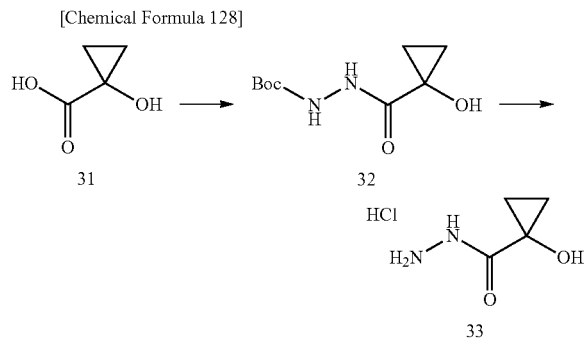

Step 1 Synthesis of Compound 32

Compound 31 (1 g, 9.8 mmol) was dissolved into N,N-dimethylformamide (20 mL), and Boc-hydrazine (1.3 g, 9.8 mmol), HATU (3.72 g, 9.8 mmol) and DIEA (3.42 mL, 20 mmol) were added. The mixture was stirred for 16 hours at room temperature. Water was added to the reaction mixture, and the mixture was extracted with ethyl acetate. The organic phase was washed with brine and dried up with magnesium sulfate anhydrous, and the solvent was removed in vacuo. The obtained residue was purified by silica-gel column chromatography (hexane/ethyl acetate) to give Compound 32 (1.38 g, 65%).

1H-NMR (DMSO-d6)

δ: 0.86 (q, J=3.8 Hz, 2H), 1.01 (q, J=3.8 Hz, 2H), 1.40 (s, 9H), 6.24 (s, 1H), 8.62 (s, 1H), 9.51 (s, 1H).

Step 2 Synthesis of Compound 33

Compound 32 (1.3 g, 6.0 mmol) was dissolved into dichloromethane (10 mL), and hydrochloric acid (4 mol/L, dioxane solution, 9 mL) was added. The mixture was stirred for 7 hours at room temperature. The reaction mixture was filtrated, and the obtained solids were dried up to give Compound 33. Compound 33 was used to synthesis of Compound I-257 without purification.

Reference Example 14

Synthesis of Compound 36 (the Side Chain of Compound I-80)

[Chemical Formula 128]

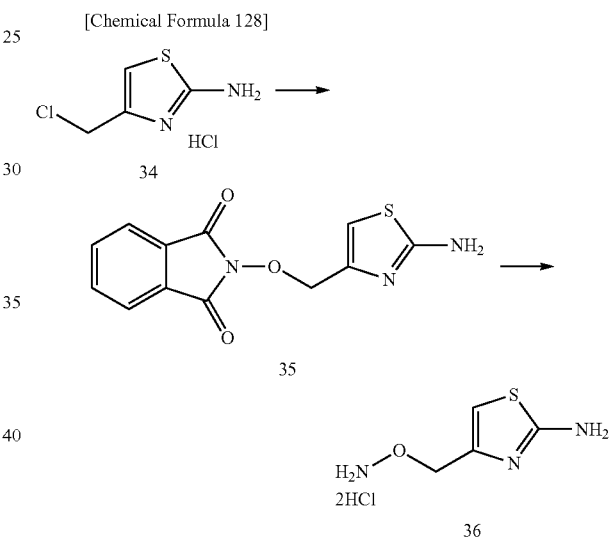

Step 1 Synthesis of Compound 35

2-Hydroxyisoindoline-1,3-dione was dissolved into N,N-dimethylformamide (60 mL), and Compound 34 (5.86 g, 36 mmol), potassium carbonate (9.12 g, 66.0 mmol) and potassium bromide (1.78 g, 15 mmol) were added. The mixture was stirred for 5 hours at room temperature. Ice was added to the reaction mixture, the resulted residue was filtrated and washed with water to give Compound 35 (5.16 g, 63%).

Mass (M+1): 276

Step 2 Synthesis of Compound 36

Compound 35 (2.202 g, 8 mmol) was dissolved into dichloromethane (40 mL), and methylhydrazine was added. The mixture was stirred for 2 hours. After concentration, the mixture was purified by silica-gel column chromatography. 4 mmol/L HCl/AcOEt (5 mL) was added to the condensed solution to give Compound 36 (1.08 g, 62%). Compound 36 was used to synthesis of Compound I-80 without purification.

$^1$H-NMR (CDCl$_3$)δ:4.56 (s, 2H),5.00-5.20 (br, 2H), 5.40-5.80 (br, 2H), 6.47 (s, 1H)

Reference Example 15

Synthesis of Compound 40 (the Side Chain of Compound I-226)

[Chemical Formula 130]

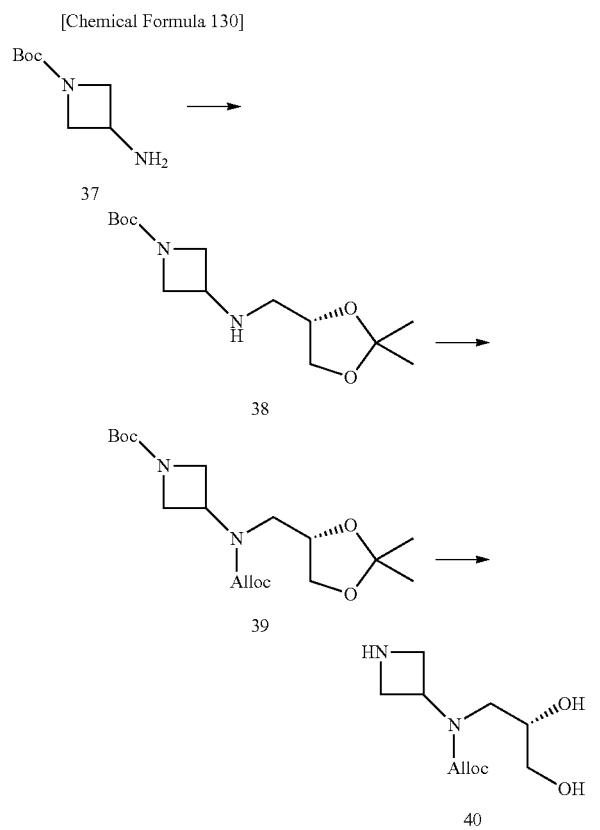

Step 1 Synthesis of Compound 38

Dichloromethane solution (6 mL) of tert-butyl 3-amino-azetidine-1-carboxylate (Compound 37: 1.26 g, 7 mmol) was added to dichloromethane solution (6 mL) of (R)-2,2-dimethyl-1,3-dioxolane-4-carbaldehyde (1.00 g, 7.70 mmol). After the reaction mixture was cooled to 0° C., Sodium Triacetoxyborohydride (2.23 g, 10.5 mmol) was added. After the mixture was stirred for 4 hours at room temperature, the mixture was incubated for 12 hours. Saturated sodium hydrogen carbonate aqueous solution was added, and the mixture was extracted with ethyl acetate and washed with brine. The organic phase was dried up with magnesium sulfate, filtrated and condensed to give Compound 38 (2 g, 99%).

Step 2 Synthesis of Compound 39

After dichloromethane solution (20 mL) of Compound 38 (2 g, 6.98 mmol) was cooled to 0° C., triethylamine (1.45 mL, 10.5 mmol) and allyl chloroformate (0.97 mL, 9.08 mmol) were added. The mixture was stirred for an hour at room temperature. After concentration, water was added. The mixture was extracted with ethyl acetate and washed with brine. The organic phase was dried up with magnesium sulfate, filtrated and condensed. The obtained residue was purified by silica-gel column chromatography to give Compound 39 (1.34 g, 52%).

$^1$H-NMR (CDCl$_3$)δ: 1.33 (s, 3H), 1.42 (s, 3H), 1.61 (s, 9H), 3.25-3.30 (m, 1H), 3.53-3.70 (m, 1H), 4.00-4.20 (m, 7H), 4.50-4.62 (m, 3H), 5.26 (dd, J=12 Hz, 24 Hz, 2H), 5.87-5.96 (m, 1H)

Step 3 Synthesis of Compound 40

Concentrated hydrochloric acid (3 mL) was added to toluene (3 mL) and tetrahydrofuran (2 mL) solution of Compound 5 (1.34 g, 3.62 mmol), and the mixture was stirred for 3 hours at 65° C. After that, concentrated hydrochloric acid (3 mL) was added, and the mixture was stirred for 1.5 hours at 70° C. Compound 40 was obtained by azeotroping with toluene. Compound 40 was used to synthesis of Compound I-226 without purification.

Reference Example 16

Synthesis of Compound 44 (the Side Chain of Compound I-227)

[Chemical Formula 131]

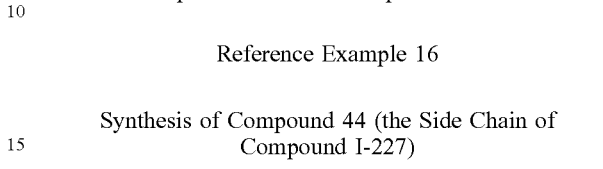

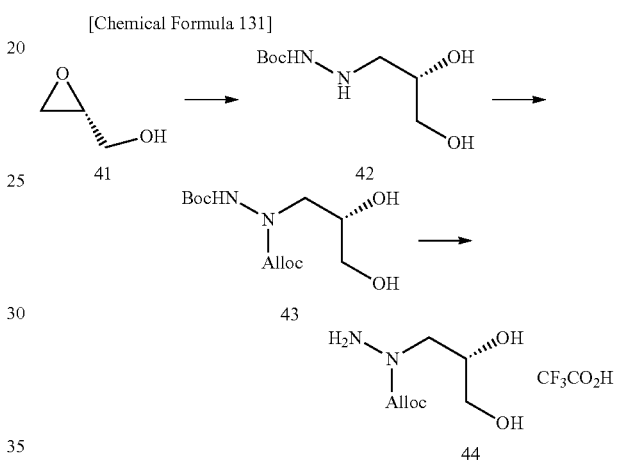

Step 1 Synthesis of Compound 42

Tert-butyl hydrazine carboxylate (37.5 g, 283 mmol) was added to ethanol solution (67 mL) of Compound 41 (7 g, 94 mmol), and the mixture was stirred for 3 days at room temperature. After concentration, the mixture was purified by silica-gel column chromatography to give Compound 42 (13.6 g, 70%).

$^1$H-NMR (CDCl$_3$)δ:1.51 (s, 9H), 2.50-3.00 (m, 2H), 3.50-3.60 (m, 3H), 3.65-3.70 (m, 1H), 3.71-3.90 (m, 1H),4.00-4.50 (br, 1H), 6.30-6.40 (br, 1H)

Step 2 Synthesis of Compound 43

Allyl 2,5-dioxopyrrolidine-1-yl carbonate (219 mg, 1.1 mmol) was added to tetrahydrofuran solution (2 mL) of Compound 42 (206 mg, 1 mmol), and the mixture was stirred for 12 hours at room temperature. Allyl 2,5-dioxopyrrolidine-1-yl carbonate (299 mg, 1.5 mmol) was added, and the mixture was stirred for 8 hours. After concentration, the mixture was purified by silica-gel column chromatography to give Compound 43 (142 mg, 49%).

$^1$H-NMR (CDCl$_3$)δ:1.54 (s, 9H), 1.70-1.75 (br, 1H), 3.80-3.98 (m, 4H), 3.99-4.02 (m, 1H), 4.86-4.74 (br, 2H), 4.82-4.90 (m, 2H), 5.27-5.42 (m, 2H), 5.88-5.90 (m, 1H)

Step 3 Synthesis of Compound 44

Dichloromethane solution (0.5 mL) of Compound 43 (58.1 mg, 0.2 mmol) was cooled to 0° C. Trifluoroacetic acid (0.3 mL) was added, and the mixture was stirred for an hour at room temperature. After concentration, Compound 44 was used for synthesis of Compound I-227

Reference Example 17

Synthesis of Compound 47 (the Side Chain of Compound I-244)

[Chemical Formula 132]

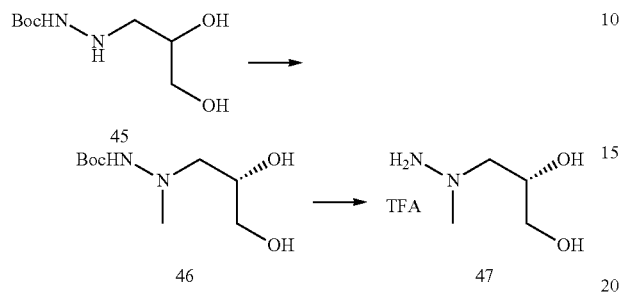

Step 1 Synthesis of Compound 46

After tetrahydrofuran:dichloromethane=1:1 (24 mL) suspension solution of Compound 45 (1.24 g, 6 mmol) was cooled to 0° C., N,N-diisopropylethylamine (5.24 mL, 30 mmol) and iodomethane (3.75 mL, 60 mmol) were added. The mixture was stirred for 4 hours at room temperature. After concentration, the mixture was extracted by adding water. After the organic phase was washed with brine, the organic phase was dried up with magnesium sulfate, filtrated and condensed to give Compound 46 (1.02 g, 77%).

$^1$H-NMR (CDCl$_3$)δ:1.46 (s, 9H), 1.62-1.73 (br, 1H), 2.55 (d, J=12 Hz, 2H), 2.67 (s, 3H), 2.80 (t, J=12 Hz, 1H), 3.48-3.60 (br, 1H), 3.50-3.80 (m, 2H), 5.58-5.60 (br, 1H)

Step 2 Synthesis of Compound 47

After dichloromethane solution (5 mL) of Compound 11 (551 mg, 2.5 mmol) was cooled to 0° C., trifluoroacetic acid (3.8 mL) was added. The mixture was stirred for 40 minutes at 10° C. After that, the mixture was heated to room temperature and stirred for 40 minutes. Trifluoroacetic acid (1.9 mL) was added, and the mixture was stirred for 40 minutes at room temperature. Compound 47 was obtained by azeotroping with toluene. Compound 47 was used to synthesis of Compound I-244 without purification.

Reference Example 18

Synthesis of Compound 51 (the Side Chain of Compound I-255)

[Chemical Formula 133]

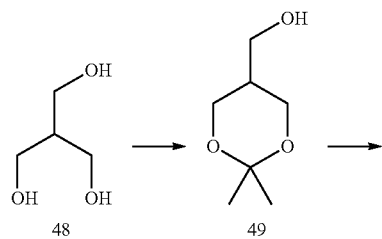

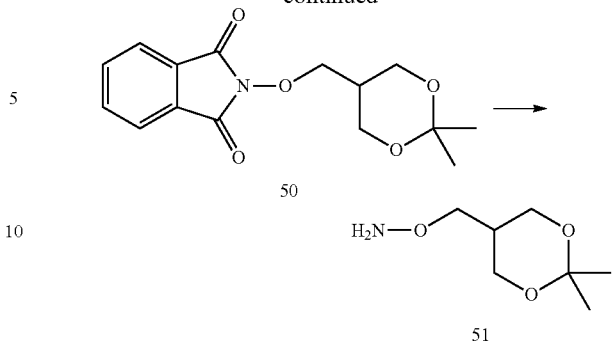

Step 1 Synthesis of Compound 49

Compound 48 (5.93 g, 55.9 mmol) was dissolved into tetrahydrofuran (25 mL), and 2,2-dimethoxypropane (10.27 mL, 84 mmol) and p-toluenesulfonic acid (1.063 g, 5.59 mmol) were added. The mixture was stirred for an hour at 50° C. After that, the mixture was incubated for 12 hours. Potassium carbonate (1.54 g, 11.2 mmol) was added, and the mixture was stirred for 30 minutes. The mixture was filtrated and condensed. Brine was added, and the mixture was extracted with chloroform. The organic phase was washed with brine and dried up with magnesium sulfate, and filtrated and condensed to give Compound 40.

Step 2 Synthesis of Compound 50

N-hydroxyphthalimide (6.36 g, 39.0 mmol), triphenylphosphine (11.8 g, 45.0 mmol) were added to tetrahydrofuran solution (80 mL) of Compound 49 (4.39 g, 30 mmol), and the mixture was cooled to 0° C. Diisopropyl Azodicarboxylate (8.75 mL, 45.0 mmol) was added, and the mixture was stirred for 2 hours. After concentration, the crude Compound 50 obtained by silica-gel column chromatography was used to next reaction.

Step 3 Synthesis of Compound 51

After dichloromethane:methanol=2:1 solution (15 mL) of Compound 15 (628 mg, 2.5 mmol) was cooled, methylhydrazine (0.146 mL, 2.75 mmol) was added. After the mixture was stirred for an hour, the mixture was condensed to give Compound 51. Compound 51 was used to synthesis of Compound I-255 without purification.

$^1$H-NMR (CDCl$_3$)δ:1.80-2.00 (m, 1H), 3.40 (d, J=8 Hz, 4H), 3.52 (d, J=8 Hz, 2H)

The following compounds were synthesized by above examples. "No." in tables means compound No.; "LC-MS" in tables means molecular weight of each compounds measured by liquid column chromatography/mass analysis; "Method" means method of liquid column chromatography/mass analysis.

(Method A)
Column: ACQUITY UPLC BEH C18 (1.7 μm, 2.1×50 mm) (Waters)
Column temperature: room temperature
Flow speed: 0.4 mL/minutes
UV wavelength of detection: 200 to 400 nm
Mobile phase: [A] aqueous solution with 0.1% formic acid, [B] acetonitrile solution with 0.1% formic acid
Gradient: linear gradient of 10%-95% of [B] for 8 minutes
Ionization: ESI Positive/Negative (Method B)
Column: ACQUITY UPLC BEH C18 (1.7 μm, 2.1×50 mm) (Waters)
Column temperature: room temperature
Flow speed: 0.8 mL/minutes
UV wavelength of detection: 200 to 400 nm
Mobile phase: [A] aqueous solution with 0.1% formic acid, [B] acetonitrile solution with 0.1% formic acid
Gradient: linear gradient of 5%-100% of [B] for 3.5 minutes, and hold 100% of [B] for 0.5 minutes
Ionization: ESI Positive/Negative

[Chemical Formula 134]
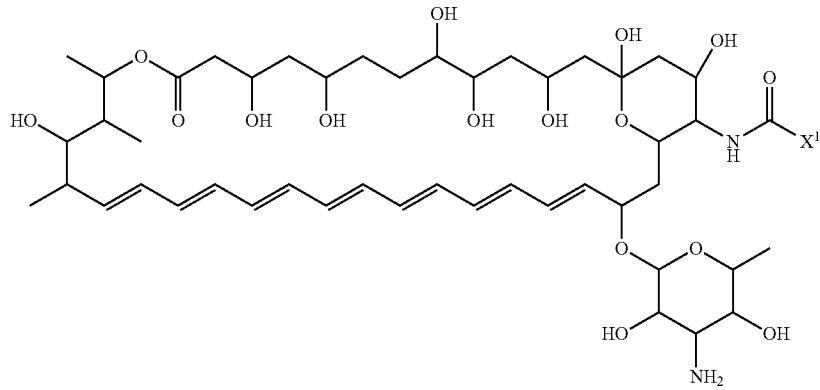
(XIV)
The structure and physical property of compound (XIV) are shown below.
TABLE 1
| No. | X¹ | LC-MS | Method |
|---|---|---|---|
| I-1 | (aminopropyl glucoside) | 1158.6 [M + H]+ | B |
| I-2 | (morpholinyl) | 1008.4 [M + H]+, 1030.5 [M + Na]+ | A |
| I-3 | (3-hydroxypropylamino) | 996.9 [M + H]+ | B |
| I-4 | (3-fluoropropylamino) | 998.5 [M + H]+ | B |
| I-5 | (histamine) | 1032.5 [M + H]+ | A |
| I-6 | (hydroxymethyl histidinyl) | 1062.5 [M + H]+ | B |
| I-7 | (3-dimethylaminopropylamino) | 1023.6 [M + H]+ | A |

TABLE 1-continued
| No. | X¹ | LC-MS | Method |
|---|---|---|---|
| I-8 | 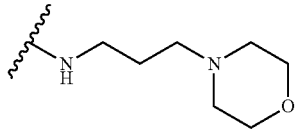 [SMILES: *NCCCN1CCOCC1] | 1065.6 [M + H]+ | B |
| I-9 | 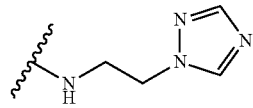 [SMILES: *NCCn1cncn1] | 1033.4 [M + H]+ | B |
TABLE 2
| No | X¹ | LC-MS | Method |
|---|---|---|---|
| I-10 | 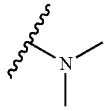 [SMILES: *N(C)C] | 966.5 [M + H]+ | B |
| I-11 | 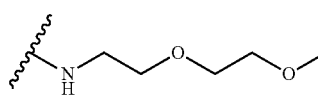 | 1070.5 [M + H]+, 1092.5 [M + Na]+ | A |
| I-12 | 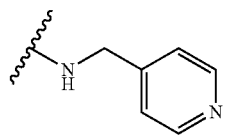 [SMILES: *NCc1ccncc1] | 1029.6 [M + H]+, 1051.6 [M + Na]+ | A |
| I-13 | 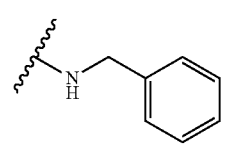 [SMILES: *NCc1ccccc1] | 1028.6 [M + H]+, 1050.6 [M + Na]+ | A |
| I-14 | 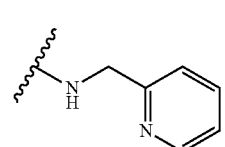 | 1029.6 [M + H]+ | B |
| I-15 | 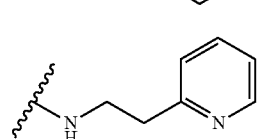 | 1043.5 [M + H]+ | A |
| I-16 | 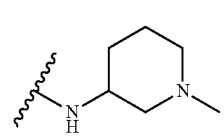 [SMILES: *NC1CCCN(C)C1] | 1035.6 [M + H]+ | A |
| I-17 | 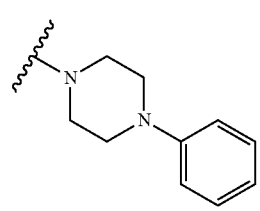 | 1083.9 [M + H]+ | B |

TABLE 3
| No. | X¹ | LC-MS | Method |
|---|---|---|---|
| I-18 | 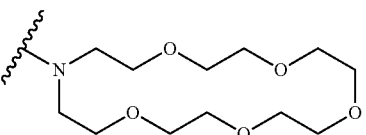 | 1184.9 [M + H]+ | B |
| I-19 | 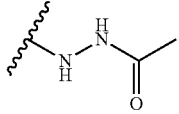 [SMILES: *NNC(C)=O] | 995.5 [M + H]+ | A |
| I-20 | 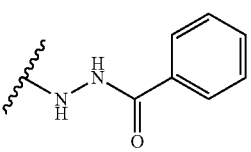 [SMILES: *NNC(=O)c1ccccc1] | 1057.7 [M + H]+ | B |
| I-21 | 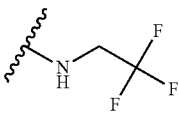 [SMILES: *NCC(F)(F)F] | 1020.5 [M + H]+ | B |
| I-22 | 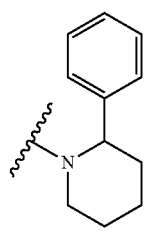 [SMILES: *N1CCCCC1c1ccccc1] | 1082.6 [M + H]+ | B |
| I-23 | 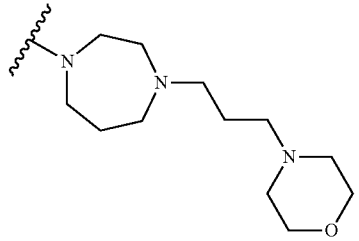 [SMILES: *N1CCCN(CCCN2CCOCC2)CC1] | 1148.8 [M + H]+ | B |
| I-24 | 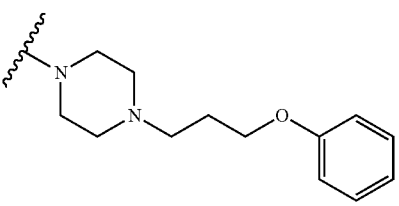 [SMILES: *N1CCN(CCCOc2ccccc2)CC1] | 1141.6 [M + H]+ | B |
TABLE 4
| No. | X¹ | LC-MS | Method |
|---|---|---|---|
| I-25 | 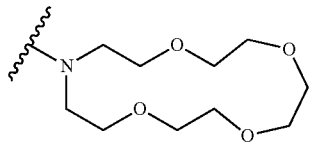 [SMILES: *N1CCOCCOCCOCCOCC1] | 1140.7 [M + H]+ | B |

TABLE 4-continued
| No. | X¹ | LC-MS | Method |
|---|---|---|---|
| I-26 | 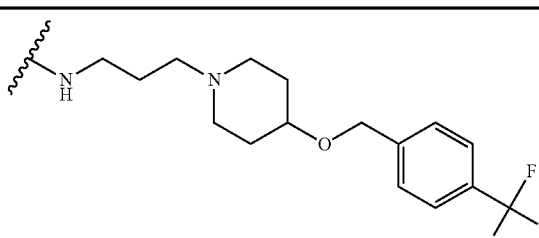 | 1237.9 [M + H]+ | B |
| I-27 | 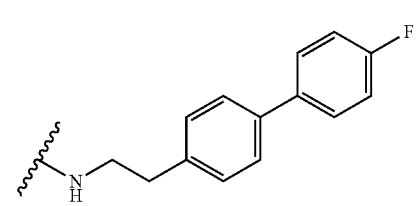 [SMILES: *NCCc1ccc(-c2ccc(F)cc2)cc1] | 1136.7 [M + H]+ | B |
| I-28 | 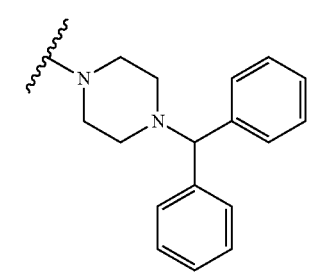 [SMILES: *N1CCN(C(c2ccccc2)c2ccccc2)CC1] | 1173.9 [M + H]+ | B |
| I-29 | 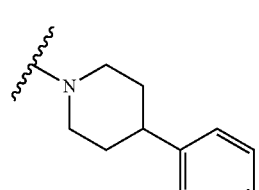 | 1082.7 [M + H]+ | B |
| I-30 | 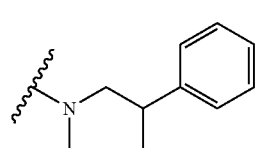 | 1082.7 [M + H]+ | B |
TABLE 5
| No. | X¹ | LC-MS | Method |
|---|---|---|---|
| I-31 | 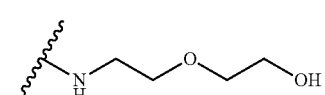 | 1026.4 [M + H]+ | A |
| I-32 | 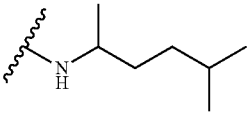 [SMILES: *NC(C)CCC(C)C] | 1036.9 [M + H]+ | B |

TABLE 5-continued

| No. | X¹ | LC-MS | Method |
|---|---|---|---|
| I-33 | —NH—CH2—CH(OH)—CH2OH | 1012.8 [M + H]+ | B |
| I-34 | —N(cyclohexyl)2 | 1102.8 [M + H]+ | B |
| I-35 | 4-(ethoxycarbonyl)piperidin-1-yl-NH— (ethyl 4-aminopiperidine-1-carboxylate) | 1094 [M + H]+ | B |
| I-36 | —NH2 | 938.5 [M + H]+ | A |
| I-37 | —NH—CH2—COOH | 996.2 [M + H]+, 1018.3 [M + Na]+ | A |
| I-38 | —NH—(CH2)3—COOH | 1024.6 [M + H]+ | A |
| I-39 | —N(CH2CH2OH)2 | 1026.6 [M + H]+, 1048.6 [M + Na]+ | A |

TABLE 6

| No. | X¹ | LC-MS | Method |
|---|---|---|---|
| I-40 | —NH—CH(CH2OH)2 | 1012.4 [M + H]+, 1034.5 [M + Na]+ | B |
| I-41 | —NH—cyclopropyl | 978.3 [M + H]+, 1000.4 [M + Na]+ | A |
| I-42 | —NH—CH2—(4-dimethylamino-phenyl) | 1071.6 [M + H]+ | B |
| I-43 | —NH—NH—CHO | 981.4 [M + H]+ | A |
| I-44 | —NH—NH—C(O)-pyridin-2-yl | 1058.7 [M + H]+ | B |
| I-45 | —NH—NH—C(O)-pyridin-3-yl | 1058.7 [M + H]+ | B |
| I-46 | —NH—NH—C(O)-pyridin-4-yl | 1058.7 [M + H]+ | B |
| I-47 | —NH—NH—C(O)—O—CH3 | 1011.4 [M + H]+, 1033.4 [M + Na]+ | A |
| I-48 | —NH-(1-methylpiperidin-4-yl) | 1035.6 [M + H]+ | A |

TABLE 7

| No. | X¹ | LC-MS | Method |
|---|---|---|---|
| I-49 | 3-(dimethylamino)pyrrolidin-1-yl | 1035.7 [M + H]+ | B |
| I-50 | 3-(dimethylamino)pyrrolidin-1-yl (stereoisomer) | 1035.7 [M + H]+ | B |
| I-51 | —NH—CH2CH2—N(CH3)2 | 1009.5 [M + H]+, 1031.5 [M + Na]+ | A |

TABLE 7-continued

| No. | X¹ | LC-MS | Method |
|---|---|---|---|
| I-53 | (structure) | 1023.7 [M + H]+ | A |
| I-54 | (structure) | 1049.7 [M + H]+ | B |
| I-55 | (structure) | 1038.6 [M + H]+, 1060.6 [M + Na]+ | A |
| I-56 | (structure) | 1031.5 [M + H]+ | A |
| I-57 | (structure) | 1014.5 [M + H]+ | A |
| I-58 | (structure) | 981.4 [M + H]+ | A |

TABLE 8

| No. | X¹ | LC-MS | Method |
|---|---|---|---|
| I-59 | (structure) | 968.5 [M + H]+ | A |
| I-60 | (structure) | 996.5 [M + H]+ | A |
| I-61 | (structure) | 994.5 [M + H]+, 1016.5 [M + Na]+ | A |
| I-62 | (structure) | 1007.5 [M + H]+, 1029.5 [M + Na]+ | A |
| I-63 | (structure) | 1012.5 [M + H]+ | A |

TABLE 8-continued

| No. | X¹ | LC-MS | Method |
|---|---|---|---|
| I-64 | (structure) | 1059.5 [M + H]+, 1081.5 [M + Na]+ | A |
| I-65 | (structure) | 1060.5 [M + H]+, 1082.5 [M + Na]+ | A |
| I-66 | (structure) | 1036.5 [M + H]+, 1058.5 [M + Na]+ | A |
| I-67 | (structure) | 1023.5 [M + H]+ | A |
| I-68 | (structure) | 1067.5 [M + H]+ | A |

TABLE 9

| No. | X¹ | LC-MS | Method |
|---|---|---|---|
| I-69 | (structure) | 1034.5 [M + H]+ | A |
| I-70 | (structure) | 1039.5 [M + H]+ | A |
| I-71 | (structure) | 1100.4 [M + H]+, 1122.5 [M + Na]+ | A |
| I-72 | (structure) | 1099.4 [M + H]+, 1121.5 [M + Na]+ | A |
| I-73 | (structure) | 1026.5 [M + H]+ | A |

TABLE 9-continued

| No. | X¹ | LC-MS | Method |
|---|---|---|---|
| I-74 | [structure: NH-O-tetrahydropyran with 3 OH and CH2OH] | 1116.5 [M + H]+ | A |
| I-75 | [structure: NH-O-CH2CH2-OH] | 998.4 [M + H]+ | A |
| I-76 | [structure: NH-piperazine-CH2CH2-OH] | 1066.6 [M + H]+ | A |
| I-77 | [structure: NH-CH2-C(O)-O-CH3] | 1010.5 [M + H]+ | A |

TABLE 10

| No. | X¹ | LC-MS | Method |
|---|---|---|---|
| I-78 | [structure: NH-NH-CH2CH2-N(CH3)2] | 1024.5 [M + H]+ | A |
| I-79 | [structure: NH-O-CH2CH2-N(CH3)2] | 1025.7 [M + H]+ | A |
| I-80 | [structure: NH-O-CH2-thiazole-NH2] | 1066.5 [M + H]+ | A |
| I-81 | [structure: NH-CH2CH2-C(O)-NH2] | 1009.6 [M + H]+, 1031.6 [M + Na]+ | A |
| I-82 | [structure: NH-CH2-CH(OH)-CH2OH] | 1012.4 [M + H]+, 1034.4 [M + Na]+ | B |
| I-83 | [structure: NH-CH(CH2OH)2] | 1026.5 [M + H]+ | A |
| I-84 | [structure: NH-CH(CH2-C(O)OCH3)-C(O)OCH3] | 1082.5 [M + H]+, 1140.5 [M + Na]+ | A |

TABLE 10-continued

| No. | X¹ | LC-MS | Method |
|---|---|---|---|
| I-85 | [structure: NH-CH(CH3)-C(O)-OCH3] | 1024.5 [M + H]+, 1046.5 [M + Na]+ | A |
| I-86 | [structure: NH-CH(CH3)-C(O)-OH] | 1010.5 [M + H]+ | A |
| I-87 | [structure: NH-CH(CH2OH)-C(O)-OCH3] | 1040.4 [M + H]+, 1062.5 [M + Na]+ | A |

TABLE 11

| No. | X¹ | LC-MS | Method |
|---|---|---|---|
| I-88 | [structure: NH-CH(CH2OCH3)2] | 1040.6 [M + H]+, 1062.6 [M + Na]+ | A |
| I-89 | [structure: NH-CH2-C(O)-NH-CH2-C(O)OH] | 1053.5 [M + H]+, 1075.5 [M + Na]+ | A |
| I-90 | [structure: NH-CH2-C(O)-NH2] | 995.5 [M + H]+ | A |
| I-91 | [structure: NH-CH2-C(O)-NH-CH2-C(O)OCH3] | 1067.5 [M + H]+, 1089.5 [M + Na]+ | A |
| I-92 | [structure: NH-CH2CH2-imidazole] | 1032.4 [M + H]+, 1054.4 [M + Na]+ | A |
| I-93 | [structure: NH-CH2CH2-NH-C(O)-NH2] | 1024.4 [M + H]+, 1046.4 [M + Na]+ | A |
| I-94 | [structure: NH-CH2CH2-NH-benzothiazole-CF3] | 1182.5 [M + H]+, 1204.5 [M + Na]+ | A |

TABLE 11-continued

| No. | X¹ | LC-MS | Method |
|---|---|---|---|
| I-95 | aminoethoxy-thiazol-2-amine group | 1080.4 [M + H]+, 1102.4 [M + Na]+ | A |
| I-96 | aminoethoxy-imidazol-1-yl group | 1048.5 [M + H]+, 1070.5 [M + Na]+ | A |

TABLE 12

| No. | X¹ | LC-MS | Method |
|---|---|---|---|
| I-97 | diethyl (2-aminoethyl)phosphonate | 1102.4 [M + H]+, 1124.4 [M + Na]+ | A |
| I-98 | N-(3-aminopropyl)-N-methyl-2-methoxybenzylamine | 1129.6 [M + H]+ | A |
| I-99 | tris(hydroxymethyl)aminomethane | 1042.5 [M + H]+ | A |
| I-100 | N,N-dimethyl-β-alaninamide | 1037.5 [M + H]+ | A |
| I-101 | 3-aminobenzamide | 1057.6 [M + H]+ | A |
| I-102 | aminoacetonitrile | 977.4 [M + H]+ | A |
| I-103 | 2-amino-3-methyl-1-butanol | 1024.6 [M + H]+ | A |

TABLE 12-continued

| No. | X¹ | LC-MS | Method |
|---|---|---|---|
| I-104 | 2-methoxybenzylamine | 1058.6 [M + H]+ | A |

TABLE 13

| No. | X¹ | LC-MS | Method |
|---|---|---|---|
| I-105 | 1-aminocyclopropanecarbonitrile | 1003.5 [M + H]+ | A |
| I-106 | L-alaninamide | 1009.6 [M + H]+ | A |
| I-107 | taurine | 1046.5 [M + H]+, 1068.4 [M + Na]+ | A |
| I-109 | 3-(aminomethyl)benzoic acid | 1072.5 [M + H]+ | A |
| I-110 | 4-(aminomethyl)benzamide | 1071.6 [M + H]+ | A |
| I-111 | N-methylglycinamide | 1009.6 [M + H]+ | A |
| I-112 | diethyl L-glutamate | 1124.6 [M + H]+ | A |

TABLE 13-continued

| No. | X¹ | LC-MS | Method |
|---|---|---|---|
| I-113 | (3-carbamoylbenzyl)amino group | 1071.6 [M + H]+ | A |

TABLE 14

| No. | X¹ | LC-MS | Method |
|---|---|---|---|
| I-114 | (2-carbamoylbenzyl)amino group | 1071.6 [M + H]+, 1093.6 [M + Na]+ | A |
| I-115 | 2-sulfamoylethylamino group | 1045.5 [M + H]+ | A |
| I-116 | tyrosine methyl ester group | 1116.6 [M + H]+ | A |
| I-117 | tryptophan amide group | 1124.6 [M + H]+ | A |
| I-118 | tryptamine group | 1081.6 [M + H]+ | A |
| I-119 | (2R)-2,3-dihydroxypropylamino group | 1012.5 [M + H]+ | A |
| I-120 | (3-carbamoyl-1,2,4-oxadiazol-5-yl)methylamino group | 1063.6 [M + H]+ | A |

TABLE 15

| No. | X¹ | LC-MS | Method |
|---|---|---|---|
| I-121 | 2-(pyridin-2-yl)hydrazinyl group | 1030.6 [M + H]+, 1052.6 [M + Na]+ | A |
| I-122 | (quinuclidin-4-yl)methylamino group | 1061.6 [M + H]+ | A |
| I-123 | 2-(3-(pyridin-3-yl)ureido)acetohydrazide group | 1130.7 [M + H]+ | A |
| I-124 | 2-(3-(trifluoromethyl)pyridin-2-yl)hydrazinyl group | 1098.6 [M + H]+ | A |
| I-125 | 2-(5-(trifluoromethyl)pyridin-2-yl)hydrazinyl group | 1098.6 [M + H]+ | A |
| I-126 | (2-hydroxybenzyl)amino group | 1044.6 [M + H]+ | A |
| I-127 | (1-(2-amino-2-oxoethyl)azetidin-3-yl)amino group | 1050.6 [M + H]+, 1072.6 [M + Na]+ | A |
| I-128 | (3-(dimethylamino)-2,2-dimethylpropyl)amino group | 1051.7 [M + H]+ | A |

TABLE 16

| No. | X¹ | LC-MS | Method |
|---|---|---|---|
| I-129 | (1,3-dihydroxypropan-2-yl)amino group | 1026.6 [M + H]+ | A |
| I-130 | (2S)-2-hydroxy-3-amino-3-oxopropylamino group | 1025.6 [M + H]+, 1047.6 [M + Na]+ | A |
| I-131 | (5-oxopyrrolidin-2-yl)methylamino group | 1035.6 [M + H]+, 1057.6 [M + Na]+ | A |

TABLE 16-continued

| No. | X¹ | LC-MS | Method |
|---|---|---|---|
| I-132 | (azetidine-N-linked 2-thiazolyl, NH-linker) | 1076.5 [M + H]+ | A |
| I-133 | -NH-CH₂CH₂CH₂-NH₂ | 995.6 [M + H]+, 1017.6 [M + Na]+ | A |
| I-134 | -NH-CH₂-(pyrrolizidine) | 1061.7 [M + H]+ | A |
| I-135 | -NH-CH₂CH₂CH₂-(pyrrolidin-1-yl) | 1049.6 [M + H]+ | A |
| I-136 | -NH-CH₂-(5-yl-2-pyridone) | 1045.5 [M + H]+, 1067.5 [M + Na]+ | A |

TABLE 17

| No. | X¹ | LC-MS | Method |
|---|---|---|---|
| I-137 | -NH-CH₂CH₂-NH-C(O)-NH-(2-pyridyl) | 1101.6 [M + H]+, 1123.6 [M + Na]+ | A |
| I-138 | -NH-CH₂-(4,6-dimethylpyrimidin-2-yl) | 1058.6 [M + H]+, 1080.6 [M + Na]+ | A |
| I-139 | (thiazolidine-N-linked) | 1010.5 [M + H]+ | A |
| I-140 | -NH-CH₂-C(cyclopropyl)(CH₂-imidazol-1-yl) | 1072.6 [M + H]+ | A |
| I-141 | -NH-CH₂-(4-sulfamoylphenyl) | 1107.6 [M + H]+ | A |

TABLE 17-continued

| No. | X¹ | LC-MS | Method |
|---|---|---|---|
| I-142 | -NH-CH₂CH₂-NH-C(O)-CH₃ | 1023.6 [M + H]+ | A |
| I-143 | -NH-CH₂-(5-methylpyrazin-2-yl) | 1044.5 [M + H]+ | A |
| I-144 | -NH-CH₂-CH(NH₂)-COOH (L) | 1025.5 [M + H]+ | B |

TABLE 18

| No. | X¹ | LC-MS | Method |
|---|---|---|---|
| I-145 | (pyrrolidin-1-yl)-3-carboxamide | 1035.6 [M + H]+ | B |
| I-146 | -NH-CH₂CH₂-CH(OH)-CH₂OH | 1026.6 [M + H]+ | A |
| I-147 | -NH-CH₂-(4-amino-2-methylpyrimidin-5-yl) | 1059.6 [M + H]+ | A |
| I-148 | -NH-CH₂CH₂-NH-CH₃ | 995.5 [M + H]+ | A |
| I-149 | -NH-CH(CH₂OH)-C(O)-NH₂ | 1025.6 [M + H]+ | A |
| I-150 | -NH-CH₂CH₂-NH-(2-pyridyl) | 1059.6 [M + H]+ | A |
| I-151 | -NH-CH₂-C(O)-NH-CH₂-CH(OH)-CH₂OH | 1069.6 [M + H]+ | A |
| I-152 | -NH-CH₂-(2-pyridon-3-yl) | 1045.6 [M + H]+ | A |

TABLE 18-continued

| No. | X¹ | LC-MS | Method |
|---|---|---|---|
| I-153 | (pyrrolidine-2-carboxamide, 1-methyl, 4-NH-) | 1064.5 [M + H]+ | A |

TABLE 19

| No. | X¹ | LC-MS | Method |
|---|---|---|---|
| I-154 | histidinamide | 1075.5 [M + H]+ | A |
| I-155 | -NH-CH2-C(O)-NH-CH(CH2OH)2 | 1069.6 [M + H]+ | A |
| I-156 | -NH-CH2CH2-NH-C(O)-pyrazine | 1087.6 [M + H]+ | A |
| I-157 | -NH-CH2-C(O)-NH-CH2-CN | 1034.5 [M + H]+ | A |
| I-158 | -NH-CH2-(azetidin-3-yl)-N-CH2CH2OH | 1051.6 [M + H]+ | A |
| I-159 | -NH-CH2-(1-methylazetidin-3-yl) | 1021.6 [M + H]+ | A |
| I-160 | -NH-CH2CH2-NH-C(O)-CH2-NH2 | 1038.6 [M + H]+ | A |
| I-161 | -NH-CH2-C(H)(OH)-CH2CH2OH (S) | 1026.5 [M + H]+ | A |
| I-162 | -NH-CH2-C(H)(NH2)-CH2OH (S) | 1011.5 [M + H]+ | A |

TABLE 20

| No. | X¹ | LC-MS | Method |
|---|---|---|---|
| I-163 | -NH-CH2-C(H)(NH2)-CH2CH2OH (S) | 1025.6 [M + H]+ | A |
| I-164 | -NH-CH2CH2-NH-C(O)-NH-CH(CH2OH)2 | 1098.6 [M + H]+ | A |
| I-165 | -NH-(azetidin-3-yl)-N-CH2CH2OH | 1037.5 [M + H]+ | A |
| I-166 | -N-(3-hydroxyazetidin-1-yl) | 994.5 [M + H]+ | A |
| I-167 | -NH-CH2CH2-(4-methylpiperazin-1-yl) | 1064.6 [M + H]+ | A |
| I-168 | -NH-CH(CH2NH2)-CH2CH2OH | 1025.5 [M + H]+ | A |
| I-169 | -NH-CH(CH2NH2)-CH2OH | 1011.5 [M + H]+ | A |
| I-170 | -N-(3-(hydroxymethyl)azetidin-1-yl) | 1008.4 [M + H]+ | A |
| I-171 | -NH-CH2CH2-S(O)2-NH-(pyridin-2-yl) | 1022.5 [M + H]+ | A |

TABLE 21

| No. | X¹ | LC-MS | Method |
|---|---|---|---|
| I-172 | -NH-CH2-(3-aminophenyl) | 1043.5 [M + H]+ | A |

TABLE 21-continued

| No. | X¹ | LC-MS | Method |
|---|---|---|---|
| I-173 | (aminomethyl-pyridin-2-amine) | 1044.5 [M + H]+ | A |
| I-174 | (bis(2-hydroxyethyl)aminoethylamine) | 1069.5 [M + H]+, 1091.5 [M + Na]+ | A |
| I-175 | (tetrazol-5-ylmethylamine) | 1020.5 [M + H]+ | A |
| I-176 | (2-(dimethylamino)benzylamine) | 1071.5 [M + H]+ | A |
| I-177 | (glucosamine) | 1100.5 [M + H]+ | A |
| I-178 | (methyl 3-aminopropanoate) | 1024.5 [M + H]+, 1046.6 [M + Na]+ | A |
| I-179 | (3-(dimethylamino)-2-hydroxymethyl-propylamine) | 1039.5 [M + H]+, 1061.6 [M + Na]+ | A |

TABLE 22

| No. | X¹ | LC-MS | Method |
|---|---|---|---|
| I-180 | (3-hydroxypyrrolidine) | 1030.5 [M + Na]+ | A |
| I-181 | (cyanamide) | 963 [M + H]+ | A |
| I-182 | (2-((2-aminoethyl)amino)propane-1,3-diol) | 1055.6 [M + H]+, 1077.6 [M + Na]+ | A |

TABLE 22-continued

| No. | X¹ | LC-MS | Method |
|---|---|---|---|
| I-183 | (N,N-bis(carbamoylmethyl)ethylenediamine) | 1095.5 [M + H]+ | A |
| I-184 | (aminomethyl-pyridin-2-amine) | 1044.4 [M + H]+ | A |
| I-185 | (3-((2-methylimidazol-1-yl)pyridin-3-yl)methylamine) | 1109.5 [M + H]+, 1131.5 [M + Na]+ | A |
| I-186 | (N-(2-aminoethyl)acetimidamide) | 1022.5 [M + H]+ | A |
| I-187 | (3,4-dihydroxybenzylamine) | 1060.4 [M + H]+ | A |

TABLE 23

| No. | X¹ | LC-MS | Method |
|---|---|---|---|
| I-188 | (3-(pyridin-3-yl)-1,2,4-oxadiazol-5-yl)methylamine | 1097.5 [M + H]+ | A |
| I-189 | (3-(dimethylamino)azetidine) | 1021.5 [M + H]+ | A |
| I-190 | (glucamine) | 1102.4 [M + H]+ | A |
| I-191 | (3-amino-2,2-dimethylpropanamide) | 1037.4 [M + H]+ | A |

TABLE 23-continued

| No. | X¹ | LC-MS | Method |
|---|---|---|---|
| I-192 | (aminomethyl-isoxazole-pyridine) | 1096.4 [M + H]+ | A |
| I-193 | (aminomethyl-oxetane-methanol) | 1038.5 [M + H]+ | A |
| I-194 | (morpholino-pyridine carbohydrazide) | 1143.4 [M + H]+ | A |
| I-195 | (1-methyl-pyrrolidine carboxamide) | 1064.5 [M + H]+ | A |

TABLE 24

| No. | X¹ | LC-MS | Method |
|---|---|---|---|
| I-196 | (aminomethyl-pyridine-bis(hydroxymethyl)amino) | 1118.5 [M + H]+ | A |
| I-197 | (3-aminopyridine-2-carbohydrazide) | 1073.4 [M + H]+ | A |
| I-198 | (2-aminopyridine-3-carbohydrazide) | 1073.6 [M + H]+ | A |
| I-199 | (aminopropyl urea) | 1038.6 [M + H]+ | A |
| I-200 | (aminomethyl-isoxazole-2-aminopyridine) | 1111.6 [M + H]+, 1133.6 [M + Na]+ | A |
| I-201 | (pyrrolidine carboxylic acid) | 1036.5 [M + H]+ | A |

TABLE 24-continued

| No. | X¹ | LC-MS | Method |
|---|---|---|---|
| I-202 | (aminomethyl-cyclopropane carboxylic acid) | 1036.5 [M + H]+ | A |
| I-203 | (asparagine derivative) | 1053.3 [M + H]+, 1075.4 [M + Na]+ | A |

TABLE 25

| No. | X¹ | LC-MS | Method |
|---|---|---|---|
| I-204 | (1-amino-cyclopropane carboxylic acid) | 1022.4 [M + H]+ | A |
| I-205 | (2-amino-2-methylpropanoic acid) | 1024.4 [M + H]+, 1046.4 [M + Na]+ | A |
| I-206 | (4-amino-2,2-dimethylbutanoic acid) | 1052.6 [M + H]+ | A |
| I-207 | (2-aminocyclopentanol) | 1022.6 [M + H]+ | A |
| I-208 | (hydroxybutanoyl hydrazide) | 1039.5 [M + H]+, 1061.6 [M + Na]+ | A |
| I-209 | (butanoyl hydrazide) | 1023.5 [M + H]+ | A |
| I-210 | (dimethylamino-acetyl hydrazide) | 1038.6 [M + H]+ | A |
| I-211 | (isobutanoyl hydrazide) | 1023.5 [M + H]+, 1045.6 [M + Na]+ | A |
| I-212 | (2-amino-ethanolamine) | 997.8 [M + H]+ | B |
| I-213 | (2-amino-2-methyl-1,3-propanediol) | 1026.9 [M + H]+ | B |

TABLE 26

| No. | X¹ | LC-MS | Method |
|---|---|---|---|
| I-214 | (imidazole sulfonyl hydrazide) | 1083.4 [M + H]+, 1105.4 [M + Na]+ | A |
| I-215 | (methyl thiosemicarbazide) | 1026.3 [M + H]+, 1048.4 [M + Na]+ | A |
| I-216 | (phenyl thiosemicarbazide) | 1088.4 [M + H]+, 1110.4 [M + Na]+ | A |

TABLE 26-continued

| No. | X¹ | LC-MS | Method |
|---|---|---|---|
| I-217 | (thiosemicarbazide-propyl-morpholine) | 1139.5 [M + H]+, 1161.5 [M + Na]+ | A |
| I-218 | (semicarbazide-NHOH) | 1012.4 [M + H]+ | A |
| I-219 | (NH-OH) | 954.4 [M + H]+, 976.5 [M + Na]+ | A |
| I-220 | (semicarbazide-CH2-C(O)NH2) | 1053.5 [M + H]+ | A |
| I-221 | (semicarbazide-2-pyridyl) | 1073.5 [M + H]+ | A |
| I-222 | (azetidine-CH2-CH(OH)-CH2OH) | 1067.5 [M + H]+, 1089.5 [M + Na]+ | A |

TABLE 27

| No. | X¹ | LC-MS | Method |
|---|---|---|---|
| I-223 | (hydrazide-CH(OH)-CH2OH) | 1041.4 [M + H]+, 1063.5 [M + Na]+ | A |
| I-224 | (semicarbazide-pyridazinyl) | 1074.4 [M + H]+ | A |
| I-225 | (semicarbazide-CH2-CH(OH)-CH2OH) | 1070.4 [M + H]+, 1192.4 [M + Na]+ | A |
| I-226 | (azetidine-NH-CH2-CH(OH)-CH2OH) | 1067.5 [M + H]+, 1089.5 [M + Na]+ | A |

TABLE 27-continued

| No. | X¹ | LC-MS | Method |
|---|---|---|---|
| I-227 | (hydrazine-CH2-CH(OH)-CH2OH) | 1027.4 [M + H]+ | A |
| I-228 | (hydrazine-C(O)-NH-CH3) | 1010.4 [M + H]+ | A |
| I-229 | (hydrazine-C(O)-NH-CH2-CH(OH)-CH2-OCH3) | 1088.4 [M + H]+, 1110.4 [M + Na]+ | A |
| I-230 | (4-hydroxypyrrolidine-2-carboxylic acid) | 1052.4 [M + H]+ | A |
| I-231 | (3-aminotetrahydrothiophene 1,1-dioxide) | 1056.4 [M + H]+, 1078.5 [M + Na]+ | A |

TABLE 28

| No. | X¹ | LC-MS | Method |
|---|---|---|---|
| I-232 | (hydrazine-C(O)-C(CH3)2-CH2OH) | 1053.6 [M + H]+, 1075.6 [M + Na]+ | A |
| I-233 | (hydrazine-C(O)-cyclohexane tetraol) | 1027.6 [M + H]+, 1049.7 [M + Na]+ | A |
| I-234 | (sulfamide-CH2-CH(NH)-CH2-N(CH3)2) | 1117.5 [M + H]+ | B |
| I-235 | (hydrazone-CH(OH)-CH2OH) | 1025.5 [M + H]+, 1047 [M + Na]+ | A |
| I-236 | (O-CH2-CH(OH)-CH2OH aminoxy) | 1028.6 [M + H]+ | A |
| I-237 | (hydrazine-C(O)-CH2-CH(OH)-CH2OH) | 1055.5 [M + H]+, 1077.6 [M + Na]+ | A |
| I-238 | (hydrazine-C(O)-4-hydroxycyclohexane) | 1027.6 [M + H]+, 1049.7 [M + Na]+ | A |
| I-239 | (hydrazine-C(O)-4-hydroxycyclohexane) | 1079.6 [M + H]+ | A |
| I-240 | (hydrazine-C(O)-CH(CH2OH)2) | 1055.6 [M + H]+ | A |

TABLE 29

| No. | X¹ | LC MS | Method |
|---|---|---|---|
| I-241 | [structure: -NH-NH-CH2CH2-O-CH2CH2-S(O)2-CH3] | 1088.5 [M + H]+ | A |
| I-242 | [structure: hydrazide of gluconic acid-type polyol] | 1131.4 [M + H]+ | A |
| I-243 | [structure: -NH-NH-C(O)-CH2-OH] | 1011.3 [M + H]+ | A |
| I-244 | [structure: -NH-N(CH3)-CH2-CH(OH)-CH2OH] | 1041.4 [M + H]+ | A |
| I-245 | [structure: -NH-NH-C(O)-CH(OH)-C(CH3)2-CH2OH] | 1083.4 [M + H]+ | A |
| I-246 | [structure: -NH-NH-SO2-(1H-1,2,4-triazol-3-yl)] | 1084.4 [M + H]+ | A |
| I-247 | [structure: -NH-NH-C(O)-cyclopropyl-CH2OH] | 1051.4 [M + H]+ | A |

TABLE 30

| No. | X¹ | LC-MS | Method |
|---|---|---|---|
| I-248 | [structure: trisaccharide-linked pentaerythritol-type amine] | 1529.3 [M + H]+ | A |

TABLE 30-continued

| No. | X¹ | LC-MS | Method |
|---|---|---|---|
| I-249 | (structure: NH-CH(CH2OH)-COOH, homoserine-like) | 1040.4 [M + H]+, 1062.5 [M + Na]+ | A |
| I-250 | (structure: NH-CH2-CH(OH)-CH2-COOH) | 1040.4 [M + H]+, 1062.5 [M + Na]+ | A |
| I-251 | (structure: NH-O-CH(CH2OH)2) | 1028.4 [M + H]+, 1050.4 [M + Na]+ | A |
| I-252 | (structure: NH-oxetane-COOH) | 1038.4 [M + H]+ | A |
| I-253 | (structure: NH-NH-C(O)-CH2-CH(OH)-COOH) | 1069.4 [M + H]+ | A |
| I-254 | (structure: diglycoside-NH) | 1336.6 [M + H]+ | A |

TABLE 31

| No. | X¹ | LC-MS | Method |
|---|---|---|---|
| I-255 | (structure: NH-O-CH(CH2OH)2) | 1042.4 [M + H]+, 1064.5 [M + Na]+ | A |
| I-256 | (structure: NH-NH-C(O)-cyclopropyl-C(O)NH2) | 1064.5 [M + H]+, 1086.5 [M + Na]+ | A |
| I-257 | (structure: NH-NH-C(O)-cyclopropyl-OH) | 1037.4 [M + H]+, 1059.5 [M + Na]+ | A |
| I-258 | (structure: NH-oxetane-CN) | 1019.6 [M + H]+ | A |
| I-259 | (structure: NH-CH2-CH(OH)-COOH) | 1026.5 [M + H]+ | A |
| I-260 | (structure: 3,4-dihydroxypyrrolidine) | 1024.5 [M + H]+, 1046.6 [M + Na]+ | A |

TABLE 31-continued

| No. | X¹ | LC-MS | Method |
|---|---|---|---|
| I-261 | (hydrazide-succinic acid) | 1053.5 [M + H]+, 1075.6 [M + Na]+ | A |
| I-262 | (3,4-dihydroxypyrrolidinyl) | 1024.3 [M + H]+ | A |
| I-263 | (hydrazide-cyclopropyl methylsulfonyl) | 1099.4 [M + H]+, 1121.5 [M + Na]+ | A |
| I-264 | (hydrazinyl-2,3-dihydroxypropyl) | 1027.5 [M + H]+, 1049.6 [M + Na]+ | A |

TABLE 32

| No. | X¹ | LC-MS | Method |
|---|---|---|---|
| I-265 | (hydrazinyl-1,3-dihydroxy-2-propyl) | 1027.4 [M + H]+ | B |
| I-266 | (N-methyl-N-hydroxyamino) | 968.4 [M + H]+, 990.4 [M + Na]+ | B |
| I-267 | (N-isopropyl-N-hydroxyamino) | 996.5 [M + H]+ | B |
| I-268 | (hydrazono-1,3-dihydroxy-2-propyl) | 1025.4 [M + H]+ | B |
| I-269 | (aminooxy-furanose) | 1086.4 [M + H]+, 1108.5 [M + Na]+ | A |
| I-270 | (aminooxy-hydroxy-nitrile) | 1037.4 [M + H]+, 1059.5 [M + Na]+ | A |
| I-271 | (aminooxyethoxy-pyranose) | 1160.5 [M + H]+, 1182.6 [M + Na]+ | A |
| I-272 | (hydrazinyl-1,3-dihydroxy-2-propyl) | 1027.4 [M + H]+ | A |

TABLE 32-continued

| No. | X¹ | LC-MS | Method |
|---|---|---|---|
| I-273 | (N(OH)-CH₂-C(=O)NH₂) | 1011.4 [M + H]+ | A |

TABLE 33

| No. | X¹ | LC-MS | Method |
|---|---|---|---|
| I-274 | (N(OH)-CH₂CH₂OH) | 998.4 [M + H]+, 1020.4 [M + Na]+ | A |
| I-275 | (N(OH)-CH₂-CH(OH)-CH₂OH) | 1028.4 [M + H]+ | B |
| I-276 | (N(OH)-CH₂-COOH) | 1012.5 [M + H]+ | B |
| I-277 | (azetidine-3-carboxylic acid) | 1095.5 [M + H]+ | A |
| I-278 | (NH-O-CH₂-COOH) | 1012.3 [M + H]+ | A |
| I-279 | (N(OH)-Et) | 982.4 [M + H]+ | B |
| I-280 | (N(OH)-nPr) | 996.4 [M + H]+ | B |
| I-281 | (N(OH)-CH₂-cyclopropane-COOH) | 1052.4 [M + H]+ | B |
| I-282 | (N(Me)-OMe) | 982.5 [M + H]+ | B |
| I-283 | (azetidine-2-carboxylic acid) | 1022.4 [M + H]+, 1044.5 [M + Na]+ | A |

TABLE 34

| No. | X¹ | LC-MS | Method |
|---|---|---|---|
| I-284 | (azetidine-2-carboxylic acid) | 1022.4 [M + H]+, 1044.5 [M + Na]+ | A |
| I-285 | (NH-CH₂-C(=O)NHOH) | 1011.4 [M + H]+ | A |
| I-286 | (arginine) | 1095.5 [M + H]+ | A |
| I-287 | (N(CH₂COOH)₂) | 1054.4 [M + H]+ | B |
| I-288 | (N(OH)-CH₂-C(=O)NMe₂) | 1039.5 [M + H]+ | B |
| I-289 | (4-hydroxy-pyrrolidine-3-carboxylic acid) | 1052.4 [M + H]+ | B |
| I-290 | (3,4-dihydroxypyrrolidine) | 1024.4 [M + H]+ | B |
| I-291 | (threonine) | 1040.4 [M + H]+ | A |

TABLE 35

| No. | X¹ | LC-MS | Method |
|---|---|---|---|
| I-292 | (pyrroline with two COOH groups) | 1078.5 [M + H]+ | B |
| I-293 | (NH-CH(COOH)-CH2-COOH, aspartic acid) | 1054.4 [M + H]+ | B |
| I-294 | (pyrrolidine-3,4-dicarboxylic acid) | 1080.4 [M + H]+ | B |
| I-295 | (N(OH)-CH2-CH(OH)-COOH) | 1042.4 [M + H]+, 1064.5 [M + Na]+ | A |

TABLE 35-continued

| No. | X¹ | LC-MS | Method |
|---|---|---|---|
| I-296 | (3-hydroxyazetidine-3-yl-acetic acid) | 1052.5 [M + H]+, 1074.5 [M + Na]+ | A |
| I-297 | (glutamic acid) | 1068.4 [M + H]+, 1090.5 [M + Na]+ | A |
| I-298 | (3,4-dihydroxy-pyrrolidine-3,4-dicarboxylic acid) | 1112.4 [M + H]+ | B |

TABLE 36

| No. | X¹ | LC-MS | Method |
|---|---|---|---|
| I-299 | (1-aminocyclobutane-1-carboxylic acid) | 1036.4 [M + H]+ | B |
| I-300 | (2-aminocyclopentane-1-carboxylic acid) | 1050.4 [M + H]+ | B |
| I-301 | (2-aminocyclopentane-1-carboxylic acid isomer) | 1050.4 [M + H]+ | B |
| I-302 | (β-hydroxy diacid amino acid) | 1070.4 [M + H]+ | B |

TABLE 36-continued

| No. | X¹ | LC-MS | Method |
|---|---|---|---|
| I-303 | (azetidine-N-linked, O-linked to pyranose with OH, OH, OH, CH2OH) | 1156.5 [M + H]+, 1178.5 [M + Na]+ | A |
| I-304 | (cyclopropane with NH, COOH, CH2OH substituents) | 1052.5 [M + H]+, 1074.5 [M + Na]+ | A |
| I-305 | (3-hydroxy-3-carboxyazetidine) | 1038.5 [M + H]+ | A |
| I-306 | (azetidin-3-ylidene acetic acid) | 1034.4 [M + H]+ | A |

TABLE 37

| No. | X¹ | LC-MS | Method |
|---|---|---|---|
| I-307 | (4-hydroxyproline) | 1052.5 [M + H]+, 1074.5 [M + Na]+ | A |
| I-308 | (4-hydroxyproline, other stereochemistry) | 1052.5 [M + H]+, 1074.6 [M + Na]+ | A |
| I-309 | (hydrazine-N,N-diacetic acid) | 1069.4 [M + H]+ | A |
| I-310 | (hydrazine-CH2-CH(OH)-COOH) | 1041.6 [M + H]+ | A |
| I-311 | (NH-CH2-CH(OH)-COOH) | 1026.6 [M + H]+ | A |

[Chemical Formula 135]

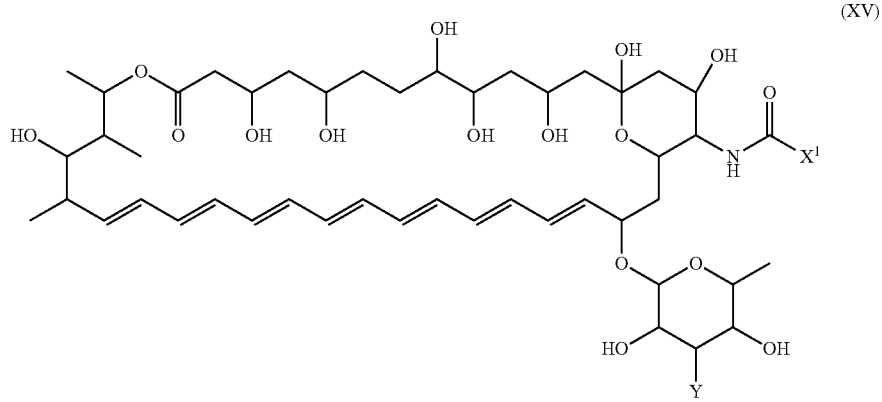

(XV)

The structure and physical property of compound (XV) are shown below.

TABLE 38

| No. | X¹ | Y | LC-MS | Method |
|---|---|---|---|---|
| I-312 | -NH-CH₃ | aminomethyl tetrahydropyran tetraol | 1114.5 [M + H]+ | B |
| I-313 | -NH-CH₃ | (1-methylpiperidin-4-yl)methylamino | 1064.2 [M + H]+ | B |

TABLE 38-continued

| No. | X¹ | Y | LC-MS | Method |
|---|---|---|---|---|
| I-314 | -NH-CH₃ | 4-(dimethylamino)benzylamino | 1085.91 [M + H]+ | B |
| I-315 | -NH-CH₃ | 2-(piperidin-4-yl)ethylamino | 1063.3 [M + H]+ | B |
| I-316 | -NH-CH₃ | (pyrrolidin-2-yl)methylamino | 1035.3 [M + H]+ | B |

TABLE 39
| No. | X¹ | Y | LC-MS | Method |
|---|---|---|---|---|
| I-317 |  | 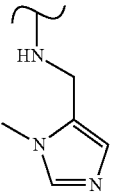 | 1046.2 [M + H]+ | B |
| I-318 |  | 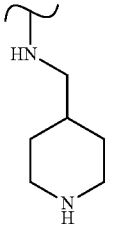 | 1049.3 [M + H]+ | B |
| I-319 |  | 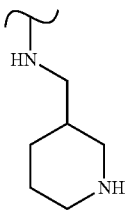 | 1049.6 [M + H]+ | B |
| I-320 |  | 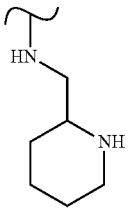 | 1049.5 [M + H]+ | B |
| I-321 | 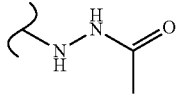 | 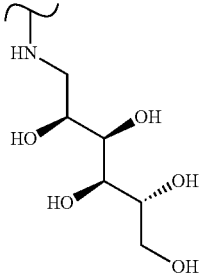 | 1159.5 [M + H]+ | B |
TABLE 40
| No. | X¹ | Y | LC-MS | Method |
|---|---|---|---|---|
| I-322 | 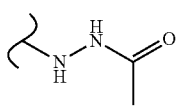 | 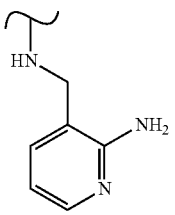 | 1101.5 [M + H]+ | B |

TABLE 40-continued

| No. | X¹ | Y | LC-MS | Method |
|---|---|---|---|---|
| I-323 | hydrazide-acetyl | guanidine | 1037.5 [M + H]+ | B |
| I-324 | hydrazide-acetyl | -NH-C(=O)-CH2-N(CH3)2 | 1080.5 [M + H]+ | B |
| I-325 | -NH2 | -NH-C(=O)-CH2-N(CH3)2 | 1023.5 [M + H]+ | B |
| I-326 | semicarbazide | -NH-C(=O)-CH2-N(CH3)2 | 1081.5 [M + H]+ | B |
| I-327 | -NH-CH2CH2-N(CH3)2 | -NH-C(=O)-CH2-N(CH3)2 | 1094.5 [M + H]+, 1116.5 [M + Na]+ | A |

TABLE 41

| No. | X¹ | Y | LC-MS | Method |
|---|---|---|---|---|
| I-328 | -NH-CH2CH2-N(CH3)2 | -NH-CH2-(2-aminopyridin-3-yl) | 1115.7 [M + H]+ | B |
| I-329 | -NH2 | guanidine | 980.5 [M + H]+ | A |
| I-330 | semicarbazide | guanidine | 1038.5 [M + H]+ | A |

TABLE 41-continued
| No. | X¹ | Y | LC-MS | Method |
|---|---|---|---|---|
| I-331 | 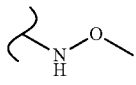 | 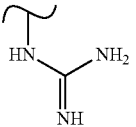 | 1010.6 [M + H]+ | A |
| I-332 | 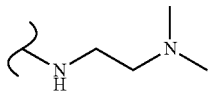 | 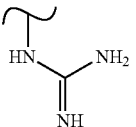 | 1051.5 [M + H]+ | A |
| I-333 | 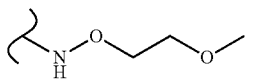 | 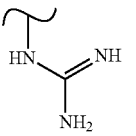 | 1054.5 [M + H]+ | A |
| I-334 | 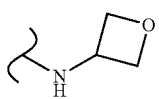 | 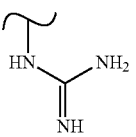 | 1036.5 [M + H]+ | A |
TABLE 42
| No. | X¹ | Y | LC-MS | Method |
|---|---|---|---|---|
| I-335 | 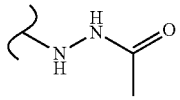 | 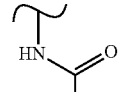 | 1109.6 [M + H]+, 1131.6 [M + Na]+ | A |
| I-336 | 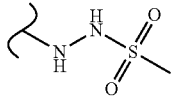 | 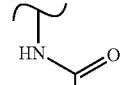 | 1159.5 [M + H]+ | B |
| I-337 | 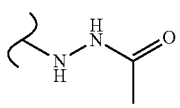 | 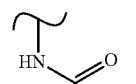 | 1123.6 [M + H]+, 1145.6 [M + Na]+ | A |

TABLE 42-continued

| No. | X¹ | Y | LC-MS | Method |
|---|---|---|---|---|
| I-338 | NH-NH-S(O)₂-CH₃ | HN-C(O)-CH(NH₂)-(CH₂)₃-NH₂ | 1145.5 [M + H]+ | A |
| I-339 | NH-NH-C(O)-CH₃ | HN-C(O)-CH(NH₂)-CH₂-C(O)NH₂ | 1109.5 [M + H]+ | A |

TABLE 43

| No. | X¹ | Y | LC-MS | Method |
|---|---|---|---|---|
| I-340 | NH₂ | HN-C(O)-CH(NH₂)-(CH₂)₄-NH₂ | 1066.5 [M + H]+ | A |
| I-341 | NH-NH-S(O)₂-CH₃ | HN-C(=NH)-NH₂ (guanidine) | 1073.4 [M + H]+ | B |
| I-342 | NH-NH-C(O)-CH₃ | HN-tetrahydropyran-4-yl | 1079.5 [M + H]+ | A |
| I-343 | NH-CH₂-CH₂-C(O)NH₂ | HN-C(=NH)-NH₂ (guanidine) | 1051.6 [M + H]+ | A |

TABLE 43-continued

| No. | X¹ | Y | LC-MS | Method |
|---|---|---|---|---|
| I-344 | [β-alanine amide group] | [N,N-dimethylglycinamide group] | 1094.6 [M + H]+ | A |
| I-345 | [glycinamide group] | [N,N-dimethylglycinamide group] | 1080.6 [M + H]+ | A |
| I-346 | [glycinamide group] | [guanidine group] | 1037.5 [M + H]+ | A |

TABLE 44

| No. | X¹ | Y | LC-MS | Method |
|---|---|---|---|---|
| I-347 | [aminoethyl urea group] | [N,N-dimethylglycinamide group] | 1109.6 [M + H]+, 1131.6 [M + Na]+ | A |
| I-348 | [aminoethyl urea group] | [guanidine group] | 1066.7 [M + H]+ | A |
| I-349 | [2,3-dihydroxypropylamino group] | [4-(dimethylamino)benzylamino group] | 1145.5 [M + H]+ | A |
| I-350 | [2,3-dihydroxypropylamino group] | [guanidine group] | 1054.5 [M + H]+ | A |

TABLE 44-continued

| No. | X¹ | Y | LC-MS | Method |
|---|---|---|---|---|
| I-351 | ⎰N(H)–CH2–CH(OH)–CH2OH (with HO) | ⎰NH–C(=O)–CH2–N(CH3)2 | 1097.5 [M + H]+ | A |
| I-352 | ⎰N(H)–CH2–CH(OH)–CH2OH (with HO) | ⎰NH–CH2–CH(OH)–CH(OH)–CH(OH)–CH(OH)–CH(OH)–CH3 | 1160.5 [M + H]+ | A |

TABLE 45

| No. | X¹ | Y | LC-MS | Method |
|---|---|---|---|---|
| I-353 | ⎰N(H)–CH2–CH(OH)–CH2OH (with HO) | ⎰HN–CH2–C6H4–C(=NH)NH2 | 1145.5 [M + H]+ | A |
| I-354 | ⎰N(H)–CH2–CH(OH)–CH2OH (with HO) | ⎰HN–C(=O)–CH2–CH2–C(=O)OH | 1112.5 [M + H]+ | A |
| I-355 | ⎰N(H)–CH2–CH(OH)–CH2OH (with HO) | ⎰HN–CH2–CH2–CH2–NH2 | 1069.5 [M + H]+ | B |
| I-356 | ⎰NH–CH(CH2OH)2 | ⎰HN–C(=NH)NH2 | 1054.5 [M + H]+ | A |

TABLE 45-continued

| No. | X¹ | Y | LC-MS | Method |
|---|---|---|---|---|
| I-357 | -NH-CH2-COOH (glycine) | -NH-C(=NH)-NH2 (guanidine) | 1038.6 [M + H]+ | B |
| I-358 | -NH-CH2-COOH (glycine) | -NH-C(=O)-CH2-N(CH3)2 | 1081.7 [M + H]+ | B |

TABLE 46

| No. | X¹ | Y | LC-MS | Method |
|---|---|---|---|---|
| I-359 | -NH-CH2-CH(OH)-CH2OH | -NH-C(=NH)-NHCH3 | 1068.7 [M + H]+ | B |
| I-360 | -NH-CH2-CH(OH)-CH2OH | -NH-(CH2)3-NH-C(=NH)-NH2 | 1111.8 [M + H]+ | B |
| I-361 | -NH-CH2-CH(OH)-CH2OH | -NH-C(=N-CN)-NHCH3 | 1093.5 [M + H]+, 1115.5 [M + Na]+ | A |
| I-362 | -NH-CH2-CH(OH)-CH2OH | -NH-C(=N-Et)-NH-(CH2)3-N(CH3)2 | 1167.6 [M + H]+ | A |

TABLE 46-continued
| No. | X¹ | Y | LC-MS | Method |
|---|---|---|---|---|
| I-363 | 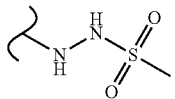 | | 1170.6 [M + H]+ | A |
TABLE 47
| No. | X¹ | Y | LC-MS | Method |
|---|---|---|---|---|
| I-364 | 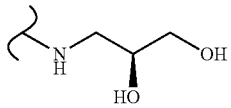 | 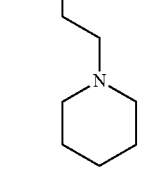 | 1151.6 [M + H]+ | A |
| I-365 | | | 1071 [M + H]+ | B |
| I-366 | | | 1061.8 [M − H₂O + H]+ | B |
| I-367 | 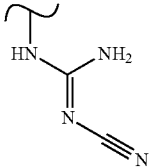 | 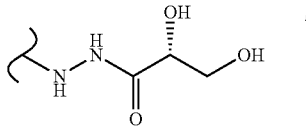 | 1083.3 [M + H]+ | A |
| I-368 | | 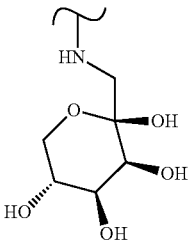 | 1174 [M + H]+ | B |

TABLE 47-continued
| No. | X¹ | Y | LC-MS | Method |
|---|---|---|---|---|
| I-369 | 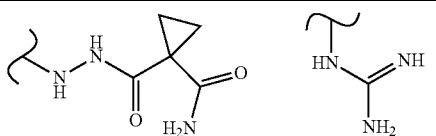 | 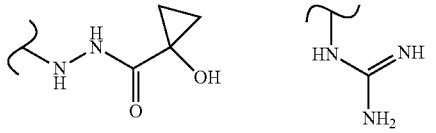 | 1093.4 [M + H]+ | A |
TABLE 48
| No. | X¹ | Y | LC-MS | Method |
|---|---|---|---|---|
| I-370 |  |  | 1106.4 [M + H]+, 1128.6 [M + Na]+ | A |
| I-371 | 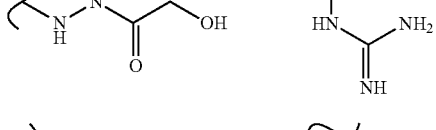 | 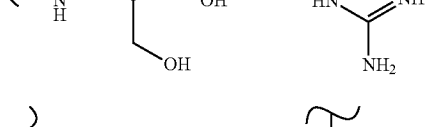 | 1079.5 [M + H]+ | A |
| I-372 | 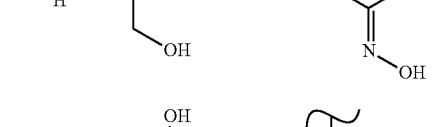 | 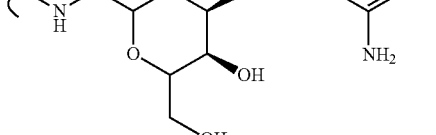 | 996.4 [M + H]+, 1018.5 [M + Na]+ | A |
| I-373 |  |  | 1012.4 [M+ H]+ | A |
| I-374 |  |  | 1053.5 [M + H]+, 1075.6 [M + Na]+ | A |
| I-375 |  |  | 1070.5 [M + H]+, 1092.5 [M + Na]+ | A |
| I-376 |  |  | 1086.5 [M + H]+, 1108.6 [M + Na]+ | A |
| I-377 |  |  | 1158.5 [M + H]+, 1180.6 [M + Na]+ | A |

TABLE 49

| No. | X¹ | Y | LC-MS | Method |
|---|---|---|---|---|
| I-378 | NH-O-sugar(OH,OH,OH,CH2OH) | HN-C(=N-OH)-NH2 | 1174.5 [M + H]+ | A |
| I-379 | NH-NH-C(=O)-CH2-OH | HN-C(=NH)-NH-OH | 1069.4 [M + H]+ | A |
| I-380 | NH-NH-C(=O)-CH(OH)-CH2OH | HN-C(=NH)-NH-OH | 1099.5 [M + H]+, 1121.6 [M + Na]+ | A |
| I-381 | N(CH3)-OH | HN-C(=NH)-NH2 | 1010.4 [M + H]+, 1032.5 [M + Na]+ | A |
| I-382 | NH-CH2-C(=O)-OH | HN-CH2-C(=O)-OH | 1054.4 [M + H]+ | A |
| I-383 | NH-CH3 | N(CH2CH2CH2NH2)(CH2CH2CH2NH2) | 1066.8 [M + H]+ | B |
| I-384 | NH-CH2-CH(OH)-CH2OH | N(CH3)2 | 1040.5 [M + H]+ | A |

TABLE 50

| No. | X¹ | Y | LC-MS | Method |
|---|---|---|---|---|
| I-385 | NH-CH2-CH(OH)-CH2OH | N(CH2CH2CH2NH2)(CH2CH2CH2NH2) | 1126.6 [M + H]+ | A |

TABLE 50-continued
| No. | X¹ | Y | LC-MS | Method |
|---|---|---|---|---|
| I-386 | 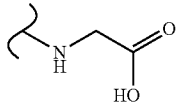 | 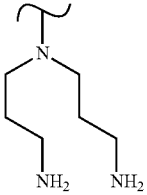 | 1110.6 [M + H]+ | B |
| I-387 | 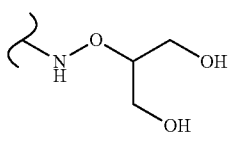 | 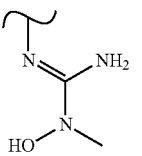 | 1100.5 [M + H]+, 1122.5 [M + Na]+ | A |
| I-388 | 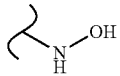 | 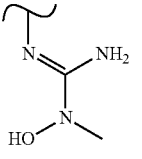 | 1026.5 [M + H]+, 1048.5 [M + Na]+ | A |
| I-389 | 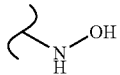 | 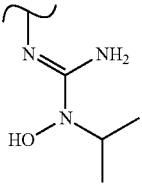 | 1054.5 [M + H]+ | A |
TABLE 51
| No. | X | Y | LC-MS | Method |
|---|---|---|---|---|
| I-390 | 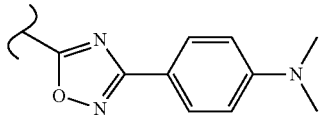 |  | 1067.5 [M + H]+ | B |
| I-391 | 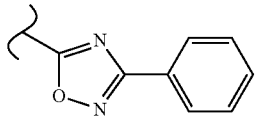 |  | 1024.5 [M + H]+ | B |
| I-392 | 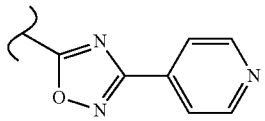 |  | 1025.5 [M + H]+ | B |

TABLE 51-continued
| No. | X | Y | LC-MS | Method |
|---|---|---|---|---|
| I-394 | 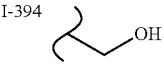 | 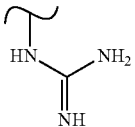 | 952.8 [M + H]+ | A |
| I-395 |  | 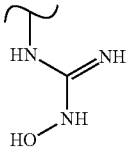 | 968.5 [M + H]+ | A |
| I-396 | 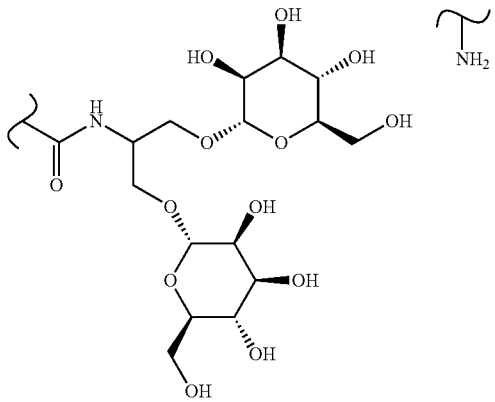 |  | 1321.7 [M + H]+ | A |
In addition, the following compounds were prepared.
TABLE 52
| No. | Structure | LC-MS | Method |
|---|---|---|---|
| I-393 | 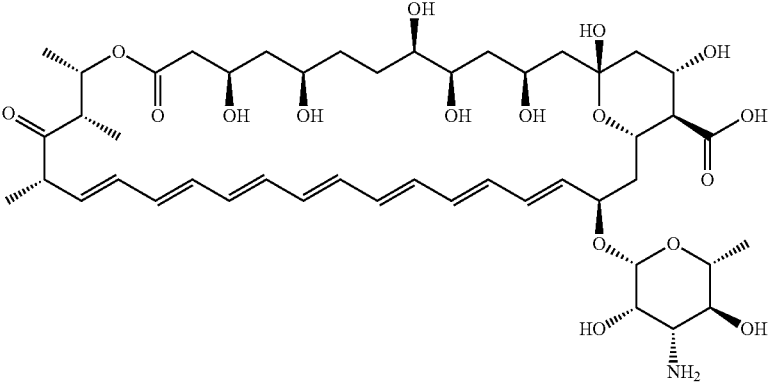 [SMILES: C[C@@H]1OC(=O)C[C@H](O)C[C@H](O)CC[C@@H](O)[C@H](O)C[C@H](O)C[C@]2(O)C[C@H](O)[C@@H](C(=O)O)[C@H](C[C@@H](O[C@@H]3O[C@H](C)[C@@H](O)[C@H](N)[C@@H]3O)/C=C/C=C/C=C/C=C/C=C/C=C/C=C/[C@H](C)C(=O)[C@H]1C)O2] | 922.9 [M + H]+ | B |
The structures of AmBMU, AmBCU and AmBAU described in non-patent documents 4, 5 and patent document 11 are shown below.

TABLE 53

AmBMU
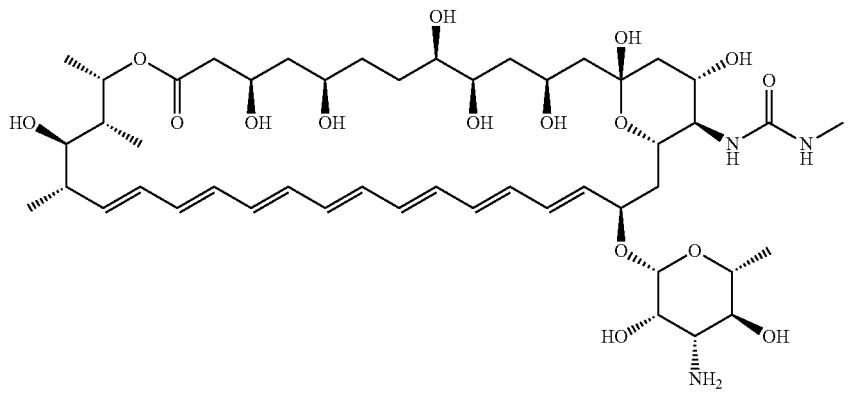 [SMILES: CNC(=O)N[C@H]1[C@@H]2C[C@@H](O[C@@H]3O[C@H](C)[C@@H](O)[C@H](N)[C@@H]3O)/C=C/C=C/C=C/C=C/C=C/C=C/C=C/[C@H](C)[C@@H](O)[C@@H](C)[C@H](C)OC(=O)C[C@H](O)C[C@H](O)CC[C@@H](O)[C@H](O)C[C@H](O)C[C@](O)(C[C@@H]1O)O2]

AmBCU
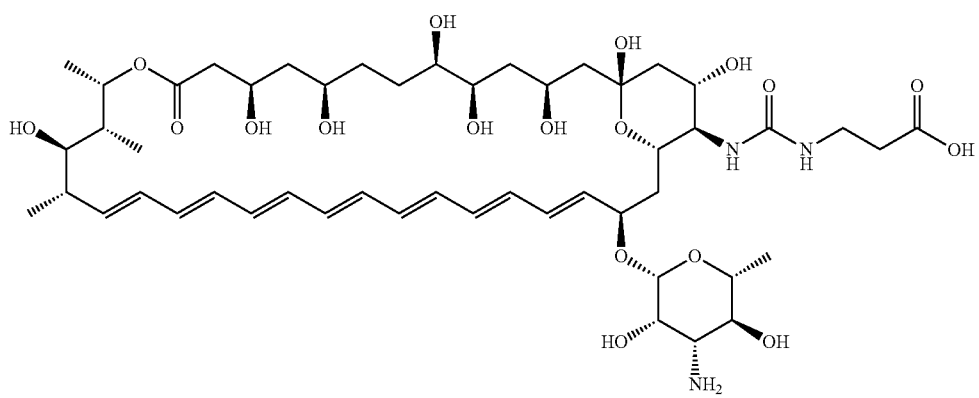 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NCCC(=O)O]

AmBAU
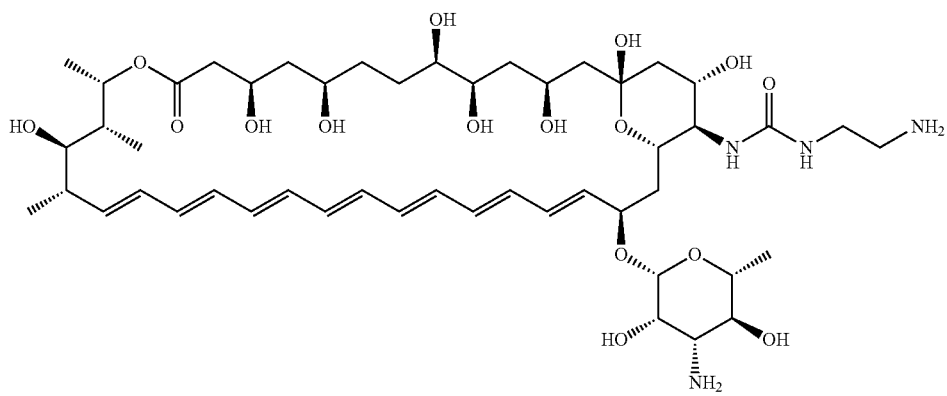 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NCCN]

Biological test examples for compounds of the present invention were described below.

Test Example 1

Antifungal Activity Test

The Minimum Inhibitory Concentration (MIC) values of the present compound against yeast and filamentous fungi were determined by broth microdilution assay according to the Clinical Laboratory Standards Institute (CLSI) guidelines outlined in documents M27-A3 and M38-A2. The medium used in the assay consisted of RPMI1640 (with glutamine, without bicarbonate) with 2% glucose and 0.165 mol/L morpholinepropanesulfonic acid (MOPS) with pH adjusted to 7.0 using 1 mol/L sodium hydroxide. The present compound was dissolved in dimethyl sulfoxide (DMSO). A series of two-fold dilutions were prepared in DMSO, and then 2 μL of the diluted compound was added to each well in 96-well sterile plates. Each inoculum was prepared by diluting a suspension of *Candida* spp. or a conidia suspension of *Aspergillus* spp. suspended in sterile saline solution, and then 200 μL was added to each well to a predetermined concentration using RPMI/MOPS (final concentration for each solution: approximately 1×103 cells/mL and approximately 1×104 CFU/mL). Plates of *Candida* spp. and *Aspergillus* spp. were incubated at 35° C. for 24-48 hours. The MIC was defined as the lowest concentration giving 100% inhibition compared to the growth control.

The results are shown below.

TABLE 54

| No. | C. albicans ATCC90028 MIC (µg/mL) | A. flavus ATCC204304 MIC (µg/mL) | A. fumigatus ATCC204305 MIC (µg/mL) |
|---|---|---|---|
| I-19 | 0.25 | 1 | 1 |
| I-36 | 0.25 | 1 | 1 |
| I-40 | 0.125 | 0.5 | 0.25 |
| I-43 | 0.25 | 1 | 1 |
| I-45 | 0.25 | 0.5 | 1 |
| I-59 | 0.25 | 1 | 1 |
| I-60 | 0.125 | 0.5 | 0.5 |
| I-67 | 0.25 | 1 | 1 |
| I-90 | 0.25 | 0.5 | 0.5 |
| I-119 | 0.25 | 0.5 | 1 |
| I-155 | 0.5 | 0.5 | 1 |
| I-157 | 0.5 | 0.5 | 1 |
| I-158 | 0.25 | 1 | 1 |
| I-159 | 0.25 | 0.5 | 1 |
| I-162 | 0.25 | 1 | 1 |
| I-163 | 0.25 | 1 | 1 |
| I-165 | 0.25 | 1 | 1 |
| I-166 | 0.25 | 0.5 | 1 |
| I-169 | 0.25 | 1 | 1 |
| I-189 | 0.25 | 0.5 | 0.5 |
| I-190 | 0.25 | 1 | 0.5 |
| I-193 | 0.25 | 0.5 | 1 |

TABLE 55

| No. | C. albicans ATCC90028 MIC (µg/mL) | A. flavus ATCC204304 MIC (µg/mL) | A. fumigatus ATCC204305 MIC (µg/mL) |
|---|---|---|---|
| I-202 | 0.5 | 0.5 | 1 |
| I-218 | 0.25 | 0.5 | 1 |
| I-227 | 0.5 | 0.5 | 1 |
| I-230 | 0.5 | 0.5 | 1 |
| I-237 | 0.5 | 0.5 | 1 |
| I-240 | 0.5 | 0.5 | 1 |
| I-250 | 0.5 | 0.5 | 1 |
| I-259 | 0.5 | 0.5 | 1 |
| I-260 | 0.5 | 0.5 | 1 |
| I-261 | 0.5 | 0.5 | 1 |
| I-266 | 0.25 | 0.5 | 0.5 |
| I-272 | 0.25 | 0.5 | 0.5 |
| I-273 | 0.25 | 0.5 | 0.5 |
| I-274 | 0.5 | 0.5 | 0.5 |
| I-275 | 0.5 | 1 | 0.5 |
| I-276 | 0.5 | 0.5 | 0.5 |
| I-278 | 0.5 | 0.5 | 0.5 |
| I-284 | 0.5 | 0.5 | 1 |
| I-298 | 0.5 | 1 | 0.5 |
| I-310 | 0.5 | 0.5 | 1 |
| I-311 | 0.5 | 0.5 | 0.5 |

TABLE 56

| No. | C. albicans ATCC90028 MIC (µg/ml) | A. flavus ATCC204304 MIC (µg/mL) | A. fumigatus ATCC204305 MIC (µg/mL) |
|---|---|---|---|
| I-325 | 0.25 | 0.5 | 1 |
| I-326 | 0.25 | 1 | 1 |
| I-330 | 0.25 | 1 | 1 |
| I-331 | 0.25 | 1 | 1 |
| I-343 | 0.25 | 0.5 | 1 |
| I-344 | 0.5 | 0.5 | 1 |
| I-346 | 0.5 | 0.5 | 1 |
| I-350 | 0.25 | 0.5 | 0.5 |
| I-367 | 0.25 | 0.5 | 1 |
| I-380 | 0.5 | 0.5 | 1 |
| I-383 | 0.25 | 1 | 1 |

The results of the compounds as comparative example are shown below.

TABLE 57

| No. | C. albicans ATCC90028 MIC (µg/ml) | A. flavus ATCC204304 MIC (µg/mL) | A. fumigatus ATCC204305 MIC (µg/mL) |
|---|---|---|---|
| AmBMU | 0.5 | 1 | 1 |
| AmBCU | 0.5 | 1 | 1 |
| AmBAU | 0.5 | 1 | 1 |

Test Example 2

Hemolytic Activity Test

Nephrotoxic potentials of the compounds of the present invention except the compounds whose X is —N($R^F$)—CO—$X^1$ and $X^1$ is the group represented by formula (III) and T is —N($R^{a5}$)— were investigated by in vitro hemolytic activity test under the condition, in that, the upper limit was 50 µmol/L, 80 µmol/L, 100 µmol/L, or 200 µmol/L as the required concentration to 50% of hemolysis ($IC_{50}$).

Defibrinated sterile blood was centrifuged at 700×g for 3 minutes and, and the supernatant was removed for 100% of red blood cells. After the cleaning with physiological saline, the washed blood cells was suspended in the medium (Earle's balanced salt sodium, bicarbonate, 0.1 g/L L-glutamine without phenol red), and was diluted by 5% (5% RBC suspension).

The washed blood was diluted by 5% in water for injection (solution of complete hemolysis), and was used as the indication of optical density for complete hemolysis.

The compounds of the present invention solution in DMSO (several and doubling dilutions starting from 2.5 mmol/L, 4 mmol/L, 5 mmol/L, or 10 mmol/L), DMSO as the negative control, and Amphotericin B as the positive control were used, and each 5 µL of these was added in to a well of V-form 96 well type microplate.

Finally, the maximum concentration of the compounds of the present invention solution in DMSO was 50 µmol/L, 80 µmol/L, 100 µmol/L, or 200 µmol/L by adding 245 µL of the medium or 5% RBC suspension into the well.

Two hundred fifty µL of the solution of complete hemolysis was added into another well and the microplate was incubated at 37° C. in 5% of $CO_2$ concentration for an hour.

After the incubation, each 100 µL of supernatants in wells was collected by centrifugation of the microplate at 300×g for 5 minutes and was located on a well of flat-form 96 well type microplate. An absorbance of each supernatant was measured at wavelength of 540 nm.

Percent hemolysis was calculated by using the followed equation. The required concentration to 50% of hemolysis ($IC_{50}$) was calculated based on the percent hemolysis. Smallness of $IC_{50}$ shows that the compound has potential of kidney toxicity.

Hemolysis (%)=(CR−VM)×100÷(VL−VR)

Where:
CR: Absorbance of 5% RBC suspension incubated with the compounds of the present invention solution in DMSO
VM: Absorbance of medium incubated with the compounds of the present invention solution in DMSO
VL: Absorbance of solution of complete hemolysis
VR: Absorbance of 5% RBC suspension incubated with DMSO The results are shown below. The "hemolysis method" in the table means any tests the upper concentration of above $IC_{50}$ are 50 µmol/L, 80 µmol/L, 100 µmol/L or 200 µmol/L.

The ">50", ">80", ">100" or ">200" in the table means above IC$_{50}$ value exceeded the each upper concentration.

TABLE 58

| No. | hemolysis IC50 (μmol/L) | hemolysis method | No. | hemolysis IC50 (μmol/L) | hemolysis method |
|---|---|---|---|---|---|
| I-5 | 94 | 100 | I-54 | >80 | 80 |
| I-6 | 75 | 100 | I-55 | >50 | 50 |
| I-7 | 81 | 100 | I-62 | 50 | 100 |
| I-8 | 96 | 100 | I-81 | >50 | 50 |
| I-9 | >100 | 100 | I-93 | >50 | 50 |
| I-10 | >100 | 100 | I-105 | >200 | 200 |
| I-11 | >50 | 50 | I-146 | >50 | 50 |
| I-15 | >80 | 80 | I-207 | >100 | 100 |
| I-17 | >80 | 80 | I-212 | >100 | 100 |
| I-18 | >80 | 80 | I-213 | >100 | 100 |
| I-21 | >80 | 80 | I-226 | >50 | 50 |
| I-22 | >80 | 80 | I-231 | >50 | 50 |
| I-23 | 79 | 80 | I-234 | >50 | 50 |
| I-24 | >80 | 80 | I-241 | >50 | 50 |
| I-38 | >50 | 50 | I-249 | >50 | 50 |
| I-39 | >80 | 80 | I-250 | >50 | 50 |
| I-40 | >80 | 80 | I-252 | >50 | 50 |
| I-41 | >50 | 50 | I-254 | >50 | 50 |
| I-48 | >80 | 80 | I-255 | >50 | 50 |
| I-49 | >80 | 80 | I-258 | >50 | 50 |
| I-50 | >80 | 80 | I-259 | >50 | 50 |
| I-51 | >80 | 80 | I-279 | >50 | 50 |
| I-53 | >80 | 80 | I-280 | >50 | 50 |
| I-282 | >50 | 50 | I-328 | >50 | 100 |

TABLE 59

| No. | hemolysis IC50 (μmol/L) | hemolysis method |
|---|---|---|
| I-283 | >50 | 50 |
| I-284 | >50 | 50 |
| I-291 | >50 | 50 |
| I-295 | >50 | 50 |
| I-303 | >50 | 50 |
| I-311 | >50 | 50 |
| I-314 | >80 | 100 |
| I-327 | >50 | 100 |
| I-365 | >50 | 50 |
| I-366 | >50 | 50 |
| I-368 | >50 | 50 |
| I-390 | >50 | 50 |
| I-391 | >50 | 50 |
| I-392 | >50 | 50 |
| I-396 | >100 | 100 |

Test Example 2

Hemolytic Activity Test

Nephrotoxic potentials of the compounds of the present invention whose X is —N(R$^F$)—CO—X$^1$ and X$^1$ is the group represented by formula (III) and T is —N(R$^{a5}$)— were investigated by in vitro hemolytic activity test under the condition that the upper limit was 200 μmol/L as the required concentration to 50% of hemolysis (IC$_{50}$).

Defibrinated sterile blood was centrifuged at 700×g for 3 minutes and, and the supernatant was removed for 100% of red blood cells. After the cleaning with physiological saline, the washed blood cells was suspended in the medium (Earle's balanced salt sodium, bicarbonate, 0.1 g/L L-glutamine without phenol red), and was diluted by 5% (5% RBC suspension).

The washed blood was diluted by 5% in water for injection (solution of complete hemolysis), and was used as the indication of optical density for complete hemolysis.

The compounds of the present invention solution in DMSO (several and doubling dilutions starting from 10 mmol/L), DMSO as the negative control, and Amphotericin B as the positive control were used, and each 5 μL of these was added in to a well of V-form 96 well type microplate. Finally, the maximum concentration of the compounds of the present invention solution in DMSO was 200 μmol/L by adding 245 μL of the medium or 5% RBC suspension into the well.

Two hundred fifty μL of the solution of complete hemolysis was added into another well and the microplate was incubated at 37° C. in 5% of CO$_2$ concentration for an hour.

After the incubation, each 100 μL of supernatants in wells was collected by centrifugation of the microplate at 300×g for 5 minutes and was located on a well of flat-form 96 well type microplate. An absorbance of each supernatant was measured at wavelength of 540 nm.

Percent hemolysis was calculated by using the followed equation. The required concentration to 50% of hemolysis (IC$_{50}$) was calculated based on the percent hemolysis. Smallness of IC$_{50}$ shows that the compound has potential of kidney toxicity.

$$\text{Hemolysis (\%)} = (CR - VM) \times 100 \div (VL - VR)$$

Where:
CR: Absorbance of 5% RBC suspension incubated with the compounds of the present invention solution in DMSO
VM: Absorbance of medium incubated with the compounds of the present invention solution in DMSO
VL: Absorbance of solution of complete hemolysis
VR: Absorbance of 5% RBC suspension incubated with DMSO The results are shown below. The ">200" in the table means above IC$_{50}$ value exceeded the upper concentration 200 μmol/L.

TABLE 60

| No. | hemolysis IC50 (μmol/L) | hemolysis method |
|---|---|---|
| I-19 | >200 | 200 |
| I-43 | >200 | 200 |
| I-44 | >200 | 200 |
| I-45 | >200 | 200 |
| I-47 | >200 | 200 |
| I-60 | >200 | 200 |
| I-78 | >200 | 200 |
| I-123 | >200 | 200 |
| I-124 | >200 | 200 |
| I-125 | >200 | 200 |
| I-194 | >200 | 200 |
| I-197 | >200 | 200 |
| I-198 | >200 | 200 |
| I-209 | >200 | 200 |
| I-214 | >200 | 200 |
| I-215 | >200 | 200 |
| I-216 | >200 | 200 |
| I-217 | >200 | 200 |
| I-218 | >200 | 200 |
| I-220 | >200 | 200 |
| I-221 | >200 | 200 |
| I-223 | >200 | 200 |
| I-224 | >200 | 200 |
| I-225 | >200 | 200 |
| I-228 | >200 | 200 |
| I-229 | >200 | 200 |
| I-232 | >200 | 200 |
| I-233 | >200 | 200 |
| I-237 | >200 | 200 |
| I-238 | >200 | 200 |
| I-239 | >200 | 200 |
| I-240 | >200 | 200 |

TABLE 60-continued

| No. | hemolysis IC50 (μmol/L) | hemolysis method |
|---|---|---|
| I-242 | >200 | 200 |
| I-243 | >200 | 200 |
| I-245 | >200 | 200 |
| I-246 | >200 | 200 |
| I-247 | >200 | 200 |
| I-253 | >200 | 200 |
| I-256 | >200 | 200 |
| I-257 | >200 | 200 |
| I-261 | >200 | 200 |
| I-263 | >200 | 200 |
| I-272 | >200 | 200 |
| I-310 | >200 | 200 |

The results of the comparative example are shown below.

TABLE 61

| | hemolysis IC50 (μmol/L) | hemolysis method |
|---|---|---|
| AmB | 1.6 | 200 |
| AmBMU | 129.8 | 200 |
| AmBAU | 58 | 200 |

Test Example 3

Cytotoxicity Assay

The Cytotoxicity of the compounds of the present invention was evaluated by measuring cell numbers automatically using the cell image analyzer, Toxinsight® (Thermofisher Scientific).

HepG2 cells were seeded in 384-well black plates (100000 cells/mL) and allowed to attach for approximately 24 hours at 37° C. in humidified $CO_2$ incubator. Test compounds and positive control (Fungizone®) were initially dissolved as concentrated 20 mmol/L stock solutions in DMSO and added to culture medium, to the final concentration; 1.6, 3.1, 6.3, 12.5, 25, 50, 100 μmol/L. The negative control well was treated with DMSO alone. After exposure of each test compound for approximately 71 hours, each well were added with Hoechst 33342, for staining of nuclei, diluted in D-PBS to the final concentration; 1 μg/mL, and after that, fixed with 4% paraformaldehyde. The cell number, stained with Hoechst 33342, was counted by Toxinsight® (Thermofisher Scientific) in each well. The mean value of cell number and the standard deviation (SD) was calculated (N=4). The lowest cytotoxicity concentration was evaluated as the concentration showed the cell numbers decreased more than 2SD from vehicle control values. The lower the cell numbers is indicated that the risk of cytotoxicity is higher.

The results are shown below.

TABLE 62

| No. | cytotoxicity (μmol/L) |
|---|---|
| I-214 | >100 |
| I-215 | >100 |
| I-216 | >100 |
| I-253 | >100 |
| I-310 | >100 |

The results of the comparative example are shown below.

TABLE 63

| | cytotoxicity (μmol/L) |
|---|---|
| AmB | <1.6 |
| AmBMU | 12.5 |
| AmBCU | 25.2 |
| AmBAU | 51.0 |

Test Example 4

Hemolytic Activity Test

The expression level of marker genes for nephrotoxicity was determined by quantitative RT-PCR to evaluate nephrotoxicity of the compound of the present invention. The compound of the present invention or vehicle was intravenously administered to mice and their kidneys were isolated. After removal of the kidney capsule, all of the kidneys were sliced into two equal halves, and stored at −80° C. in RNAlater® (Ambion) until use. Samples were disrupted and homogenized in QIAzol Lysis Reagent with TissueLyser (Qiagen), and total RNA was extracted using an RNeasy® Mini kit (Qiagen). Total RNA concentrations were determined to read OD260 by absorptiometer.

The level of expression of the following target genes was determined using one-step quantitative real-time PCR: Kim1, Timp1, and Lcn2. Total RNA (80 ng/2 μL) was used as the template, and TaqMan Gene Expression Assays (Applied Biosystems, for Havcr1 (Kim1), assay ID: Mm00506686_m1; Timp1, Mm01341361_m1; Lcn2, Mm01324470_m1) or TaqMan Endogenous Controls (Gapdh, predesigned assay reagent supplied by ABI, Applied Biosystems) were employed as gene-specific probe and primer sets. Quantitative RT-PCR was performed using a QuantiTect™ Probe RT-PCR kit (Qiagen), and transcript levels were quantitated with an Applied Biosystems 7900HT Fast Real Time PCR System (Applied Biosystems). Reverse transcription and amplification conditions were set as follows: 50° C. for 30 min, 95° C. for 15 min, followed by 40 cycles at 95° C. for 15 s and 60° C. for 1 min. The resulting cycle threshold (Ct) value was processed based on the comparative Ct method (ΔΔCt Method), where Gapdh was used as an endogenous reference gene to normalize the expression level of target genes.

The ΔCt was calculated as follows: $Ct_{Gapdh} - Ct_{target\ gene}$.
The ΔΔCt was calculated as follows: $\Delta Ct_{treated\ sample} - \Delta Ct_{average\ of\ vehicle\ control\ sample}$.

Higher ΔΔCt values indicate higher expression rates of the target gene and therefore high risk for nephrotoxicity. When ΔΔCt values of two-third of target genes showed >3, it was considered to be nephrotoxicity positive.

The results are shown below.

TABLE 64

| No. | nephrotoxicity MTD (mg/kg) |
|---|---|
| I-105 | >24 |
| I-219 | 16 |
| I-235 | >24 |
| I-394 | >24 |
| I-396 | 16 |

The results of the comparative example are shown below.

TABLE 65

| | nephrotoxicity MTD (mg/kg) |
|---|---|
| AmB | 1 |
| AmBMU | 12 |
| AmBCU | 3 |
| AmBAU | 12* |

The mark * in above table is indicated that all mouses of 3 cases at 16 mg/kg dosing was died. It is showed that AmBAU has possibilities of acute toxicity.

INDUSTRIAL APPLICABILITY

The compound of the present invention has antifungal activity against fungi. Therefore, the compound of the present invention is useful for prevention or treatment against various infections associated with fungi (examples: deep mycosis, fungemia, respiratory mycosis, fungal meningitis, disseminated mycosis and the like).

The invention claimed is:
1. A compound represented by formula (I):

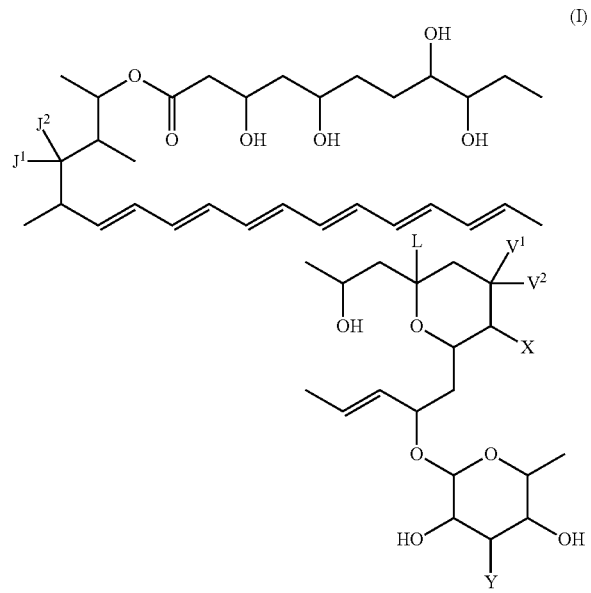

wherein X is a group of formula (II):

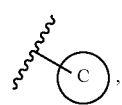

or —N(R$^F$)—CO—X$^1$,
wherein in formula (II) Ring C is substituted or unsubstituted aromatic carbocycle, substituted or unsubstituted non-aromatic carbocycle, substituted or unsubstituted aromatic heterocycle or substituted or unsubstituted non-aromatic heterocycle;
wherein R$^F$ is hydrogen, substituted or unsubstituted alkyl, substituted or unsubstituted alkenyl or substituted or unsubstituted alkynyl; and X$^1$ is any one of following groups (III)-(VI):

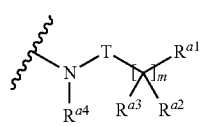 (III)

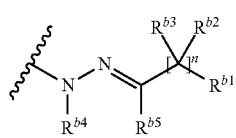 (IV)

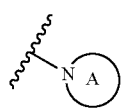 (V)

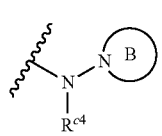 (VI)

wherein in formula (I) L, J$^1$ and V$^1$ are each independently hydrogen, halogen, hydroxy, substituted or unsubstituted amino or substituted or unsubstituted alkyloxy;
J$^2$ and V$^2$ are each independently hydrogen, substituted or unsubstituted alkyl, substituted or unsubstituted alkenyl or substituted or unsubstituted alkynyl;
or J$^1$ and J$^2$ and/or V$^1$ and V$^2$ may be taken together to form oxo;
wherein in formula (III) or (IV) R$^{a1}$ and R$^{b1}$ are each independently, hydrogen, halogen, hydroxy, carboxy, substituted or unsubstituted amino, formyl, substituted or unsubstituted carbamoyl, substituted or unsubstituted sulfamoyl, sulfo, cyano, substituted or unsubstituted ureido, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkyl ammonium, substituted or unsubstituted alkylsulfonyl, substituted or unsubstituted alkenylsulfonyl, substituted or unsubstituted alkynylsulfonyl, substituted or unsubstituted alkylphosphonyl, substituted or unsubstituted dialkynylphosphonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl or substituted or unsubstituted non-aromatic heterocyclylsulfonyl;

$R^{a2}$ and $R^{b2}$ are each independently hydrogen, halogen, hydroxy, carboxy, substituted or unsubstituted amino, substituted or unsubstituted carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl;

$R^{a3}$ and $R^{b3}$ are each independently, hydrogen, halogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted non-aromatic heterocyclyloxyalkyl, substituted or unsubstituted non-aromatic heterocyclyloxyalkenyl or substituted or unsubstituted non-aromatic heterocyclyloxyalkynyl;

or $R^{a2}$ and $R^{a3}$ and/or $R^{b2}$ and $R^{b3}$ are each independently may be taken together to form oxo, substituted or unsubstituted imino or thioxo, or may be taken together with neighboring atoms to form substituted or unsubstituted non-aromatic carbocycle or substituted or unsubstituted non-aromatic heterocycle;

$R^{a4}$, $R^{b4}$ and $R^{c4}$ are each independently, hydrogen, hydroxy, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl or substituted or unsubstituted non-aromatic carbocyclyl;

$R^{b5}$ is hydrogen, substituted or unsubstituted alkyl, substituted or unsubstituted alkenyl or substituted or unsubstituted alkynyl;

wherein in formula (V) or (VI) Ring A and Ring B are each independently, substituted or unsubstituted nitrogen-containing aromatic heterocycle or substituted or unsubstituted nitrogen-containing non-aromatic heterocycle;

wherein in formula (III) T is a bond, —N($R^{a5}$)— or —O—;

wherein the $R^{a5}$ is hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl or substituted or unsubstituted alkynylcarbonyl;

wherein in formula (III) or (IV) m and n are each independently an integer of 0 to 10;

wherein in formula (I) Y is any one of following groups:

(VII)

(VIII)

wherein in formula (VII) $R^A$ is hydrogen, substituted or unsubstituted alkyl, substituted or unsubstituted alkenyl or substituted or unsubstituted alkynyl;

$R^B$ and $R^C$ are each independently hydrogen, hydroxy, substituted or unsubstituted amino, substituted or unsubstituted alkyl, substituted or unsubstituted alkenyl or substituted or unsubstituted alkynyl;

or $R^B$ and $R^C$ may be taken together to form oxo, substituted or unsubstituted imino or thioxo, or may be taken together with neighboring atoms to form substituted or unsubstituted non-aromatic carbocycle or substituted or unsubstituted non-aromatic heterocycle;

wherein in formula (VII) or (VIII) $R^D$ is hydrogen, hydroxy, carboxy, substituted or unsubstituted amino, substituted or unsubstituted carbamoyl, substituted or unsubstituted amidino, substituted or unsubstituted guanidino, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl;

wherein in formula (VIII) $R^E$ is hydrogen, hydroxy or substituted or unsubstituted amino;

wherein in formula (VII) q is an integer of 0 to 10;

provided that the following compounds are excluded:
the compounds which X is either of following groups; and Y is —NH$_2$;

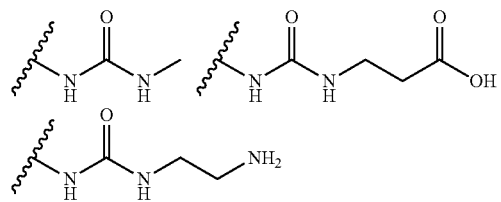

or a pharmaceutically acceptable salt thereof.

2. The compound or its pharmaceutically acceptable salt according to claim 1, wherein $J^1$, L and $V^1$ are hydroxy; and $J^2$ and $V^2$ are hydrogen.

3. The compound or its pharmaceutically acceptable salt according to claim 1, wherein X is a group of formula: —N($R^F$)—CO—$X^1$; $X^1$ is a group represented by formula (III); and T is a bond.

4. The compound or its pharmaceutically acceptable salt according to claim 3, wherein $R^{a1}$ is halogen, hydroxy, carboxy, substituted or unsubstituted amino, substituted or unsubstituted aromatic heterocyclylamino, substituted or unsubstituted non-aromatic heterocyclylamino, substituted or unsubstituted alkylammonium, carbamoyl, sulfamoyl, sulfo, cyano, substituted or unsubstituted ureido, guanidino, substituted or unsubstituted alkyloxy, substituted or unsubstituted non-aromatic heterocyclyloxy, substituted or unsubstituted alkylphosphonyl, substituted sulfamoyl, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl;

wherein said substituted or unsubstituted amino is selected from unsubstituted amino, hydroxyamino, sulfamoylamino, substituted or unsubstituted alkylamino, substituted or unsubstituted alkylsulfonylamino, substituted or unsubstituted non-aromatic carbocyclylcarbonylamino, substituted or unsubstituted aromatic carbocyclylcarbonylamino, substituted or unsubstituted aromatic heterocyclylcarbonylamino and substituted or unsubstituted non-aromatic heterocyclylcarbonylamino;

wherein said substituted or unsubstituted ureido is selected from ureido, substituted or unsubstituted alkylureido, substituted or unsubstituted aromatic heterocyclylureido and substituted or unsubstituted aromatic heterocyclylureido;

wherein said substituted sulfamoyl is substituted or unsubstituted aromatic heterocyclylsulfamoyl.

5. The compound or its pharmaceutically acceptable salt according to claim 3, wherein $R^{a2}$ are each independently hydrogen, halogen, hydroxy, carboxy, amino, carbamoyl, substituted or unsubstituted alkyl, substituted or unsubstituted non-aromatic heterocyclyloxyalkyl or substituted or unsubstituted alkylcarbonyl;

$R^{a3}$ are each independently, hydrogen, halogen, substituted or unsubstituted alkyl or substituted or unsubstituted non-aromatic heterocyclyloxyalkyl;

or $R^{a2}$ and $R^{a3}$ may be taken together to form oxo, or may be taken together with neighboring atoms to form non-aromatic carbocycle or non-aromatic heterocycle.

6. The compound or its pharmaceutically acceptable salt according to claim 3, wherein $R^{a4}$ is hydrogen, hydroxy, amino, substituted or unsubstituted alkyl or substituted or unsubstituted non-aromatic carbocyclyl.

7. The compound or its pharmaceutically acceptable salt according to claim 1, wherein X is a group of formula: —N($R^F$)—CO—$X^1$; $X^1$ is a group represented by formula (III); and T is —N($R^{a5}$)— or —O—.

8. The compound or its pharmaceutically acceptable salt according to claim 7, wherein $R^{a1}$ is hydroxy, carboxy, substituted amino, substituted or unsubstituted aromatic heterocyclylamino, formyl, carbamoyl, cyano, guanidino, substituted or unsubstituted alkyloxy, substituted or unsubstituted non-aromatic heterocyclyloxy, substituted or unsubstituted alkylcarbonyl, substituted or unsubstituted alkyloxycarbonyl, substituted or unsubstituted alkylsulfonyl, substituted or unsubstituted aromatic heterocyclylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted ureido;

wherein said substituted amino is hydroxyamino or substituted or unsubstituted alkylamino;

wherein said substituted ureido is substituted or unsubstituted aromatic heterocyclylureido.

9. The compound or its pharmaceutically acceptable salt according to claim 7, wherein $R^{a2}$ are each independently hydrogen, hydroxy or substituted or unsubstituted alkyl;

$R^{a3}$ are each independently hydrogen or substituted or unsubstituted alkyl;

or $R^{a2}$ and $R^{a3}$ may be taken together to form oxo or thioxo, or may be taken together with neighboring atoms to form substituted or unsubstituted non-aromatic carbocycle.

10. The compound or its pharmaceutically acceptable salt according to claim 7, wherein $R^{a4}$ is hydrogen.

11. The compound or its pharmaceutically acceptable salt according to claim 1, wherein X is a group of formula: —N($R^F$)—CO—X hu 1 ; and $X^1$ is a group represented by formula (IV).

12. The compound or its pharmaceutically acceptable salt according to claim 11, wherein $R^{b1}$ is hydroxy.

13. The compound or its pharmaceutically acceptable salt according to claim 11, wherein n is 1 or 2; $R^{b2}$ are each independently hydrogen or hydroxy; and $R^{b3}$ is hydrogen.

14. The compound or its pharmaceutically acceptable salt according to claim 11, wherein $R^{b4}$ is hydrogen; and $R^{b5}$ is hydrogen or substituted or unsubstituted alkyl.

15. The compound or its pharmaceutically acceptable salt according to claim 1, wherein X is —N($R^F$)—CO—$X^1$; and $X^1$ is a group represented by formula (V).

16. The compound or its pharmaceutically acceptable salt according to claim 15, wherein ring A is substituted or unsubstituted nitrogen-containing non-aromatic heterocycle.

17. The compound or its pharmaceutically acceptable salt according to claim 1, wherein X is a group of formula: —N($R^F$)—CO—$X^1$; $X^1$ is a group represented by formula (VI).

18. The compound or its pharmaceutically acceptable salt according to claim 17, wherein ring B is substituted or unsubstituted nitrogen-containing non-aromatic heterocycle.

19. The compound or its pharmaceutically acceptable salt according to claim 17, wherein $R^{c4}$ is hydrogen.

20. The compound or its pharmaceutically acceptable salt according to claim 1, wherein $R^F$ is hydrogen.

21. The compound or its pharmaceutically acceptable salt according to claim 1, wherein X is a group represented by formula (II); and said group is represent by formula (IX):

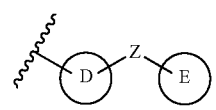

(IX)

wherein ring D and ring E are each independently substituted or unsubstituted aromatic carbocycle, substituted or unsubstituted non-aromatic carbocycle, substituted or unsubstituted aromatic heterocycle or substituted or unsubstituted non-aromatic heterocycle; and Z is a bond, alkylene, —O—, —S— or —N(H)—.

22. The compound or its pharmaceutically acceptable salt according to claim 21, wherein ring D is substituted or unsubstituted aromatic heterocycle; and ring E is substituted or unsubstituted aromatic carbocycle or substituted or unsubstituted aromatic heterocycle.

23. The compound or its pharmaceutically acceptable salt according to claim 21, wherein Z is a bond.

24. The compound or its pharmaceutically acceptable salt according to claim 21, wherein the substituent(s) on ring E is/are alkylamino.

25. The compound or its pharmaceutically acceptable salt according to claim 1, wherein $R^A$ are each independently hydrogen or substituted or unsubstituted alkyl; $R^B$ are each independently hydrogen or hydroxy or substituted or unsubstituted amino; $R^C$ are each independently hydrogen or hydroxy or substituted or unsubstituted amino; or $R^B$ and $R^C$ may be taken together to form oxo, substituted or unsubstituted imino, hydroxyimino or cyanoimino;

$R^D$ is hydrogen, hydroxy, carboxy, substituted or unsubstituted amino, carbamoyl, guanidine, substituted or unsubstituted aromatic carbocyclyl, substituted or unsubstituted aromatic heterocyclyl or substituted or unsubstituted non-aromatic heterocyclyl;

$R^E$ is amino;
wherein said substituted or unsubstituted amino is unsubstituted amino or substituted or unsubstituted alkylamino;
wherein said substituted or unsubstituted imino is unsubstituted imino, hydroxyimino or cyanoimino.

26. The compound or its pharmaceutically acceptable salt according to claim 1, wherein Y is $NH_2$.

27. The compound or its pharmaceutically acceptable salt according to claim 2, wherein X is a group of formula: $-N(R^F)-CO-X^1$, wherein $X^1$ is a group represented by formula (III);
T is $-N(H)-$; $R^{a1}$ is carboxy, carbamoyl or substituted amino; $R^{a2}$ is each independently hydrogen or hydroxy; and $R^{a3}$ and $R^{a4}$ are hydrogen; m is 2; and Y is $NH_2$.

28. A pharmaceutical composition containing the compound or its pharmaceutically acceptable salt according to claim 1.

29. A pharmaceutical composition of claim 28 having antifungal activity.

30. A compound represented by formula (X), (XI), (XVI) or (XVII):

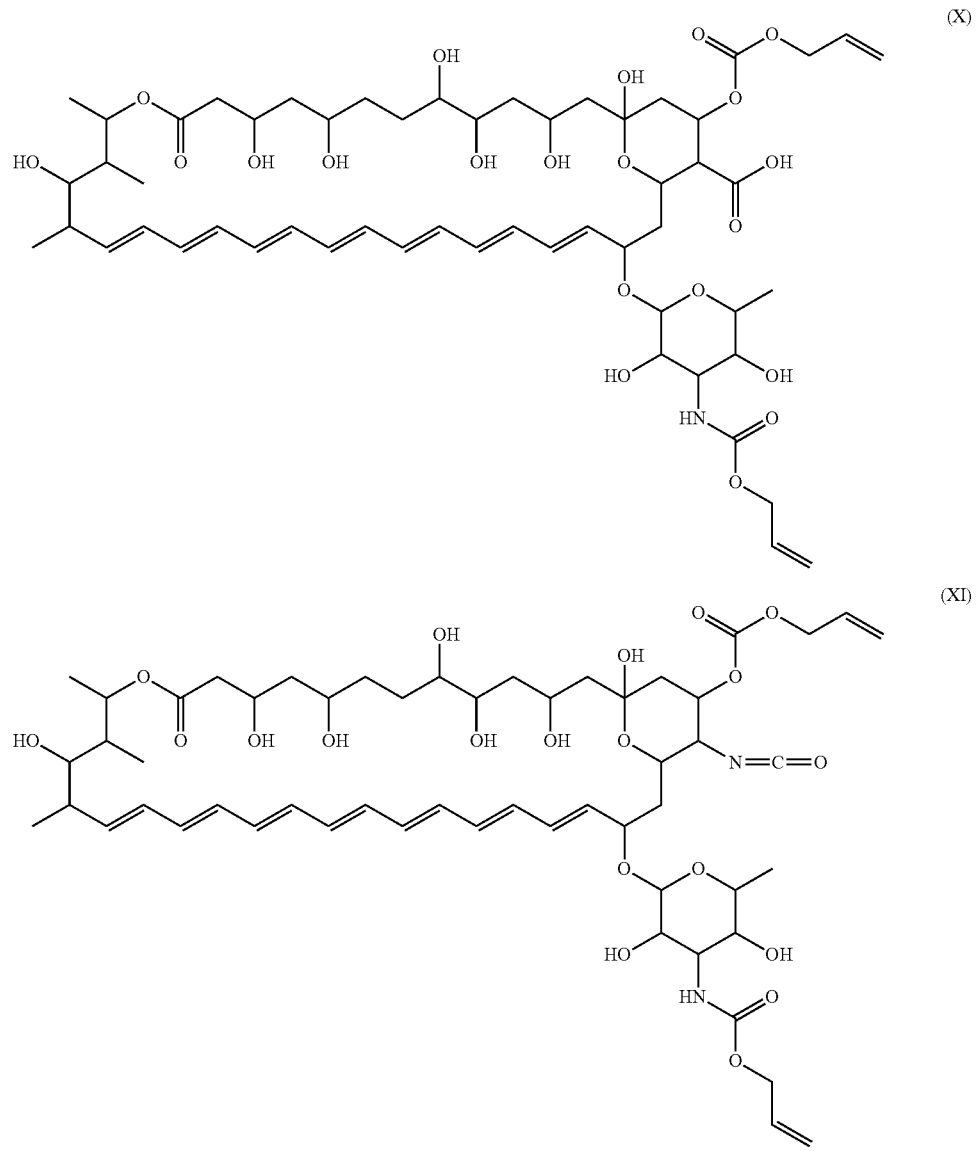

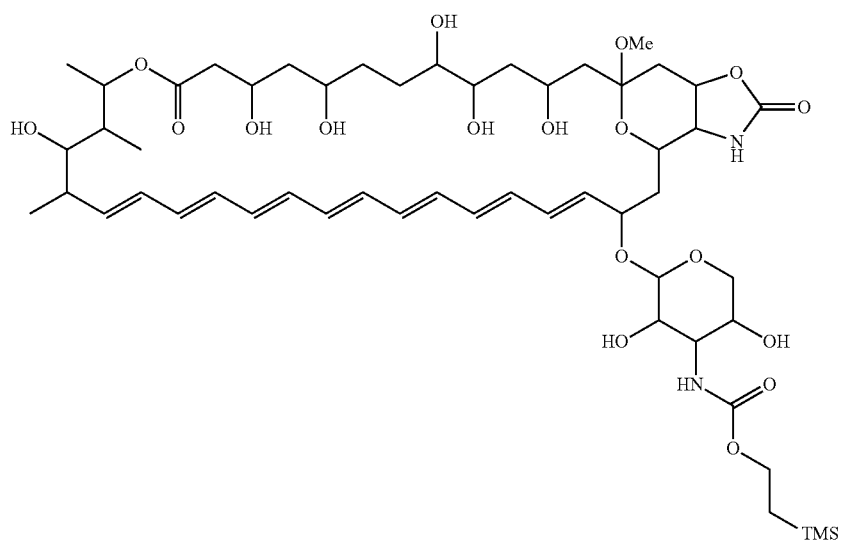
(XII)
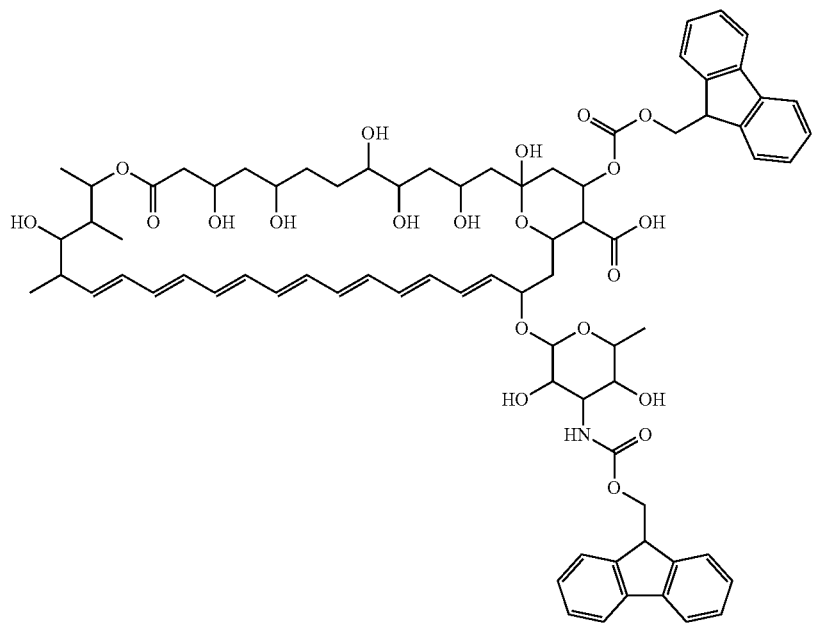
(XVI)

-continued
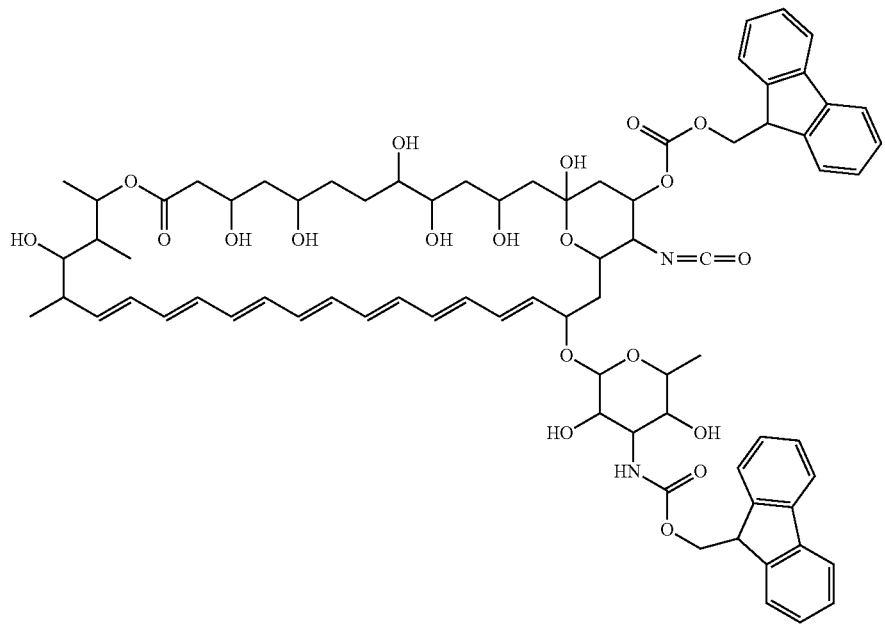
(XVII)
or its pharmaceutically acceptable salt.
31. The compound or its pharmaceutically acceptable salt according to claim 1,
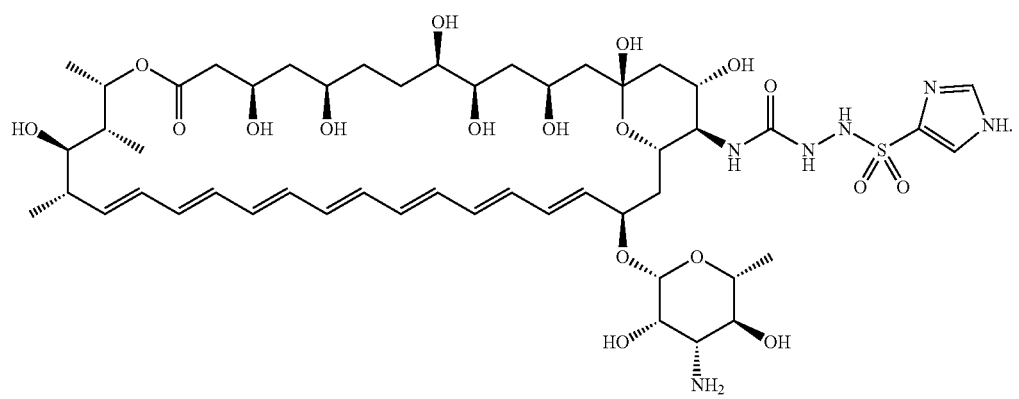 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NNS(=O)(=O)c1c[nH]cn1]
32. A pharmaceutical composition comprising the compound according to claim 31, or its pharmaceutically acceptable salt.

33. The compound or its pharmaceutically acceptable salt according to claim 1, said compound being:

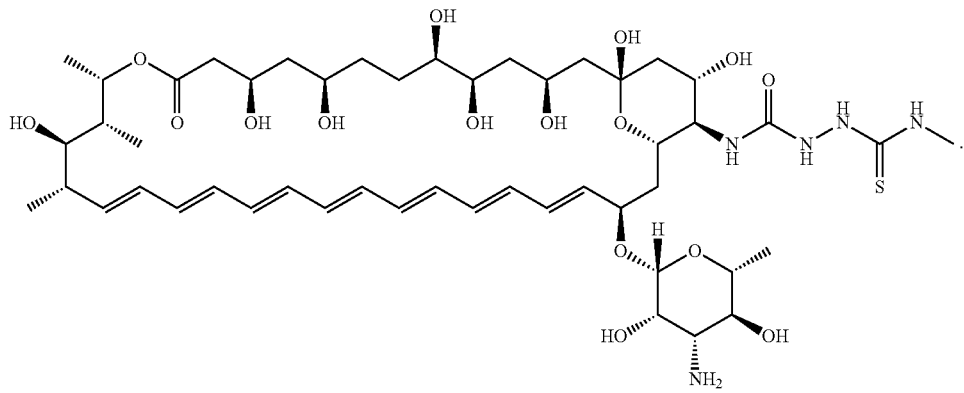

34. A pharmaceutical composition comprising the compound according to claim 33, or its pharmaceutically acceptable salt.

35. The compound or its pharmaceutically acceptable salt according to claim 1, said compound being:

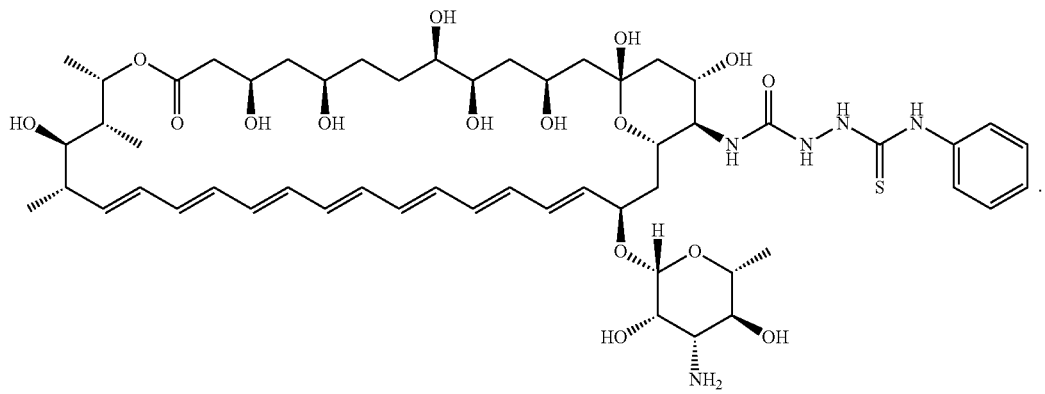 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NNC(=S)Nc1ccccc1]

36. A pharmaceutical composition comprising the compound according to claim 35, or its pharmaceutically acceptable salt.

37. The compound or its pharmaceutically acceptable salt according to claim 1, said compound being:

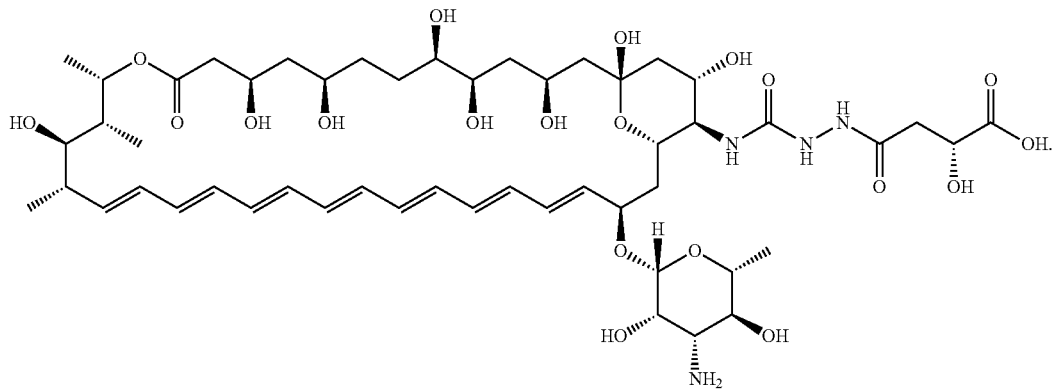 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NNC(=O)C[C@@H](O)C(=O)O]

38. A pharmaceutical composition comprising the compound according to claim 37, or its pharmaceutically acceptable salt.

39. The compound or its pharmaceutically acceptable salt according to claim 1, said compound being:

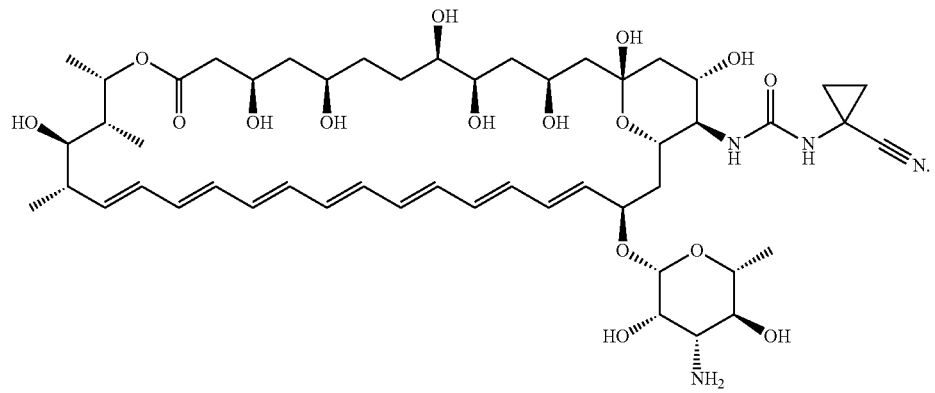 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NC1(C#N)CC1]

40. A pharmaceutical composition comprising the compound according to claim 39, or its pharmaceutically acceptable salt.

41. The compound or its pharmaceutically acceptable salt according to claim 1, said compound being:

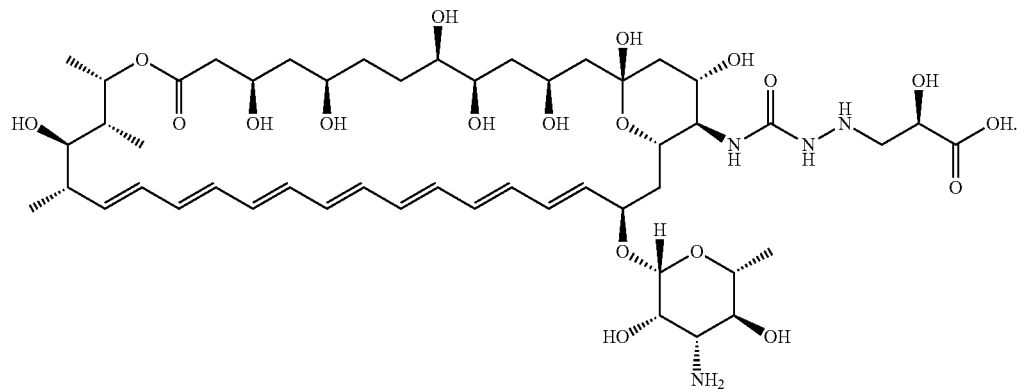 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2NC(=O)NNC[C@@H](O)C(=O)O]

42. A pharmaceutical composition comprising the compound according to claim 21, or its pharmaceutically acceptable salt.

* * * * *